United States Patent
Liu et al.

(10) Patent No.: US 11,124,570 B2
(45) Date of Patent: Sep. 21, 2021

(54) ANTI-PD1 AND ANTI-CTLA4 ANTIBODIES

(71) Applicant: QILU PUGET SOUND BIOTHERAPEUTICS CORPORATION, Bothell, WA (US)

(72) Inventors: Zhi Liu, Shoreline, WA (US); Zhonghua Hu, Kenmore, WA (US); William C. Fanslow, Normandy Park, WA (US); Wei Yan, Samamish, WA (US)

(73) Assignee: QILU PUGET SOUND BIOTHERAPEUTICS CORPORATION, Bothell, WA (US)

( * ) Notice: Subject to any disclaimer, the term of this patent is extended or adjusted under 35 U.S.C. 154(b) by 216 days.

(21) Appl. No.: 16/347,554

(22) PCT Filed: Nov. 6, 2017

(86) PCT No.: PCT/US2017/060122
§ 371 (c)(1),
(2) Date: May 3, 2019

(87) PCT Pub. No.: WO2018/089293
PCT Pub. Date: May 17, 2018

(65) Prior Publication Data
US 2019/0276542 A1 Sep. 12, 2019

Related U.S. Application Data

(60) Provisional application No. 62/419,157, filed on Nov. 8, 2016.

(51) Int. Cl.
*C07K 16/28* (2006.01)
*A61P 35/00* (2006.01)
*A61K 9/00* (2006.01)
*C07K 16/30* (2006.01)
*A61K 39/00* (2006.01)

(52) U.S. Cl.
CPC ........ *C07K 16/2818* (2013.01); *A61K 9/0019* (2013.01); *A61P 35/00* (2018.01); *C07K 16/30* (2013.01); *A61K 2039/507* (2013.01); *C07K 2317/14* (2013.01); *C07K 2317/21* (2013.01); *C07K 2317/522* (2013.01); *C07K 2317/55* (2013.01); *C07K 2317/56* (2013.01); *C07K 2317/74* (2013.01); *C07K 2317/76* (2013.01); *C07K 2317/92* (2013.01)

(58) Field of Classification Search
CPC .................................................. C07K 16/2818
See application file for complete search history.

(56) References Cited

U.S. PATENT DOCUMENTS

| 5,863,892 | A | 1/1999 | Stern et al. |
|---|---|---|---|
| 6,682,736 | B1 | 1/2004 | Hanson et al. |
| 8,008,449 | B2 | 8/2011 | Korman et al. |
| 8,101,724 | B2 | 1/2012 | MacDonald et al. |
| 8,592,562 | B2 | 11/2013 | Kannan et al. |
| 9,346,889 | B2 | 5/2016 | Muraro et al. |
| 9,724,413 | B2 | 8/2017 | Maecker et al. |
| 2008/0269466 | A1 | 10/2008 | Humphreys |
| 2009/0182127 | A1 | 7/2009 | Kjaergaard et al. |
| 2009/0311187 | A1 | 12/2009 | Berman et al. |
| 2014/0010814 | A1 | 1/2014 | Benhar et al. |
| 2014/0154254 | A1 | 6/2014 | Kannan et al. |
| 2015/0274807 | A1 | 10/2015 | Xu et al. |
| 2016/0152726 | A1 | 6/2016 | Kim |
| 2017/0088615 | A1 | 3/2017 | Korman et al. |
| 2019/0161548 | A1* | 5/2019 | Johnson ................. C07K 16/44 |

FOREIGN PATENT DOCUMENTS

| EP | 2170959 B | 10/2013 |
|---|---|---|
| WO | 2000037504 A2 | 6/2000 |
| WO | 2007113648 A2 | 10/2007 |
| WO | 2009100140 A1 | 8/2009 |
| WO | 2011045704 A1 | 4/2011 |
| WO | 2015112800 A1 | 7/2015 |

OTHER PUBLICATIONS

Nivolumab, PubChem Substance Record, available at http://pubchem.ncbi/nlm.nih.gov/substance/178103907, accessed Oct. 11, 2019.
Boutros et al. (2016), Safety profiles of anti-CTLA-4 and anti-PD-1 antibodies alone and in combination, Nat. Rev. Clin. Oncol. 13: 473-486.
Buchbinder and Desai (2016), CTLA-4 and PD-1 pathways: similarities, differences, and implications of their inhibition, Am J. Clin. Oncol. 39(1): 98-106.
Choi et al. (2015), Antibody humanization by structure-based computational protein design, mAbs 7(6): 1045-1057.
Gijsen et al. (2010), HER2 phophorylation is maintained by a PKB negative feedback loop in response to anti-HER2 Herceptin in breast cancer, PLoS Biol. 8(12): e1000563.
Gijsen et al. (2016), Correction: HER2 phophorylation is maintained by a PKB negative feedback loop in response to anti-HER2 Herceptin in breast cancer, PLoS Biol., DOI:10.1371/journal.pbio.1002414.
Klein et al. (2012), Progress in overcoming the chain association issue in bispecific heterodimeric IgG antibodies, mAbs 4(6): 653-663.
Li et al. (2010), Cell culture processes for monoclonal antibody Production, mAbs 2(5): 466-477.
Lin and Nemunaitis (2004), Oncolytic viral therapies, Cancer Gene Therapy, 11: 643-664.

(Continued)

*Primary Examiner* — Laura B Goddard
(74) *Attorney, Agent, or Firm* — Procopio, Cory, Hargreaves & Savitch LLP

(57) ABSTRACT

Anti-CTLA4 antibodies, anti-PD1 antibodies, mixtures thereof, polynucleotides encoding such antibodies or mixtures, optionally carried on vectors, and methods of treatment utilizing such antibodies, mixtures, polynucleotides, or vectors are described herein. The anti-CTLA4 and anti-PD1 antibodies have particular sequences and properties. The methods of treatment include uses in treatment of cancer, infections, and immunodeficiency disorders.

12 Claims, 22 Drawing Sheets

Specification includes a Sequence Listing.

(56) References Cited

OTHER PUBLICATIONS

Lindzen et al. (2010), Tailored cancer immunotherapy using combinations of chemotherapy and a mixture of antibodies against EGF-receptor ligands, Proc. Natl. Acad. Sci. 107(28): 12559-12563.
KEGG DRUG: Nivolumab. Available at https://www.genome.jp/dbget-bin/www_bget?dr:D10316, downloaded Oct. 11, 2019.
Lewis et al. (2014), Generation of bispecific IgG antibodies by structure-based design of an orthogonal Fab interface, Nature Biotechnol. 32(2); 191-198.
Liu et al. (2015), A novel antibody engineering strategy for making monovalent bispecific heterodimeric IgG antibodies by electrostatic steering mechanism, J. Biol. Chem. 290(12): 7535-7562.
Logtenberg (2007), Antibody cocktails: next-generation biopharmaceuticals with improved potency, Trends in Biotechnology, Elsevier Publications, Cambridge, GB, 25(9): 390-394.
Mazor et al. (2015), Improving target cell specificity using a novel monovalent bispecific IgG design, mAbs 7(2): 377-389.
Pardoll (2012), The blockade of immune checkpoints in cancer immunotherapy, Nature Reviews Cancer 12: 252-264.
Rasmussen et al. (2012), Recombinant antibody mixtures: production strategies and cost considerations, Archives of Biochem. Biophys. 526(2): 139-145.
Rasmussen et al. (2007), Manufacture of recombinant polyclonal antibodies, Biotechnol. Lett. 29: 845-852.
Reiter et al. (1996), Engineering antibody Fv fragments for cancer detection and therapy: disulfide-stabilized Fv rragments, Nature Biotechnol. 14: 1239-1245.
Robak (2013), The emerging therapeutic role of antibody mixtures, Expert Opinion Bio. Ther. 13(7): 953-958. doi:10.1517/14712598. 2013.799133.
Ulrich Storz (2016), Intellectual property issues of immune checkpoint inhibitors mAbs 8(1): 10-26.
Thakur and Lum (2010), Cancer therapy with bispecific antibodies: Clinical experience, Curr. Opin. Mol. Ther. 12(3): 340-349.
Walker and Sansom (2011), The emerging role of CTLA4 as a cell-extrinsic regulator of T cell responses, Nature Reviews Immunology 11: 852-863.
Wolchok et al. (2013), Nivolumab plus ipilimumab in advanced melanoma, N. Engl. J. Med. 369(2): 122-133.
Larkin, et al. "Combined Nivolumab and Ipilimumab or Monotherapy in Untreated Melanoma," The New England Journal of Medicine, vol. 373, No. 1, Jul. 2, 2015, United States, pp. 23-34.
Liu, et al. "A Novel Antibody Engineering Strategy for Making Monovalent Bispecific Heterodimeric IgG Antibodies by Electrostatic Steering Mechanism," Journal of Biological Chemistry, vol. 290, No. 12, Mar. 20, 2015, pp. 7535-7562.
International Search Report for International Patent Application No. PCT/US2017/060122, dated Jan. 4, 2019, 8 pages.
Written Opinion for International Patent Application No. PCT/US2017/060122, dated Jan. 4, 2019, 9 pages.

* cited by examiner

Anti-hCTLA VH CDRs

| antibody | CDR1 | CDR2 | CDR3 |
|---|---|---|---|
| 1E1 | SYGMH (SEQ ID NO:3) | VIWYNPSEKDYADSAKG (SEQ ID NO:4) | AGLLGYFDY (SEQ ID NO:5) |
| 2F1 | SYGMH (SEQ ID NO:3) | VIWY*HR*SEKDYADSAKG (SEQ ID NO:13) | AGLLGYFDY (SEQ ID NO:5) |
| 3G1 | SYGMH (SEQ ID NO:3) | VIWY*KS*SEK*YY*ADSAKG (SEQ ID NO:20) | *G*GLLGYFDY (SEQ ID NO:21) |
| 4H1 | SYGMH (SEQ ID NO:3) | VIWYNPS*KK*DYADSAKG (SEQ ID NO:24) | *G*GL*F*GYFDY (SEQ ID NO:25) |
| 5B2 | SYGMH (SEQ ID NO:3) | VIWY*KS*SEKDYADSAKG (SEQ ID NO:31) | AGLLGYFDY (SEQ ID NO:5) |
| 6E3 | SYGMH (SEQ ID NO:3) | VIWY*KT*SEKDYADSAKG (SEQ ID NO:37) | AGLLGYFDY (SEQ ID NO:5) |
| 7A4 | SYGMH (SEQ ID NO:3) | VIWY*QT*SEKDYADSAKG (SEQ ID NO:43) | AGLLGYFDY (SEQ ID NO:5) |
| 8B4 | SYGMH (SEQ ID NO:3) | VIWY*Q*PSEKDYADSAKG (SEQ ID NO:46) | AG*F*LGYFDY (SEQ ID NO:47) |
| 9C4 | SYGMH (SEQ ID NO:3) | VIWY*KS*SEKDYADSAKG (SEQ ID NO:31) | AGLLGYFDY (SEQ ID NO:5) |
| 10D4 | SYGMH (SEQ ID NO:3) | VIWY*H*PS*K*KDYADSAKG (SEQ ID NO:59) | AGLLGYFDY (SEQ ID NO:5) |
| 11F4 | SYGMH (SEQ ID NO:3) | VIWY*K*PSEKDYADSAKG (SEQ ID NO:65) | *G*GLLGYFDY (SEQ ID NO:21) |
| 12G4 | SYGMH (SEQ ID NO:3) | VIWYN*TS**K*KDYADSAKG (SEQ ID NO:70) | *G*GLLGYFDY (SEQ ID NO:21) |
|  | SYGMH (SEQ ID NO:3) | VIWYKPSEKDYADSAKG<br>NS K Y<br>QT<br>HR<br>(SEQ ID NO:75) | AGLLGYFDY<br>G FF<br>(SEQ ID NO:77) |

FIGURE 1

Anti-hCTLA4 VL CDRs

| antibody | CDR1 | CDR2 | CDR3 |
|---|---|---|---|
| 1E1 | RASQSISSYLA (SEQ ID NO:8) | GVSSRAT (SEQ ID NO:9) | QQYGMSPFT (SEQ ID NO:10) |
| 2F1 | RASQSI*N*SYLA (SEQ ID NO:16) | GVSSRAT (SEQ ID NO:9) | QQYGM*Y*PFT (SEQ ID NO:17) |
| 3G1 | RASQSI*N*SYLA (SEQ ID NO:16) | GVSSRAT (SEQ ID NO:9) | QQYGM*Y*PFT (SEQ ID NO:17) |
| 4H1 | RASQS*V*SSYLA (SEQ ID NO:28) | GVSSRAT (SEQ ID NO:9) | QQYGM*Y*PFT (SEQ ID NO:17) |
| 5B2 | RASQS*L*SSYLA (SEQ ID NO:34) | GVSSRAT (SEQ ID NO:9) | QQYGM*Y*PFT (SEQ ID NO:17) |
| 6E3 | RASQS*VT*SYLA (SEQ ID NO:40) | GVSSRAT (SEQ ID NO:9) | QQYGMSPFT (SEQ ID NO:10) |
| 7A4 | RASQS*V*SSYLA (SEQ ID NO:28) | GVSSRAT (SEQ ID NO:9) | QQYGM*Y*PFT (SEQ ID NO:17) |
| 8B4 | RASQS*VN*SYLA (SEQ ID NO:50) | GVSSRAT (SEQ ID NO:9) | QQYGM*Y*PFT (SEQ ID NO:17) |
| 9C4 | RASQS*LN*SYLA (SEQ ID NO:55) | GVSSRAT (SEQ ID NO:9) | QQYG*IY*PFT (SEQ ID NO:56) |
| 10D4 | RASQS*VT*SYLA (SEQ ID NO:40) | GVSSRAT (SEQ ID NO:9) | QQYG*R*YPFT (SEQ ID NO:62) |
| 11F4 | RASQSI*N*SYLA (SEQ ID NO:16) | GVSSRAT (SEQ ID NO:9) | QQYG*RY*PFT (SEQ ID NO:62) |
| 12G4 | RASQSI*T*SYLA (SEQ ID NO:73) | GVSSRAT (SEQ ID NO:9) | QQYG*RY*PFT (SEQ ID NO:62) |
| | RASQSINSYLA<br>VS<br>LT<br>(SEQ ID NO:79) | GVSSRAT<br><br><br>(SEQ ID NO:9) | QQYGMYPFT<br>RS<br>I<br>(SEQ ID NO:81) |

FIGURE 2

Anti-hCTLA4 VH Sequences

```
                    20                              40
                     *                               *
1E1   QVQLVESGGG VVEPGRSLRL SCAASGFTFS SYGMHWVRQA PGKGL
2F1   QVQLVESGGG VVEPGRSLRL SCAASGFTFS SYGMHWVRQA PGKGL
3G1   QVQLVESGGG VVEPGRSLRL SCTASGFTFS SYGMHWVRQA PGKGL
4H1   QVQLVESGGG VVEPGRSLRL SCTASGFTFS SYGMHWVRQA PGKGL
5B2   QVQLVESGGG VVEPGRSLRL SCTASGFTFS SYGMHWVRQA PGKGL
6E3   QVQLVESGGG VVEPGRSLRL SCAASGFTFS SYGMHWVRQA PGKGL
7A4   QVQLVESGGG VVEPGRSLRL SCTASGFTFS SYGMHWVRQA PGKGL
8B4   QVQLVESGGG VVEPGRSLRL SCAASGFTFS SYGMHWVRQA PGKGL
9C4   QVQLVESGGG VVEPGRSLRL SCAASGFTFS SYGMHWVRQA PGKGL
10D4  QVQLVESGGG VVEPGRSLRL SCTASGFTFS SYGMHWVRQA PGKGL
11F4  QVQLVESGGG VVEPGRSLRL SCAASGFTFS SYGMHWVRQA PGKGL
12G4  QVQLVESGGG VVEPGRSLRL SCAASGFTFS SYGMHWVRQA PGKGL 60                            80
               #       *                        *   ###
1E1   EWVAV IWYNPSEKDY ADSAKGRFTI SRDNSKNTLY LQMNSLRAED
2F1   EWVAV IWYHRSEKDY ADSAKGRFTI SRDNSKNTLY LQMNSLRAED
3G1   EWVAV IWYKSSEKYY ADSAKGRFTI SRDNSKNTLY LQMNSLRAED
4H1   EWVAV IWYNPSKKDY ADSAKGRFTI SRDNSKNTLY LQMNSLRAED
5B2   EWVAV IWYKSSEKDY ADSAKGRFTI SRDNSKNTLY LQMNSLRAED
6E3   EWVAV IWYKTSEKDY ADSAKGRFTI SRDNSKNTLY LQMNSLRAED
7A4   EWVAV IWYQTSEKDY ADSAKGRFTI SRDNSKNTLY LQMNSLRAED
8B4   EWVAV IWYQPSEKDY ADSAKGRFTI SRDNSKNTLY LQMNSLRAED
9C4   EWVAV IWYKSSEKDY ADSAKGRFTI SRDNSKNTLY LQMNSLRAED
10D4  EWVAV IWYHPSKKDY ADSAKGRFTI SRDNSKNTLY LQMNSLRAED
11F4  EWVAV IWYKPSEKDY ADSAKGRFTI SRDNSKNTLY LQMNSLRAED
12G4  EWVAV IWYNTSKKDY ADSAKGRFTI SRDNSKNTLY LQMNSLRAED

100
              *#
1E1   TAVYYCARAG LLGYFDYWGQ GTLVTVSS (SEQ ID NO:2)
2F1   TAVYYCARAG LLGYFDYWGQ GTLVTVSS (SEQ ID NO:12)
3G1   TAVYYCARGG LLGYFDYWGQ GTLVTVSS (SEQ ID NO:19)
4H1   TAVYYCARGG LFGYFDYWGQ GTLVTVSS (SEQ ID NO:23)
5B2   TAVYYCARAG LLGYFDYWGQ GTLVTVSS (SEQ ID NO:30)
6E3   TAVYYCARAG LLGYFDYWGQ GTLVTVSS (SEQ ID NO:36)
7A4   TAVYYCARAG LLGYFDYWGQ GTLVTVSS (SEQ ID NO:42)
8B4   TAVYYCARAG FLGYFDYWGQ GTLVTVSS (SEQ ID NO:45)
9C4   TAVYYCARAG LLGYFDYWGQ GTLVTVSS (SEQ ID NO:52)
10D4  TAVYYCARAG LLGYFDYWGQ GTLVTVSS (SEQ ID NO:58)
11F4  TAVYYCARGG LLGYFDYWGQ GTLVTVSS (SEQ ID NO:64)
12G4  TAVYYCARGG LLGYFDYWGQ GTLVTVSS (SEQ ID NO:69)
```

FIGURE 3

Anti-hCTLA4 VL Sequences

```
                    20                           40
                     *                            *
1E1   EIVLTQSPGT LSLSPGERAT LSCRASQSIS SYLAWYQQKP
2F1   EIVLTQSPGT LSLSPGERAT LSCRASQSIN SYLAWYQQKP
3G1   EIVLTQSPGT LSLSPGERAT LSCRASQSIN SYLAWYQQKP
4H1   EIVLTQSPGT LSLSPGERAT LSCRASQSVS SYLAWYQQKP
5B2   EIVLTQSPGT LSLSPGERAT LSCRASQSLS SYLAWYQQKP
6E3   EIVLTQSPGT LSLSPGERAT LSCRASQSVT SYLAWYQQKP
7A4   EIVLTQSPGT LSLSPGERAT LSCRASQSVS SYLAWYQQKP
8B4   EIVLTQSPGT LSLSPGERAT LSCRASQSVN SYLAWYQQKP
9C4   EIVLTQSPGT LSLSPGERAT LSCRASQSLN SYLAWYQQKP
10D4  EIVLTQSPGT LSLSPGERAT LSCRASQSVT SYLAWYQQKP
11F4  EIVLTQSPGT LSLSPGERAT LSCRASQSIN SYLAWYQQKP
12G4  EIVLTQSPGT LSLSPGERAT LSCRASQSIT SYLAWYQQKP 60                           80
                     *                            *
1E1   GQAPRPLIYG VSSRATGIPD RFSGSGSGTD FTLTISRLEP
2F1   GQAPRPLIYG VSSRATGIPD RFSGSGSGTD FTLTISRLEP
3G1   GQAPRPLIYG VSSRATGIPD RFSGSGSGTD FTLTISRLEP
4H1   GQAPRPLIYG VSSRATGIPD RFSGSGSGTD FTLTISRLEP
5B2   GQAPRLLIYG VSSRATGIPD RFSGSGSGTD FTLTISRLEP
6E3   GQAPRPLIYG VSSRATGIPD RFSGSGSGTD FTLTISRLEP
7A4   GQAPRPLIYG VSSRATGIPD RFSGSGSGTD FTLTISRLEP
8B4   GQAPRPLIYG VSSRATGIPD RFSGSGSGTD FTLTISRLEP
9C4   GQAPRPLIYG VSSRATGIPD RFSGSGSGTD FTLTISRLEP
10D4  GQAPRPLIYG VSSRATGIPD RFSGSGSGTD FTLTISRLEP
11F4  GQAPRPLIYG VSSRATGIPD RFSGSGSGTD FTLTISRLEP
12G4  GQAPRPLIYG VSSRATGIPD RFSGSGSGTD FTLTISRLEP

100
                    *
1E1   EDFAVYYCQQ YGMSPFTFGP GTKVDIK (SEQ ID NO:7)
2F1   EDFAVYYCQQ YGMYPFTFGP GTKVDIK (SEQ ID NO:15)
3G1   EDFAVYYCQQ YGMYPFTFGP GTKVDIK (SEQ ID NO:15)
4H1   EDFAVYYCQQ YGMYPFTFGP GTKVDIK (SEQ ID NO:27)
5B2   EDFAVYYCQQ YGMYPFTFGP GTKVDIK (SEQ ID NO:33)
6E3   EDFAVYYCQQ YGMSPFTFGP GTKVDIK (SEQ ID NO:39)
7A4   EDFAVYYCQQ YGMYPFTFGP GTKVDIK (SEQ ID NO:27)
8B4   EDFAVYYCQQ YGMYPFTFGP GTKVDIK (SEQ ID NO:49)
9C4   EDFAVYYCQQ YGIYPFTFGP GTKVDIK (SEQ ID NO:54)
10D4  EDFAVYYCQQ YGRYPFTFGP GTKVDIK (SEQ ID NO:61)
11F4  EDFAVYYCQQ YGRYPFTFGP GTKVDIK (SEQ ID NO:67)
12G4  EDFAVYYCQQ YGRYPFTFGP GTKVDIK (SEQ ID NO:72)
```

FIGURE 4

Anti-hPD1 VH CDRs

| Antibody | CDR1 | CDR2 | CDR3 |
|---|---|---|---|
| 1 | NYWIH (SEQ ID NO:88) | EIDPYDSYTNYNQKFKG (SEQ ID NO:89) | PGFTYGGMDF (SEQ ID NO:90) |
| 2 | *SYWMH* (SEQ ID NO:98) | EIDPYDSYTNYNQKFKG (SEQ ID NO:89) | PG*N*TYGGMD*Y* (SEQ ID NO:99) |
| 3 | NYWMH (SEQ ID NO:105) | EIDPYDSYTNYNQKFKG (SEQ ID NO:89) | PGFTYGGMDF (SEQ ID NO:90) |
| 4 | NYWMH (SEQ ID NO:105) | EIDP*F*DSYTNYNQKFKG (SEQ ID NO:111) | PG*Y*TYGGMDF (SEQ ID NO:112) |
| 5 | NYWIH (SEQ ID NO:88) | EIDP*F*DSYTNYNQKFKG (SEQ ID NO:111) | PGFTYGGMDF (SEQ ID NO:90) |
| 6 | NYWIH (SEQ ID NO:88) | EIDPYDSYTNYNQKFKG (SEQ ID NO:89) | PG*Y*TYGGMDF (SEQ ID NO:112) |
| 7 | NYWIH (SEQ ID NO:88) | EIDPYDSYTNYNQKFKG (SEQ ID NO:89) | PG*L*TYGGMDF (SEQ ID NO:127) |
| 8 | NYWIH (SEQ ID NO:88) | EIDPYDSYTNYNQKFKG (SEQ ID NO:89) | PG*N*TYGGMDF (SEQ ID NO:134) |
| 9 | *SYWMH* (SEQ ID NO:98) | EIDPYDSYTNYNQKFKG (SEQ ID NO:89) | PGFTYGGMDF (SEQ ID NO:90) |
| 10 | *SYWMH* (SEQ ID NO:98) | EIDP*F*DSYTNYNQKFKG (SEQ ID NO:111) | PG*Y*TYGGMDF (SEQ ID NO:112) |
| 11 | *SY*WIH (SEQ ID NO:149) | EIDP*S*DSYTNYNQKFKG (SEQ ID NO:150) | PG*Y*TYGGMDF (SEQ ID NO:112) |
| 12 | NYWMH (SEQ ID NO:105) | EIDP*F*DSYTNYNQKFKG (SEQ ID NO:111) | PGFTYGGMDF (SEQ ID NO:90) |
| 13 | *SY*WIH (SEQ ID NO:149) | EIDPYDSYTNYNQKFKG (SEQ ID NO:89) | PG*L*TYGGMDF (SEQ ID NO:127) |
| 14 | NYWIH (SEQ ID NO:88) | EIDPYDSYTNYNQKFKG (SEQ ID NO:89) | PG*Y*TYGGMDF (SEQ ID NO:112) |
| 15 | NYWMH (SEQ ID NO:105) | EIDPYDSYTNYNQKFKG (SEQ ID NO:89) | PG*L*TYGGMDF (SEQ ID NO:127) |
| | NYWMH (SEQ ID NO:170) | EIDPYDSYTNYNQKFKG (SEQ ID NO:172) | PGFTYGGMDF (SEQ ID NO:174) |
| | S I | F    S | Y Y<br>L<br>N |

FIGURE 5

Anti-hPD1 VL CDRs

| Antibody | CDR1 | CDR2 | CDR3 |
|---|---|---|---|
| 1 | KSSQSLFNSGNQKNYLA (SEQ ID NO:93) | GASTRDS (SEQ ID NO:94) | QNDHYYPYT (SEQ ID NO:95) |
| 2 | RSSQSLFNSGNQKNYLA (SEQ ID NO:102) | GASTRDS (SEQ ID NO:94) | QNDHYYPYT (SEQ ID NO:95) |
| 3 | KSSQSLFNSGNQKNYLA (SEQ ID NO:93) | GASTRES (SEQ ID NO:108) | QNDHYYPYT (SEQ ID NO:95) |
| 4 | KSSQSLLNSGNQKNYLA (SEQ ID NO:115) | GASTRDS (SEQ ID NO:94) | QNDHYYPYT (SEQ ID NO:95) |
| 5 | KSSQSLLNSGNQKNYLA (SEQ ID NO:120) | GASTRES (SEQ ID NO:108) | QNDHYYPYT (SEQ ID NO:95) |
| 6 | RSSQSLFNSGNQKNYLA (SEQ ID NO:102) | GASTRES (SEQ ID NO:108) | QNDHYYPYT (SEQ ID NO:95) |
| 7 | RSSQSLFISGNQKNYLA (SEQ ID NO:130) | GASTRDS (SEQ ID NO:94) | QNMHYYPYT (SEQ ID NO:131) |
| 8 | KSSQSLFISGNQKNYLA (SEQ ID NO:137) | GASTRDS (SEQ ID NO:94) | QNMHYYPYT (SEQ ID NO:131) |
| 9 | RSSQSLLISGNQKNYLA (SEQ ID NO:142) | GASTRDS (SEQ ID NO:94) | QNMHYYPYT (SEQ ID NO:131) |
| 10 | RSSQSLFISGNQKNYLA (SEQ ID NO:130) | GASTRDS (SEQ ID NO:94) | QNMHYYPYT (SEQ ID NO:131) |
| 11 | RSSQSLFISGNQKNYLA (SEQ ID NO:130) | GASTRDS (SEQ ID NO:94) | QNMHYYPYT (SEQ ID NO:131) |
| 12 | RSSQSLLISGNQKNYLA (SEQ ID NO:142) | GASTRDS (SEQ ID NO:94) | QNMHYYPYT (SEQ ID NO:131) |
| 13 | KSSQSLLNSGNQKNYLA (SEQ ID NO:115) | GASTRDS (SEQ ID NO:94) | QNDHYYPYT (SEQ ID NO:95) |
| 14 | KSSQSLFNSGNQKNYLA (SEQ ID NO:93) | GASTRDS (SEQ ID NO:94) | QNDHYYPYT (SEQ ID NO:95) |
| 15 | RSSQSLFNSGNQKNYLA (SEQ ID NO:102) | GASTRES (SEQ ID NO:108) | QNDHYYPYT (SEQ ID NO:95) |
|  | RSSQSLFNSGNQKNYLA (SEQ ID NO:176) | GASTRDS (SEQ ID NO:177) | QNDHYYPYT (SEQ ID NO:179) |
|  | K        LI | E | N |

FIGURE 6

Anti-hPD1 VH Sequences

```
                    20                              40
                     *                               *
1   QVQLVQSGAE  VKKPGASVKV  SCKASGYTFT  NYWIHWVRQA  PGQGL
2   QVQLVQSGAE  VKKPGASVKV  SCKASGYTFT  SYWMHWVRQA  PGQGL
3   QVQLVQSGAE  VKKPGASVKV  SCKASSYTFT  NYWMHWVRQA  PGQGL
4   QVQLVQSGAE  VKKPGASVKV  SCKASGYTFT  NYWMHWVRQA  PGQGL
5   QVQLVQSGAE  VKKPGASVKV  SCKASGYTFT  NYWMHWVRQA  PGQGL
6   QVQLVQSGAE  VKKPGASVKV  SCKASGYTFT  NYWIHWVRQA  PGQGL
7   QVQLVQSGAE  VKKPGASVKV  SCKASGYTFT  NYWIHWVRQA  PGQGL
8   QVQLVQSGAE  VKKPGASVKV  SCKASGYTFT  NYWIHWVRQA  PGQGL
9   QVQLVQSGAE  VKKPGASVKV  SCKASGYTFT  SYWMHWVRQA  PGQGL
10  QVQLVQSGAE  VKKPGASVKV  SCKASGYTFT  SYWMHWVRQA  PGQGL
11  QVQLVQSGAE  VKKPGASVKV  SCKASGYTFT  SYWIHWVRQA  PGQGL
12  QVQLVQSGAE  VKKPGASVKV  SCKASGYTFT  NYWMHWVRQA  PGQGL
13  QVQLVQSGAE  VKKPGASVKV  SCKASGYTFT  SYWIHWVRQA  PGQGL
14  QVQLVQSGAE  VKKPGASVKV  SCKASGYTFT  NYWIHWVRQA  PGQGL
15  QVQLVQSGAE  VKKPGASVKV  SCKASGYTFT  NYWMHWVRQA  PGQGL 60                              80
           #    *                           *    ###
1   EWMGE  IDPYDSYTNY  NQKFKGRVTM  TVDKSTSTVY  MELSSLRSED
2   EWMGE  IDPYDSYTNY  NQKFKGRVTM  TVDKSTSTVY  MELSSLRSED
3   EWMGE  IDPYDSYTNY  NQKFKGRVTM  TIDTSTSTVY  MELSSLTSED
4   EWMGE  IDPFDSYTNY  NQKFKGRVTM  TRDTSTSTVY  MELSSLTSED
5   EWMGE  IDPFDSYTNY  NQKFKGRVTM  TRDKSTSTVY  MELSSLRSED
6   EWMGE  IDPYDSYTNY  NQKFKGRVTM  TGDTSTSTVY  MELSSLTSED
7   EWMGE  IDPYDSYTNY  NQKFKGRVTM  TIDKSTNTVY  MELSSLRSED
8   EWMGE  IDPYDSYTNY  NQKFKGRVTM  TIDTSTSTVY  MELSSLRSED
9   EWMGE  IDPYDSYTNY  NQKFKGRVTM  TIDKSTSTVY  MELSSLTSED
10  EWMGE  IDPFDSYTNY  NQKFKGRVTM  TIDKSTNTVY  MELSSLGSED
11  EWMGE  IDPSDSYTNY  NQKFKGRVTM  TGDTSTNTVY  MELSSLTSED
12  EWMGE  IDPFDSYTNY  NQKFKGRVTM  TIDTSTNTVY  MELSSLRSED
13  EWMGE  IDPYDSYTNY  NQKFKGRVTM  TVDKSTNTVY  MELSSLTSED
14  EWMGE  IDPYDSYTNY  NQKFKGRVTM  TGDKSTSTVY  MELSSLTSED
15  EWMGE  IDPYDSYTNY  NQKFKGRVTM  TRDTSTNTVY  MELSSLRSED

100
           *     *##
1   TAVYYCARPG  FTYGGMDFWG  QGTLVTVSS  (SEQ ID NO:87)
2   TAVYYCARPG  NTYGGMDYWG  QGTLVTVSS  (SEQ ID NO:97)
3   TAVYYCARPG  FTYGGMDFWG  QGTLVTVSS  (SEQ ID NO:104)
4   TAVYYCARPG  YTYGGMDFWG  QGTLVTVSS  (SEQ ID NO:110)
5   TAVYYCARPG  FTYGGMDFWG  QGTLVTVSS  (SEQ ID NO:117)
6   TAVYYCARPG  YTYGGMDFWG  QGTLVTVSS  (SEQ ID NO:122)
7   TAVYYCARPG  LTYGGMDFWG  QGTLVTVSS  (SEQ ID NO:126)
8   TAVYYCARPG  NTYGGMDFWG  QGTLVTVSS  (SEQ ID NO:133)
9   TAVYYCARPG  FTYGGMDFWG  QGTLVTVSS  (SEQ ID NO:139)
10  TAVYYCARPG  YTYGGMDFWG  QGTLVTVSS  (SEQ ID NO:144)
11  TAVYYCARPG  YTYGGMDFWG  QGTLVTVSS  (SEQ ID NO:148)
12  TAVYYCARPG  FTYGGMDFWG  QGTLVTVSS  (SEQ ID NO:154)
13  TAVYYCARPG  LTYGGMDFWG  QGTLVTVSS  (SEQ ID NO:158)
14  TAVYYCARPG  YTYGGMDFWG  QGTLVTVSS  (SEQ ID NO:162)
15  TAVYYCARPG  LTYGGMDFWG  QGTLVTVSS  (SEQ ID NO:166)
```

FIGURE 7

Anti-hPD1 VL Sequences

```
                   20                ### ###
                   *
 1  DIQMTQSPSS LSASVGDRVT ITCKSSQSLF NSGNQKNYLA WYQ
 2  DIQMTQSPSS LSASVGDRVT ITCRSSQSLF NSGNQKNYLA WYQ
 3  DIQMTQSPSS LSASVGDRVT ITCKSSQSLF NSGNQKNYLA WYQ
 4  DIQMTQSPSS LSASVGDRVT ITCKSSQSLL NSGNQKNYLA WYQ
 5  DIQMTQSPSS LSASVGDRVT ITCRSSQSLL NSGNQKNYLA WYQ
 6  DIQMTQSPSS LSASVGDRVT ITCRSSQSLF NSGNQKNYLA WYQ
 7  DIVMTQSPDS LAVSLGERAT INCRSSQSLF ISGNQKNYLA WYQ
 8  DIVMTQSPDS LAVSLGERAT INCKSSQSLF ISGNQKNYLA WYQ
 9  DIVMTQSPDS LAVSLGERAT INCRSSQSLL ISGNQKNYLA WYQ
10  DIVMTQSPDS LAVSLGERAT INCRSSQSLF ISGNQKNYLA WYQ
11  DIVMTQSPDS LAVSLGERAT ISCRSSQSLF ISGNQKNYLA WYQ
12  DIVMTQSPDS LAVSLGERAT ISCRSSQSLL ISGNQKNYLA WYQ
13  DIQMTQSPSS LSASVGDRVT ITCKSSQSLL NSGNQKNYLA WYQ
14  DIQMTQSPSS LSASVGDRVT ITCKSSQSLF NSGNQKNYLA WYQ
15  DIQMTQSPSS LSASVGDRVT ITCRSSQSLF NSGNQKNYLA WYQ 40                  60
        *                   *
 1  QKPGKVP KLLIYGASTR DSGVPYRFSG SGSGTDFTLT ISSLQ
 2  QKPGKVP KLLIYGASTR DSGVPYRFSG SGSGTDFTLT ISSLQ
 3  QKPGKVP KLLIYGASTR ESGVPARFSG SGSGTDFTLT ISSLQ
 4  QKPGKPP KLLIYGASTR DSGVPSRFSG SGSGTDFTLT ISSLQ
 5  QKPGKLP KLLIYGASTR DSGVPSRFSG SGSGTDFTLT ISSLQ
 6  QKPGKPP KLLIYGASTR ESGVPARFSG SGSGTDFTLT ISSLQ
 7  QKPGQPP KLLIYGASTR ESGVPDRFSG SGSGTDFTLT ISSLQ
 8  QKPGQPP KLLIYGASTR DSGVPDRFSG SGSGTDFTLT ISSLQ
 9  QKPGQPP KLLIYGASTR DSGVPDRFSG SGSGTDFTLT ISSLQ
10  QKPGQPP KLLIYGASTR DSGVPDRFSG SGSGTDFTLT ISSLQ
11  QKPGQPP KLLIYGASTR DSGVPDRFSG SGSGTDFTLT ISSLQ
12  QKPGQPP KLLIYGASTR DSGVPDRFSG SGSGTDFTLT ISSLQ
13  QKPGKPP KLLIYGASTR DSGVPAKFSG SGSGTDFTLT ISSLQ
14  QKPGKLP KLLIYGASTR DSGVPSRFSG SGSGTDFTLT ISSLQ
15  QKPGKPP KLLIYGASTR ESGVPYRFSG SGSGTDFTLT ISSLQ 80                100
    *                 *
 1  PEDVA TYYCQNDHYY PYTFGGGTKV EIK (SEQ ID NO:92)
 2  PEDVA TYYCQNDHYY PYTFGGGTKV EIK (SEQ ID NO:101)
 3  AEDVA TYYCQNDHYY PYTFGGGTKV EIK (SEQ ID NO:107)
 4  PEDVA TYYCQNDHYY PYTFGGGTKV EIK (SEQ ID NO:114)
 5  AEDVA TYYCQNDHYY PYTFGGGTKV EIK (SEQ ID NO:119)
 6  PEDVA TYYCQNDHYY PYTFGGGTKV EIK (SEQ ID NO:124)
 7  AEDVA VYYCQNNHYY PYTFGGGTKV EIK (SEQ ID NO:129)
 8  AEDVA VYYCQNNHYY PYTFGGGTKV EIK (SEQ ID NO:136)
 9  AEDVA VYYCQNNHYY PYTFGGGTKV EIK (SEQ ID NO:141)
10  AEDVA VYYCQNNHYY PYTFGGGTKV EIK (SEQ ID NO:146)
11  AEDVA VYYCQNNHYY PYTFGGGTKV EIK (SEQ ID NO:152)
12  AEDVA VYYCQNNHYY PYTFGGGTKV EIK (SEQ ID NO:156)
13  PEDVA TYYCQNDHYY PYTFGGGTKV EIK (SEQ ID NO:160)
14  PEDVA TYYCQNDHYY PYTFGGGTKV EIK (SEQ ID NO:164)
15  PEDVA TYYCQNDHYY PYTFGGGTKV EIK (SEQ ID NO:168)
```

FIGURE 8

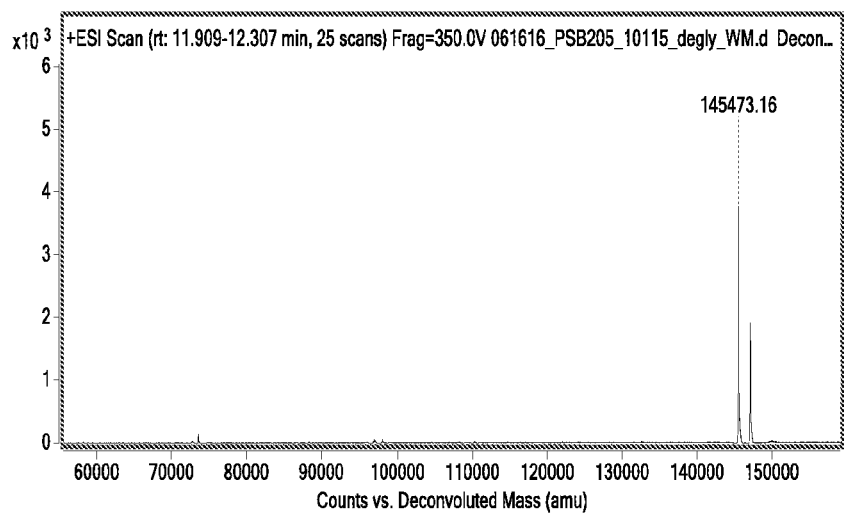
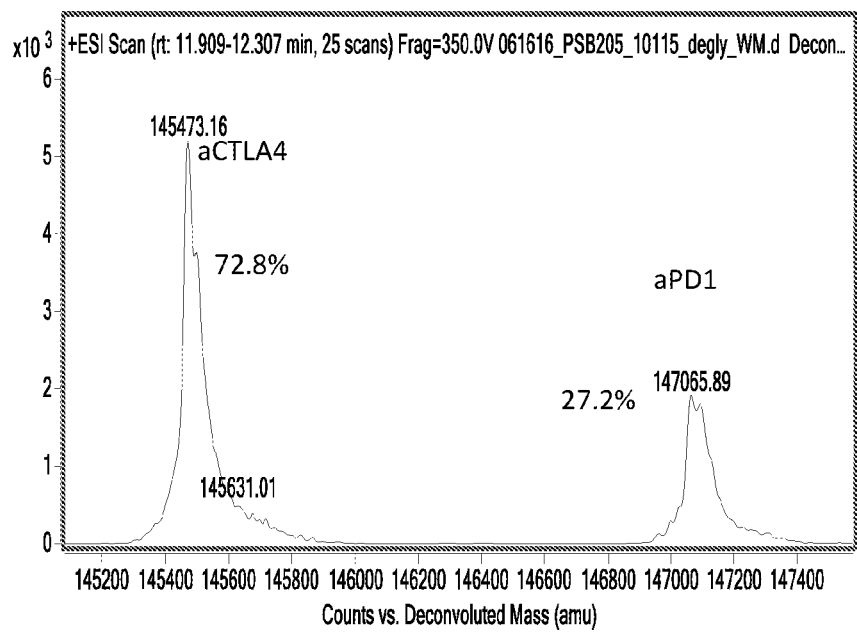
FIGURE 18

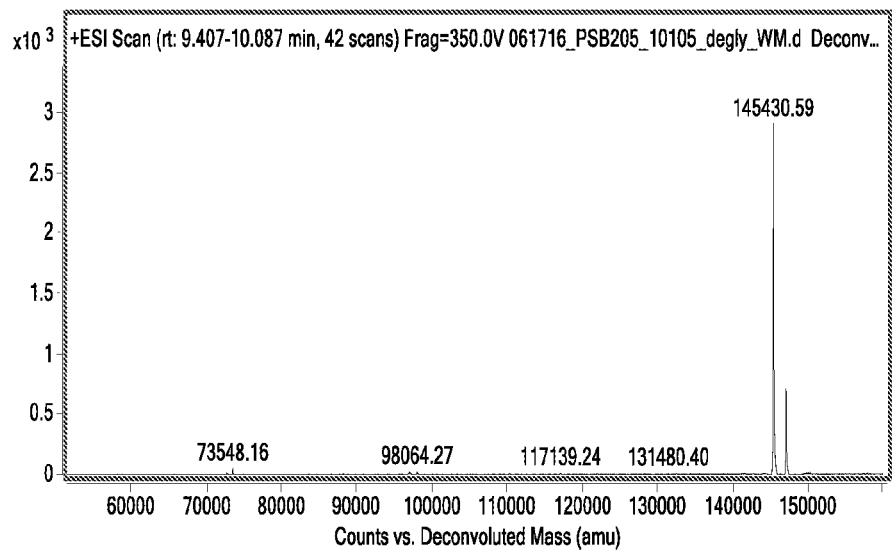
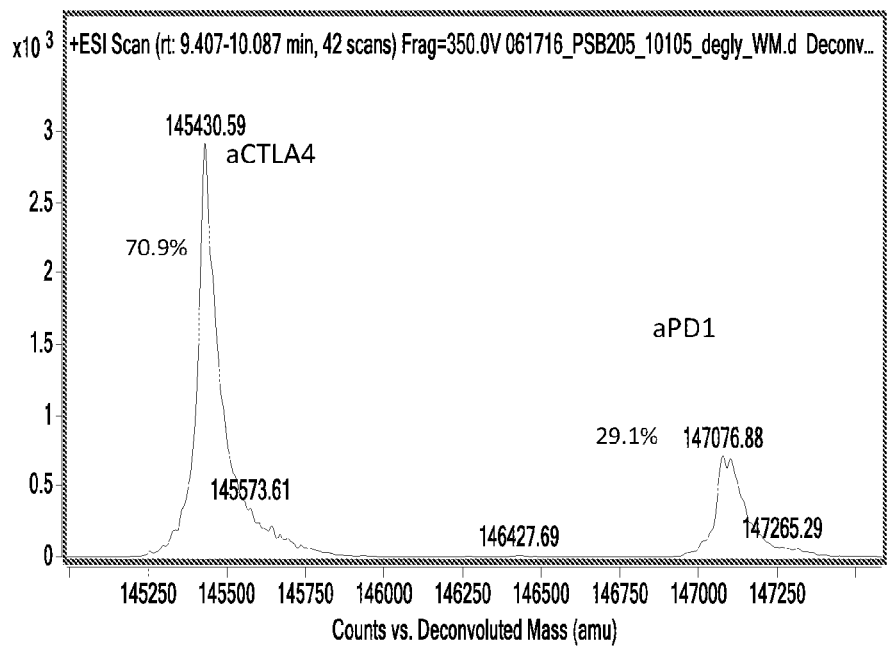
FIGURE 19

SEQUENCE LISTING

```
<160> NUMBER OF SEQ ID NOS: 208

<210> SEQ ID NO 1
<211> LENGTH: 354
<212> TYPE: DNA
<213> ORGANISM: Artificial Sequence
<220> FEATURE:
<223> OTHER INFORMATION: DNA sequence encoding the VH domain of the
      anti-hCTLA4 antibody designated 1E1

<400> SEQUENCE: 1
caggtgcagc ttgtcgaaag cggtggtggg gtagttgaac cagggcgttc tttacgttta      60
tcttgtgcag cctccggttt caccttcagt tcatacggga tgcactgggt tagacaagct     120
ccaggaaaag gattagaatg ggtagctgtt atttggtaca accctagcga gaaggattac     180
gccgattcag ctaagggtag gtttaccatt agtagagaca atagtaaaaa cactctatat     240
ctacaaatga acagcttgcg tgccgaggat actgcagttt actactgcgc gagggctggt     300
cttctcggtt atttcgacta ctgggggtcag gggacattgg taactgtttc aagc          354

<210> SEQ ID NO 2
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 1E1

<400> SEQUENCE: 2
```

```
Gln Val Gln Leu Val Glu Ser Gly Gly Val Val Glu Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Asn Pro Ser Glu Lys Asp Tyr Ala Asp Ser Ala
50                      55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Gly Tyr Phe Asp Tyr Trp Gly Gln Gly Thr
            100                 105                 110

Leu Val Thr Val Ser Ser
        115
```

<210> SEQ ID NO 3
<211> LENGTH: 5
<212> TYPE: PRT
<213> ORGANISM: Artificial Sequence
<220> FEATURE:
<223> OTHER INFORMATION: Amino acid sequence of the CDR1 of the VH
      domain of the anti-hCTLA4 antibodies designated 1E1, 2F1, 3G1,
      4H1, 5B2, 6E3, 7A4, 8B4, 9C4, 10D4, 11F4, and 12G4

<400> SEQUENCE: 3

```
Ser Tyr Gly Met His
1               5
```

<210> SEQ ID NO 4
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibody designated 1E1

<400> SEQUENCE: 4

```
Val Ile Trp Tyr Asn Pro Ser Glu Lys Asp Tyr Ala Asp Ser Ala Lys
1               5                   10                  15

Gly
```

<210> SEQ ID NO 5
<211> LENGTH: 9
<212> TYPE: PRT
<213> ORGANISM: Artificial Sequence
<220> FEATURE:
<223> OTHER INFORMATION: Amino acid sequence of the CDR3 of the VH
      domain of the anti-hCTLA4 antibodies designated 1E1, 2F1, 5B2,
      6E3, 7A4, 9C4, and 10D4

<400> SEQUENCE: 5

```
Ala Gly Leu Leu Gly Tyr Phe Asp Tyr
1               5
```

<210> SEQ ID NO 6
<211> LENGTH: 321
<212> TYPE: DNA
<213> ORGANISM: Artificial Sequence
<220> FEATURE:
<223> OTHER INFORMATION: DNA sequence encoding the VL domain of the
      anti-hCTLA4 antibody designated 1E1

<400> SEQUENCE: 6

```
gagattgttc tgacacagag tcctggtaca ttatctttgt cccctggtga aagggcaact    60
ctatcttgta gggcctctca atctattagc agctacttgg cttggtatca acaaaaacca   120
ggtcaagcgc cgagaccatt gatttatggt gtctcctcta gagcaacagg gataccagac   180
agatttagtg gaagcggttc aggtactgat ttcactctaa cgattagccg tttagaacct   240
gaagattttg cagtgtacta ttgtcaacag tacggcatga gccccttttac ctttggtcct   300
ggaactaaag tggatataaa g                                              321
```

<210> SEQ ID NO 7
<211> LENGTH: 107
<212> TYPE: PRT
<213> ORGANISM: Artificial Sequence
<220> FEATURE:
<223> OTHER INFORMATION: Amino acid sequence of the VL domain of the anti-hCTLA4 antibody designated 1E1

<400> SEQUENCE: 7

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Ser Ser Tyr
            20                  25                  30

Leu Ala Trp Tyr Gln Gln Lys Pro Gly Gln Ala Pro Arg Pro Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Met Ser Pro Phe
                85                  90                  95

Thr Phe Gly Pro Gly Thr Lys Val Asp Ile Lys
            100                 105
```

<210> SEQ ID NO 8
<211> LENGTH: 11
<212> TYPE: PRT
<213> ORGANISM: Artificial Sequence
<220> FEATURE:
<223> OTHER INFORMATION: Amino acid sequence of the CDR1 of the VL domain of the anti-hCTLA4 antibody designated 1E1

<400> SEQUENCE: 8

```
Arg Ala Ser Gln Ser Ile Ser Ser Tyr Leu Ala
1               5                   10
```

<210> SEQ ID NO 9
<211> LENGTH: 7
<212> TYPE: PRT
<213> ORGANISM: Artificial Sequence
<220> FEATURE:
<223> OTHER INFORMATION: Amino acid sequence of the CDR2 of the VL domain of the anti-hCTLA4 antibodies designated 1E1, 2F1, 3G1, 4H1, 5B2, 6E3, 7A4, 8B4, 9C4, 10D4, 11F4, and 12G4

<400> SEQUENCE: 9

```
Gly Val Ser Ser Arg Ala Thr
1               5
```

<210> SEQ ID NO 10
<211> LENGTH: 9

```
<212> TYPE: PRT
<213> ORGANISM: Artificial Sequence
<220> FEATURE:
<223> OTHER INFORMATION: Amino acid sequence of the CDR3 of the VL
      domain of the anti-hCTLA4 antibodies designated 1E1 and 6E3

<400> SEQUENCE: 10

Gln Gln Tyr Gly Met Ser Pro Phe Thr
1               5

<210> SEQ ID NO 11
<211> LENGTH: 354
<212> TYPE: DNA
<213> ORGANISM: Artificial Sequence
<220> FEATURE:
<223> OTHER INFORMATION: DNA sequence encoding the VH domain of the
      anti-hCTLA4 antibody designated 2F1

<400> SEQUENCE: 11
caggtgcagc ttgtcgaaag cggtggtggg gtagttgaac cagggcgttc tttacgttta    60
tcttgtgcag cctccggttt caccttcagt tcatacggga tgcactgggt tagacaagct   120
ccaggaaaag gattagaatg ggtagctgtt atttggtacc accgtagcga gaaggattac   180
gccgattcag ctaagggtag gtttaccatt agtagagaca atagtaaaaa cactctatat   240
ctacaaatga acagcttgcg tgccgaggat actgcagttt actactgcgc gagggctggt   300
cttctcggtt atttcgacta ctggggtcag gggacattgg taactgtttc aagc         354

<210> SEQ ID NO 12
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 2F1

<400> SEQUENCE: 12

Gln Val Gln Leu Val Glu Ser Gly Gly Gly Val Val Glu Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr His Arg Ser Glu Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Gly Tyr Phe Asp Tyr Trp Gly Gln Gly Thr
            100                 105                 110

Leu Val Thr Val Ser Ser
        115

<210> SEQ ID NO 13
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibody designated 2F1

<400> SEQUENCE: 13
```

Val Ile Trp Tyr His Arg Ser Glu Lys Asp Tyr Ala Asp Ser Ala Lys
1               5                   10                  15

Gly

<210> SEQ ID NO 14
<211> LENGTH: 321
<212> TYPE: DNA
<213> ORGANISM: Artificial Sequence
<220> FEATURE:
<223> OTHER INFORMATION: DNA sequence encoding the VL domain of the
      anti-hCTLA4 antibodies designated 2F1 and 3G1

<400> SEQUENCE: 14
gagattgttc tgacacagag tcctggtaca ttatctttgt ccccctggtga aagggcaact      60 ctatcttgta gggcctctca atctattaac agctacttgg cttggtatca acaaaaacca     120
ggtcaagcgc cgagaccatt gatttatggt gtctcctcta gagcaacagg gataccagac     180
agatttagtg gaagcggttc aggtactgat ttcactctaa cgattagccg tttagaacct     240
gaagattttg cagtgtacta ttgtcaacag tacggcatgt acccctttac ctttggtcct     300
ggaactaaag tggatataaa g                                               321

<210> SEQ ID NO 15
<211> LENGTH: 107
<212> TYPE: PRT
<213> ORGANISM: Artificial Sequence
<220> FEATURE:
<223> OTHER INFORMATION: Amino acid sequence of the VL domain of the
      anti-hCTLA4 antibodies designated 2F1 and 3G1

<400> SEQUENCE: 15

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Asn Ser Tyr
            20                  25                  30

Leu Ala Trp Tyr Gln Gln Lys Pro Gly Gln Ala Pro Arg Pro Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Met Tyr Pro Phe
                85                  90                  95

Thr Phe Gly Pro Gly Thr Lys Val Asp Ile Lys
            100                 105

<210> SEQ ID NO 16
<211> LENGTH: 11
<212> TYPE: PRT
<213> ORGANISM: Artificial Sequence
<220> FEATURE:
<223> OTHER INFORMATION: Amino acid sequence of the CDR1 of the VL
      domain of the anti-hCTLA4 antibodies designated 2F1, 3G1, and 11F4

<400> SEQUENCE: 16

Arg Ala Ser Gln Ser Ile Asn Ser Tyr Leu Ala
1               5                   10

<210> SEQ ID NO 17
<211> LENGTH: 9
<212> TYPE: PRT

<210> SEQ ID NO 17
<211> LENGTH: 8
<212> TYPE: PRT
<213> ORGANISM: Artificial Sequence
<220> FEATURE:
<223> OTHER INFORMATION: Amino acid sequence of the CDR3 of the VL
domain of the anti-hCTLA4 antibodies designated 2F1, 3G1,4H1, 5B2,
7A4, and 8B4

<400> SEQUENCE: 17

Gln Gln Tyr Gly Met Tyr Pro Phe Thr
1               5

<210> SEQ ID NO 18
<211> LENGTH: 354
<212> TYPE: DNA
<213> ORGANISM: Artificial Sequence
<220> FEATURE:
<223> OTHER INFORMATION: DNA sequence encoding the VH domain of the
anti-hCTLA4 antibody designated 3G1

<400> SEQUENCE: 18
caggtgcagc ttgtcgaaag cggtggtggg gtagttgaac agggcgttc tttacgttta        60 tcttgtacag cctccggttt cacc ttcagt tcatacggga tgcactgggt tagacaagct     120
ccaggaaaag gattagaatg ggtagctgtt atttggtaca agagtagcga aaagtattac     180
gccgattcag ctaagggtag gtttaccatt agtagagaca atagtaaaaa cactctatat     240
ctacaaatga acagcttgcg tgccgaggat actgcagttt actactgcgc gaggggtggt     300
cttctcggtt atttcgacta ctggggtcag gggacattgg taactgtttc aagc           354

<210> SEQ ID NO 19
<211> LENGTH: 118
<212> TYPE: PRT
<213> ORGANISM: Artificial Sequence
<220> FEATURE:
<223> OTHER INFORMATION: Amino acid sequence of the VH domain of the
anti-hCTLA4 antibody designated 3G1

<400> SEQUENCE: 19

Gln Val Gln Leu Val Glu Ser Gly Gly Gly Val Val Glu Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Lys Ser Ser Glu Lys Tyr Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Leu Gly Tyr Phe Asp Tyr Trp Gly Gln Gly Thr
            100                 105                 110

Leu Val Thr Val Ser Ser
        115

<210> SEQ ID NO 20
<211> LENGTH: 17
<212> TYPE: PRT
<213> ORGANISM: Artificial Sequence
<220> FEATURE:
<223> OTHER INFORMATION: Amino acid sequence of the CDR2 of the VH
domain of the anti-hCTLA4 antibody designated 3G1

<400> SEQUENCE: 20

```
Val Ile Trp Tyr Lys Ser Ser Glu Lys Tyr Tyr Ala Asp Ser Ala Lys
1               5                   10                  15

Gly

<210> SEQ ID NO 21
<211> LENGTH: 9
<212> TYPE: PRT
<213> ORGANISM: Artificial Sequence
<220> FEATURE:
<223> OTHER INFORMATION: Amino acid sequence of the CDR3 of the VH
      domain of the anti-hCTLA4 antibody designated 3G1, 11F4, and 12G4

<400> SEQUENCE: 21

Gly Gly Leu Leu Gly Tyr Phe Asp Tyr
1               5

<210> SEQ ID NO 22
<211> LENGTH: 354
<212> TYPE: DNA
<213> ORGANISM: Artificial Sequence
<220> FEATURE:
<223> OTHER INFORMATION: DNA sequence encoding the VH domain of the
      anti-hCTLA4 antibody designated 4H1

<400> SEQUENCE: 22
caggtgcagc ttgtcgaaag cggtggtggg gtagttgaac cagggcgttc tttacgttta      60
tcttgtacag cctccggttt caccttcagt tcatacggga tgcactgggt tagacaagct     120
ccaggaaaag gattagaatg ggtagctgtt atttggtaca accctagcaa aaaggattac     180
gccgattcag ctaagggtag gtttaccatt agtagagaca atagtaaaaa cactctatat     240
ctacaaatga acagcttgcg tgccgaggat actgcagttt actactgcgc gaggggtggt     300
cttttcggtt atttcgacta ctggggtcag gggacattgg taactgtttc aagc           354

<210> SEQ ID NO 23
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 4H1

<400> SEQUENCE: 23

Gln Val Gln Leu Val Glu Ser Gly Gly Gly Val Val Glu Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asn Pro Ser Lys Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Phe Gly Tyr Phe Asp Tyr Trp Gly Gln Gly Thr
            100                 105                 110

Leu Val Thr Val Ser Ser
        115
```

-continued

```
<210> SEQ ID NO 24
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibody designated 4H1

<400> SEQUENCE: 24

Val Ile Trp Tyr Asn Pro Ser Lys Lys Asp Tyr Ala Asp Ser Ala Lys
1               5                   10                  15

Gly

<210> SEQ ID NO 25
<211> LENGTH: 9
<212> TYPE: PRT
<213> ORGANISM: Artificial Sequence
<220> FEATURE:
<223> OTHER INFORMATION: Amino acid sequence of the CDR3 of the VH
      domain of the anti-hCTLA4 antibody designated 4H1

<400> SEQUENCE: 25

Gly Gly Leu Phe Gly Tyr Phe Asp Tyr
1               5

<210> SEQ ID NO 26
<211> LENGTH: 321
<212> TYPE: DNA
<213> ORGANISM: Artificial Sequence
<220> FEATURE:
<223> OTHER INFORMATION: DNA sequence encoding the VL domain of the
      anti-hCTLA4 antibodies designated 4H1 and 7A4

<400> SEQUENCE: 26
gagattgttc tgacacagag tcctggtaca ttatctttgt cccctggtga aagggcaact      60
ctatcttgta gggcctctca atctgttagc agctacttgg cttggtatca acaaaaacca    120
ggtcaagcgc cgagaccatt gatttatggt gtctcctcta gagcaacagg gataccagac    180
agatttagtg gaagcggttc aggtactgat ttcactctaa cgattagccg tttagaacct    240
gaagattttg cagtgtacta ttgtcaacag tacggcatgt accccttac ctttggtcct    300 ggaactaaag tggatataaa g                                              321

<210> SEQ ID NO 27
<211> LENGTH: 107
<212> TYPE: PRT
<213> ORGANISM: Artificial Sequence
<220> FEATURE:
<223> OTHER INFORMATION: Amino acid sequence of the VL domain of the
      anti-hCTLA4 antibodies designated 4H1 and 7A4

<400> SEQUENCE: 27

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Tyr
                20                  25                  30

Leu Ala Trp Tyr Gln Gln Lys Pro Gly Gln Ala Pro Arg Pro Leu Ile
            35                  40                  45

Tyr Gly Val Ser Ser Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Met Tyr Pro Phe
```

```
                        85                  90                  95
Thr Phe Gly Pro Gly Thr Lys Val Asp Ile Lys
            100                 105

<210> SEQ ID NO 28
<211> LENGTH: 11
<212> TYPE: PRT
<213> ORGANISM: Artificial Sequence
<220> FEATURE:
<223> OTHER INFORMATION: Amino acid sequence of the CDR1 of the VL
      domain of the anti-hCTLA4 antibodies designated 4H1 and 7A4

<400> SEQUENCE: 28

Arg Ala Ser Gln Ser Val Ser Ser Tyr Leu Ala
1               5                   10

<210> SEQ ID NO 29
<211> LENGTH: 354
<212> TYPE: DNA
<213> ORGANISM: Artificial Sequence
<220> FEATURE:
<223> OTHER INFORMATION: DNA sequence encoding the VH domain of the
      anti-hCTLA4 antibody designated 5B2

<400> SEQUENCE: 29
caggtgcagc ttgtcgaaag cggtggtggg gtagttgaac agggcgttc tttacgttta      60 tcttgtacag cctccggttt caccttcagt tcatacggga tgcactgggt tagacaagct    120
ccaggaaaag gattagaatg ggtagctgtt atttggtaca agagtagcga aaaggattac    180
gccgattcag ctaagggtag gtttaccatt agtagagaca atagtaaaaa cactctatat    240
ctacaaatga acagcttgcg tgccgaggat actgcagttt actactgcgc gagggctggt    300
cttctcggtt atttcgacta ctggggtcag gggacattgg taactgtttc aagc          354

<210> SEQ ID NO 30
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 5B2

<400> SEQUENCE: 30

Gln Val Gln Leu Val Glu Ser Gly Gly Gly Val Val Glu Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Lys Ser Ser Glu Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Gly Tyr Phe Asp Tyr Trp Gly Gln Gly Thr
            100                 105                 110

Leu Val Thr Val Ser Ser
        115

<210> SEQ ID NO 31
```

```
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibodies designated 5B2 and 9C4

<400> SEQUENCE: 31

Val Ile Trp Tyr Lys Ser Ser Glu Lys Asp Tyr Ala Asp Ser Ala Lys
1               5                   10                  15

Gly

<210> SEQ ID NO 32
<211> LENGTH: 321
<212> TYPE: DNA
<213> ORGANISM: Artificial Sequence
<220> FEATURE:
<223> OTHER INFORMATION: DNA sequence encoding the VL domain of the
      anti-hCTLA4 antibody designated 5B2

<400> SEQUENCE: 32
gagattgttc tgacacagag tcctggtaca ttatctttgt cccctggtga aagggcaact    60
ctatcttgta gggcctctca atctcttagc agctacttgg cttggtatca acaaaaacca   120
ggtcaagcgc cgagactatt gatttatggt gtctcctcta gagcaacagg gataccagac   180
agatttagtg aagcggttc aggtactgat ttcactctaa cgattagtcg tttagaacct    240
gaagattttg cagtgtacta ttgtcaacag tacggcatgt acccctttac ctttggtcct   300
ggaactaaag tggatataaa g                                             321

<210> SEQ ID NO 33
<211> LENGTH: 107
<212> TYPE: PRT
<213> ORGANISM: Artificial Sequence
<220> FEATURE:
<223> OTHER INFORMATION: Amino acid sequence of the VL domain of the
      anti-hCTLA4 antibody designated 5B2

<400> SEQUENCE: 33

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Ser Ser Tyr
                20                  25                  30

Leu Ala Trp Tyr Gln Gln Lys Pro Gly Gln Ala Pro Arg Leu Leu Ile
            35                  40                  45

Tyr Gly Val Ser Ser Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Met Tyr Pro Phe
                85                  90                  95

Thr Phe Gly Pro Gly Thr Lys Val Asp Ile Lys
            100                 105

<210> SEQ ID NO 34
<211> LENGTH: 11
<212> TYPE: PRT
<213> ORGANISM: Artificial Sequence
<220> FEATURE:
<223> OTHER INFORMATION: Amino acid sequence of the CDR1 of the VL
      domain of the anti-hCTLA4 antibody designated 5B2

<400> SEQUENCE: 34
```

Arg Ala Ser Gln Ser Leu Ser Ser Tyr Leu Ala
1               5                   10

<210> SEQ ID NO 35
<211> LENGTH: 354
<212> TYPE: DNA
<213> ORGANISM: Artificial Sequence
<220> FEATURE:
<223> OTHER INFORMATION: DNA sequence encoding the VH domain of the
      anti-hCTLA4 antibody designated 6E3

<400> SEQUENCE: 35
caggtgcagc ttgtcgaaag cggtggtggg gtagttgaac cagggcgttc tttacgttta      60
tcttgtgcag cctccggttt caccttcagt tcatacggga tgcactgggt tagacaagct     120
ccaggaaaag gattagaatg ggtagctgtt atttggtaca agactagcga gaaggattac     180
gccgattcag ctaagggtag gtttaccatt agtagagaca atagtaaaaa cactctatat     240
ctacaaatga acagcttgcg tgccgaggat actgcagttt actactgcgc gagggctggt     300
cttctcggtt atttcgacta ctggggtcag gggacattgg taactgtttc aagc           354

<210> SEQ ID NO 36
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 6E3

<400> SEQUENCE: 36

Gln Val Gln Leu Val Glu Ser Gly Gly Gly Val Val Glu Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Lys Thr Ser Glu Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Gly Tyr Phe Asp Tyr Trp Gly Gln Gly Thr
            100                 105                 110

Leu Val Thr Val Ser Ser
        115

<210> SEQ ID NO 37
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibody designated 6E3

<400> SEQUENCE: 37

Val Ile Trp Tyr Lys Thr Ser Glu Lys Asp Tyr Ala Asp Ser Ala Lys
1               5                   10                  15

Gly

```
<210> SEQ ID NO 38
<211> LENGTH: 321
<212> TYPE: DNA
<213> ORGANISM: Artificial Sequence
<220> FEATURE:
<223> OTHER INFORMATION: DNA sequence encoding the VL domain of the
      anti-hCTLA4 antibody designated 6E3

<400> SEQUENCE: 38
gagattgttc tgacacagag tcctggtaca ttatctttgt ccctggtga aagggcaact      60 ctatcttgta gggcctctca atctgttacc agctacttgg cttggtatca acaaaaacca   120
ggtcaagcgc cgagaccatt gatttatggt gtctcctcta gagcaacagg gataccagac   180
agatttagtg gaagcggttc aggtactgat ttcactctaa cgattagccg tttagaacct   240
gaagattttg cagtgtacta ttgtcaacag tacggcatga gccccttttac ctttggtcct   300 ggaactaaag tggatataaa g                                              321

<210> SEQ ID NO 39
<211> LENGTH: 107
<212> TYPE: PRT
<213> ORGANISM: Artificial Sequence
<220> FEATURE:
<223> OTHER INFORMATION: Amino acid sequence of the VL domain of the
      anti-hCTLA4 antibody designated 6E3

<400> SEQUENCE: 39

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Tyr
            20                  25                  30

Leu Ala Trp Tyr Gln Gln Lys Pro Gly Gln Ala Pro Arg Pro Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Met Ser Pro Phe
                85                  90                  95

Thr Phe Gly Pro Gly Thr Lys Val Asp Ile Lys
            100                 105

<210> SEQ ID NO 40
<211> LENGTH: 11
<212> TYPE: PRT
<213> ORGANISM: Artificial Sequence
<220> FEATURE:
<223> OTHER INFORMATION: Amino acid sequence of the CDR1 of the VL
      domain of the anti-hCTLA4 antibodies designated 6E3 and 10D4

<400> SEQUENCE: 40

Arg Ala Ser Gln Ser Val Thr Ser Tyr Leu Ala
1               5                   10

<210> SEQ ID NO 41
<211> LENGTH: 354
<212> TYPE: DNA
<213> ORGANISM: Artificial Sequence
<220> FEATURE:
<223> OTHER INFORMATION: Nucleotide sequence encoding the VH domain of
      the anti-hCTLA4 antibody designated 7A4

<400> SEQUENCE: 41
```

-continued

```
caggtgcagc ttgtcgaaag cggtggtggg gtagttgaac cagggcgttc tttacgttta    60
tcttgtacag cctccggttt caccttcagt tcatacggga tgcactgggt tagacaagct   120
ccaggaaaag gattagaatg ggtagctgtt atttggtacc agactagcga aaaggattac   180
gccgattcag ctaagggtag gtttaccatt agtagagaca atagtaaaaa cactctatat   240
ctacaaatga acagcttgcg tgccgaggat actgcagttt actactgcgc gagggctggt   300
cttctcggtt atttcgacta ctggggtcag gggacattgg taactgtttc aagc          354
```

<210> SEQ ID NO 42
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 7A4

<400> SEQUENCE: 42

Gln Val Gln Leu Val Glu Ser Gly Gly Val Val Glu Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Gln Thr Ser Glu Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Gly Tyr Phe Asp Tyr Trp Gly Gln Gly Thr
            100                 105                 110

Leu Val Thr Val Ser Ser
        115

<210> SEQ ID NO 43
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibody designated 7A4

<400> SEQUENCE: 43

Val Ile Trp Tyr Gln Thr Ser Glu Lys Asp Tyr Ala Asp Ser Ala Lys
1               5                   10                  15

Gly

<210> SEQ ID NO 44
<211> LENGTH: 354
<212> TYPE: DNA
<213> ORGANISM: Artificial Sequence
<220> FEATURE:
<223> OTHER INFORMATION: DNA sequence encoding the VH domain of the
      anti-hCTLA4 antibody designated 8B4

<400> SEQUENCE: 44

```
caggtgcagc ttgtcgaaag cggtggtggg gtagttgaac cagggcgttc tttacgttta    60
tcttgtgcag cctccggttt caccttcagt tcatacggga tgcactgggt tagacaagct   120
ccaggaaaag gattagaatg ggtagctgtt atttggtacc agcctagcga gaaggattac   180
```

```
gccgattcag ctaagggtag gtttaccatt agtagagaca atagtaaaaa cactctatat    240
ctacaaatga acagcttgcg tgccgaggat actgcagttt actactgcgc gagggctggt    300
tttctcggtt atttcgacta ctggggtcag gggacattgg taactgtttc aagc          354
```

<210> SEQ ID NO 45
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 8B4

<400> SEQUENCE: 45

```
Gln Val Gln Leu Val Glu Ser Gly Gly Gly Val Val Glu Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Gln Pro Ser Glu Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Phe Leu Gly Tyr Phe Asp Tyr Trp Gly Gln Gly Thr
            100                 105                 110

Leu Val Thr Val Ser Ser
        115
```

<210> SEQ ID NO 46
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibody designated 8B4

<400> SEQUENCE: 46

```
Val Ile Trp Tyr Gln Pro Ser Glu Lys Asp Tyr Ala Asp Ser Ala Lys
1               5                   10                  15

Gly
```

<210> SEQ ID NO 47
<211> LENGTH: 9
<212> TYPE: PRT
<213> ORGANISM: Artificial Sequence
<220> FEATURE:
<223> OTHER INFORMATION: Amino acid sequence of the CDR3 of the VH
      domain of the anti-hCTLA4 antibody designated 8B4

<400> SEQUENCE: 47

```
Ala Gly Phe Leu Gly Tyr Phe Asp Tyr
1               5
```

<210> SEQ ID NO 48
<211> LENGTH: 321
<212> TYPE: DNA
<213> ORGANISM: Artificial Sequence
<220> FEATURE:
<223> OTHER INFORMATION: DNA sequence encoding the VL domain of the anti-hCTLA4 antibody designated 8B4

<400> SEQUENCE: 48

```
gagattgttc tgacacagag tcctggtaca ttatctttgt cccctggtga agggcaact      60
ctatcttgta gggcctctca atctgttaac agctacttgg cttggtatca acaaaaacca   120
ggtcaagcgc cgagaccatt gatttatggt gtctcctcta gagcaacagg gataccagac   180
agatttagtg gaagcggttc aggtactgat ttcactctaa cgattagccg tttagaacct   240
gaagattttg cagtgtacta ttgtcaacag tacggcatgt acccctttac ctttggtcct   300
ggaactaaag tggatataaa g                                              321
```

<210> SEQ ID NO 49
<211> LENGTH: 107
<212> TYPE: PRT
<213> ORGANISM: Artificial Sequence
<220> FEATURE:
<223> OTHER INFORMATION: Amino acid sequence of the VL domain of the
anti-hCTLA4 antibody designated 8B4

<400> SEQUENCE: 49

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Asn Ser Tyr
            20                  25                  30

Leu Ala Trp Tyr Gln Gln Lys Pro Gly Gln Ala Pro Arg Pro Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Met Tyr Pro Phe
                85                  90                  95

Thr Phe Gly Pro Gly Thr Lys Val Asp Ile Lys
            100                 105
```

<210> SEQ ID NO 50
<211> LENGTH: 11
<212> TYPE: PRT
<213> ORGANISM: Artificial Sequence
<220> FEATURE:
<223> OTHER INFORMATION: Amino acid sequence of the CDR1 of the VL
domain of the anti-hCTLA4 antibody designated 8B4

<400> SEQUENCE: 50

```
Arg Ala Ser Gln Ser Val Asn Ser Tyr Leu Ala
1               5                   10
```

<210> SEQ ID NO 51
<211> LENGTH: 354
<212> TYPE: DNA
<213> ORGANISM: Artificial Sequence
<220> FEATURE:
<223> OTHER INFORMATION: DNA sequence encoding the VH domain of the
anti-hCTLA4 antibody designated 9C4

<400> SEQUENCE: 51

```
caggtgcagc ttgtcgaaag cggtggtggg gtagttgaac cagggcgttc tttacgttta    60
tcttgtgcag cctccggttt caccttcagt tcatacggga tgcactgggt tagacaagct   120
ccaggaaaag gattagaatg ggtagctgtt atttggtaca gagtagcga aaaggattac   180
```

```
gccgattcag ctaagggtag gtttaccatt agtagagaca atagtaaaaa cactctatat    240
ctacaaatga acagcttgcg tgccgaggat actgcagttt actactgcgc gagggctggt    300
cttctcggtt atttcgacta ctggggtcag gggacattgg taactgtttc aagc          354
```

```
<210> SEQ ID NO 52
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 9C4

<400> SEQUENCE: 52
```

Gln Val Gln Leu Val Glu Ser Gly Gly Gly Val Val Glu Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Lys Ser Glu Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Gly Tyr Phe Asp Tyr Trp Gly Gln Gly Thr
            100                 105                 110

Leu Val Thr Val Ser Ser
        115

```
<210> SEQ ID NO 53
<211> LENGTH: 321
<212> TYPE: DNA
<213> ORGANISM: Artificial Sequence
<220> FEATURE:
<223> OTHER INFORMATION: DNA sequence encoding the VL domain of the
      anti-hCTLA4 antibody designated 9C4

<400> SEQUENCE: 53
```

```
gagattgttc tgacacagag tcctggtaca ttatctttgt cccctggtga aagggcaact    60
ctatcttgta gggcctctca atctcttaac agctacttgg cttggtatca acaaaaacca   120
ggtcaagcgc cgagaccatt gatttatggt gtctcctcta gagcaacagg gataccagac   180
agatttagtg gaagcggttc aggtactgat ttcactctaa cgattagccg tttagaacct   240
gaagattttg cagtgtacta ttgtcaacag tacggcatat accccttac ctttggtcct   300 ggaactaaag tggatataaa g                                             321
```

```
<210> SEQ ID NO 54
<211> LENGTH: 107
<212> TYPE: PRT
<213> ORGANISM: Artificial Sequence
<220> FEATURE:
<223> OTHER INFORMATION: Amino acid sequence of the VL domain of the
      anti-hCTLA4 antibody designated 9C4

<400> SEQUENCE: 54
```

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Leu Asn Ser Tyr

```
                 20                  25                  30

Leu Ala Trp Tyr Gln Gln Lys Pro Gly Gln Ala Pro Arg Pro Leu Ile
            35                  40                  45

Tyr Gly Val Ser Ser Arg Ala Thr Gly Ile Pro Asp Arg Phe Ser Gly
        50                  55                  60

Ser Gly Ser Gly Thr Asp Phe Thr Leu Thr Ile Ser Arg Leu Glu Pro
 65                 70                  75                  80

Glu Asp Phe Ala Val Tyr Tyr Cys Gln Gln Tyr Gly Ile Tyr Pro Phe
                85                  90                  95

Thr Phe Gly Pro Gly Thr Lys Val Asp Ile Lys
            100                 105

<210> SEQ ID NO 55
<211> LENGTH: 11
<212> TYPE: PRT
<213> ORGANISM: Artificial Sequence
<220> FEATURE:
<223> OTHER INFORMATION: Amino acid sequence of the CDR1 of the VL
      domain of the anti-hCTLA4 antibody designated 9C4

<400> SEQUENCE: 55

Arg Ala Ser Gln Ser Leu Asn Ser Tyr Leu Ala
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Amino acid sequence of the CDR3 of the VL
      domain of the anti-hCTLA4 antibody designated 9C4

<400> SEQUENCE: 56

Gln Gln Tyr Gly Ile Tyr Pro Phe Thr
1               5

<210> SEQ ID NO 57
<211> LENGTH: 354
<212> TYPE: DNA
<213> ORGANISM: Artificial Sequence
<220> FEATURE:
<223> OTHER INFORMATION: DNA sequence encoding the VH domain of the
      anti-hCTLA4 antibody designated 10D4

<400> SEQUENCE: 57
caggtgcagc ttgtcgaaag cggtggtggg gtagttgaac cagggcgttc tttacgttta      60
tcttgtacag cctccggttt caccttcagt tcatacggga tgcactgggt tagacaagct     120
ccaggaaaag gattagaatg ggtagctgtt atttggtacc accctagcaa aaaggattac     180
gccgattcag ctaagggtag gtttaccatt agtagagaca atagtaaaaa cactctatat     240
ctacaaatga acagcttgcg tgccgaggat actgcagttt actactgcgc gagggctggt     300
cttctcggtt atttcgacta ctgggggtcag gggacattgg taactgtttc aagc           354

<210> SEQ ID NO 58
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 10D4

<400> SEQUENCE: 58
```

```
Gln Val Gln Leu Val Glu Ser Gly Gly Val Val Glu Pro Gly Arg
1               5                   10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr His Pro Ser Lys Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Ala Gly Leu Leu Gly Tyr Phe Asp Tyr Trp Gly Gln Gly Thr
            100                 105                 110

Leu Val Thr Val Ser Ser
            115
```

<210> SEQ ID NO 59
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibody designated 10D4

<400> SEQUENCE: 59

```
Val Ile Trp Tyr His Pro Ser Lys Lys Asp Tyr Ala Asp Ser Ala Lys
1               5                   10                  15

Gly
```

<210> SEQ ID NO 60
<211> LENGTH: 321
<212> TYPE: DNA
<213> ORGANISM: Artificial Sequence
<220> FEATURE:
<223> OTHER INFORMATION: DNA sequence encoding the VL domain of the
      anti-hCTLA4 antibody designated 10D4

<400> SEQUENCE: 60

```
gagattgttc tgacacagag tcctggtaca ttatctttgt cccctggtga aagggcaact    60
ctatcttgta gggcctctca atctgttacc agctacttgg cttggtatca acaaaaacca   120
ggtcaagcgc cgagaccatt gatttatggt gtctcctcta gagcaacagg gataccagac   180
agatttagtg gaagcggttc aggtactgat ttcactctaa cgattagccg tttagaacct   240
gaagattttg cagtgtacta ttgtcaacag tacggcagat accccttta cctttggtcct   300 ggaactaaag tggatataaa g                                             321
```

<210> SEQ ID NO 61
<211> LENGTH: 107
<212> TYPE: PRT
<213> ORGANISM: Artificial Sequence
<220> FEATURE:
<223> OTHER INFORMATION: Amino acid sequence of the VL domain of the
      anti-hCTLA4 antibody designated 10D4

<400> SEQUENCE: 61

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Tyr
            20                  25                  30
```

```
Leu Ala Trp Tyr Gln Gln Lys Pro Gly Gln Ala Pro Arg Pro Leu Ile
        35                  40                  45

Tyr Gly Val Ser Ser Arg Ala Thr Gly Ile Pro Asp Arg Phe Ser Gly
     50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Arg Tyr Pro Phe
                 85                  90                  95

Thr Phe Gly Pro Gly Thr Lys Val Asp Ile Lys
            100                 105
```

<210> SEQ ID NO 62
<211> LENGTH: 9
<212> TYPE: PRT
<213> ORGANISM: Artificial Sequence
<220> FEATURE:
<223> OTHER INFORMATION: Amino acid sequence of the CDR3 of the VL
      domain of the anti-hCTLA4 antibodies designated 10D4, 11F4, and
      12G4

<400> SEQUENCE: 62

```
Gln Gln Tyr Gly Arg Tyr Pro Phe Thr
1               5
```

<210> SEQ ID NO 63
<211> LENGTH: 354
<212> TYPE: DNA
<213> ORGANISM: Artificial Sequence
<220> FEATURE:
<223> OTHER INFORMATION: DNA sequence encoding the VH domain of the
      anti-hCTLA4 antibody designated 11F4

<400> SEQUENCE: 63

```
caggtgcagc ttgtcgaaag cggtggtggg gtagttgaac agggcgttc tttacgttta      60 tcttgtgcag cctccggttt caccttcagt tcatacggga tgcactgggt tagacaagct    120
ccaggaaaag gattagaatg ggtagctgtt atttggtaca agcctagcga agaggattac    180
gccgattcag ctaagggtag gtttaccatt agtagagaca atagtaaaaa cactctatat    240
ctacaaatga acagcttgcg tgccgaggat actgcagttt actactgcgc gaggggtggt    300
cttctcggtt atttcgacta ctgggggtcag gggacattgg taactgtttc aagc          354
```

<210> SEQ ID NO 64
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 11F4

<400> SEQUENCE: 64

```
Gln Val Gln Leu Val Glu Ser Gly Gly Gly Val Val Glu Pro Gly Arg
1               5                   10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ala Val Ile Trp Tyr Lys Pro Ser Glu Lys Asp Tyr Ala Asp Ser Ala
     50                  55                  60

Lys Gly Arg Phe Thr Ile Ser Arg Asp Asn Ser Lys Asn Thr Leu Tyr
65                  70                  75                  80
```

```
Leu Gln Met Asn Ser Leu Arg Ala Glu Asp Thr Ala Val Tyr Tyr Cys
                85                  90                  95

Ala Arg Gly Gly Leu Leu Gly Tyr Phe Asp Tyr Trp Gly Gln Gly Thr
            100                 105                 110

Leu Val Thr Val Ser Ser
        115

<210> SEQ ID NO 65
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibody designated 11F4

<400> SEQUENCE: 65

Val Ile Trp Tyr Lys Pro Ser Glu Lys Asp Tyr Ala Asp Ser Ala Lys
1               5                   10                  15

Gly

<210> SEQ ID NO 66
<211> LENGTH: 321
<212> TYPE: DNA
<213> ORGANISM: Artificial Sequence
<220> FEATURE:
<223> OTHER INFORMATION: DNA sequence encoding the VL domain of the
      anti-hCTLA4 antibody designated 11F4

<400> SEQUENCE: 66
gagattgttc tgacacagag tcctggtaca ttatctttgt cccctggtga agggcaact     60 ctatcttgta gggcctctca atctattaac agctacttgg cttggtatca acaaaaacca   120
ggtcaagcgc cgagaccatt gatttatggt gtctcctcta gagcaacagg gataccagac   180
agatttagtg gaagcggttc aggtactgat ttcactctaa cgattagccg tttagaacct   240
gaagattttg cagtgtacta ttgtcaacag tacggcaggt acccctttac ctttggtcct   300
ggaactaaag tggatataaa g                                             321

<210> SEQ ID NO 67
<211> LENGTH: 107
<212> TYPE: PRT
<213> ORGANISM: Artificial Sequence
<220> FEATURE:
<223> OTHER INFORMATION: Amino acid sequence of the VL domain of the
      anti-hCTLA4 antibody designated 11F4

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Asn Ser Tyr
            20                  25                  30

Leu Ala Trp Tyr Gln Gln Lys Pro Gly Gln Ala Pro Arg Pro Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Arg Tyr Pro Phe
                85                  90                  95

Thr Phe Gly Pro Gly Thr Lys Val Asp Ile Lys
            100                 105
```

<210> SEQ ID NO 68
<211> LENGTH: 354
<212> TYPE: DNA
<213> ORGANISM: Artificial Sequence
<220> FEATURE:
<223> OTHER INFORMATION: DNA sequence encoding the VH domain of the
      anti-hCTLA4 antibody designated 12G4

<400> SEQUENCE: 68
caggtgcagc ttgtcgaaag cggtggtggg gtagttgaac cagggcgttc tttacgttta      60
tcttgtgcag cctctggttt caccttcagt tcatacggga tgcactgggt tagacaagct     120
ccaggaaaag gattagaatg ggtagctgtt atttggtaca acactagcaa gaaggattac     180
gccgattcag ctaagggtag gtttaccatt agtagagaca atagtaaaaa cactctatat     240
ctacaaatga acagcttgcg tgccgaggat actgcagttt actactgcgc gagggggtggt    300 cttctcggtt atttcgacta ctggggtcag gggacattgg taactgtttc aagc           354

<210> SEQ ID NO 69
<211> LENGTH: 118
<212> TYPE: PRT
<213> ORGANISM: Artificial Sequence
<220> FEATURE:
<223> OTHER INFORMATION: Amino acid sequence of the VH domain of the
      anti-hCTLA4 antibody designated 12G4

<400> SEQUENCE: 69

Gln Val Gln Leu Val Glu Ser Gly Gly Gly Val Val Glu Pro Gly Arg
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ala Val Ile Trp Tyr Asn Thr Ser Lys Lys Asp Tyr Ala Asp Ser Ala
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Gly Leu Leu Gly Tyr Phe Asp Tyr Trp Gly Gln Gly Thr
            100                 105                 110

Leu Val Thr Val Ser Ser
        115

<210> SEQ ID NO 70
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hCTLA4 antibody designated 12G4

<400> SEQUENCE: 70

Val Ile Trp Tyr Asn Thr Ser Lys Lys Asp Tyr Ala Asp Ser Ala Lys
1               5                   10                  15

Gly

<210> SEQ ID NO 71
<211> LENGTH: 321

-continued

```
<212> TYPE: DNA
<213> ORGANISM: Artificial Sequence
<220> FEATURE:
<223> OTHER INFORMATION: DNA sequence encoding the VL domain of the
      anti-hCTLA4 antibody designated 12G4

<400> SEQUENCE: 71
gagattgttc tgacacagag tcctggtaca ttatctttgt cccctggtga aagggcaact    60
ctatcttgta gggcctctca atctattacc agctacttgg cttggtatca acaaaaacca   120
ggtcaagcgc cgagaccatt gatttatggt gtctcctcta gagcaacagg gataccagac   180
agatttagtg gaagcggttc aggtactgat ttcactctaa cgattagccg tttagaacct   240
gaagattttg cagtgtacta ttgtcaacag tacggcagat acccctttac ctttggtcct   300
ggaactaaag tggatataaa g                                             321

<210> SEQ ID NO 72
<211> LENGTH: 107
<212> TYPE: PRT
<213> ORGANISM: Artificial Sequence
<220> FEATURE:
<223> OTHER INFORMATION: Amino acid sequence of the VL domain of the
      anti-hCTLA4 antibody designated 12G4

<400> SEQUENCE: 72

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Thr Ser Tyr
            20                  25                  30

Leu Ala Trp Tyr Gln Gln Lys Pro Gly Gln Ala Pro Arg Pro Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Arg Tyr Pro Phe
                85                  90                  95

Thr Phe Gly Pro Gly Thr Lys Val Asp Ile Lys
            100                 105

<210> SEQ ID NO 73
<211> LENGTH: 11
<212> TYPE: PRT
<213> ORGANISM: Artificial Sequence
<220> FEATURE:
<223> OTHER INFORMATION: Amino acid sequence of the CDR1 of the VL
      domain of the anti-hCTLA4 antibody designated 12G4

<400> SEQUENCE: 73

Arg Ala Ser Gln Ser Ile Thr Ser Tyr Leu Ala
1               5                   10

<210> SEQ ID NO 74
<211> LENGTH: 17
<212> TYPE: PRT
<213> ORGANISM: Artificial Sequence
<220> FEATURE:
<223> OTHER INFORMATION: Consensus amino acid sequence for anti-hCTLA4
      VH CDR2s
<220> FEATURE:
<221> NAME/KEY: X
<222> LOCATION: (5)..(5)
<223> OTHER INFORMATION: X is asparagine, lysine, arginine, glutamine,
      or histidine
```

```
<220> FEATURE:
<221> NAME/KEY: X
<222> LOCATION: (6)..(6)
<223> OTHER INFORMATION: X is proline, alanine, serine, threonine,
      lysine, glutamine, asparagine, or arginine
<220> FEATURE:
<221> NAME/KEY: X
<222> LOCATION: (8)..(8)
<223> OTHER INFORMATION: X is glutamate, aspartate, arginine, or lysine
<220> FEATURE:
<221> NAME/KEY: X
<222> LOCATION: (10)..(10)
<223> OTHER INFORMATION: X is aspartate, glutamate, tryptophan,
      phenylalanine, threonine, serine, or tyrosine

<400> SEQUENCE: 74

Val Ile Trp Tyr Xaa Xaa Ser Xaa Lys Xaa Tyr Ala Asp Ser Ala Lys
1               5                   10                  15
Gly

<210> SEQ ID NO 75
<211> LENGTH: 17
<212> TYPE: PRT
<213> ORGANISM: Artificial Sequence
<220> FEATURE:
<223> OTHER INFORMATION: Second consensus amino acid sequence for
      anti-hCTLA4 VH CDR2s
<220> FEATURE:
<221> NAME/KEY: X
<222> LOCATION: (5)..(5)
<223> OTHER INFORMATION: X is asparagine, lysine, glutamine, or
      histidine
<220> FEATURE:
<221> NAME/KEY: X
<222> LOCATION: (6)..(6)
<223> OTHER INFORMATION: X is proline, serine, threonine, or arginine
<220> FEATURE:
<221> NAME/KEY: X
<222> LOCATION: (8)..(8)
<223> OTHER INFORMATION: X is glutamate or lysine
<220> FEATURE:
<221> NAME/KEY: X
<222> LOCATION: (10)..(10)
<223> OTHER INFORMATION: X is aspartate or tyrosine

<400> SEQUENCE: 75

Val Ile Trp Tyr Xaa Xaa Ser Xaa Lys Xaa Tyr Ala Asp Ser Ala Lys
1               5                   10                  15
Gly

<210> SEQ ID NO 76
<211> LENGTH: 9
<212> TYPE: PRT
<213> ORGANISM: Artificial Sequence
<220> FEATURE:
<223> OTHER INFORMATION: Consensus amino acid sequence for anti-hCTLA4
      VH CDR3s
<220> FEATURE:
<221> NAME/KEY: X
<222> LOCATION: (1)..(1)
<223> OTHER INFORMATION: X is alanine, valine, leucine, isoleucine, or
      glycine
<220> FEATURE:
<221> NAME/KEY: X
<222> LOCATION: (3)..(4)
<223> OTHER INFORMATION: X is leucine, isoleucine, valine, methionine,
      alanine, or phenylalanine

<400> SEQUENCE: 76

Xaa Gly Xaa Xaa Gly Tyr Phe Asp Tyr
1               5
```

```
<210> SEQ ID NO 77
<211> LENGTH: 9
<212> TYPE: PRT
<213> ORGANISM: Artificial Sequence
<220> FEATURE:
<223> OTHER INFORMATION: Second consensus amino acid sequence for
      anti-hCTLA4 VH CDR3
<220> FEATURE:
<221> NAME/KEY: X
<222> LOCATION: (1)..(1)
<223> OTHER INFORMATION: X is alanine or glycine
<220> FEATURE:
<221> NAME/KEY: X
<222> LOCATION: (3)..(4)
<223> OTHER INFORMATION: X is leucine or phenylalanine

<400> SEQUENCE: 77

Xaa Gly Xaa Xaa Gly Tyr Phe Asp Tyr
1               5

<210> SEQ ID NO 78
<211> LENGTH: 11
<212> TYPE: PRT
<213> ORGANISM: Artificial Sequence
<220> FEATURE:
<223> OTHER INFORMATION: Consensus amino acid sequence for anti-hCTLA4
      VL CDR1s
<220> FEATURE:
<221> NAME/KEY: X
<222> LOCATION: (6)..(6)
<223> OTHER INFORMATION: X is isoleucine, valine, leucine, methionine,
      alanine, or phenylalanine
<220> FEATURE:
<221> NAME/KEY: X
<222> LOCATION: (7)..(7)
<223> OTHER INFORMATION: X is serine asparagine, threonine, glutamine,
      alanine, or cysteine

<400> SEQUENCE: 78

Arg Ala Ser Gln Ser Xaa Xaa Ser Tyr Leu Ala
1               5                   10

<210> SEQ ID NO 79
<211> LENGTH: 11
<212> TYPE: PRT
<213> ORGANISM: Artificial Sequence
<220> FEATURE:
<223> OTHER INFORMATION: Second consensus amino acid sequence for
      anti-hCTLA4 VL CDR1s
<220> FEATURE:
<221> NAME/KEY: X
<222> LOCATION: (6)..(6)
<223> OTHER INFORMATION: X is isoleucine, valine, or leucine
<220> FEATURE:
<221> NAME/KEY: X
<222> LOCATION: (7)..(7)
<223> OTHER INFORMATION: X is serine, asparagine, or threonine

<400> SEQUENCE: 79

Arg Ala Ser Gln Ser Xaa Xaa Ser Tyr Leu Ala
1               5                   10

<210> SEQ ID NO 80
<211> LENGTH: 9
<212> TYPE: PRT
<213> ORGANISM: Artificial Sequence
<220> FEATURE:
<223> OTHER INFORMATION: Consensus amino acid sequence for anti-hCTLA4
      VL CDR3
<220> FEATURE:
<221> NAME/KEY: X
<222> LOCATION: (5)..(5)
```

```
<223> OTHER INFORMATION: X is methionine, arginine, or isoleucine
<220> FEATURE:
<221> NAME/KEY: X
<222> LOCATION: (6)..(6)
<223> OTHER INFORMATION: X is tyrosine, tryptophan, phenylalanine,
      threonine, or serine

<400> SEQUENCE: 80

Gln Gln Tyr Gly Xaa Xaa Pro Phe Thr
1               5

<210> SEQ ID NO 81
<211> LENGTH: 9
<212> TYPE: PRT
<213> ORGANISM: Artificial Sequence
<220> FEATURE:
<223> OTHER INFORMATION: Second consensus amino acid sequence for
      anti-hCTLA4 VL CDR3s
<220> FEATURE:
<221> NAME/KEY: X
<222> LOCATION: (5)..(5)
<223> OTHER INFORMATION: X is methionine, arginine, or isoleucine
<220> FEATURE:
<221> NAME/KEY: X
<222> LOCATION: (6)..(6)
<223> OTHER INFORMATION: X is tyrosine or serine

<400> SEQUENCE: 81

Gln Gln Tyr Gly Xaa Xaa Pro Phe Thr
1               5

<210> SEQ ID NO 82
<211> LENGTH: 118
<212> TYPE: PRT
<213> ORGANISM: Artificial Sequence
<220> FEATURE:
<223> OTHER INFORMATION: Consensus amino acid sequence for anti-hCTLA4
      VH domains
<220> FEATURE:
<221> NAME/KEY: X
<222> LOCATION: (23)..(23)
<223> OTHER INFORMATION: X is threonine, alanine, serine, valine,
      leucine, or isoleucine
<220> FEATURE:
<221> NAME/KEY: X
<222> LOCATION: (54)..(54)
<223> OTHER INFORMATION: X is asparagine, histidine, lysine, glutamine,
      or arginine
<220> FEATURE:
<221> NAME/KEY: X
<222> LOCATION: (55)..(55)
<223> OTHER INFORMATION: X is proline, arginine, serine, threonine,
      lysine, glutamine, asparagine, alanine, or threonine
<220> FEATURE:
<221> NAME/KEY: X
<222> LOCATION: (57)..(57)
<223> OTHER INFORMATION: X is glutamate, lysine, aspartate, arginine,
      glutamine, or asparagine
<220> FEATURE:
<221> NAME/KEY: X
<222> LOCATION: (59)..(59)
<223> OTHER INFORMATION: X is aspartate, tyrosine, glutamate,
      tryptophan, phenylalanine, threonine, or serine
<220> FEATURE:
<221> NAME/KEY: X
<222> LOCATION: (99)..(99)
<223> OTHER INFORMATION: X is alanine, glycine, valine, leucine,
      isoleucine, or proline
<220> FEATURE:
<221> NAME/KEY: X
<222> LOCATION: (101)..(102)
<223> OTHER INFORMATION: X is leucine, phenylalanine, isoleucine,
      valine, methionine, alanine, or tyrosine

<400> SEQUENCE: 82
```

Gln Val Gln Leu Val Glu Ser Gly Gly Gly Val Val Glu Pro Gly Arg
1               5                   10                  15

Ser Leu Arg Leu Ser Cys Xaa Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Xaa Xaa Ser Xaa Lys Xaa Tyr Ala Asp Ser Ala
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Xaa Gly Xaa Xaa Gly Tyr Phe Asp Tyr Trp Gly Gln Gly Thr
            100                 105                 110

Leu Val Thr Val Ser Ser
            115

<210> SEQ ID NO 83
<211> LENGTH: 118
<212> TYPE: PRT
<213> ORGANISM: Artificial Sequence
<220> FEATURE:
<223> OTHER INFORMATION: Second consensus amino acid sequence for
      anti-hCTLA4 VH domains
<220> FEATURE:
<221> NAME/KEY: X
<222> LOCATION: (23)..(23)
<223> OTHER INFORMATION: X is threonine or alanine
<220> FEATURE:
<221> NAME/KEY: X
<222> LOCATION: (54)..(54)
<223> OTHER INFORMATION: X is asparagine, histidine, lysine, or
      glutamine
<220> FEATURE:
<221> NAME/KEY: X
<222> LOCATION: (55)..(55)
<223> OTHER INFORMATION: X is proline, arginine, serine, or threonine
<220> FEATURE:
<221> NAME/KEY: X
<222> LOCATION: (57)..(57)
<223> OTHER INFORMATION: X is glutamate or lysine
<220> FEATURE:
<221> NAME/KEY: X
<222> LOCATION: (59)..(59)
<223> OTHER INFORMATION: X is aspartate or tyrosine
<220> FEATURE:
<221> NAME/KEY: X
<222> LOCATION: (99)..(99)
<223> OTHER INFORMATION: X is alanine or glycine
<220> FEATURE:
<221> NAME/KEY: X
<222> LOCATION: (101)..(102)
<223> OTHER INFORMATION: X is leucine or phenylalanine

<400> SEQUENCE: 83

Gln Val Gln Leu Val Glu Ser Gly Gly Gly Val Val Glu Pro Gly Arg
1               5                   10                  15

Ser Leu Arg Leu Ser Cys Xaa Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Trp Tyr Xaa Xaa Ser Xaa Lys Xaa Tyr Ala Asp Ser Ala
        50                  55                  60

Lys Gly Arg Phe Thr Ile Ser Arg Asp Asn Ser Lys Asn Thr Leu Tyr
65                  70                  75                  80

```
Leu Gln Met Asn Ser Leu Arg Ala Glu Asp Thr Ala Val Tyr Tyr Cys
                85                  90                  95

Ala Arg Xaa Gly Xaa Xaa Gly Tyr Phe Asp Tyr Trp Gly Gln Gly Thr
            100                 105                 110

Leu Val Thr Val Ser Ser
        115

<210> SEQ ID NO 84
<211> LENGTH: 107
<212> TYPE: PRT
<213> ORGANISM: Artificial Sequence
<220> FEATURE:
<223> OTHER INFORMATION: Consensus amino acid sequence for anti-hCTLA4
      VL domains
<220> FEATURE:
<221> NAME/KEY: X
<222> LOCATION: (29)..(29)
<223> OTHER INFORMATION: X is isoleucine, valine, leucine, methionine,
      alanine, or phenylalanine
<220> FEATURE:
<221> NAME/KEY: X
<222> LOCATION: (30)..(30)
<223> OTHER INFORMATION: X is serine, asparagine, threonine, alanine, or
      glutamine
<220> FEATURE:
<221> NAME/KEY: X
<222> LOCATION: (46)..(46)
<223> OTHER INFORMATION: X is proline, leucine, alanine, isoleucine,
      valine, methionine, or phenylalanine
<220> FEATURE:
<221> NAME/KEY: X
<222> LOCATION: (93)..(93)
<223> OTHER INFORMATION: X is methionine, isoleucine, arginine, leucine,
      phenylalanine, valine, alanine lysine, glutamine, or asparagine
<220> FEATURE:
<221> NAME/KEY: X
<222> LOCATION: (94)..(94)
<223> OTHER INFORMATION: X is serine, tyrosine, threonine, alanine,
      tryptophan, or phenylalanine

<400> SEQUENCE: 84

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Xaa Xaa Ser Tyr
            20                  25                  30

Leu Ala Trp Tyr Gln Gln Lys Pro Gly Gln Ala Pro Arg Xaa Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Xaa Xaa Pro Phe
                85                  90                  95

Thr Phe Gly Pro Gly Thr Lys Val Asp Ile Lys
            100                 105

<210> SEQ ID NO 85
<211> LENGTH: 107
<212> TYPE: PRT
<213> ORGANISM: Artificial Sequence
<220> FEATURE:
<223> OTHER INFORMATION: Second consensus amino acid sequence for
      anti-hCTLA4 VL domains
<220> FEATURE:
<221> NAME/KEY: X
<222> LOCATION: (29)..(29)
<223> OTHER INFORMATION: X is isoleucine, valine, or leucine
```

```
<220> FEATURE:
<221> NAME/KEY: X
<222> LOCATION: (30)..(30)
<223> OTHER INFORMATION: X is serine asparagine, or threonine
<220> FEATURE:
<221> NAME/KEY: X
<222> LOCATION: (46)..(46)
<223> OTHER INFORMATION: X is proline or leucine
<220> FEATURE:
<221> NAME/KEY: X
<222> LOCATION: (93)..(93)
<223> OTHER INFORMATION: X is methionine, isoleucine, or arginine
<220> FEATURE:
<221> NAME/KEY: X
<222> LOCATION: (94)..(94)
<223> OTHER INFORMATION: X is serine or tyrosine

<400> SEQUENCE: 85

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Xaa Xaa Ser Tyr
             20                  25                  30

Leu Ala Trp Tyr Gln Gln Lys Pro Gly Gln Ala Pro Arg Xaa Leu Ile
         35                  40                  45

Tyr Gly Val Ser Ser Arg Ala Thr Gly Ile Pro Asp Arg Phe Ser Gly
 50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Xaa Xaa Pro Phe
                 85                  90                  95

Thr Phe Gly Pro Gly Thr Lys Val Asp Ile Lys
            100                 105

<210> SEQ ID NO 86
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #1

<400> SEQUENCE: 86
caagttcaat tggttcaatc tggtgctgaa gtcaaaaagc caggtgcctc tgtcaaggtt      60
tcttgtaaag cttccggtta caccttcact aattactgga ttcactgggt tagacaagct    120
ccaggtcaag gtttggaatg gatgggtgag atcgacccat atgattctta tactaattac    180
aatcaaaagt tcaagggtcg tgttactatg accgtagaca atccactag taccgtttac     240 atggaattat cttccttgag atccgaggac actgctgttt attattgcgc tcgtccaggt    300
tttacctacg gtggtatgga ttttgggggt caaggtactt tggttaccgt ttcttct        357

<210> SEQ ID NO 87
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #1

<400> SEQUENCE: 87

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
             20                  25                  30
```

```
Trp Ile His Trp Val Arg Gln Ala Pro Gly Gln Gly Leu Glu Trp Met
        35                  40                  45

Gly Glu Ile Asp Pro Tyr Asp Ser Tyr Thr Asn Tyr Asn Gln Lys Phe
    50                  55                  60

Lys Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Gly Phe Thr Tyr Gly Gly Met Asp Phe Trp Gly Gln Gly
            100                 105                 110

Thr Leu Val Thr Val Ser Ser
        115
```

```
<210> SEQ ID NO 88
<211> LENGTH: 5
<212> TYPE: PRT
<213> ORGANISM: Artificial Sequence
<220> FEATURE:
<223> OTHER INFORMATION: Amino acid sequence of the CDR1 of the VH
      domain of the anti-hPD1 antibodies designated #1, #6, #7, #8, and
      #14

<400> SEQUENCE: 88

Asn Tyr Trp Ile His
1               5
```

```
<210> SEQ ID NO 89
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hPD1 antibodies designated #1, #2, #3, #6, #7,
      #8, #9, #13, #14, and #15

<400> SEQUENCE: 89

Glu Ile Asp Pro Tyr Asp Ser Tyr Thr Asn Tyr Asn Gln Lys Phe Lys
1               5                   10                  15

Gly
```

```
<210> SEQ ID NO 90
<211> LENGTH: 10
<212> TYPE: PRT
<213> ORGANISM: Artificial Sequence
<220> FEATURE:
<223> OTHER INFORMATION: Amino acid sequence of the CDR3 of the VH
      domain of the anti-hPD1 antibodies designated #1, #3, #5, #9, and
      #12

<400> SEQUENCE: 90

Pro Gly Phe Thr Tyr Gly Gly Met Asp Phe
1               5                   10
```

```
<210> SEQ ID NO 91
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #1

<400> SEQUENCE: 91
gatattcaaa tgacccaatc cccatcctct ttgtccgctt ctgttggtga cagagtcacc     60
```

```
atcacttgta agtcctctca atccttgttt aattctggta accaaaaaaa ctacttggcc    120
tggtaccaac aaaagccagg taaggttcct aaattgttga tttatggtgc ctccactaga   180
gattctggtg tcccatatag attctctggt tctggttccg gtactgactt tactttgact   240
atttcttcct tgcaaccaga agacgtcgcc acctattact gtcaaaatga ccactactac    300
ccatacactt ttggtggtgg tactaaggtt gaaattaaa    339
```

<210> SEQ ID NO 92
<211> LENGTH: 113
<212> TYPE: PRT
<213> ORGANISM: Artificial Sequence
<220> FEATURE:
<223> OTHER INFORMATION: Amino acid sequence of the VL domain of the anti-hPD1 antibody designated #1

<400> SEQUENCE: 92

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Gly Asn Gln Lys Asn Tyr Leu Ala Trp Tyr Gln Gln Lys Pro Gly Lys
        35                  40                  45

Val Pro Lys Leu Leu Ile Tyr Gly Ala Ser Thr Arg Asp Ser Gly Val
    50                  55                  60

Pro Tyr Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp His Tyr Tyr Pro Tyr Thr Phe Gly Gly Gly Thr Lys Val Glu Ile
            100                 105                 110

Lys
```

<210> SEQ ID NO 93
<211> LENGTH: 17
<212> TYPE: PRT
<213> ORGANISM: Artificial Sequence
<220> FEATURE:
<223> OTHER INFORMATION: Amino acid sequence of the CDR1 of the VL domain of the anti-hPD1 antibodies designated #1, #3, and #14

<400> SEQUENCE: 93

```
Lys Ser Ser Gln Ser Leu Phe Asn Ser Gly Asn Gln Lys Asn Tyr Leu
1               5                   10                  15

Ala
```

<210> SEQ ID NO 94
<211> LENGTH: 7
<212> TYPE: PRT
<213> ORGANISM: Artificial Sequence
<220> FEATURE:
<223> OTHER INFORMATION: Amino acid sequence of the CDR2 of the VL domain of the anti-hPD1 antibodies designated #1, #2, #4, #5, #8, #9, #10, #11, #12, #13, and #14

<400> SEQUENCE: 94

```
Gly Ala Ser Thr Arg Asp Ser
1               5
```

<210> SEQ ID NO 95
<211> LENGTH: 9
<212> TYPE: PRT

```
<213> ORGANISM: Artificial Sequence
<220> FEATURE:
<223> OTHER INFORMATION: Amino acid sequence of the CDR3 of the VL
      domain of the anti-hPD1 antibodies designated #1, #2, #3, #4, #5,
      #6, #13, #14, and #15

<400> SEQUENCE: 95

Gln Asn Asp His Tyr Tyr Pro Tyr Thr
1               5

<210> SEQ ID NO 96
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #2

<400> SEQUENCE: 96
caagttcaat tggttcaatc tggtgctgaa gtcaaaaagc caggtgcctc tgtcaaggtt     60
tcttgtaaag cttccggtta caccttcact tcttactgga tgcactgggt tagacaagct    120
ccaggtcaag gtttggaatg gatgggtgag atcgacccat atgattctta tactaattac    180
aatcaaaagt tcaagggtcg tgttactatg accgtagaca atccactag taccgtttac    240 atggaattat cttccttgag atccgaggac actgctgttt attattgcgc tcgtccaggt    300
aatacctacg gtggtatgga ttattggggt caaggtactt tggttaccgt ttcttct      357

<210> SEQ ID NO 97
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #2

<400> SEQUENCE: 97

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Asp Pro Tyr Asp Ser Tyr Thr Asn Tyr Asn Gln Lys Phe
    50                  55                  60

Lys Gly Arg Val Thr Met Thr Val Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Gly Asn Thr Tyr Gly Gly Met Asp Tyr Trp Gly Gln Gly
            100                 105                 110

Thr Leu Val Thr Val Ser Ser
        115

<210> SEQ ID NO 98
<211> LENGTH: 5
<212> TYPE: PRT
<213> ORGANISM: Artificial Sequence
<220> FEATURE:
<223> OTHER INFORMATION: Amino acid sequence of the CDR1 of the VH
      domain of the anti-hPD1 antibodies designated #2, #9, and #10

<400> SEQUENCE: 98
```

Ser Tyr Trp Met His
1               5

<210> SEQ ID NO 99
<211> LENGTH: 10
<212> TYPE: PRT
<213> ORGANISM: Artificial Sequence
<220> FEATURE:
<223> OTHER INFORMATION: Amino acid sequence of the CDR3 of the VH
      domain of the anti-hPD1 antibody designated #2

<400> SEQUENCE: 99

Pro Gly Asn Thr Tyr Gly Gly Met Asp Tyr
1               5                   10

<210> SEQ ID NO 100
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #2

<400> SEQUENCE: 100
gatattcaaa tgacccaatc cccatcctct ttgtccgctt ctgttggtga cagagtcacc      60
atcacttgta ggtcctctca atccttgttt aattctggta accaaaaaaa ctacttggcc     120
tggtaccaac aaaagccagg taaggttcct aaattgttga tttatggtgc ctccactaga     180
gattctggtg tcccatatag attctctggt tctggttccg gtactgactt tactttgact     240
atttcttcct tgcaaccaga agacgtcgcc acctattact gtcaaaatga ccactactac     300
ccatacactt ttggtggtgg tactaaggtt gaaattaaa                            339

<210> SEQ ID NO 101
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #2

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Phe Asn Ser
            20                  25                  30

Gly Asn Gln Lys Asn Tyr Leu Ala Trp Tyr Gln Gln Lys Pro Gly Lys
        35                  40                  45

Val Pro Lys Leu Leu Ile Tyr Gly Ala Ser Thr Arg Asp Ser Gly Val
    50                  55                  60

Pro Tyr Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp His Tyr Tyr Pro Tyr Thr Phe Gly Gly Gly Thr Lys Val Glu Ile
            100                 105                 110

Lys

<210> SEQ ID NO 102
<211> LENGTH: 17
<212> TYPE: PRT

<213> ORGANISM: Artificial Sequence
<220> FEATURE:
<223> OTHER INFORMATION: Amino acid sequence of the CDR1 of the VL
      domain of the anti-hPD1 antibodies designated #2, #6, and #15

<400> SEQUENCE: 102

Arg Ser Ser Gln Ser Leu Phe Asn Ser Gly Asn Gln Lys Asn Tyr Leu
1               5                   10                  15

Ala

<210> SEQ ID NO 103
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #3

<400> SEQUENCE: 103
caagttcaat tggttcaatc tggtgctgaa gtcaaaaagc caggtgcctc tgtcaaggtt      60
tcttgtaaag cttccagtta caccttcact aattactgga tgcactgggt tagacaagct     120
ccaggtcaag gtttggaatg gatgggtgag atcgacccat atgattctta tactaattac     180
aatcaaaagt tcaagggtcg tgttactatg accatagaca catccactag taccgtttac     240
atggaattat cttccttgac atccgaggac actgctgttt attattgcgc tcgtccaggt     300
tttacctacg gtggtatgga tttttgggt caaggtactt tggttaccgt ttcttct         357

<210> SEQ ID NO 104
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #3

<400> SEQUENCE: 104

Gln Val Gln Leu Val Gln Ser Gly Ala Glu Val Lys Lys Pro Gly Ala
1               5                   10                  15

Ser Val Lys Val Ser Cys Lys Ala Ser Ser Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asp Pro Tyr Asp Ser Tyr Thr Asn Tyr Asn Gln Lys Phe
    50                  55                  60

Lys Gly Arg Val Thr Met Thr Ile Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Pro Gly Phe Thr Tyr Gly Gly Met Asp Phe Trp Gly Gln Gly
            100                 105                 110

Thr Leu Val Thr Val Ser Ser
        115

<210> SEQ ID NO 105
<211> LENGTH: 5
<212> TYPE: PRT
<213> ORGANISM: Artificial Sequence
<220> FEATURE:
<223> OTHER INFORMATION: Amino acid sequence of the CDR1 of the VH
      domain of the anti-hPD1 antibodies designated #3, #4, #5, #12, and
      #15

<400> SEQUENCE: 105

Asn Tyr Trp Met His
1               5

<210> SEQ ID NO 106
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #3

<400> SEQUENCE: 106
gatattcaaa tgacccaatc cccatcctct ttgtccgctt ctgttggtga cagagtcacc    60
atcacttgta gtcctctca atccttgttt aattctggta accaaaaaaa ctacttggcc   120
tggtaccaac aaaagccagg taaggttcct aaattgttga tttatggtgc ctccactaga   180
gaatctggtg tcccagctag attctctggt tctggttccg gtactgactt tactttgact   240
atttcttcct tgcaagcaga agacgtcgcc acctattact gtcaaaatga ccactactac   300
ccatacactt ttggtggtgg tactaaggtt gaaattaaa                          339

<210> SEQ ID NO 107
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #3

<400> SEQUENCE: 107

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Gly Asn Gln Lys Asn Tyr Leu Ala Trp Tyr Gln Gln Lys Pro Gly Lys
        35                  40                  45

Val Pro Lys Leu Leu Ile Tyr Gly Ala Ser Thr Arg Glu Ser Gly Val
    50                  55                  60

Pro Ala Arg Phe Ser Gly Ser Gly Ser Gly Thr Asp Phe Thr Leu Thr
65                  70                  75                  80

Ile Ser Ser Leu Gln Ala Glu Asp Val Ala Thr Tyr Tyr Cys Gln Asn
                85                  90                  95

Asp His Tyr Tyr Pro Tyr Thr Phe Gly Gly Gly Thr Lys Val Glu Ile
            100                 105                 110

Lys

<210> SEQ ID NO 108
<211> LENGTH: 7
<212> TYPE: PRT
<213> ORGANISM: Artificial Sequence
<220> FEATURE:
<223> OTHER INFORMATION: Amino acid sequence of the CDR2 of the VL
      domain of the anti-hPD1 antibodies designated #3, #6, #7, and #15

<400> SEQUENCE: 108

Gly Ala Ser Thr Arg Glu Ser
1               5

<210> SEQ ID NO 109

<211> LENGTH: 357
<212> TYPE: DNA
<213> ORGANISM: Artificial Sequence
<220> FEATURE:
<223> OTHER INFORMATION: DNA sequence encoding the VH domain of the anti-hPD1 antibody designated #4

<400> SEQUENCE: 109

```
caagttcaat tggttcaatc tggtgctgaa gtcaaaaagc caggtgcctc tgtcaaggtt    60
tcttgtaaag cttccggtta caccttcact aattactgga tgcactgggt tagacaagct   120
ccaggtcaag gtttggaatg gatgggtgag atcgacccat ttgattctta tactaattac   180
aatcaaaagt tcaagggtcg tgttactatg accagagaca catccactag taccgtttac   240
atggaattat cttccttgac atccgaggac actgctgttt attattgcgc tcgtccaggt   300
tatacctacg gtggtatgga ttttgggggt caaggtactt tggttaccgt ttcttct      357
```

<210> SEQ ID NO 110
<211> LENGTH: 119
<212> TYPE: PRT
<213> ORGANISM: Artificial Sequence
<220> FEATURE:
<223> OTHER INFORMATION: Amino acid sequence of the VH domain of the anti-hPD1 antibody designated #4

<400> SEQUENCE: 110

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asp Pro Phe Asp Ser Tyr Thr Asn Tyr Asn Gln Lys Phe
    50                  55                  60

Lys Gly Arg Val Thr Met Thr Arg Asp Thr Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Pro Gly Tyr Thr Tyr Gly Gly Met Asp Phe Trp Gly Gln Gly
            100                 105                 110

Thr Leu Val Thr Val Ser Ser
        115

<210> SEQ ID NO 111
<211> LENGTH: 17
<212> TYPE: PRT
<213> ORGANISM: Artificial Sequence
<220> FEATURE:
<223> OTHER INFORMATION: Amino acid sequence of the CDR2 of the VH domain of the anti-hPD1 antibodies designated #4, #5, #10, and #12

<400> SEQUENCE: 111

Glu Ile Asp Pro Phe Asp Ser Tyr Thr Asn Tyr Asn Gln Lys Phe Lys
1               5                   10                  15

Gly

<210> SEQ ID NO 112
<211> LENGTH: 10
<212> TYPE: PRT
<213> ORGANISM: Artificial Sequence
<220> FEATURE:
<223> OTHER INFORMATION: Amino acid sequence of the CDR3 of the VH domain of the anti-hPD1 antibodies designated #4, #6, #10, #11, and #14

<400> SEQUENCE: 112

Pro Gly Tyr Thr Tyr Gly Gly Met Asp Phe
1               5                   10

<210> SEQ ID NO 113
<211> LENGTH: 339
<212> TYPE: DNA
<213> ORGANISM: Artificial Sequence
<220> FEATURE:
<223> OTHER INFORMATION: DNA sequence encoding the VL domain of the anti-hPD1 antibody designated #4

<400> SEQUENCE: 113

```
gatattcaaa tgacccaatc cccatcctct ttgtccgctt ctgttggtga cagagtcacc      60
atcacttgta agtcctctca atccttgttg aattctggta accaaaaaaa ctacttggcc     120
tggtaccaac aaaagccagg taagcctcct aaattgttga tttatggtgc ctccactaga     180
gattctggtg tcccatctag attctctggt tctggttccg gtactgactt tactttgact     240
atttcttcct tgcaaccaga agacgtcgcc acctattact gtcaaaatga ccactactac     300
ccatacactt ttggtggtgg tactaaggtt gaaattaaa                            339
```

<210> SEQ ID NO 114
<211> LENGTH: 113
<212> TYPE: PRT
<213> ORGANISM: Artificial Sequence
<220> FEATURE:
<223> OTHER INFORMATION: Amino acid sequence of the VL domain of the anti-hPD1 antibody designated #4

<400> SEQUENCE: 114

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Asn Tyr Leu Ala Trp Tyr Gln Gln Lys Pro Gly Lys
        35                  40                  45

Pro Pro Lys Leu Leu Ile Tyr Gly Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp His Tyr Tyr Pro Tyr Thr Phe Gly Gly Gly Thr Lys Val Glu Ile
            100                 105                 110

Lys

<210> SEQ ID NO 115
<211> LENGTH: 17
<212> TYPE: PRT
<213> ORGANISM: Artificial Sequence
<220> FEATURE:
<223> OTHER INFORMATION: Amino acid sequence of the CDR1 of the VL domain of the anti-hPD1 antibodies designated #4 and #13

<400> SEQUENCE: 115

Lys Ser Ser Gln Ser Leu Leu Asn Ser Gly Asn Gln Lys Asn Tyr Leu
1               5                   10                  15

Ala

<210> SEQ ID NO 116
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #5

<400> SEQUENCE: 116

```
caagttcaat tggttcaatc tggtgctgaa gtcaaaaagc caggtgcctc tgtcaaggtt    60
tcttgtaaag cttccggtta caccttcact aattactgga tgcactgggt tagacaagct   120
ccaggtcaag gtttggaatg gatgggtgag atcgacccat tgattctta tactaattac   180 aatcaaaagt tcaagggtcg tgttactatg accagagaca atccactag taccgtttac   240 atggaattat cttccttgag atccgaggac actgctgttt attattgcgc tcgtccaggt   300
tttacctacg gtggtatgga tttttggggt caaggtactt tggttaccgt ttcttct     357
```

<210> SEQ ID NO 117
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #5

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asp Pro Phe Asp Ser Tyr Thr Asn Tyr Asn Gln Lys Phe
    50                  55                  60

Lys Gly Arg Val Thr Met Thr Arg Asp Lys Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Gly Phe Thr Tyr Gly Gly Met Asp Phe Trp Gly Gln Gly
            100                 105                 110

Thr Leu Val Thr Val Ser Ser
        115

<210> SEQ ID NO 118
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #5

<400> SEQUENCE: 118

```
gatattcaaa tgacccaatc ccatcctct tgtccgctt ctgttggtga cagagtcacc    60
atcacttgta gatcctctca atccttgttg aattctggta ccaaaaaaa ctacttggcc   120 tggtaccaac aaaagccagg taagcttcct aaattgttga tttatggtgc ctccactaga   180
gattctggtg tcccatctag attctctggt tctggttccg gtactgactt tactttgact   240
```

```
atttcttcct tgcaagcaga agacgtcgcc acctattact gtcaaaatga ccactactac    300
ccatacactt tggtggtgg tactaaggtt gaaattaaa                            339
```

<210> SEQ ID NO 119
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #5

<400> SEQUENCE: 119

```
Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Leu Asn Ser
            20                  25                  30

Gly Asn Gln Lys Asn Tyr Leu Ala Trp Tyr Gln Gln Lys Pro Gly Lys
        35                  40                  45

Leu Pro Lys Leu Leu Ile Tyr Gly Ala Ser Thr Arg Asp Ser Gly Val
    50                  55                  60

Pro Ser Arg Phe Ser Gly Ser Gly Ser Gly Thr Asp Phe Thr Leu Thr
65                  70                  75                  80

Ile Ser Ser Leu Gln Ala Glu Asp Val Ala Thr Tyr Tyr Cys Gln Asn
                85                  90                  95

Asp His Tyr Tyr Pro Tyr Thr Phe Gly Gly Gly Thr Lys Val Glu Ile
            100                 105                 110

Lys
```

<210> SEQ ID NO 120
<211> LENGTH: 17
<212> TYPE: PRT
<213> ORGANISM: Artificial Sequence
<220> FEATURE:
<223> OTHER INFORMATION: Amino acid sequence of the CDR1 of the VL
      domain of the anti-hPD1 antibody designated #5

<400> SEQUENCE: 120

```
Arg Ser Ser Gln Ser Leu Leu Asn Ser Gly Asn Gln Lys Asn Tyr Leu
1               5                   10                  15

Ala
```

<210> SEQ ID NO 121
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #6

<400> SEQUENCE: 121

```
caagttcaat tggttcaatc tggtgctgaa gtcaaaaagc caggtgcctc tgtcaaggtt     60
tcttgtaaag cttccggtta caccttcact aattactgga ttcactgggt tagacaagct    120
ccaggtcaag gtttggaatg gatgggtgag atcgacccat atgattctta tactaattac    180
aatcaaaagt tcaagggtcg tgttactatg accggagaca catccactag taccgtttac    240
atggaattat cttccttgac atccgaggac actgctgttt attattgcgc tcgtccaggt    300
tatacctacg gtggtatgga tttttggggt caaggtactt tggttaccgt ttcttct      357
```

<210> SEQ ID NO 122

```
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #6

<400> SEQUENCE: 122

Gln Val Gln Leu Val Gln Ser Gly Ala Glu Val Lys Pro Gly Ala
1               5                   10                  15

Ser Val Lys Val Ser Cys Lys Ala Ser Gly Tyr Thr Phe Thr Asn Tyr
                20                  25                  30

Trp Ile His Trp Val Arg Gln Ala Pro Gly Gln Gly Leu Glu Trp Met
            35                  40                  45

Gly Glu Ile Asp Pro Tyr Asp Ser Tyr Thr Asn Tyr Asn Gln Lys Phe
50                  55                  60

Lys Gly Arg Val Thr Met Thr Gly Asp Thr Ser Ser Thr Val Tyr
65                  70                  75                  80

Met Glu Leu Ser Ser Leu Thr Ser Glu Asp Thr Ala Val Tyr Tyr Cys
                85                  90                  95

Ala Arg Pro Gly Tyr Thr Tyr Gly Gly Met Asp Phe Trp Gly Gln Gly
            100                 105                 110

Thr Leu Val Thr Val Ser Ser
        115

<210> SEQ ID NO 123
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #6

<400> SEQUENCE: 123
gatattcaaa tgacccaatc cccatcctct ttgtccgctt ctgttggtga cagagtcacc      60
atcacttgta ggtcctctca atccttgttt aattctggta accaaaaaaa ctacttggcc     120
tggtaccaac aaaagccagg taagcctcct aaattgttga tttatggtgc ctccactaga     180
gaatctggtg tcccagctag attctctggt tctggttccg gtactgactt tactttgact     240
atttcttcct tgcaaccaga agacgtcgcc acctattact gtcaaaatga ccactactac     300
ccatacactt tggtggtgg tactaaggtt gaaattaaa                             339

<210> SEQ ID NO 124
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #6

<400> SEQUENCE: 124

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Phe Asn Ser
                20                  25                  30

Gly Asn Gln Lys Asn Tyr Leu Ala Trp Tyr Gln Gln Lys Pro Gly Lys
            35                  40                  45

Pro Pro Lys Leu Leu Ile Tyr Gly Ala Ser Thr Arg Glu Ser Gly Val
50                  55                  60
```

```
Pro Ala Arg Phe Ser Gly Ser Gly Ser Gly Thr Asp Phe Thr Leu Thr
 65                  70                  75                  80

Ile Ser Ser Leu Gln Pro Glu Asp Val Ala Thr Tyr Tyr Cys Gln Asn
                 85                  90                  95

Asp His Tyr Tyr Pro Tyr Thr Phe Gly Gly Gly Thr Lys Val Glu Ile
            100                 105                 110

Lys

<210> SEQ ID NO 125
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #7

<400> SEQUENCE: 125
caagttcaat tggttcaatc tggtgctgaa gtcaaaaagc caggtgcctc tgtcaaggtt      60
tcttgtaaag cttccggtta caccttcact aattactgga ttcactgggt tagacaagct     120
ccaggtcaag gtttggaatg gatgggtgag atcgacccat atgattctta tactaattac    180
aatcaaaagt tcaagggtcg tgttactatg accatagaca atccactaa taccgtttac      240 atggaattat cttccttgag atccgaggac actgctgttt attattgcgc tcgtccaggt    300
cttacctacg gtggtatgga ttttgggggt caaggtactt tggttaccgt ttcttct      357

<210> SEQ ID NO 126
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #7

<400> SEQUENCE: 126

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Asn Tyr
                 20                  25                  30

Trp Ile His Trp Val Arg Gln Ala Pro Gly Gln Gly Leu Glu Trp Met
             35                  40                  45

Gly Glu Ile Asp Pro Tyr Asp Ser Tyr Thr Asn Tyr Asn Gln Lys Phe
         50                  55                  60

Lys Gly Arg Val Thr Met Thr Ile Asp Lys Ser Thr Asn Thr Val Tyr
 65                  70                  75                  80

Met Glu Leu Ser Ser Leu Arg Ser Glu Asp Thr Ala Val Tyr Tyr Cys
                 85                  90                  95

Ala Arg Pro Gly Leu Thr Tyr Gly Gly Met Asp Phe Trp Gly Gln Gly
            100                 105                 110

Thr Leu Val Thr Val Ser Ser
            115

<210> SEQ ID NO 127
<211> LENGTH: 10
<212> TYPE: PRT
<213> ORGANISM: Artificial Sequence
<220> FEATURE:
<223> OTHER INFORMATION: Amino acid sequence of the CDR3 of the VH
      domain of the anti-hPD1 antibody designated #7, #13, and #15

<400> SEQUENCE: 127
```

```
Pro Gly Leu Thr Tyr Gly Gly Met Asp Phe
1               5                   10
```

<210> SEQ ID NO 128
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #7

<400> SEQUENCE: 128

```
gatattgtta tgacccaatc cccagattcc ttggctgtct ctttgggtga aagagctact      60
attaattgta gatcttccca atctttgttt atatccggta accaaaagaa ctatttggcc     120
tggtatcaac aaaagccagg tcaaccacct aagttattga tctacggtgc ttccaccaga     180
gaatctggtg ttccagatcg tttctctggt tctggttctg gtactgattt caccttaact     240
atttcttctt tgcaagccga agacgtcgct gtttactact gtcaaaacaa ccattattac     300
ccttacacct tcggtggtgg taccaaggtc gaaattaag                            339
```

<210> SEQ ID NO 129
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #7

<400> SEQUENCE: 129

```
Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Phe Ile Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn His Tyr Tyr Pro Tyr Thr Phe Gly Gly Gly Thr Lys Val Glu Ile
            100                 105                 110

Lys
```

<210> SEQ ID NO 130
<211> LENGTH: 17
<212> TYPE: PRT
<213> ORGANISM: Artificial Sequence
<220> FEATURE:
<223> OTHER INFORMATION: Amino acid sequence of the CDR1 of the VL
      domain of the anti-hPD1 antibodies designated #7, #10, and #11

<400> SEQUENCE: 130

```
Arg Ser Ser Gln Ser Leu Phe Ile Ser Gly Asn Gln Lys Asn Tyr Leu
1               5                   10                  15

Ala
```

<210> SEQ ID NO 131

```
<211> LENGTH: 9
<212> TYPE: PRT
<213> ORGANISM: Artificial Sequence
<220> FEATURE:
<223> OTHER INFORMATION: Amino acid sequence of the CDR3 of the VL
      domain of the anti-hPD1 antibodies designated #7, #8, #9, #10,
      #11, and #12

<400> SEQUENCE: 131

Gln Asn Asn His Tyr Tyr Pro Tyr Thr
1               5

<210> SEQ ID NO 132
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #8

<400> SEQUENCE: 132
caagttcaat tggttcaatc tggtgctgaa gtcaaaaagc caggtgcctc tgtcaaggtt      60
tcttgtaaag cttccggtta caccttcact aattactgga ttcactgggt tagacaagct    120
ccaggtcaag gtttggaatg gatgggtgag atcgacccgt atgattctta tactaattac    180
aatcaaaagt tcaagggtcg tgttactatg accatagaca catccactag taccgtttac    240
atggaattat cttccttgag atccgaggac actgctgttt attattgcgc tcgtccaggt    300 aataccacg gtggtatgga tttttggggt caaggtactt tggttaccgt ttcttct       357

<210> SEQ ID NO 133
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #8

<400> SEQUENCE: 133

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Glu Ile Asp Pro Tyr Asp Ser Tyr Thr Asn Tyr Asn Gln Lys Phe
    50                  55                  60

Lys Gly Arg Val Thr Met Thr Ile Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Pro Gly Asn Thr Tyr Gly Gly Met Asp Phe Trp Gly Gln Gly
            100                 105                 110

Thr Leu Val Thr Val Ser Ser
        115

<210> SEQ ID NO 134
<211> LENGTH: 10
<212> TYPE: PRT
<213> ORGANISM: Artificial Sequence
<220> FEATURE:
<223> OTHER INFORMATION: Amino acid sequence of the CDR3 of the VH
      domain of the anti-hPD1 antibody designated #8
```

<400> SEQUENCE: 134

Pro Gly Asn Thr Tyr Gly Gly Met Asp Phe
1               5                   10

<210> SEQ ID NO 135
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #8

<400> SEQUENCE: 135
gatattgtta tgacccaatc cccagattcc ttggctgtct ctttgggtga aagagctact      60
attaattgta atcttccca atctttgttt atatccggta accaaaagaa ctatttggcc     120
tggtatcaac aaaagccagg tcaaccacct aagttattga tctacggtgc ttccaccaga    180
gattctggtg ttccagatcg tttctctggt tctggttctg gtactgattt caccttaact    240
atttcttctt tgcaagccga agacgtcgct gtttactact gtcaaaacaa ccattattac    300
ccttacacct cggtggtgg taccaaggtc gaaattaag                            339

<210> SEQ ID NO 136
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #8

<400> SEQUENCE: 136

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Leu Phe Ile Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn His Tyr Tyr Pro Tyr Thr Phe Gly Gly Gly Thr Lys Val Glu Ile
            100                 105                 110

Lys

<210> SEQ ID NO 137
<211> LENGTH: 17
<212> TYPE: PRT
<213> ORGANISM: Artificial Sequence
<220> FEATURE:
<223> OTHER INFORMATION: Amino acid sequence of the CDR1 of the VL
      domain of the anti-hPD1 antibody designated #8

<400> SEQUENCE: 137

Lys Ser Ser Gln Ser Leu Phe Ile Ser Gly Asn Gln Lys Asn Tyr Leu
1               5                   10                  15

Ala

<210> SEQ ID NO 138
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #9

<400> SEQUENCE: 138

```
caagttcaat tggttcaatc tggtgctgaa gtcaaaaagc caggtgcctc tgtcaaggtt      60
tcttgtaaag cttccggtta caccttcact tcttactgga tgcactgggt tagacaagct     120
ccaggtcaag gtttggaatg gatgggtgag atcgacccat atgattctta tactaattac     180
aatcaaaagt tcaagggtcg tgttactatg accatagaca atccactag taccgtttac     240 atggaattat cttccttgac atccgaggac actgctgttt attattgcgc tcgtccaggt     300
tttacctacg gtggtatgga tttttggggt caaggtactt tggttaccgt ttcttct       357
```

<210> SEQ ID NO 139
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #9

<400> SEQUENCE: 139

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Asp Pro Tyr Asp Ser Tyr Thr Asn Tyr Asn Gln Lys Phe
    50                  55                  60

Lys Gly Arg Val Thr Met Thr Ile Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Pro Gly Phe Thr Tyr Gly Gly Met Asp Phe Trp Gly Gln Gly
            100                 105                 110

Thr Leu Val Thr Val Ser Ser
        115
```

<210> SEQ ID NO 140
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #9

<400> SEQUENCE: 140

```
gatattgtta tgacccaatc cccagattcc ttggctgtct ctttgggtga aagagctact      60
attaattgta gatcttccca atctttgttg atttccggta accaaaagaa ctatttggcc    120
tggtatcaac aaaagccagg tcaaccacct aagttattga tctacggtgc ttccaccaga    180
gattctggtg ttccagatcg ttttctctggt tctggttctg gtactgattt cacccttaact   240 atttcttctt tgcaagccga agacgtcgct gtttactact gtcaaaacaa ccattattac    300
```

```
ccttacacct tcggtggtgg taccaaggtc gaaattaag                    339
```

<210> SEQ ID NO 141
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #9

<400> SEQUENCE: 141

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Leu Ile Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn His Tyr Tyr Pro Tyr Thr Phe Gly Gly Gly Thr Lys Val Glu Ile
            100                 105                 110

Lys

<210> SEQ ID NO 142
<211> LENGTH: 17
<212> TYPE: PRT
<213> ORGANISM: Artificial Sequence
<220> FEATURE:
<223> OTHER INFORMATION: Amino acid sequence of the CDR1 of the VL
      domain of the anti-hPD1 antibodies designated #9 and #12

<400> SEQUENCE: 142

Arg Ser Ser Gln Ser Leu Leu Ile Ser Gly Asn Gln Lys Asn Tyr Leu
1               5                   10                  15

Ala

<210> SEQ ID NO 143
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #10

<400> SEQUENCE: 143

```
caagttcaat tggttcaatc tggtgctgaa gtcaaaaagc caggtgcctc tgtcaaggtt    60
tcttgtaaag cttccggtta cacctttcact tcttactgga tgcactgggt tagacaagct   120
ccaggtcaag gtttggaatg gatgggtgag atcgacccat tgattcttta tactaattac   180
aatcaaaagt tcaagggtcg tgttactatg accatagaca aatccactaa taccgtttac   240
atggaattat cttccttggg atccgaggac actgctgttt attattgcgc tcgtccaggt   300
tatacctacg gtggtatgga ttttgggggt caaggtactt tggttaccgt tcttcct      357
```

<210> SEQ ID NO 144
<211> LENGTH: 119
<212> TYPE: PRT

<213> ORGANISM: Artificial Sequence
<220> FEATURE:
<223> OTHER INFORMATION: Amino acid sequence of the VH domain of the anti-hPD1 antibody designated #10

<400> SEQUENCE: 144

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Met His Trp Val Arg Gln Ala Pro Gly Gln Gly Leu Glu Trp Met
        35                  40                  45

Gly Glu Ile Asp Pro Phe Asp Ser Tyr Thr Asn Tyr Asn Gln Lys Phe
    50                  55                  60

Lys Gly Arg Val Thr Met Thr Ile Asp Lys Ser Thr Asn Thr Val Tyr
65                  70                  75                  80

Met Glu Leu Ser Ser Leu Gly Ser Glu Asp Thr Ala Val Tyr Tyr Cys
                85                  90                  95

Ala Arg Pro Gly Tyr Thr Tyr Gly Gly Met Asp Phe Trp Gly Gln Gly
            100                 105                 110

Thr Leu Val Thr Val Ser Ser
        115

<210> SEQ ID NO 145
<211> LENGTH: 339
<212> TYPE: DNA
<213> ORGANISM: Artificial Sequence
<220> FEATURE:
<223> OTHER INFORMATION: DNA sequence encoding the VL domain of the anti-hPD1 antibody designated #10

<400> SEQUENCE: 145
gatattgtta tgacccaatc cccagattcc ttggctgtct ctttgggtga aagagctact    60
attaattgta gatcttccca atctttgttt atttccggta accaaaagaa ctatttggcc   120
tggtatcaac aaaagccagg tcaaccacct aagttattga tctacggtgc ttccaccaga   180
gattctggtg ttccagatcg tttctctggt tctggttctg gtactgattt caccttaact   240
atttcttctt tgcaagccga agacgtcgct gtttactact gtcaaaacaa ccattattac   300
ccttacacct tcggtggtgg taccaaggtc gaaattaag                           339

<210> SEQ ID NO 146
<211> LENGTH: 113
<212> TYPE: PRT
<213> ORGANISM: Artificial Sequence
<220> FEATURE:
<223> OTHER INFORMATION: Amino acid sequence of the VL domain of the anti-hPD1 antibody designated #10

<400> SEQUENCE: 146

Asp Ile Val Met Thr Gln Ser Pro Asp Ser Leu Ala Val Ser Leu Gly
1               5                   10                  15

Glu Arg Ala Thr Ile Asn Cys Arg Ser Ser Gln Ser Leu Phe Ile Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

```
Ile Ser Ser Leu Gln Ala Glu Asp Val Ala Val Tyr Tyr Cys Gln Asn
                85                  90                  95

Asn His Tyr Tyr Pro Tyr Thr Phe Gly Gly Thr Lys Val Glu Ile
            100                 105                 110

Lys
```

<210> SEQ ID NO 147
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #11

<400> SEQUENCE: 147

```
caagttcaat tggttcaatc tggtgctgaa gtcaaaaagc caggtgcctc tgtcaaggtt      60
tcttgtaaag cttccggtta caccttcact tcttactgga ttcactgggt tagacaagct     120
ccaggtcaag gtttggaatg gatgggtgag atcgacccat ctgattctta tactaattac     180
aatcaaaagt tcaagggtcg tgttactatg accggagaca catccactaa taccgtttac     240
atggaattat cttccttgac atccgaggac actgctgttt attattgcgc tcgtccaggt     300
tatacctacg gtggtatgga tttttggggt caaggtactt tggttaccgt ttcttct        357
```

<210> SEQ ID NO 148
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #11

<400> SEQUENCE: 148

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Trp Ile His Trp Val Arg Gln Ala Pro Gly Gln Gly Leu Glu Trp Met
            35                  40                  45

Gly Glu Ile Asp Pro Ser Asp Ser Tyr Thr Asn Tyr Asn Gln Lys Phe
        50                  55                  60

Lys Gly Arg Val Thr Met Thr Gly Asp Thr Ser Thr Asn Thr Val Tyr
65                  70                  75                  80

Met Glu Leu Ser Ser Leu Thr Ser Glu Asp Thr Ala Val Tyr Tyr Cys
                85                  90                  95

Ala Arg Pro Gly Tyr Thr Tyr Gly Gly Met Asp Phe Trp Gly Gln Gly
            100                 105                 110

Thr Leu Val Thr Val Ser Ser
        115
```

<210> SEQ ID NO 149
<211> LENGTH: 5
<212> TYPE: PRT
<213> ORGANISM: Artificial Sequence
<220> FEATURE:
<223> OTHER INFORMATION: Amino acid sequence of the CDR1 of the VH
      domain of the anti-hPD1 antibodies designated #11 and #13

<400> SEQUENCE: 149

Ser Tyr Trp Ile His

<210> SEQ ID NO 150
<211> LENGTH: 17
<212> TYPE: PRT
<213> ORGANISM: Artificial Sequence
<220> FEATURE:
<223> OTHER INFORMATION: Amino acid sequence of the CDR2 of the VH
      domain of the anti-hPD1 antibody designated #11

<400> SEQUENCE: 150

Glu Ile Asp Pro Ser Asp Ser Tyr Thr Asn Tyr Asn Gln Lys Phe Lys
1               5                   10                  15

Gly

<210> SEQ ID NO 151
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #11

<400> SEQUENCE: 151
gatattgtta tgacccaatc cccagattcc ttggctgtct ctttgggtga agagctact       60 attagttgta gatcttccca atctttgttt atatccggta accaaaagaa ctatttggcc    120
tggtatcaac aaaagccagg tcaaccacct aagttattga tctacggtgc ttccaccaga    180
gattctggtg ttccagatcg tttctctggt tctggttctg gtactgattt caccttaact    240
atttcttctt tgcaagccga agacgtcgct gtttactact gtcaaaacaa ccattattac    300
ccttacacct tcggtggtgg taccaaggtc gaaattaag                           339

<210> SEQ ID NO 152
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #11

<400> SEQUENCE: 152

Asp Ile Val Met Thr Gln Ser Pro Asp Ser Leu Ala Val Ser Leu Gly
1               5                   10                  15

Glu Arg Ala Thr Ile Ser Cys Arg Ser Ser Gln Ser Leu Phe Ile Ser
                20                  25                  30

Gly Asn Gln Lys Asn Tyr Leu Ala Trp Tyr Gln Gln Lys Pro Gly Gln
            35                  40                  45

Pro Pro Lys Leu Leu Ile Tyr Gly Ala Ser Thr Arg Asp Ser Gly Val
        50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn His Tyr Tyr Pro Tyr Thr Phe Gly Gly Gly Thr Lys Val Glu Ile
            100                 105                 110

Lys

<210> SEQ ID NO 153
<211> LENGTH: 357
<212> TYPE: DNA

<213> ORGANISM: Artificial Sequence
<220> FEATURE:
<223> OTHER INFORMATION: DNA sequence encoding the VH domain of the
      anti-hPD1 antibody designated #12

<400> SEQUENCE: 153

```
caagttcaat tggttcaatc tggtgctgaa gtcaaaaagc caggtgcctc tgtcaaggtt      60
tcttgtaaag cttccggtta caccttcact aattactgga tgcactgggt tagacaagct     120
ccaggtcaag gtttggaatg gatgggtgag atcgacccat ttgattctta tactaattac     180
aatcaaaagt tcaagggtcg tgttactatg accatagaca catccactaa taccgtttac     240
atggaattat cttccttgag atccgaggac actgctgttt attattgcgc tcgtccaggt     300
tttacctacg gtggtatgga tttttgggt caaggtactt tggttaccgt ttcttct        357
```

<210> SEQ ID NO 154
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #12

<400> SEQUENCE: 154

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asp Pro Phe Asp Ser Tyr Thr Asn Tyr Asn Gln Lys Phe
    50                  55                  60

Lys Gly Arg Val Thr Met Thr Ile Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Pro Gly Phe Thr Tyr Gly Gly Met Asp Phe Trp Gly Gln Gly
            100                 105                 110

Thr Leu Val Thr Val Ser Ser
        115
```

<210> SEQ ID NO 155
<211> LENGTH: 339
<212> TYPE: DNA
<213> ORGANISM: Artificial Sequence
<220> FEATURE:
<223> OTHER INFORMATION: Nucleotide sequence encoding the VL domain of
      the anti-hPD1 antibody designated #12

<400> SEQUENCE: 155

```
gatattgtta tgacccaatc cccagattcc ttggctgtct ctttgggtga agagctact      60 attagttgta gatcttccca atctttgttg atttccggta ccaaaagaa ctatttggcc     120 tggtatcaac aaaagccagg tcaaccacct aagttattga tctacggtgc ttccaccaga    180
gattctggtg ttccagatcg tttctctggt tctggttctg gtactgattt cacccttaact   240 atttcttctt tgcaagccga agacgtcgct gtttactact gtcaaaacaa ccattattac    300
ccttacacct cggtggtgg taccaaggtc gaaattaag                             339
```

<210> SEQ ID NO 156

<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #12

<400> SEQUENCE: 156

Asp Ile Val Met Thr Gln Ser Pro Asp Ser Leu Ala Val Ser Leu Gly
1               5                   10                  15

Glu Arg Ala Thr Ile Ser Cys Arg Ser Ser Gln Ser Leu Leu Ile Ser
            20                  25                  30

Gly Asn Gln Lys Asn Tyr Leu Ala Trp Tyr Gln Gln Lys Pro Gly Gln
        35                  40                  45

Pro Pro Lys Leu Leu Ile Tyr Gly Ala Ser Thr Arg Asp Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Asn
                85                  90                  95

Asn His Tyr Tyr Pro Tyr Thr Phe Gly Gly Gly Thr Lys Val Glu Ile
            100                 105                 110

Lys

<210> SEQ ID NO 157
<211> LENGTH: 357
<212> TYPE: DNA
<213> ORGANISM: Artificial Sequence
<220> FEATURE:
<223> OTHER INFORMATION: Nucleotide sequence encoding the VH domain of
      the anti-hPD1 antibody designated #13

<400> SEQUENCE: 157
caagttcaat tggttcaatc tggtgctgaa gtcaaaaagc caggtgcctc tgtcaaggtt      60
tcttgtaaag cttccggtta caccttcact tcttactgga ttcactgggt tagacaagct    120
ccaggtcaag gtttggaatg gatgggtgag atcgacccat atgattctta tactaattac    180
aatcaaaagt tcaagggtcg tgttactatg accgtagaca aatccactaa taccgtttac    240
atggaattat cttccttaac atccgaggac actgctgttt attattgcgc tcgtccaggt    300
cttacctacg gtggtatgga ttttgggggt caaggtactt tggttaccgt ttcttct       357

<210> SEQ ID NO 158
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #13

<400> SEQUENCE: 158

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Trp Ile His Trp Val Arg Gln Ala Pro Gly Gln Gly Leu Glu Trp Met
        35                  40                  45

Gly Glu Ile Asp Pro Tyr Asp Ser Tyr Thr Asn Tyr Asn Gln Lys Phe
    50                  55                  60

Lys Gly Arg Val Thr Met Thr Val Asp Lys Ser Thr Asn Thr Val Tyr

```
                65                  70                  75                  80
Met Glu Leu Ser Ser Leu Thr Ser Glu Asp Thr Ala Val Tyr Tyr Cys
                        85                  90                  95

Ala Arg Pro Gly Leu Thr Tyr Gly Gly Met Asp Phe Trp Gly Gln Gly
                100                 105                 110

Thr Leu Val Thr Val Ser Ser
        115
```

<210> SEQ ID NO 159
<211> LENGTH: 339
<212> TYPE: DNA
<213> ORGANISM: Artificial Sequence
<220> FEATURE:
<223> OTHER INFORMATION: DNA sequence encoding the VL domain of the anti-hPD1 antibody designated #13

<400> SEQUENCE: 159

```
gatattcaaa tgacccaatc cccatcctct ttgtccgctt ctgttggtga cagagtcacc    60
atcacttgta agtcctctca atccttgttg aattctggta accaaaaaaa ctacttggcc   120
tggtaccaac aaaagccagg taagcctcct aaattgttga tttatggtgc ctccactaga   180
gattctggtg tcccagctaa attctctggt tctggttccg gtactgactt tactttgact   240
atttcttcct tgcaaccaga agacgtcgcc acctattact gtcaaaatga ccactactac   300
ccatacactt ttggtggtgg tactaaggtt gaaattaaa                          339
```

<210> SEQ ID NO 160
<211> LENGTH: 113
<212> TYPE: PRT
<213> ORGANISM: Artificial Sequence
<220> FEATURE:
<223> OTHER INFORMATION: Amino acid sequence of the VL domain of the anti-hPD1 antibody designated #13

<400> SEQUENCE: 160

```
Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Leu Asn Ser
            20                  25                  30

Gly Asn Gln Lys Asn Tyr Leu Ala Trp Tyr Gln Gln Lys Pro Gly Lys
        35                  40                  45

Pro Pro Lys Leu Leu Ile Tyr Gly Ala Ser Thr Arg Asp Ser Gly Val
    50                  55                  60

Pro Ala Lys Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp His Tyr Tyr Pro Tyr Thr Phe Gly Gly Gly Thr Lys Val Glu Ile
                100                 105                 110

Lys
```

<210> SEQ ID NO 161
<211> LENGTH: 357
<212> TYPE: DNA
<213> ORGANISM: Artificial Sequence
<220> FEATURE:
<223> OTHER INFORMATION: Nucleotide sequence encoding the VH domain of the anti-hPD1 antibody designated #14

<400> SEQUENCE: 161

```
caagttcaat tggttcaatc tggtgctgaa gtcaaaaagc aggtgcctc tgtcaaggtt      60 tcttgtaaag cttccggtta caccttcact aattactgga ttcactgggt tagacaagct    120
ccaggtcaag gtttggaatg gatgggtgag atcgacccat atgattctta tactaattac    180
aatcaaaagt tcaagggtcg tgttactatg accggagaca atccactag taccgtttac     240 atggaattat cttccttgac atccgaggac actgctgttt attattgcgc tcgtccaggt    300
tatacctacg gtggtatgga tttttggggt caaggtactt tggttaccgt ttcttct       357
```

<210> SEQ ID NO 162
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #14

<400> SEQUENCE: 162

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Met
        35                  40                  45

Gly Glu Ile Asp Pro Tyr Asp Ser Tyr Thr Asn Tyr Asn Gln Lys Phe
    50                  55                  60

Lys Gly Arg Val Thr Met Thr Gly Asp Lys Ser Thr Ser Thr Val Tyr
65                  70                  75                  80

Met Glu Leu Ser Ser Leu Thr Ser Glu Asp Thr Ala Val Tyr Tyr Cys
                85                  90                  95

Ala Arg Pro Gly Tyr Thr Tyr Gly Gly Met Asp Phe Trp Gly Gln Gly
            100                 105                 110

Thr Leu Val Thr Val Ser Ser
        115

<210> SEQ ID NO 163
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #14

<400> SEQUENCE: 163

```
gatattcaaa tgacccaatc cccatcctct ttgtccgctt ctgttggtga cagagtcacc     60
atcacttgta gtcctctca atccttgttt aattctggta accaaaaaaa ctacttggcc    120
tggtaccaac aaaagccagg taagcttcct aaattgttga tttatggtgc ctccactaga    180
gattctggtg tcccatctag attctctggt tctggttccg gtactgactt tactttgact    240
atttcttcct tgcaaccaga agacgtcgcc acctattact gtcaaaatga ccactactac    300
ccatacactt ttggtggtgg tactaaggtt gaaattaaa                           339
```

<210> SEQ ID NO 164
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #14

<400> SEQUENCE: 164

Asp Ile Gln Met Thr Gln Ser Pro Ser Ser Leu Ser Ala Ser Val Gly
1               5                   10                  15

Asp Arg Val Thr Ile Thr Cys Lys Ser Ser Gln Ser Leu Phe Asn Ser
            20                  25                  30

Gly Asn Gln Lys Asn Tyr Leu Ala Trp Tyr Gln Gln Lys Pro Gly Lys
        35                  40                  45

Leu Pro Lys Leu Leu Ile Tyr Gly Ala Ser Thr Arg Asp Ser Gly Val
50                  55                  60

Pro Ser Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp His Tyr Tyr Pro Tyr Thr Phe Gly Gly Gly Thr Lys Val Glu Ile
            100                 105                 110

Lys

<210> SEQ ID NO 165
<211> LENGTH: 357
<212> TYPE: DNA
<213> ORGANISM: Artificial Sequence
<220> FEATURE:
<223> OTHER INFORMATION: DNA sequence encoding the VH domain of the
      anti-hPD1 antibody designated #15

<400> SEQUENCE: 165
caagttcaat tggttcaatc tggtgctgaa gtcaaaaagc caggtgcctc tgtcaaggtt      60
tcttgtaaag cttccggtta caccttcact aattactgga tgcactgggt tagacaagct     120
ccaggtcaag gtttggaatg gatgggtgag atcgacccat atgattctta tactaattac     180
aatcaaaagt tcaagggtcg tgttactatg accagagaca catccactaa taccgtttac     240
atggaattat cttccttgag atccgaggac actgctgttt attattgcgc tcgtccaggt     300
cttacctacg gtggtatgga ttttgggggt caaggtactt tggttaccgt ttcttct        357

<210> SEQ ID NO 166
<211> LENGTH: 119
<212> TYPE: PRT
<213> ORGANISM: Artificial Sequence
<220> FEATURE:
<223> OTHER INFORMATION: Amino acid sequence of the VH domain of the
      anti-hPD1 antibody designated #15

<400> SEQUENCE: 166

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Met His Trp Val Arg Gln Ala Pro Gly Gln Gly Leu Glu Trp Met
        35                  40                  45

Gly Glu Ile Asp Pro Tyr Asp Ser Tyr Thr Asn Tyr Asn Gln Lys Phe
50                  55                  60

Lys Gly Arg Val Thr Met Thr Arg Asp Thr Ser Thr Asn Thr Val Tyr
65                  70                  75                  80

Met Glu Leu Ser Ser Leu Arg Ser Glu Asp Thr Ala Val Tyr Tyr Cys
                85                  90                  95

Ala Arg Pro Gly Leu Thr Tyr Gly Gly Met Asp Phe Trp Gly Gln Gly
            100                 105                 110

```
Thr Leu Val Thr Val Ser Ser
        115

<210> SEQ ID NO 167
<211> LENGTH: 339
<212> TYPE: DNA
<213> ORGANISM: Artificial Sequence
<220> FEATURE:
<223> OTHER INFORMATION: DNA sequence encoding the VL domain of the
      anti-hPD1 antibody designated #15

<400> SEQUENCE: 167
gatattcaaa tgacccaatc cccatcctct ttgtccgctt ctgttggtga cagagtcacc        60
atcacttgta ggtcctctca atccttgttt aattctggta accaaaaaaa ctacttggcc       120
tggtaccaac aaaagccagg taagcctcct aaattgttga tttatggtgc ctccactaga       180
gaatctggtg tcccatatag attctctggt tctggttccg gtactgactt tacttttgact      240 atttcttcct tgcaaccaga agacgtcgcc acctattact gtcaaaatga ccactactac       300
ccatacactt ttggtggtgg tactaaggtt gaaattaaa                              339

<210> SEQ ID NO 168
<211> LENGTH: 113
<212> TYPE: PRT
<213> ORGANISM: Artificial Sequence
<220> FEATURE:
<223> OTHER INFORMATION: Amino acid sequence of the VL domain of the
      anti-hPD1 antibody designated #15

<400> SEQUENCE: 168

Asp Ile Gln Met Thr Gln Ser Pro Ser Ser Leu Ser Ala Ser Val Gly
1               5                   10                  15

Asp Arg Val Thr Ile Thr Cys Arg Ser Ser Gln Ser Leu Phe Asn Ser
            20                  25                  30

Gly Asn Gln Lys Asn Tyr Leu Ala Trp Tyr Gln Gln Lys Pro Gly Lys
        35                  40                  45

Pro Pro Lys Leu Leu Ile Tyr Gly Ala Ser Thr Arg Glu Ser Gly Val
    50                  55                  60

Pro Tyr Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp His Tyr Tyr Pro Tyr Thr Phe Gly Gly Gly Thr Lys Val Glu Ile
            100                 105                 110

Lys

<210> SEQ ID NO 169
<211> LENGTH: 5
<212> TYPE: PRT
<213> ORGANISM: Artificial Sequence
<220> FEATURE:
<223> OTHER INFORMATION: Consensus amino acid sequence for anti-hPD1 VH
      CDR1s
<220> FEATURE:
<221> NAME/KEY: X
<222> LOCATION: (1)..(1)
<223> OTHER INFORMATION: X is asparagine, glutamine, threonine, alanine,
      or serine
<220> FEATURE:
<221> NAME/KEY: X
<222> LOCATION: (4)..(4)
<223> OTHER INFORMATION: X is methionine, leucine, phenylalanine,
      valine, alanine, or isoleucine
```

```
<400> SEQUENCE: 169

Xaa Tyr Trp Xaa His
1               5

<210> SEQ ID NO 170
<211> LENGTH: 5
<212> TYPE: PRT
<213> ORGANISM: Artificial Sequence
<220> FEATURE:
<223> OTHER INFORMATION: Second consensus amino acid sequence for
      anti-hPD1 VH CDR1s
<220> FEATURE:
<221> NAME/KEY: X
<222> LOCATION: (1)..(1)
<223> OTHER INFORMATION: X is asparagine or serine
<220> FEATURE:
<221> NAME/KEY: X
<222> LOCATION: (4)..(4)
<223> OTHER INFORMATION: X is methionine or isoleucine

<400> SEQUENCE: 170

Xaa Tyr Trp Xaa His
1               5

<210> SEQ ID NO 171
<211> LENGTH: 17
<212> TYPE: PRT
<213> ORGANISM: Artificial Sequence
<220> FEATURE:
<223> OTHER INFORMATION: Consensus amino acid sequence for anti-hPD1 VH
      CDR2s
<220> FEATURE:
<221> NAME/KEY: X
<222> LOCATION: (1)..(17)
<223> OTHER INFORMATION: X is tyrosine, tryptophan, phenylalanine,
      threonine, alanine, or serine

<400> SEQUENCE: 171

Glu Ile Asp Pro Xaa Asp Ser Tyr Thr Asn Tyr Asn Gln Lys Phe Lys
1               5                   10                  15

Gly

<210> SEQ ID NO 172
<211> LENGTH: 17
<212> TYPE: PRT
<213> ORGANISM: Artificial Sequence
<220> FEATURE:
<223> OTHER INFORMATION: Second consensus amino acid sequence for
      anti-hPD1 VH CDR2s
<220> FEATURE:
<221> NAME/KEY: X
<222> LOCATION: (1)..(17)
<223> OTHER INFORMATION: X is tyrosine, phenylalanine, or serine

<400> SEQUENCE: 172

Glu Ile Asp Pro Xaa Asp Ser Tyr Thr Asn Tyr Asn Gln Lys Phe Lys
1               5                   10                  15

Gly

<210> SEQ ID NO 173
<211> LENGTH: 10
<212> TYPE: PRT
<213> ORGANISM: Artificial Sequence
<220> FEATURE:
<223> OTHER INFORMATION: Consensus amino acid sequence for anti-hPD1 VH
      CDR3s
<220> FEATURE:
<221> NAME/KEY: X
```

```
<222> LOCATION: (3)..(3)
<223> OTHER INFORMATION: X is phenylalanine, tyrosine, leucine,
      isoleucine, valine, methionine, alanine, asparagine, or glutamine
<220> FEATURE:
<221> NAME/KEY: X
<222> LOCATION: (10)..(10)
<223> OTHER INFORMATION: X is phenylalanine, or tyrosine

<400> SEQUENCE: 173

Pro Gly Xaa Thr Tyr Gly Gly Met Asp Xaa
1               5                   10

<210> SEQ ID NO 174
<211> LENGTH: 10
<212> TYPE: PRT
<213> ORGANISM: Artificial Sequence
<220> FEATURE:
<223> OTHER INFORMATION: Second consensus amino acid sequence for
      anti-hPD1 VH CDR3s
<220> FEATURE:
<221> NAME/KEY: X
<222> LOCATION: (3)..(3)
<223> OTHER INFORMATION: X is phenylalanine, tyrosine, leucine, or
      asparagine
<220> FEATURE:
<221> NAME/KEY: X
<222> LOCATION: (10)..(10)
<223> OTHER INFORMATION: X is phenylalanine or tyrosine

<400> SEQUENCE: 174

Pro Gly Xaa Thr Tyr Gly Gly Met Asp Xaa
1               5                   10

<210> SEQ ID NO 175
<211> LENGTH: 17
<212> TYPE: PRT
<213> ORGANISM: Artificial Sequence
<220> FEATURE:
<223> OTHER INFORMATION: Consensus amino acid sequence for anti-hPD1 VL
      CDR1s
<220> FEATURE:
<221> NAME/KEY: X
<222> LOCATION: (1)..(1)
<223> OTHER INFORMATION: X is arginine, glutamine, asparagine, or lysine
<220> FEATURE:
<221> NAME/KEY: X
<222> LOCATION: (7)..(7)
<223> OTHER INFORMATION: X is phenylalanine, valine, isoleucine,
      alanine, tyrosine, methionine, or leucine
<220> FEATURE:
<221> NAME/KEY: X
<222> LOCATION: (8)..(8)
<223> OTHER INFORMATION: X is asparagine, glutamine, leucine, valine,
      methionine, alanine, phenylalanine, or isoleucine

<400> SEQUENCE: 175

Xaa Ser Ser Gln Ser Leu Xaa Xaa Ser Gly Asn Gln Lys Asn Tyr Leu
1               5                   10                  15

Ala

<210> SEQ ID NO 176
<211> LENGTH: 17
<212> TYPE: PRT
<213> ORGANISM: Artificial Sequence
<220> FEATURE:
<223> OTHER INFORMATION: Second consensus amino acid sequence for
      anti-hPD1 VL CDR1s
<220> FEATURE:
<221> NAME/KEY: X
<222> LOCATION: (1)..(1)
<223> OTHER INFORMATION: X is arginine or lysine
<220> FEATURE:
```

```
<221> NAME/KEY: X
<222> LOCATION: (7)..(7)
<223> OTHER INFORMATION: X is phenylalanine or leucine
<220> FEATURE:
<221> NAME/KEY: X
<222> LOCATION: (8)..(8)
<223> OTHER INFORMATION: X is asparagine or isoleucine

<400> SEQUENCE: 176

Xaa Ser Ser Gln Ser Leu Xaa Xaa Ser Gly Asn Gln Lys Asn Tyr Leu
1               5                   10                  15

Ala

<210> SEQ ID NO 177
<211> LENGTH: 7
<212> TYPE: PRT
<213> ORGANISM: Artificial Sequence
<220> FEATURE:
<223> OTHER INFORMATION: Consensus amino acid sequence for anti-hPD1 VL
      CDR2s
<220> FEATURE:
<221> NAME/KEY: X
<222> LOCATION: (1)..(7)
<223> OTHER INFORMATION: X is aspartate or glutamate

<400> SEQUENCE: 177

Gly Ala Ser Thr Arg Xaa Ser
1               5

<210> SEQ ID NO 178
<211> LENGTH: 9
<212> TYPE: PRT
<213> ORGANISM: Artificial Sequence
<220> FEATURE:
<223> OTHER INFORMATION: Consensus amino acid sequence for anti-hPD1 VL
      CDR3s
<220> FEATURE:
<221> NAME/KEY: X
<222> LOCATION: (1)..(9)
<223> OTHER INFORMATION: X is aspartate, glutamate, glutamine, or
      asparagine

<400> SEQUENCE: 178

Gln Asn Xaa His Tyr Tyr Pro Tyr Thr
1               5

<210> SEQ ID NO 179
<211> LENGTH: 9
<212> TYPE: PRT
<213> ORGANISM: Artificial Sequence
<220> FEATURE:
<223> OTHER INFORMATION: Second consensus amino acid sequence for
      anti-hPD1 VL CDR3s
<220> FEATURE:
<221> NAME/KEY: X
<222> LOCATION: (1)..(9)
<223> OTHER INFORMATION: X is aspartate or asparagine

<400> SEQUENCE: 179

Gln Asn Xaa His Tyr Tyr Pro Tyr Thr
1               5

<210> SEQ ID NO 180
<211> LENGTH: 119
<212> TYPE: PRT
<213> ORGANISM: Artificial Sequence
<220> FEATURE:
<223> OTHER INFORMATION: Consensus amino acid sequence for anti-hPD1 VH
      domains
<220> FEATURE:
```

```
<221> NAME/KEY: X
<222> LOCATION: (26)..(26)
<223> OTHER INFORMATION: X is glycine, alanine, threonine, or serine
<220> FEATURE:
<221> NAME/KEY: X
<222> LOCATION: (31)..(31)
<223> OTHER INFORMATION: X is asparagine, glutamine, threonine, alanine,
      or serine
<220> FEATURE:
<221> NAME/KEY: X
<222> LOCATION: (34)..(34)
<223> OTHER INFORMATION: X is isoleucine, leucine, valine, alanine,
      phenylalanine, or methionine
<220> FEATURE:
<221> NAME/KEY: X
<222> LOCATION: (54)..(54)
<223> OTHER INFORMATION: X is tyrosine, tryptophan, threonine,
      phenylalanine, leucine, valine, isoleucine, alanine, threonine, or
      serine
<220> FEATURE:
<221> NAME/KEY: X
<222> LOCATION: (72)..(72)
<223> OTHER INFORMATION: X is valine, methionine, leucine,
      phenylalanine, alanine, isoleucine, valine, arginine, lysine,
      glutamine, asparagine, or glycine
<220> FEATURE:
<221> NAME/KEY: X
<222> LOCATION: (74)..(74)
<223> OTHER INFORMATION: X is lysine, arginine, glutamine, asparagine,
      serine, or threonine
<220> FEATURE:
<221> NAME/KEY: X
<222> LOCATION: (77)..(77)
<223> OTHER INFORMATION: X is asparagine, glutamine, threonine, alanine,
      or serine
<220> FEATURE:
<221> NAME/KEY: X
<222> LOCATION: (87)..(87)
<223> OTHER INFORMATION: X is arginine, lysine, glutamine, asparagine,
      serine, threonine, alanine, proline, or glycine
<220> FEATURE:
<221> NAME/KEY: X
<222> LOCATION: (101)..(101)
<223> OTHER INFORMATION: X is phenylalanine, valine, isoleucine,
      alanine, asparagine, glutamine, tyrosine, tryptophan, threonine,
      serine, methionine, or leucine
<220> FEATURE:
<221> NAME/KEY: X
<222> LOCATION: (108)..(108)
<223> OTHER INFORMATION: X is phenylalanine, leucine, valine,
      isoleucine, alanine, tryptophan, threonine, serine, or tyrosine

<400> SEQUENCE: 180

Gln Val Gln Leu Val Gln Ser Gly Ala Glu Val Lys Lys Pro Gly Ala
1               5                   10                  15

Ser Val Lys Val Ser Cys Lys Ala Ser Xaa Tyr Thr Phe Thr Xaa Tyr
            20                  25                  30

Trp Xaa His Trp Val Arg Gln Ala Pro Gly Gln Gly Leu Glu Trp Met
        35                  40                  45

Gly Glu Ile Asp Pro Xaa Asp Ser Tyr Thr Asn Tyr Asn Gln Lys Phe
    50                  55                  60

Lys Gly Arg Val Thr Met Thr Xaa Asp Xaa Ser Thr Xaa Thr Val Tyr
65                  70                  75                  80

Met Glu Leu Ser Ser Leu Xaa Ser Glu Asp Thr Ala Val Tyr Tyr Cys
                85                  90                  95

Ala Arg Pro Gly Xaa Thr Tyr Gly Gly Met Asp Xaa Trp Gly Gln Gly
            100                 105                 110

Thr Leu Val Thr Val Ser Ser
        115
```

```
<210> SEQ ID NO 181
<211> LENGTH: 119
<212> TYPE: PRT
<213> ORGANISM: Artificial Sequence
<220> FEATURE:
<223> OTHER INFORMATION: Second consensus amino acid sequence for
      anti-hPD1 VH domains
<220> FEATURE:
<221> NAME/KEY: X
<222> LOCATION: (26)..(26)
<223> OTHER INFORMATION: X is glycine or serine
<220> FEATURE:
<221> NAME/KEY: X
<222> LOCATION: (31)..(31)
<223> OTHER INFORMATION: X is asparagine or serine
<220> FEATURE:
<221> NAME/KEY: X
<222> LOCATION: (34)..(34)
<223> OTHER INFORMATION: X is isoleucine or methionine
<220> FEATURE:
<221> NAME/KEY: X
<222> LOCATION: (54)..(54)
<223> OTHER INFORMATION: X is tyrosine, phenylalanine, or serine
<220> FEATURE:
<221> NAME/KEY: X
<222> LOCATION: (72)..(72)
<223> OTHER INFORMATION: X is valine, isoleucine, arginine, or glycine
<220> FEATURE:
<221> NAME/KEY: X
<222> LOCATION: (74)..(74)
<223> OTHER INFORMATION: X is lysine or threonine
<220> FEATURE:
<221> NAME/KEY: X
<222> LOCATION: (77)..(77)
<223> OTHER INFORMATION: X is asparagine or serine
<220> FEATURE:
<221> NAME/KEY: X
<222> LOCATION: (87)..(87)
<223> OTHER INFORMATION: X is arginine, threonine, or glycine
<220> FEATURE:
<221> NAME/KEY: X
<222> LOCATION: (101)..(101)
<223> OTHER INFORMATION: X is phenylalanine, asparagine, tyrosine, or
      leucine
<220> FEATURE:
<221> NAME/KEY: X
<222> LOCATION: (108)..(108)
<223> OTHER INFORMATION: X is phenylalanine or tyrosine

<400> SEQUENCE: 181

Gln Val Gln Leu Val Gln Ser Gly Ala Glu Val Lys Lys Pro Gly Ala
1               5                   10                  15

Ser Val Lys Val Ser Cys Lys Ala Ser Xaa Tyr Thr Phe Thr Xaa Tyr
                20                  25                  30

Trp Xaa His Trp Val Arg Gln Ala Pro Gly Gln Gly Leu Glu Trp Met
            35                  40                  45

Gly Glu Ile Asp Pro Xaa Asp Ser Tyr Thr Asn Tyr Asn Gln Lys Phe
        50                  55                  60

Lys Gly Arg Val Thr Met Thr Xaa Asp Xaa Ser Thr Xaa Thr Val Tyr
65                  70                  75                  80

Met Glu Leu Ser Ser Leu Xaa Ser Glu Asp Thr Ala Val Tyr Tyr Cys
                85                  90                  95

Ala Arg Pro Gly Xaa Thr Tyr Gly Gly Met Asp Xaa Trp Gly Gln Gly
                100                 105                 110

Thr Leu Val Thr Val Ser Ser
            115

<210> SEQ ID NO 182
<211> LENGTH: 113
<212> TYPE: PRT
```

```
<213> ORGANISM: Artificial Sequence
<220> FEATURE:
<223> OTHER INFORMATION: Consensus amino acid sequence for anti-hPD1 VL
      domains
<220> FEATURE:
<221> NAME/KEY: X
<222> LOCATION: (3)..(3)
<223> OTHER INFORMATION: X is valine, isoleucine, methionine, leucine,
      phenylalanine, alanine, asparagine, or glutamine
<220> FEATURE:
<221> NAME/KEY: X
<222> LOCATION: (9)..(9)
<223> OTHER INFORMATION: X is serine, threonine, alanine, glutamate, or
      aspartate
<220> FEATURE:
<221> NAME/KEY: X
<222> LOCATION: (12)..(12)
<223> OTHER INFORMATION: X is serine, threonine, valine, leucine,
      isoleucine, or alanine
<220> FEATURE:
<221> NAME/KEY: X
<222> LOCATION: (13)..(13)
<223> OTHER INFORMATION: X is alanine, leucine, isoleucine, methionine,
      phenylalanine, or valine
<220> FEATURE:
<221> NAME/KEY: X
<222> LOCATION: (15)..(15)
<223> OTHER INFORMATION: X is valine, isoleucine, methionine,
      phenylalanine, alanine, or leucine
<220> FEATURE:
<221> NAME/KEY: X
<222> LOCATION: (17)..(17)
<223> OTHER INFORMATION: X is aspartate or glutamate
<220> FEATURE:
<221> NAME/KEY: X
<222> LOCATION: (19)..(19)
<223> OTHER INFORMATION: X is valine, isoleucine, methionine, leucine,
      phenylalanine or alanine
<220> FEATURE:
<221> NAME/KEY: X
<222> LOCATION: (22)..(22)
<223> OTHER INFORMATION: X is threonine, asparagine, glutamine, alanine,
      or serine
<220> FEATURE:
<221> NAME/KEY: X
<222> LOCATION: (24)..(24)
<223> OTHER INFORMATION: X is lysine, glutamine, asparagine, or arginine
<220> FEATURE:
<221> NAME/KEY: X
<222> LOCATION: (30)..(30)
<223> OTHER INFORMATION: X is phenylalanine, valine, isoleucine,
      alanine, tyrosine, methionine, or leucine
<220> FEATURE:
<221> NAME/KEY: X
<222> LOCATION: (31)..(31)
<223> OTHER INFORMATION: X is asparagine, glutamine, leucine, valine,
      methionine, alanine, phenylalanine, or isoleucine
<220> FEATURE:
<221> NAME/KEY: X
<222> LOCATION: (48)..(48)
<223> OTHER INFORMATION: X is lysine, arginine, asparagine, or glutamine
<220> FEATURE:
<221> NAME/KEY: X
<222> LOCATION: (49)..(49)
<223> OTHER INFORMATION: X is valine, isoleucine, methionine,
      phenylalanine, alanine, proline, or leucine
<220> FEATURE:
<221> NAME/KEY: X
<222> LOCATION: (61)..(61)
<223> OTHER INFORMATION: X is aspartate or glutamate
<220> FEATURE:
<221> NAME/KEY: X
<222> LOCATION: (66)..(66)
<223> OTHER INFORMATION: X is tyrosine, tryptophan, phenylalanine,
      threonine, alanine, valine, leucine, isoleucine, serine,
      glutamate, or aspartate
<220> FEATURE:
<221> NAME/KEY: X
<222> LOCATION: (67)..(67)
```

```
<223> OTHER INFORMATION: X is arginine, lysine, asparagine, or
      glutatmine
<220> FEATURE:
<221> NAME/KEY: X
<222> LOCATION: (86)..(86)
<223> OTHER INFORMATION: X is proline, valine, leucine, isoleucine, or
      alanine
<220> FEATURE:
<221> NAME/KEY: X
<222> LOCATION: (91)..(91)
<223> OTHER INFORMATION: X is threonine, serine, isoleucine, methionine,
      leucine, phenylalanine, alanine, or valine
<220> FEATURE:
<221> NAME/KEY: X
<222> LOCATION: (97)..(97)
<223> OTHER INFORMATION: X is aspartate, glutamate, glutamine, or
      asparagine

<400> SEQUENCE: 182

Asp Ile Xaa Met Thr Gln Ser Pro Xaa Ser Leu Xaa Xaa Ser Xaa Gly
1               5                   10                  15

Xaa Arg Xaa Thr Ile Xaa Cys Xaa Ser Ser Gln Ser Leu Xaa Xaa Ser
            20                  25                  30

Gly Asn Gln Lys Asn Tyr Leu Ala Trp Tyr Gln Gln Lys Pro Gly Xaa
        35                  40                  45

Xaa Pro Lys Leu Leu Ile Tyr Gly Ala Ser Thr Arg Xaa Ser Gly Val
    50                  55                  60

Pro Xaa Xaa Phe Ser Gly Ser Gly Ser Gly Thr Asp Phe Thr Leu Thr
65                  70                  75                  80

Ile Ser Ser Leu Gln Xaa Glu Asp Val Ala Xaa Tyr Tyr Cys Gln Asn
                85                  90                  95

Xaa His Tyr Tyr Pro Tyr Thr Phe Gly Gly Gly Thr Lys Val Glu Ile
            100                 105                 110

Lys

<210> SEQ ID NO 183
<211> LENGTH: 113
<212> TYPE: PRT
<213> ORGANISM: Artificial Sequence
<220> FEATURE:
<223> OTHER INFORMATION: Second consensus amino acid sequence for
      anti-hPD1 VL domains
<220> FEATURE:
<221> NAME/KEY: X
<222> LOCATION: (3)..(3)
<223> OTHER INFORMATION: X is valine or glutamine
<220> FEATURE:
<221> NAME/KEY: X
<222> LOCATION: (9)..(9)
<223> OTHER INFORMATION: X is serine or aspartate
<220> FEATURE:
<221> NAME/KEY: X
<222> LOCATION: (12)..(12)
<223> OTHER INFORMATION: X is serine or alanine
<220> FEATURE:
<221> NAME/KEY: X
<222> LOCATION: (13)..(13)
<223> OTHER INFORMATION: X is alanine or valine
<220> FEATURE:
<221> NAME/KEY: X
<222> LOCATION: (15)..(15)
<223> OTHER INFORMATION: X is valine or leucine
<220> FEATURE:
<221> NAME/KEY: X
<222> LOCATION: (17)..(17)
<223> OTHER INFORMATION: X is aspartate or glutamate
<220> FEATURE:
<221> NAME/KEY: X
<222> LOCATION: (19)..(19)
<223> OTHER INFORMATION: X is valine or alanine
```

```
<220> FEATURE:
<221> NAME/KEY: X
<222> LOCATION: (22)..(22)
<223> OTHER INFORMATION: X is threonine, asparagine, or serine
<220> FEATURE:
<221> NAME/KEY: X
<222> LOCATION: (24)..(24)
<223> OTHER INFORMATION: X is lysine or arginine
<220> FEATURE:
<221> NAME/KEY: X
<222> LOCATION: (30)..(30)
<223> OTHER INFORMATION: X is phenylalanine or leucine
<220> FEATURE:
<221> NAME/KEY: X
<222> LOCATION: (31)..(31)
<223> OTHER INFORMATION: X is asparagine or isoleucine
<220> FEATURE:
<221> NAME/KEY: X
<222> LOCATION: (48)..(48)
<223> OTHER INFORMATION: X is lysine or glutamine
<220> FEATURE:
<221> NAME/KEY: X
<222> LOCATION: (49)..(49)
<223> OTHER INFORMATION: X is valine, proline, or leucine
<220> FEATURE:
<221> NAME/KEY: X
<222> LOCATION: (61)..(61)
<223> OTHER INFORMATION: X is aspartate or glutamate
<220> FEATURE:
<221> NAME/KEY: X
<222> LOCATION: (66)..(66)
<223> OTHER INFORMATION: X is tyrosine, alanine, serine, or aspartate
<220> FEATURE:
<221> NAME/KEY: X
<222> LOCATION: (67)..(67)
<223> OTHER INFORMATION: X is arginine or lysine
<220> FEATURE:
<221> NAME/KEY: X
<222> LOCATION: (86)..(86)
<223> OTHER INFORMATION: X is proline or alanine
<220> FEATURE:
<221> NAME/KEY: X
<222> LOCATION: (91)..(91)
<223> OTHER INFORMATION: X is threonine or valine
<220> FEATURE:
<221> NAME/KEY: X
<222> LOCATION: (97)..(97)
<223> OTHER INFORMATION: X is aspartate or asparagine

<400> SEQUENCE: 183

Asp Ile Xaa Met Thr Gln Ser Pro Xaa Ser Leu Xaa Xaa Ser Xaa Gly
1               5                   10                  15

Xaa Arg Xaa Thr Ile Xaa Cys Xaa Ser Ser Gln Ser Leu Xaa Xaa Ser
            20                  25                  30

Gly Asn Gln Lys Asn Tyr Leu Ala Trp Tyr Gln Gln Lys Pro Gly Xaa
        35                  40                  45

Xaa Pro Lys Leu Leu Ile Tyr Gly Ala Ser Thr Arg Xaa Ser Gly Val
    50                  55                  60

Pro Xaa Xaa Phe Ser Gly Ser Gly Ser Gly Thr Asp Phe Thr Leu Thr
65                  70                  75                  80

Ile Ser Ser Leu Gln Xaa Glu Asp Val Ala Xaa Tyr Tyr Cys Gln Asn
                85                  90                  95

Xaa His Tyr Tyr Pro Tyr Thr Phe Gly Gly Gly Thr Lys Val Glu Ile
            100                 105                 110

Lys

<210> SEQ ID NO 184
<211> LENGTH: 1338
<212> TYPE: DNA
<213> ORGANISM: Artificial Sequence
```

<220> FEATURE:
<223> OTHER INFORMATION: DNA sequence encoding the human IgG4 HC of an altered anti-PD1 antibody #1 with the alterations G44D, Q105R, K147R, H168R, and V173C

<400> SEQUENCE: 184

```
caggtgcagc tggtgcagtc tggcgccgaa gtgaagaaac tggcgcctc cgtgaaggtg      60
tcctgcaagg cttccggcta cacctttacc aactactgga tccactgggt gcgacaggcc    120
ccaggccagg acctggaatg gatgggcgag atcgaccct acgactccta caccaactac    180
aaccagaaat tcaagggccg cgtgaccatg accgtggaca gtccacctc accgtgtac     240
atggaactgt cctccctgcg gagcgaggac accgccgtgt actactgtgc cagacccggc    300
ttcacctacg gcggcatgga tttctggggc agaggcaccc tcgtgaccgt gtcctctgct    360
tccaccaagg gcccctccgt gtttcctctg gccccttgct ccagatccac ctccgagtct    420
accgccgctc tgggatgtct cgtgcgggac tacttccccg agcccgtgac agtgtcttgg    480
aactctggcg ccctgacctc tggcgtgcg acctttcctg cttgcctgca gtctagcggc    540
ctgtactccc tgtcctccgt cgtgactgtg ccctccagct ctctgggcac caagacctac    600
acctgtaacg tggaccacaa gcctccaac accaaggtgg acaagcgggt ggaatctaag    660
tacggccctc cctgccctcc ttgcccagcc cctgagtttc tgggcggacc cagcgtgttc    720
ctgttccccc caaagcccaa ggacaccctg atgatctccc ggaccccga agtgacctgc    780
gtggtggtgg atgtgtccca ggaagatccc gaggtgcagt tcaattggta cgtggacggc    840
gtggaagtgc acaacgccaa gaccaagcct agagaggaac agttcaactc cacctaccgg    900
gtggtgtccg tgctgaccgt gctgcaccag gattggctga acggcaaaga gtacaagtgc    960
aaggtgtcca acaagggcct gcccagctcc atcgaaaaga ccatctccaa ggccaagggc   1020
cagccccggg aaccccaggt gtacacactg cctccaagcc aggaagagat gaccaagaac   1080
caggtgtccc tgacctgtct cgtgaaaggc ttctacccct ccgacatcgc cgtggaatgg   1140
gagtccaacg gccagcctga gaacaactac aagaccaccc cccctgtgct ggactccgac   1200
ggctccttct cctgtactc tcggctgaca gtggataagt cccggtggca ggaaggcaac   1260
gtgttctcct gctccgtgat gcacgaggcc ctgcacaacc actacaccca gaagtccctg   1320
tccctgtctc tgggaaag                                                1338
```

<210> SEQ ID NO 185
<211> LENGTH: 446
<212> TYPE: PRT
<213> ORGANISM: Artificial Sequence
<220> FEATURE:
<223> OTHER INFORMATION: Amino acid sequence of the human IgG4 HC of an altered anti-PD1 antibody #1 with the alterations G44D, Q105R, K147R, H168R, and V173C

<400> SEQUENCE: 185

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Asp Leu Glu Trp Met
        35                  40                  45

Gly Glu Ile Asp Pro Tyr Asp Ser Tyr Thr Asn Tyr Asn Gln Lys Phe
    50                  55                  60

Lys Gly Arg Val Thr Met Thr Val Asp Lys Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Pro Gly Phe Thr Tyr Gly Gly Met Asp Phe Trp Gly Arg Gly
                100                 105                 110

Thr Leu Val Thr Val Ser Ser Ala Ser Thr Lys Gly Pro Ser Val Phe
            115                 120                 125

Pro Leu Ala Pro Cys Ser Arg Ser Thr Ser Glu Ser Thr Ala Ala Leu
130             135                 140

Gly Cys Leu Val Arg Asp Tyr Phe Pro Glu Pro Val Thr Val Ser Trp
145             150                 155                 160

Asn Ser Gly Ala Leu Thr Ser Gly Val Arg Thr Phe Pro Ala Cys Leu
                165                 170                 175

Gln Ser Ser Gly Leu Tyr Ser Leu Ser Ser Val Val Thr Val Pro Ser
                180                 185                 190

Ser Ser Leu Gly Thr Lys Thr Tyr Thr Cys Asn Val Asp His Lys Pro
            195                 200                 205

Ser Asn Thr Lys Val Asp Lys Arg Val Glu Ser Lys Tyr Gly Pro Pro
210                 215                 220

Cys Pro Pro Cys Pro Ala Pro Glu Phe Leu Gly Gly Pro Ser Val Phe
225             230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser Gln Glu Asp Pro Glu Val
                260                 265                 270

Gln Phe Asn Trp Tyr Val Asp Gly Val Glu Val His Asn Ala Lys Thr
            275                 280                 285

Lys Pro Arg Glu Glu Gln Phe Asn Ser Thr Tyr Arg Val Val Ser Val
290                 295                 300

Leu Thr Val Leu His Gln Asp Trp Leu Asn Gly Lys Glu Tyr Lys Cys
305                 310                 315                 320

Lys Val Ser Asn Lys Gly Leu Pro Ser Ser Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Gln Glu Glu Met Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Arg Leu Thr Val Asp Lys Ser Arg Trp
                405                 410                 415

Gln Glu Gly Asn Val Phe Ser Cys Ser Val Met His Glu Ala Leu His
                420                 425                 430

Asn His Tyr Thr Gln Lys Ser Leu Ser Leu Ser Leu Gly Lys
            435                 440                 445

<210> SEQ ID NO 186
<211> LENGTH: 660
<212> TYPE: DNA
<213> ORGANISM: Artificial Sequence
<220> FEATURE:
<223> OTHER INFORMATION: DNA sequence encoding the human LC of an
      altered anti-PD1 antibody #1 with the alterations V43D, G100R,
      S131D, S162C, and S174D
```

<400> SEQUENCE: 186

```
gacatccaga tgacccagtc cccctccagc ctgtctgcct ctgtgggcga cagagtgacc    60
atcacatgca agtcctccca gtccctgttc aactccggca accagaagaa ctacctggcc   120
tggtatcagc agaagcccgg caaggacccc aagctgctga tctacggcgc ctccaccaga   180
gactctggcg tgccctacag attctccggc tctggctctg gcaccgactt taccctgacc   240
atcagctccc tgcagcccga ggatgtggcc acctactact gccagaacga ccactactac   300
ccctacacct tcggcagagg caccaaggtg gaaatcaagc ggaccgtggc cgctccctcc   360
gtgttcatct tcccaccttc cgacgagcag ctgaagtccg gcaccgctga tgtcgtgtgc   420
ctgctgaaca acttctaccc ccgcgaggcc aaggtgcagt ggaaggtgga caacgccctg   480
cagtccggca actcccagga atgcgtgacc gagcaggact ccaaggacag cacctacgac   540
ctgtcctcca ccctgaccct gtccaaggcc gactacgaga agcacaaggt gtacgcctgc   600
gaagtgaccc accagggcct gtctagcccc gtgaccaagt ctttcaaccg gggcgagtgc   660
```

<210> SEQ ID NO 187
<211> LENGTH: 220
<212> TYPE: PRT
<213> ORGANISM: Artificial Sequence
<220> FEATURE:
<223> OTHER INFORMATION: Amino acid sequence of the human LC of an altered anti-PD1 antibody #1 with the alterations V43D, G100R, S131D, S162C, and S174D

<400> SEQUENCE: 187

```
Asp Ile Gln Met Thr Gln Ser Pro Ser Ser Leu Ser Ala Ser Val Gly
1               5                  10                  15

Asp Arg Val Thr Ile Thr Cys Lys Ser Ser Gln Ser Leu Phe Asn Ser
            20                  25                  30

Gly Asn Gln Lys Asn Tyr Leu Ala Trp Tyr Gln Gln Lys Pro Gly Lys
        35                  40                  45

Asp Pro Lys Leu Leu Ile Tyr Gly Ala Ser Thr Arg Asp Ser Gly Val
    50                  55                  60

Pro Tyr Arg Phe Ser Gly Ser Gly Ser Gly Thr Asp Phe Thr Leu Thr
65                  70                  75                  80

Ile Ser Ser Leu Gln Pro Glu Asp Val Ala Thr Tyr Tyr Cys Gln Asn
                85                  90                  95

Asp His Tyr Tyr Pro Tyr Thr Phe Gly Arg Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Asp Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Cys Val Thr Glu Gln Asp Ser Lys Asp
                165                 170                 175

Ser Thr Tyr Asp Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

<210> SEQ ID NO 188
<211> LENGTH: 1344
<212> TYPE: DNA
<213> ORGANISM: Artificial Sequence
<220> FEATURE:
<223> OTHER INFORMATION: DNA sequence encoding the human IgG1 HC of an altered anti-CTLA4 antibody 10D4 with the alterations G44R, Q105D, K147D, H168D, V173C, R255K, D399R, and K409E

<400> SEQUENCE: 188

```
caagttcagc ttgttgagtc tgggggtgga gtagttgaac ctggtagaag cctccgattg      60
agttgcactg ctagtggatt cactttcagt tcatacggga tgcactgggt acgccaagca     120
ccaggcaagc gtctcgaatg ggtggccgtt atctggtatc accctccaa aaaagactac      180
gccgacagcg ccaagggacg gtttaccatt agccgagata cagtaaaaa cactctctat      240
cttcaaatga acagccttcg cgctgaagac acagccgtct actattgtgc tagagctggc     300
cttcttggct acttcgacta ctggggagat ggcactctcg tcacagtgag ttctgctagc     360
accaagggcc catcggtctt ccccctggca cctcctcca agagcacctc tgggggcaca     420
gcggccctgg gctgcctggt cgacgactac ttccccgaac cggtgacggt gtcgtggaac     480
tcaggcgccc tgaccagcgg cgtggacacc ttccggctt gcctacagtc ctcaggactc     540
tactccctca gcagcgtggt gaccgtgccc tccagcagct gggcaccca gacctacatc     600
tgcaacgtga atcacaagcc cagcaacacc aaggtggaca gaaagttga gcccaaatct     660
tgtgacaaaa ctcacacatg cccaccgtgc ccagcacctg aactcctggg gggaccgtca     720
gtcttcctct tccccccaaa acccaaggac accctcatga tctccaagac ccctgaggtc     780
acatgcgtgg tggtggacgt gagccacgaa gaccctgagg tcaagttcaa ctggtacgtg     840
gacggcgtgg aggtgcataa tgccaagaca agccgcgggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaaccat ctccaaagcc    1020
aaagggcagc ccgagaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctgcgg    1200
tccgacggct ccttcttcct ctatagcgag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                           1344
```

<210> SEQ ID NO 189
<211> LENGTH: 448
<212> TYPE: PRT
<213> ORGANISM: Artificial Sequence
<220> FEATURE:
<223> OTHER INFORMATION: Amino acid sequence of the human IgG1 HC of an altered anti-CTLA4 antibody 10D4 with the alterations G44R, Q105D, K147D, H168D, V173C, R255K, D399R, and K409E

<400> SEQUENCE: 189

```
Gln Val Gln Leu Val Glu Ser Gly Gly Val Val Glu Pro Gly Arg
1               5                  10                  15

Ser Leu Arg Leu Ser Cys Thr Ala Ser Gly Phe Thr Phe Ser Ser Tyr
            20                  25                  30

Gly Met His Trp Val Arg Gln Ala Pro Gly Lys Arg Leu Glu Trp Val
        35                  40                  45
```

Ala Val Ile Trp Tyr His Pro Ser Lys Lys Asp Tyr Ala Asp Ser Ala
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Gly Leu Leu Gly Tyr Phe Asp Tyr Trp Gly Asp Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Asp Asp Tyr Phe Pro Glu Pro Val Thr Val Ser Trp Asn
145                 150                 155                 160

Ser Gly Ala Leu Thr Ser Gly Val Asp Thr Phe Pro Ala Cys Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Lys
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Arg
385                 390                 395                 400

Ser Asp Gly Ser Phe Phe Leu Tyr Ser Glu Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 190
<211> LENGTH: 642
<212> TYPE: DNA

<213> ORGANISM: Artificial Sequence
<220> FEATURE:
<223> OTHER INFORMATION: DNA sequence encoding the human LC of an altered anti-CTLA4 antibody 10D4 with the alterations V43R, G100D, S131R, Q160C, and S174R

<400> SEQUENCE: 190
gaaatcgtct tgacccaatc acctgggacc ctctccctgt cacctggaga gagagcaact 60
ttgagttgta gagctagtca gagtgtaacc tcatacctgg cttggtatca gcagaagcct 120
gggcaaaggc cacgccctct catatatggt gtaagtagtc gtgctactgg catccccgac 180
cgattcagcg gctccggttc tggtacagat ttcaccctta caatcagtag gctggaacca 240
gaggactttg cagtctacta ttgccaacag tatggtcgtt acccttttcac attcggggat 300 gggacaaagg tggatattaa acgtacggtg gctgcaccat ctgtcttcat cttcccgcca 360
tctgatgagc agttgaaatc tggaactgcc cgcgttgtgt gcctgctgaa taacttctat 420
cccagagagg ccaaagtaca gtggaaggtg gataacgccc tccaatcggg taactcctgc 480
gagagtgtca cagagcagga cagcaaggac agcacctaca ggctcagcag caccctgacg 540
ctgagcaaag cagactacga gaaacacaaa gtctacgcct gcgaagtcac ccatcagggc 600
ctgagctcgc ccgtcacaaa gagcttcaac aggggagagt gt 642

<210> SEQ ID NO 191
<211> LENGTH: 214
<212> TYPE: PRT
<213> ORGANISM: Artificial Sequence
<220> FEATURE:
<223> OTHER INFORMATION: Amino acid sequence of the human LC of an altered anti-CTLA4 antibody 10D4 with the alterations V43R, G100D, S131R, Q160C, and S174R

<400> SEQUENCE: 191

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Thr Ser Tyr
            20                  25                  30

Leu Ala Trp Tyr Gln Gln Lys Pro Gly Gln Arg Pro Arg Pro Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Arg Tyr Pro Phe
                85                  90                  95

Thr Phe Gly Asp Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Arg Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Cys
145                 150                 155                 160

Glu Ser Val Thr Glu Gln Asp Ser Lys Asp Ser Thr Tyr Arg Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser

```
                    195                 200                 205
Phe Asn Arg Gly Glu Cys
    210

<210> SEQ ID NO 192
<211> LENGTH: 1344
<212> TYPE: DNA
<213> ORGANISM: Artificial Sequence
<220> FEATURE:
<223> OTHER INFORMATION: DNA sequence encoding the human IgG1 HC of an
      altered anti-CTLA4 antibody 11F4 with the alterations G44R, Q105D,
      K147D, H168D, V173C, R255K, D399R, and K409E

<400> SEQUENCE: 192
caggtgcagc tggtggagtc cggcggtggt gtggtggagc ccggacgtag tctgcgtttg      60
tcctgcgctg cttccgggtt caccttctcc tcttatggaa tgcattgggt gcgtcaggcc     120
ccgggaaagc gcctggagtg ggtggccgtg atttggtaca agcccagcga aaggactat      180 gctgacagcg ccaaagggag attcaccatc agccgcgaca acagcaagaa cacactctac     240
ctgcagatga acagtctccg cgctgaggac acagcagtct actactgtgc acgcggcggc     300
ctcctgggct atttcgacta ctggggcgac ggcaccctgg tgaccgtgag ctctgctagc     360
accaagggcc catcggtctt ccccctggca ccctcctcca agagcacctc tgggggcaca     420
gcggccctgg gctgcctggt cgacgactac ttccccgaac cggtgacggt gtcgtggaac     480
tcaggcgccc tgaccagcgg cgtggacacc ttccggctt gcctacagtc ctcaggactc     540
tactccctca gcagcgtggt gaccgtgccc tccagcagct gggcacccca gacctacatc     600
tgcaacgtga atcacaagcc cagcaacacc aaggtggaca gaaagttga gcccaaatct     660 tgtgacaaaa ctcacacatg cccaccgtgc ccagcacctg aactcctggg gggaccgtca     720
gtcttcctct tccccccaaa acccaaggac accctcatga tctccaagac ccctgaggtc     780
acatgcgtgg tggtggacgt gagccacgaa gaccctgagg tcaagttcaa ctggtacgtg     840
gacggcgtgg aggtgcataa tgccaagaca agccgcggg aggagcagta caacagcacg     900
taccgtgtgg tcagcgtcct caccgtcctg caccaggact ggctgaatgg caaggagtac     960
aagtgcaagg tctccaacaa agccctccca gcccccatcg agaaaccat ctccaaagcc    1020 aaagggcagc cccgagaacc acaggtgtac accctgcccc catcccggga ggagatgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctgcgg    1200
tccgacggct ccttcttcct ctatagcgag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                           1344

<210> SEQ ID NO 193
<211> LENGTH: 447
<212> TYPE: PRT
<213> ORGANISM: Artificial Sequence
<220> FEATURE:
<223> OTHER INFORMATION: Amino acid sequence of the human IgG1 HC of an
      altered anti-CTLA4 antibody 11F4 with the alterations G44R,
      Q105D, K147D, H168D, V173C, R255K, D399R, and K409E

<400> SEQUENCE: 193

Gln Val Gln Leu Val Glu Ser Gly Gly Gly Val Val Glu Pro Gly Arg
1               5                   10                  15

Ser Leu Arg Leu Ser Cys Ala Ala Ser Gly Phe Thr Phe Ser Ser Tyr
```

```
                20                  25                  30
Gly Met His Trp Val Arg Gln Ala Pro Gly Lys Arg Leu Glu Trp Val
            35                  40                  45
Ala Val Ile Trp Tyr Lys Pro Ser Glu Lys Asp Tyr Ala Asp Ser Ala
        50                  55                  60
Lys Gly Arg Phe Thr Ile Ser Arg Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Arg Gly Gly Leu Leu Gly Tyr Phe Asp Tyr Trp Gly Asp Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
        130                 135                 140
Cys Leu Val Asp Asp Tyr Phe Pro Glu Pro Val Thr Val Ser Trp Asn
145                 150                 155                 160
Ser Gly Ala Leu Thr Ser Gly Val Asp Thr Phe Pro Ala Cys Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
        210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Lys
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
        290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
        370                 375                 380
Asn Gly Gln Pro Glu Asn Asn Tyr Lys Thr Thr Pro Pro Val Leu Arg
385                 390                 395                 400
Ser Asp Gly Ser Phe Phe Leu Tyr Ser Glu Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Lys
        435                 440                 445
```

<210> SEQ ID NO 194
<211> LENGTH: 642
<212> TYPE: DNA
<213> ORGANISM: Artificial Sequence
<220> FEATURE:
<223> OTHER INFORMATION: DNA sequence encoding the human LC of an
altered anti-CTLA4 antibody 11F4 with the alterations V43R,
G100D, S131R, Q160C, and S174R

<400> SEQUENCE: 194

```
gaaatcgtct tgacccaatc acctgggacc ctctccctgt cacctggaga gagagcaact    60
ttgagttgta gagctagtca gagtatcaac tcatacctgg cttggtatca gcagaagcct   120
gggcaaaggc cacgccctct catatatggt gtaagtagtc gtgctactgg catccccgac   180
cgattcagcg gctccggttc tggtacagat ttcaccctta caatcagtag gctggaacca   240
gaggactttg cagtctacta ttgccaacag tatggtcgtt acccttttcac attcggggat   300
gggacaaagg tggatattaa acgtacggtg gctgcaccat ctgtcttcat cttcccgcca   360
tctgatgagc agttgaaatc tggaactgcc cgcgttgtgt gcctgctgaa taacttctat   420
cccagagagg ccaaagtaca gtggaaggtg gataacgccc tccaatcggg taactcctgc   480
gagagtgtca cagagcagga cagcaaggac agcacctaca ggctcagcag cacccctgacg   540
ctgagcaaag cagactacga gaaacacaaa gtctacgcct gcgaagtcac ccatcagggc   600
ctgagctcgc ccgtcacaaa gagcttcaac aggggagagt gt                      642
```

<210> SEQ ID NO 195
<211> LENGTH: 214
<212> TYPE: PRT
<213> ORGANISM: Artificial Sequence
<220> FEATURE:
<223> OTHER INFORMATION: Amino acid sequence of the human LC of an
altered anti-CTLA4 antibody 11F4 with the alterations V43R, G100D,
S131R, Q160C, and S174R

<400> SEQUENCE: 195

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Ile Asn Ser Tyr
            20                  25                  30

Leu Ala Trp Tyr Gln Gln Lys Pro Gly Gln Arg Pro Arg Pro Leu Ile
        35                  40                  45

Tyr Gly Val Ser Ser Arg Ala Thr Gly Ile Pro Asp Arg Phe Ser Gly
    50                  55                  60

Ser Gly Ser Gly Thr Asp Phe Thr Leu Thr Ile Ser Arg Leu Glu Pro
65                  70                  75                  80

Glu Asp Phe Ala Val Tyr Tyr Cys Gln Gln Tyr Gly Arg Tyr Pro Phe
                85                  90                  95

Thr Phe Gly Asp Gly Thr Lys Val Asp Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Arg Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Cys
145                 150                 155                 160

Glu Ser Val Thr Glu Gln Asp Ser Lys Asp Ser Thr Tyr Arg Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 196
<211> LENGTH: 132
<212> TYPE: PRT
<213> ORGANISM: Artificial Sequence
<220> FEATURE:
<223> OTHER INFORMATION: Consensus amino acid sequence for a human VH
<220> FEATURE:
<221> NAME/KEY: X
<222> LOCATION: (1)..(16)
<223> OTHER INFORMATION: X is any amino acid ordinarily found in living
      organisms
<220> FEATURE:
<221> NAME/KEY: X
<222> LOCATION: (17)..(17)
<223> OTHER INFORMATION: X is serine or threonine
<220> FEATURE:
<221> NAME/KEY: X
<222> LOCATION: (18)..(18)
<223> OTHER INFORMATION: X is valine or leucine
<220> FEATURE:
<221> NAME/KEY: X
<222> LOCATION: (19)..(19)
<223> OTHER INFORMATION: X is any amino acid ordinarily found in living
      organisms
<220> FEATURE:
<221> NAME/KEY: X
<222> LOCATION: (20)..(20)
<223> OTHER INFORMATION: X is valine or leucine
<220> FEATURE:
<221> NAME/KEY: X
<222> LOCATION: (21)..(21)
<223> OTHER INFORMATION: X is serine or threonine
<220> FEATURE:
<221> NAME/KEY: X
<222> LOCATION: (23)..(35)
<223> OTHER INFORMATION: X is any amino acid ordinarily found in living
      organisms
<220> FEATURE:
<221> NAME/KEY: X
<222> LOCATION: (36)..(37)
<223> OTHER INFORMATION: X may or may not be present, but, if present,
      can be any amino acid ordinarily found in living organisms
<220> FEATURE:
<221> NAME/KEY: X
<222> LOCATION: (39)..(43)
<223> OTHER INFORMATION: X is any amino acid ordinarily found in living
      organisms
<220> FEATURE:
<221> NAME/KEY: X
<222> LOCATION: (45)..(45)
<223> OTHER INFORMATION: X is lysine or glutamine
<220> FEATURE:
<221> NAME/KEY: X
<222> LOCATION: (48)..(54)
<223> OTHER INFORMATION: X is any amino acid ordinarily found in living
      organisms
<220> FEATURE:
<221> NAME/KEY: X
<222> LOCATION: (55)..(57)
<223> OTHER INFORMATION: X may or may not be present, but, if present,
      can be any amino acid ordinarily found in living organisms
<220> FEATURE:
<221> NAME/KEY: X
<222> LOCATION: (58)..(108)
<223> OTHER INFORMATION: X is any amino acid ordinarily found in living
      organisms
<220> FEATURE:
<221> NAME/KEY: X

```
<222> LOCATION: (109)..(119)
<223> OTHER INFORMATION: X may or may not be present, but, if present,
      can be any amino acid ordinarily found in living organisms
<220> FEATURE:
<221> NAME/KEY: X
<222> LOCATION: (120)..(132)
<223> OTHER INFORMATION: X is any amino acid ordinarily found in living
      organisms

<400> SEQUENCE: 196

Xaa Xaa Xaa Leu Xaa Xaa Xaa Gly Xaa Xaa Xaa Xaa Pro Xaa Xaa
1               5                   10                  15

Xaa Xaa Xaa Xaa Xaa Cys Xaa Xaa Xaa Gly Xaa Xaa Xaa Xaa Xaa
            20                  25                  30

Xaa Xaa Xaa Xaa Xaa Trp Xaa Arg Gln Xaa Xaa Gly Xaa Gly Leu Xaa
        35                  40                  45

Trp Xaa Xaa Xaa Xaa Xaa Xaa Xaa Xaa Xaa Xaa Xaa Xaa Xaa
    50                  55                  60

Xaa Xaa Xaa Xaa Xaa Xaa Arg Xaa Xaa Xaa Xaa Xaa Xaa Ser Xaa
65              70                  75                  80

Xaa Xaa Xaa Xaa Leu Xaa Xaa Xaa Xaa Xaa Xaa Xaa Asp Xaa Xaa
            85                  90                  95

Xaa Tyr Xaa Cys Xaa Xaa Xaa Xaa Xaa Xaa Xaa Xaa Xaa Xaa Xaa
        100                 105                 110

Xaa Xaa Xaa Xaa Xaa Xaa Xaa Xaa Trp Xaa Gln Gly Xaa Xaa Val
        115                 120                 125

Xaa Val Ser Xaa
    130

<210> SEQ ID NO 197
<211> LENGTH: 98
<212> TYPE: PRT
<213> ORGANISM: Artificial Sequence
<220> FEATURE:
<223> OTHER INFORMATION: Consensus amino acid sequence for a CH1
<220> FEATURE:
<221> NAME/KEY: X
<222> LOCATION: (1)..(15)
<223> OTHER INFORMATION: X is any amino acid ordinarily found in living
      organisms
<220> FEATURE:
<221> NAME/KEY: X
<222> LOCATION: (16)..(16)
<223> OTHER INFORMATION: X is arginine or lysine
<220> FEATURE:
<221> NAME/KEY: X
<222> LOCATION: (17)..(98)
<223> OTHER INFORMATION: X is any amino acid ordinarily found in living
      organisms

<400> SEQUENCE: 197

Xaa Xaa Xaa Xaa Xaa Pro Xaa Xaa Xaa Pro Xaa Xaa Xaa Xaa Xaa
1               5                   10                  15

Xaa Xaa Xaa Xaa Xaa Xaa Xaa Xaa Xaa Xaa Cys Leu Xaa Lys Xaa Xaa
            20                  25                  30

Xaa Pro Xaa Xaa Xaa Xaa Xaa Xaa Trp Xaa Xaa Xaa Xaa Xaa Xaa
        35                  40                  45

Xaa Xaa His Xaa Phe Xaa Xaa Val Xaa Xaa Xaa Xaa Xaa Xaa Thr
    50                  55                  60

Xaa Ser Ser Xaa Xaa Xaa Xaa Xaa Xaa Xaa Xaa Xaa Xaa Xaa Xaa
65              70                  75                  80

Xaa Xaa Cys Xaa Xaa Xaa Xaa Xaa Xaa Xaa Xaa Xaa Xaa Xaa Xaa
            85                  90                  95
```

Xaa Xaa

<210> SEQ ID NO 198
<211> LENGTH: 98
<212> TYPE: PRT
<213> ORGANISM: Homo sapiens

<400> SEQUENCE: 198

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val

<210> SEQ ID NO 199
<211> LENGTH: 98
<212> TYPE: PRT
<213> ORGANISM: Homo sapiens

<400> SEQUENCE: 199

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val

<210> SEQ ID NO 200
<211> LENGTH: 98
<212> TYPE: PRT
<213> ORGANISM: Homo sapiens

<400> SEQUENCE: 200

Ala Ser Thr Lys Gly Pro Ser Val Phe Pro Leu Ala Pro Cys Ser Arg
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

```
Leu Ser Ser Val Val Thr Val Pro Ser Ser Ser Leu Gly Thr Gln Thr
 65                  70                  75                  80

Tyr Thr Cys Asn Val Asn His Lys Pro Ser Asn Thr Lys Val Asp Lys
                 85                  90                  95

Arg Val

<210> SEQ ID NO 201
<211> LENGTH: 98
<212> TYPE: PRT
<213> ORGANISM: Homo sapiens

<400> SEQUENCE: 201

Ala Ser Thr Lys Gly Pro Ser Val Phe Pro Leu Ala Pro Cys Ser Arg
  1               5                  10                  15

Ser Thr Ser Glu Ser Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
         50                  55                  60

Leu Ser Val Val Thr Val Pro Ser Ser Ser Leu Gly Thr Lys Thr Thr
 65                  70                  75                  80

Tyr Thr Cys Asn Val Asp His Lys Pro Ser Asn Thr Lys Val Asp Lys
                 85                  90                  95

Arg Val

<210> SEQ ID NO 202
<211> LENGTH: 232
<212> TYPE: PRT
<213> ORGANISM: Homo sapiens

<400> SEQUENCE: 202

Glu Pro Lys Ser Cys Asp Lys Thr His Thr Cys Pro Pro Cys Pro Ala
  1               5                  10                  15

Pro Glu Leu Leu Gly Gly Pro Ser Val Phe Leu Phe Pro Pro Lys Pro
                 20                  25                  30

Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
         50                  55                  60

Asp Gly Val Glu Val His Asn Ala Lys Thr Lys Pro Arg Glu Glu Gln
 65                  70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
                100                 105                 110

Leu Pro Ala Pro Ile Glu Lys Thr Ile Ser Lys Ala Lys Gly Gln Pro
            115                 120                 125

Arg Glu Pro Gln Val Tyr Thr Leu Pro Pro Ser Arg Glu Glu Met Thr
        130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
                180                 185                 190
```

-continued

```
Ser Lys Leu Thr Val Asp Lys Ser Arg Trp Gln Gln Gly Asn Val Phe
        195                 200                 205
Ser Cys Ser Val Met His Glu Ala Leu His Asn His Tyr Thr Gln Lys
    210                 215                 220
Ser Leu Ser Leu Ser Pro Gly Lys
225                 230

<210> SEQ ID NO 203
<211> LENGTH: 228
<212> TYPE: PRT
<213> ORGANISM: Homo sapiens

<400> SEQUENCE: 203

Glu Arg Lys Cys Cys Val Glu Cys Pro Pro Cys Pro Ala Pro Pro Val
1               5                   10                  15
Ala Gly Pro Ser Val Phe Leu Phe Pro Pro Lys Pro Lys Asp Thr Leu
            20                  25                  30
Met Ile Ser Arg Thr Pro Glu Val Thr Cys Val Val Val Asp Val Ser
        35                  40                  45
His Glu Asp Pro Glu Val Gln Phe Asn Trp Tyr Val Asp Gly Met Glu
    50                  55                  60
Val His Asn Ala Lys Thr Lys Pro Arg Glu Glu Gln Phe Asn Ser Thr
65                  70                  75                  80
Phe Arg Val Val Ser Val Leu Thr Val Val His Gln Asp Trp Leu Asn
                85                  90                  95
Gly Lys Glu Tyr Lys Cys Lys Val Ser Asn Lys Gly Leu Pro Ala Pro
            100                 105                 110
Ile Glu Lys Thr Ile Ser Lys Thr Lys Gly Gln Pro Arg Glu Pro Gln
        115                 120                 125
Val Tyr Thr Leu Pro Pro Ser Arg Glu Glu Met Thr Lys Asn Gln Val
    130                 135                 140
Ser Leu Thr Cys Leu Val Lys Gly Phe Tyr Pro Ser Asp Ile Ala Val
145                 150                 155                 160
Glu Trp Glu Ser Asn Gly Gln Pro Glu Asn Asn Tyr Lys Thr Thr Pro
                165                 170                 175
Pro Met Leu Asp Ser Asp Gly Ser Phe Phe Leu Tyr Ser Lys Leu Thr
            180                 185                 190
Val Asp Lys Ser Arg Trp Gln Gln Gly Asn Val Phe Ser Cys Ser Val
        195                 200                 205
Met His Glu Ala Leu His Asn His Tyr Thr Gln Lys Ser Leu Ser Leu
    210                 215                 220
Ser Pro Gly Lys
225

<210> SEQ ID NO 204
<211> LENGTH: 279
<212> TYPE: PRT
<213> ORGANISM: Homo sapiens

<400> SEQUENCE: 204

Glu Leu Lys Thr Pro Leu Gly Asp Thr His Thr Cys Pro Arg Cys Pro
1               5                   10                  15
Glu Pro Lys Ser Cys Asp Thr Pro Pro Pro Cys Pro Arg Cys Pro
            20                  25                  30
Glu Pro Lys Ser Cys Asp Thr Pro Pro Pro Cys Pro Arg Cys Pro Glu
        35                  40                  45
```

Pro Lys Ser Cys Asp Thr Pro Pro Cys Pro Arg Cys Pro Ala Pro
 50                  55                  60

Glu Leu Leu Gly Gly Pro Ser Val Phe Leu Phe Pro Pro Lys Pro Lys
 65                  70                  75                  80

Asp Thr Leu Met Ile Ser Arg Thr Pro Glu Val Thr Cys Val Val Val
                 85                  90                  95

Asp Val Ser His Glu Asp Pro Glu Val Gln Phe Lys Trp Tyr Val Asp
                100                 105                 110

Gly Val Glu Val His Asn Ala Lys Thr Lys Pro Arg Glu Glu Gln Tyr
            115                 120                 125

Asn Ser Thr Phe Arg Val Val Ser Val Leu Thr Val Leu His Gln Asp
            130                 135                 140

Trp Leu Asn Gly Lys Glu Tyr Lys Cys Lys Val Ser Asn Lys Ala Leu
145                 150                 155                 160

Pro Ala Pro Ile Glu Lys Thr Ile Ser Lys Thr Lys Gly Gln Pro Arg
                165                 170                 175

Glu Pro Gln Val Tyr Thr Leu Pro Pro Ser Arg Glu Glu Met Thr Lys
            180                 185                 190

Asn Gln Val Ser Leu Thr Cys Leu Val Lys Gly Phe Tyr Pro Ser Asp
            195                 200                 205

Ile Ala Val Glu Trp Glu Ser Ser Gly Gln Pro Glu Asn Asn Tyr Asn
210                 215                 220

Thr Thr Pro Pro Met Leu Asp Ser Asp Gly Ser Phe Phe Leu Tyr Ser
225                 230                 235                 240

Lys Leu Thr Val Asp Lys Ser Arg Trp Gln Gln Gly Asn Ile Phe Ser
                245                 250                 255

Cys Ser Val Met His Glu Ala Leu His Asn Arg Phe Thr Gln Lys Ser
            260                 265                 270

Leu Ser Leu Ser Pro Gly Lys
            275

<210> SEQ ID NO 205
<211> LENGTH: 229
<212> TYPE: PRT
<213> ORGANISM: Homo sapiens

<400> SEQUENCE: 205

Glu Ser Lys Tyr Gly Pro Pro Cys Pro Ser Cys Pro Ala Pro Glu Phe
 1               5                  10                  15

Leu Gly Gly Pro Ser Val Phe Leu Phe Pro Pro Lys Pro Lys Asp Thr
                 20                  25                  30

Leu Met Ile Ser Arg Thr Pro Glu Val Thr Cys Val Val Val Asp Val
             35                  40                  45

Ser Gln Glu Asp Pro Glu Val Gln Phe Asn Trp Tyr Val Asp Gly Val
 50                  55                  60

Glu Val His Asn Ala Lys Thr Lys Pro Arg Glu Glu Gln Phe Asn Ser
 65                  70                  75                  80

Thr Tyr Arg Val Val Ser Val Leu Thr Val Leu His Gln Asp Trp Leu
                 85                  90                  95

Asn Gly Lys Glu Tyr Lys Cys Lys Val Ser Asn Lys Gly Leu Pro Ser
            100                 105                 110

Ser Ile Glu Lys Thr Ile Ser Lys Ala Lys Gly Gln Pro Arg Glu Pro
            115                 120                 125

Gln Val Tyr Thr Leu Pro Pro Ser Gln Glu Glu Met Thr Lys Asn Gln

```
                130             135             140
Val Ser Leu Thr Cys Leu Val Lys Gly Phe Tyr Pro Ser Asp Ile Ala
145                 150                 155                 160

Val Glu Trp Glu Ser Asn Gly Gln Pro Glu Asn Asn Tyr Lys Thr Thr
                165                 170                 175

Pro Pro Val Leu Asp Ser Asp Gly Ser Phe Phe Leu Tyr Ser Arg Leu
            180                 185                 190

Thr Val Asp Lys Ser Arg Trp Gln Glu Gly Asn Val Phe Ser Cys Ser
        195                 200                 205

Val Met His Glu Ala Leu His Asn His Tyr Thr Gln Lys Ser Leu Ser
    210                 215                 220

Leu Ser Leu Gly Lys
225

<210> SEQ ID NO 206
<211> LENGTH: 117
<212> TYPE: PRT
<213> ORGANISM: Artificial sequence
<220> FEATURE:
<223> OTHER INFORMATION: Consensus amino acid sequence for a human VL
<220> FEATURE:
<221> NAME/KEY: X
<222> LOCATION: (1)..(27)
<223> OTHER INFORMATION: X is any amino acid ordinarily found in living
      organisms
<220> FEATURE:
<221> NAME/KEY: X
<222> LOCATION: (28)..(33)
<223> OTHER INFORMATION: X may or may not be present, but, if present,
      can be any amino acid ordinarily found in living organisms
<220> FEATURE:
<221> NAME/KEY: X
<222> LOCATION: (34)..(48)
<223> OTHER INFORMATION: X is any amino acid ordinarily found in living
      organisms
<220> FEATURE:
<221> NAME/KEY: X
<222> LOCATION: (49)..(49)
<223> OTHER INFORMATION: X is alanine, serine, or proline
<220> FEATURE:
<221> NAME/KEY: X
<222> LOCATION: (51)..(63)
<223> OTHER INFORMATION: X is any amino acid ordinarily found in living
      organisms
<220> FEATURE:
<221> NAME/KEY: X
<222> LOCATION: (64)..(64)
<223> OTHER INFORMATION: X is isoleucine or valine
<220> FEATURE:
<221> NAME/KEY: X
<222> LOCATION: (66)..(89)
<223> OTHER INFORMATION: X is any amino acid ordinarily found in living
      organisms
<220> FEATURE:
<221> NAME/KEY: X
<222> LOCATION: (90)..(90)
<223> OTHER INFORMATION: X is alanine or glycine
<220> FEATURE:
<221> NAME/KEY: X
<222> LOCATION: (91)..(91)
<223> OTHER INFORMATION: X is any amino acid ordinarily found in living
      organisms
<220> FEATURE:
<221> NAME/KEY: X
<222> LOCATION: (93)..(93)
<223> OTHER INFORMATION: X is tyrosine or phenylalanine
<220> FEATURE:
<221> NAME/KEY: X
<222> LOCATION: (94)..(101)
<223> OTHER INFORMATION: X is any amino acid ordinarily found in living
      organisms
<220> FEATURE:
```

```
<221> NAME/KEY: X
<222> LOCATION: (102)..(102)
<223> OTHER INFORMATION: X may or may not be present, but, if present,
      can be any amino acid ordinarily found in living organisms
<220> FEATURE:
<221> NAME/KEY: X
<222> LOCATION: (103)..(104)
<223> OTHER INFORMATION: X is any amino acid ordinarily found in living
      organisms
<220> FEATURE:
<221> NAME/KEY: X
<222> LOCATION: (107)..(107)
<223> OTHER INFORMATION: X is glutamine or glycine
<220> FEATURE:
<221> NAME/KEY: X
<222> LOCATION: (110)..(117)
<223> OTHER INFORMATION: X is any amino acid ordinarily found in living
      organisms

<400> SEQUENCE: 206

Xaa Xaa Xaa Xaa Xaa Xaa Xaa Xaa Xaa Xaa Xaa Xaa Xaa Xaa Gly
1               5                   10                  15

Xaa Xaa Xaa Xaa Xaa Xaa Cys Xaa Xaa Xaa Xaa Xaa Xaa Xaa Xaa
            20                  25                  30

Xaa Xaa Xaa Xaa Xaa Xaa Xaa Xaa Trp Xaa Xaa Xaa Xaa Xaa Xaa
        35                  40                  45

Xaa Pro Xaa Xaa Xaa Xaa Xaa Xaa Xaa Xaa Xaa Xaa Xaa Xaa Xaa
    50                  55                  60

Pro Xaa Arg Phe Ser Gly Ser Xaa Xaa Xaa Xaa Xaa Xaa Leu Xaa
65                  70                  75                  80

Xaa Xaa Xaa Xaa Xaa Xaa Xaa Xaa Xaa Xaa Tyr Xaa Xaa Xaa Xaa
                85                  90                  95

Xaa Xaa Xaa Xaa Xaa Xaa Xaa Xaa Phe Gly Xaa Gly Thr Xaa Xaa Xaa
            100                 105                 110

Xaa Xaa Xaa Xaa Xaa
        115

<210> SEQ ID NO 207
<211> LENGTH: 107
<212> TYPE: PRT
<213> ORGANISM: Artificial sequence
<220> FEATURE:
<223> OTHER INFORMATION: Consensus amino acid sequence for a CL kappa
<220> FEATURE:
<221> NAME/KEY: X
<222> LOCATION: (1)..(107)
<223> OTHER INFORMATION: X is any amino acid ordinarily found in living
      organisms

<400> SEQUENCE: 207

Xaa Xaa Xaa Xaa Xaa Pro Xaa Xaa Xaa Xaa Xaa Pro Pro Xaa Xaa Xaa
1               5                   10                  15

Xaa Xaa Xaa Xaa Xaa Xaa Xaa Ser Xaa Val Cys Xaa Xaa Xaa Xaa
            20                  25                  30

Xaa Pro Xaa Xaa Xaa Xaa Val Xaa Trp Xaa Xaa Xaa Xaa Xaa Xaa
        35                  40                  45

Xaa Xaa Xaa Xaa Gln Xaa Ser Xaa Thr Xaa Xaa Xaa Xaa Xaa Xaa
    50                  55                  60

Xaa Ser Xaa Ser Ser Thr Leu Thr Leu Xaa Xaa Xaa Xaa Xaa Xaa
65                  70                  75                  80

Xaa Xaa Xaa Xaa Xaa Xaa Cys Xaa Xaa Xaa His Xaa Xaa Xaa Xaa Xaa
                85                  90                  95

Xaa Xaa Xaa Xaa Xaa Xaa Xaa Xaa Xaa Xaa Cys
```

```
                100             105

<210> SEQ ID NO 208
<211> LENGTH: 107
<212> TYPE: PRT
<213> ORGANISM: Artificial sequence
<220> FEATURE:
<223> OTHER INFORMATION: Consensus amino acid sequence for a CL lambda
<220> FEATURE:
<221> NAME/KEY: X
<222> LOCATION: (1)..(66)
<223> OTHER INFORMATION: X is any amino acid ordinarily found in living
      organisms
<220> FEATURE:
<221> NAME/KEY: X
<222> LOCATION: (67)..(67)
<223> OTHER INFORMATION: X is alanine or methionine
<220> FEATURE:
<221> NAME/KEY: X
<222> LOCATION: (68)..(106)
<223> OTHER INFORMATION: X is any amino acid ordinarily found in living
      organisms

<400> SEQUENCE: 208

Xaa Xaa Xaa Xaa Xaa Pro Xaa Xaa Xaa Xaa Xaa Pro Pro Xaa Xaa Xaa
1               5                   10                  15

Xaa Xaa Xaa Xaa Xaa Xaa Xaa Ala Xaa Val Cys Xaa Xaa Xaa Xaa Xaa
                20                  25                  30

Xaa Pro Xaa Xaa Xaa Xaa Val Xaa Trp Xaa Xaa Xaa Xaa Xaa Xaa Xaa
            35                  40                  45

Xaa Xaa Xaa Xaa Glu Xaa Thr Xaa Pro Xaa Xaa Xaa Xaa Xaa Xaa Xaa
        50                  55                  60

Xaa Xaa Xaa Xaa Ser Ser Tyr Leu Ser Leu Xaa Xaa Xaa Xaa Xaa Xaa
65                  70                  75                  80

Xaa Xaa Xaa Xaa Xaa Xaa Cys Xaa Xaa Xaa His Xaa Xaa Xaa Xaa Xaa
                85                  90                  95

Xaa Xaa Xaa Xaa Xaa Xaa Xaa Xaa Xaa Xaa Cys
                100                 105
```

ANTI-PD1 AND ANTI-CTLA4 ANTIBODIES

CROSS-REFERENCE TO RELATED APPLICATIONS

This application is a U.S. National Stage entry under 35 USC § 371 of PCT Application No. PCT/US2017/060122, filed Nov. 6, 2017, which claims the benefit of U.S. Provisional Application No. 62/491,157, filed Nov. 8, 2016, both of which are incorporated herein by reference in their entirety for all purposes.

FIELD

The compositions and methods described herein are in the field of recombinant antibodies.

BACKGROUND

Immune checkpoint inhibitors represent a new class of cancer therapeutics. See, e.g., Pardoll (2012), Nat. Rev. Cancer 12: 252-264. T cell response is regulated by a balance of activating and inhibitory signals. Immune checkpoints, that is, inhibitory pathways, can help maintain self tolerance and/or modulate the duration and/or intensity of an immune response, thereby limiting collateral damage to healthy tissues. Cancer cells can develop multiple ways to upregulate these immune checkpoint pathways to dampen host immune response, which might otherwise kill cancer cells. The success of immune checkpoint inhibitors or blockers, e.g. anti-programmed cell death 1 (PD1), anti-programmed cell death 1 ligand 1 (PDL1), and anti-cytotoxic T lymphocyte-associated 4 (CTLA4) antibodies, in treating many types of cancer is evidence of the importance of immune checkpoints in regulating T cell response to cancer. See, e.g., Larkin et al. (2015), New Engl. J. Med 373(1): 23-34.

Refining this approach to improve patient responses and limit toxicity remains an ongoing challenge. Thus, there is a need in the art for improved immune checkpoint inhibitors and improved methods of treatment using such inhibitors. Such improved immune checkpoint inhibitors and improved methods of treatment are described herein.

SUMMARY

Described herein are anti-human CTLA4 (hCTLA4) antibodies, anti-human PD1 (hPD1) antibodies, mixtures thereof, nucleic acids encoding these antibodies and mixtures, host cells containing these nucleic acids, pharmaceutical compositions comprising these antibodies, mixtures, and nucleic acids, and methods of treatment comprising administering these antibodies, mixtures, nucleic acids, or pharmaceutical compositions to patients. The numbered items below describe these compositions and methods.

1. An anti-human CTLA4 (hCTLA4) antibody comprising a heavy chain variable domain (VH),
    wherein the VH comprises an amino acid sequence which comprises no more than four alterations relative to an amino acid sequence selected from the group consisting of SEQ ID NOs: 2, 12, 19, 23, 30, 36, 42, 45, 52, 58, 64, and 69, and
    wherein the anti-hCTLA4 antibody inhibits interaction of hCTLA4 with human B-lymphocyte activation antigen B7-1 (hB7-1) and/or human B-lymphocyte activation antigen B7-2 (hB7-2).

2. The anti-hCTLA4 antibody of item 1, wherein the VH comprises a VH complementarity determining region 1 (CDR1), a VH complementarity determining region 2 (CDR2), and a VH complementarity determining region 3 (CDR3) which comprise, respectively the amino acid sequences of SEQ ID NOs: 3, 4, and 5, SEQ ID NOs: 3, 13 and 5, SEQ ID NOs: 3, 20, and 21, SEQ ID NOs: 3, 24, and 25, SEQ ID NOs: 3, 31, and 5, SEQ ID NOs: 3, 37, and 5, SEQ ID NOs: 3, 43, and 5, SEQ ID NOs: 3, 46, and 47, SEQ ID NOs: 3, 59, and 5, SEQ ID NOs: 3, 65, and 21, or SEQ ID NOs: 3, 70, and 21.

3. The anti-hCTLA4 antibody of item 1 or 2, wherein the amino acid sequence comprised by the VH comprises no more than three amino acid alterations relative to the amino acid sequence selected from the group consisting of SEQ ID NOs: 2, 12, 19, 23, 30, 36, 42, 45, 52, 58, 64, and 69.

4. The anti-hCTLA4 antibody of item 3, wherein the amino acid sequence comprised by the VH comprises no more than two amino acid alterations relative to the amino acid sequence selected from the group consisting of SEQ ID NOs: 2, 12, 19, 23, 30, 36, 42, 45, 52, 58, 64, and 69.

5. The anti-hCTLA4 antibody of item 4, wherein the amino acid sequence comprised by the VH comprises no more than one amino acid alteration relative to the amino acid sequence selected from the group consisting of SEQ ID NOs: 2, 12, 19, 23, 30, 36, 42, 45, 52, 58, 64, and 69.

6. The anti-hCTLA4 antibody of any one of items 1 to 5, wherein the amino acid alteration(s) is (are) (a) substitution(s), and the substitution(s) is (are) (a) partner directing alteration(s).

7. The anti-hCTLA4 antibody of item 5, wherein the amino acid sequence comprised by the VH is selected from the group consisting of SEQ ID NOs: 2, 12, 19, 23, 30, 36, 42, 45, 52, 58, 64, and 69.

8. The anti-hCTLA4 antibody of any one of items 1 to 7, further comprising a light chain variable domain (VL), which comprises a VL CDR1, a VL CDR2, and a VL CDR3 comprising, respectively, the amino acid sequences of SEQ ID NOs: 3, 75, and 77.

9. The anti-hCTLA4 antibody of item 8, wherein the VL CDR1, VL CDR2, and VL CDR3 comprise, respectively, the amino acid sequences of SEQ ID NOs: 8, 9, and 10, SEQ ID NOs: 16, 9 and 17, SEQ ID NOs: 28, 9, and 17, SEQ ID NOs: 34, 9, and 17, SEQ ID NOs: 40, 9, and 10, SEQ ID NOs: 50, 9, and 17, SEQ ID NOs: 55, 9, and 56, SEQ ID NOs: 40, 9, and 62, SEQ ID NOs: 16, 9, and 62, or SEQ ID NOs: 73, 9, and 62.

10. The anti-hCTLA4 antibody of any one of items 1 to 7, further comprising a VL comprising an amino acid sequence which comprises no more than 4 amino acid alterations relative to an amino acid sequence selected from the group consisting of SEQ ID NOs: 7, 15, 27, 33, 39, 49, 54, 61, 67, 72, 84, and 85.

11. The anti-hCTLA4 antibody of item 10, wherein the amino acid sequence comprised by the VL comprises no more than three amino acid alterations relative to the amino acid sequence selected from the group consisting of SEQ ID NOs: 7, 15, 27, 33, 39, 49, 54, 61, 67, 72, 84, and 85.

12. The anti-hCTLA4 antibody of item 11, wherein the amino acid sequence comprised by the VL comprises no more than two amino acid alterations relative to the amino acid sequence selected from the group consisting of SEQ ID NOs: 7, 15, 27, 33, 39, 49, 54, 61, 67, 72, 84, and 85.

13. The anti-hCTLA4 antibody of item 12, wherein the amino acid sequence comprised by the VL comprises no more than one amino acid alteration relative to the amino acid sequence selected from the group consisting of SEQ ID NOs: 7, 15, 27, 33, 39, 49, 54, 61, 67, 72, 84, and 85.

14. The anti-hCTLA4 antibody of any one of items 10 to 13, wherein the amino acid alteration(s) relative to SEQ ID NOs: 7, 15, 27, 33, 39, 49, 54, 61, 67, 72, 84 or 85 is (are) substitution(s), and the substitution(s) is (are) (a) partner-directing alteration(s).

15. The anti-hCTLA4 antibody of any one of items 10 to 14, wherein the VL comprises a VL CDR1, a VL CDR2, and a VL CDR3 comprising, respectively, the amino acid sequences of SEQ ID NOs: 8, 9, and 10, SEQ ID NOs: 16, 9 and 17, SEQ ID NOs: 28, 9, and 17, SEQ ID NOs: 34, 9, and 17, SEQ ID NOs: 40, 9, and 10, SEQ ID NOs: 50, 9, and 17, SEQ ID NOs: 55, 9, and 56, SEQ ID NOs: 40, 9, and 62, SEQ ID NOs: 16, 9, and 62, or SEQ ID NOs: 73, 9, and 62.

16. The anti-hCTLA4 antibody of item 15, wherein the amino acid sequence comprised by the VL is selected from the group consisting of SEQ ID NOs: 7, 15, 27, 33, 39, 49, 54, 61, 67, 72, 84, and 85.

17. An anti-hCTLA4 antibody comprising a VL, wherein the VL comprises an amino acid sequence which comprises no more than four amino acid alterations relative to an amino acid sequence selected from the group consisting of SEQ ID NOs: 7, 15, 27, 33, 39, 49, 54, 61, 67, and 72,
wherein the VL comprises a CDR1, a CDR2, and a CDR3, which comprise, respectively, the amino acid sequences of SEQ ID NOs: 8, 9, and 10, SEQ ID NOs: 16, 9 and 17, SEQ ID NOs: 28, 9, and 17, SEQ ID NOs: 34, 9, and 17, SEQ ID NOs: 40, 9, and 10, SEQ ID NOs: 50, 9, and 17, SEQ ID NOs: 55, 9, and 56, SEQ ID NOs: 40, 9, and 62, SEQ ID NOs: 16, 9, and 62, or SEQ ID NOs: 73, 9, and 62, and
wherein the anti-hCTLA4 antibody inhibits interaction of hCTLA4 with hB7-1 and/or hB7-2.

18. The anti-hCTLA4 antibody of item 17, wherein the amino acid sequence comprised by the VL comprises no more than three amino acid alterations relative to the amino acid sequence selected from the group consisting of SEQ ID NOs: 7, 15, 27, 33, 39, 49, 54, 61, 67, and 72.

19. The anti-hCTLA4 antibody of item 18, wherein the amino acid sequence comprised by the VL comprises no more than two amino acid alterations relative to the amino acid sequence selected from the group consisting of SEQ ID NOs: 7, 15, 27, 33, 39, 49, 54, 61, 67, and 72.

20. The anti-hCTLA4 antibody of item 19, wherein the amino acid sequence comprised by the VL comprises no more than one amino acid alteration relative to the amino acid sequence selected from the group consisting of SEQ ID NOs: 7, 15, 27, 33, 39, 49, 54, 61, 67, and 72.

21. The anti-hCTLA4 antibody of any one of items 17 to 20, wherein the amino acid alteration(s) is (are) (a) substitution(s), and the substitution(s) is (are) (a) partner-directing alteration(s).

22. The anti-hCTLA4 antibody of item 20, wherein the amino acid sequence comprised by the VL is selected from the group consisting of SEQ ID NOs: 7, 15, 27, 33, 39, 49, 54, 61, 67, and 72.

23. The anti-hCTLA4 antibody of any one of items 17 to 22, further comprising a VH, which comprises a VH CDR1, a VH CDR2, and a VH CDR3 comprising, respectively, the amino acid sequences of SEQ ID NO:79, SEQ ID NO:9, and SEQ ID NO:81.

24. The anti-hCTLA4 antibody of item 23, wherein the VH CDR1, VH CDR2, and VH CDR3 comprise, respectively, the amino acid sequences of SEQ ID NOs: 3, 4, and 5, SEQ ID NOs: 3, 13 and 5, SEQ ID NOs: 3, 20, and 21, SEQ ID NOs: 3, 24, and 25, SEQ ID NOs: 3, 31, and 5, SEQ ID NOs: 3, 37, and 5, SEQ ID NOs: 3, 43, and 5, SEQ ID NOs: 3, 46, and 47, SEQ ID NOs: 3, 59, and 5, SEQ ID NOs: 3, 65, and 21, or SEQ ID NOs: 3, 70, and 21.

25. The anti-hCTLA4 antibody of any one of items 17 to 22, further comprising a VH, wherein the VH comprises an amino acid sequence which comprises no more than four amino acid alterations relative to an amino acid sequence selected from the group consisting of SEQ ID NOs: 2, 12, 19, 23, 30, 36, 42, 45, 52, 58, 64, 69, 82, and 83.

26. The anti-hCTLA4 antibody of item 25, wherein the amino acid sequence comprised by the VH comprises no more than three amino acid alterations relative to the amino acid sequence selected from the group consisting of SEQ ID NOs: 2, 12, 19, 23, 30, 36, 42, 45, 52, 58, 64, 69, 82, and 83.

27. The anti-hCTLA4 antibody of item 26, wherein the amino acid sequence comprised by the VH comprises no more than two amino acid alterations relative to the amino acid sequence selected from the group consisting of SEQ ID NOs: 2, 12, 19, 23, 30, 36, 42, 45, 52, 58, 64, 69, 82, and 83.

28. The anti-hCTLA4 antibody of item 27, wherein the amino acid sequence comprised by the VH comprises no more than one amino acid alteration relative to the amino acid sequence selected from the group consisting of SEQ ID NOs: 2, 12, 19, 23, 30, 36, 42, 45, 52, 58, 64, 69, 82, and 83.

29. The anti-hCTLA4 antibody of any one of items 25 to 28, wherein the amino acid alteration(s) is (are) (a) substitution(s), and the substitution(s) is (are) (a) partner-directing alteration(s).

30. The anti-hCTLA4 antibody of any one of items 25 to 29, wherein the VH comprises a VH CDR1, VH CDR2, and VH CDR3 comprising, respectively, the amino acid sequences of SEQ ID NOs: 3, 4, and 5, SEQ ID NOs: 3, 13 and 5, SEQ ID NOs: 3, 20, and 21, SEQ ID NOs: 3, 24, and 25, SEQ ID NOs: 3, 31, and 5, SEQ ID NOs: 3, 37, and 5, SEQ ID NOs: 3, 43, and 5, SEQ ID NOs: 3, 46, and 47, SEQ ID NOs: 3, 59, and 5, SEQ ID NOs: 3, 65, and 21, or SEQ ID NOs: 3, 70, and 21.

31. The anti-hCTLA4 antibody of item 28, wherein the amino acid sequence comprised by the VH is selected from the group consisting of SEQ ID NOs: 2, 12, 19, 23, 30, 36, 42, 45, 52, 58, 64, 69, 82, and 83.

32. An anti-hCTLA4 antibody comprising a VH CDR1, VH CDR2, VH CDR3, VL CDR1, VL CDR2, and VL CDR3, which comprise, respectively, the following amino acid sequences:
  (a) SEQ ID NOs: 3, 4, 5, 8, 9, and 10;
  (b) SEQ ID NOs: 3, 13, 5, 16, 9, and 17;
  (c) SEQ ID NOs: 3, 20, 21, 16, 9, and 17;
  (d) SEQ ID NOs: 3, 24, 25, 28, 9, and 17;
  (e) SEQ ID NOs: 3, 31, 5, 34, 9, and 17;
  (f) SEQ ID NOs: 3, 37, 5, 40, 9, and 10;
  (g) SEQ ID NOs: 3, 43, 5, 28, 9, and 17;
  (h) SEQ ID NOs: 3, 46, 47, 50, 9, and 17;
  (i) SEQ ID NOs: 3, 31, 5, 55, 9, and 56;
  (j) SEQ ID NOs: 3, 59, 5, 40, 9, and 62;
  (k) SEQ ID NOs: 3, 65, 21, 16, 9, and 62; or
  (l) SEQ ID NOs: 3, 70, 21, 73, 9, and 62;
wherein the anti-hCTLA4 antibody inhibits interaction of hCTLA4 with hB7-1 and/or hB7-2.

33. The anti-hCTLA4 antibody of item 32, wherein the VH and the VL of the anti-hCTLA4 antibody each comprise an amino acid sequence, which, together, comprise two sequences, and
wherein one of the two sequences comprises not more than four amino acid alterations relative to one sequence in a pair of sequences and the other of the two sequences comprises not more than four amino acid alterations relative to the other sequence in the pair of sequences, and wherein the pair of sequences is selected from the group consisting of: SEQ ID NOs: 2 (VH) and 7 (VL); SEQ ID NOs: 12 (VH) and 15 (VL); SEQ ID NOs: 19 (VH) and 15 (VL); SEQ ID NOs: 23 (VH) and 27 (VL); SEQ ID NOs: 30 (VH) and 33 (VL); SEQ ID NOs: 36 (VH) and 39 (VL); SEQ ID NOs: 42 (VH) and 27 (VL); SEQ ID NOs: 45 (VH) and 49 (VL); SEQ ID NOs: 52 (VH) and 54 (VL); SEQ ID NOs: 58 (VH) and 61 (VL); SEQ ID NOs: 64 (VH) and 67 (VL); and SEQ ID NOs: 69 (VH) and 72 (VL).

34. The anti-hCTLA4 antibody of item 33, wherein one of the two sequences comprises not more than three amino acid alterations relative to one sequence in the pair of sequences and the other of the two sequences comprises not more than three amino acid alterations relative to the other sequence in the pair of sequences.

35. The anti-hCTLA4 antibody of item 34, wherein one of the two sequences comprises not more than two amino acid alterations relative to one sequence in the pair of sequences and the other of the two sequences comprises not more than two amino acid alterations relative to the other sequence in the pair of sequences.

36. The anti-hCTLA4 antibody of item 35, wherein one of the two sequences comprises not more than one amino acid alteration relative to one sequence in the pair of sequences and the other of the two sequences comprises not more than one amino acid alteration relative to the other sequence in the pair of sequences.

37. The anti-hCTLA4 antibody of any one of items 33 to 36, wherein the alteration(s) is (are) (a) substitution(s), and the substitution(s) is (are) (a) partner-directing alteration(s).

38. The anti-hCTLA4 antibody of item 36, wherein one of the two sequences comprises one sequence in the pair of sequences and the other of the two sequences comprises the other sequence in the pair of sequences.

39. The anti-hCTLA4 antibody of any one of items 1 to 38, which is a human, humanized, or primate IgG antibody.

40. The anti-hCTLA4 antibody of item 39, which is (1) an IgG4 antibody or (2) an IgG1 antibody comprising the alteration K409R.

41. The anti-hCTLA4 antibody of item 39, which is an IgG1 antibody.

42. The anti-hCTLA4 antibody of any one of items 39 to 41,
wherein the heavy chain (HC) or the light chain (LC) contains a first partner-directing alteration at one or more positions selected from the group consisting of positions 44, 105, 147, 168 and 181 in the HC and positions 43, 100, 131, 174, and 178 in the LC,
wherein the first partner-directing alteration is a substitution where a charged amino acid replaces another amino acid,
wherein the substituted, charged amino acid of the first partner-directing alteration forms part of a charge pair of contacting amino acids within the antibody, and
wherein the contacting amino acids of the charge pair are selected from the group consisting of:
 (a) 44R/K (HC) and 100D/E (LC) or 44D/E (HC) and 100R/K (LC);
 (b) 105R/K (HC) and 43D/E (LC) or 105D/E (HC) and 43R/K (LC);
 (c) 147R/K (HC) and 131D/E (LC) or 147D/E (HC) and 131R/K (LC);
 (d) 168R/K (HC) and 174D/E (LC) or 168D/E (HC) and 174R/K (LC); and
 (e) 181R/K (HC) and 178D/E (LC) or 181D/E (HC) and 178R/K (LC).

43. The anti-hCTLA4 antibody of item 42, further comprising a second partner-directing alteration,
wherein the second partner-directing alteration is a substitution of a charged amino acid for another amino acid, and
wherein the substituted, charged amino acids of the first and second partner-directing alterations form the charge pair of contacting amino acids.

44. The anti-hCTLA4 antibody of item 42 or 43,
wherein the anti-hCTLA4 antibody is an IgG1 antibody,
wherein the HC or LC of the anti-hCTLA4 antibody contains a third partner-directing alteration at an amino acid in the HC or the LC,
wherein the third partner-directing alteration is a cysteine substitution, and
wherein the substituted cysteine of the third partner-directing alteration contacts a cysteine (1) in the HC if the third partner-directing alteration is in the LC or (2) in the LC if the third partner-directing alteration is in the HC, thereby forming a contacting pair of cysteines.

45. The anti-hCTLA4 antibody of item 44, wherein the contacting pair of cysteines is at positions selected from the group consisting of:
 (a) position 126 of the HC and position 121 or 124 in the LC;
 (b) position 128 in the HC and position 118 in the LC;
 (c) position 133 in the HC and position 117 or 209 in the LC;
 (d) position 134 or 141 in the HC and position 116 in the LC;
 (e) position 168 in the HC and position 174 in the LC;
 (f) position 170 in the HC and position 162 or 176 in the LC;
 (g) position 173 in the HC and position 160 in the LC; and
 (h) position 183 in the HC and position 176 in the LC.

46. The anti-hCTLA4 antibody of item 45, wherein the contacting pair of cysteines is at positions selected from the group consisting of:
 (a) position 126 of the HC and position 124 in the LC;
 (b) position 128 of the HC and position 118 in the LC;
 (c) position 133 of the HC and position 117 or 209 in the LC;
 (d) position 134 of the HC and position 116 in the LC;
 (e) position 168 of the HC and position 174 in the LC;
 (f) position 170 of the HC and position 162 or 176 in the LC; and
 (g) position 173 of the HC and position 160 in the LC.

47. The anti-hCTLA4 antibody of any one of items 44 to 46, wherein
if the third partner-directing alteration is in the HC, then the LC comprises a fourth partner-directing alteration which is a cysteine substitution at an amino acid contacting the amino acid of the third partner-directing alteration, or
if the third partner-directing alteration is in the LC, then the HC comprises a fourth partner-directing alteration, which is a cysteine substitution at an amino acid contacting the amino acid of the third partner-directing alteration.

48. The anti-hCTLA4 antibody of item 42 or 43,
wherein the anti-hCTLA4 antibody is an IgG4 antibody,
wherein the HC or LC of the anti-hCTLA4 antibody contains a third partner-directing alteration at an amino acid in the HC or LC,
wherein the third partner-directing alteration is a cysteine substitution, and
wherein the substituted cysteine of the third partner-directing alteration contacts a cysteine (1) in the HC if the third partner-directing alteration is in the LC or (2) in the LC if the third partner-directing alteration is in the HC, thereby forming a contacting pair of cysteines.

49. The anti-hCTLA4 antibody of item 48, wherein the contacting pair of cysteines is at positions within the HC and LC selected from the group consisting of:
   (a) position 126 in the HC and position 121 or 124 in the LC;
   (b) position 127 in the HC and position 121 in the LC;
   (c) position 128 in the HC and position 118 in the LC;
   (d) position 141 in the HC and position 116 in the LC;
   (e) position 168 in the HC and position 174 in the LC; and
   (f) position 170 or 173 in the HC and position 162 in the LC.

50. The anti-hCTLA4 antibody of item 48 or 49, wherein if the third partner-directing alteration is in the HC, then the LC comprises a fourth partner-directing alteration, which is a cysteine substitution at an amino acid contacting the amino acid of the third partner-directing alteration, or if the third partner-directing alteration is in the LC, then the HC comprises a fourth partner-directing alteration, which is a cysteine substitution at an amino acid contacting the amino acid of the third partner-directing alteration.

51. The anti-hCTLA4 antibody of any one of items 1 to 50, which comprises the alterations D399K/R and K/R409E/D.

52. The anti-hCTLA4 antibody of any one of items 1 to 51, wherein the anti-hCTLA4 antibody is a human, humanized, or primate IgG antibody comprising an Fc portion, wherein the Fc portion of the antibody comprises one or more alterations that increase clearance of the antibody in vivo.

53. The anti-hCTLA4 antibody of item 52, wherein the Fc portion of the antibody comprises at least one of the following alterations: M252A, M252L, M252S, M252R, R255K or H435R.

54. An anti-hCTLA4 antibody, which comprises the amino acid sequences of SEQ ID NOs: 189 and 191 or SEQ ID NOs: 193 and 195.

55. An anti-human PD1 (hPD1) antibody comprising a VH,
   wherein the VH comprises an amino acid sequence which comprises no more than four amino acid alterations relative to an amino acid sequence selected from the group consisting of SEQ ID NOs: 87, 97, 104, 110, 117, 122, 126, 133, 139, 144, 148, 154, 158, 162, and 166, and
   wherein the anti-hPD1 antibody inhibits the interaction of hPD1 with human PDL1 (hPDL1).

56. The anti-hPD1 antibody of item 55, wherein the VH comprises a VH CDR1, a VH CDR2, and a VH CDR3 comprising, respectively, the amino acid sequence of SEQ ID NOs: 88, 89, and 90, SEQ ID NOs: 98, 89 and 99, SEQ ID NOs: 105, 89, and 90, SEQ ID NOs: 105, 111, and 112, SEQ ID NOs: 105, 111, and 90, SEQ ID NOs: 88, 89, and 112, SEQ ID NOs: 88, 89, and 127, SEQ ID NOs: 88, 89, and 134, SEQ ID NOs: 98, 89, and 90, SEQ ID NOs: 98, 111, and 112, SEQ ID NOs: 149, 150, and 112, SEQ ID NOs: 105, 111, and 90, SEQ ID NOs: 149, 89, and 127, SEQ ID NOs: 88, 89, and 112, or SEQ ID NOs: 105, 89, and 127.

57. The anti-hPD1 antibody of item 55 or 56, wherein the amino acid sequence comprised by the VH comprises no more than three amino acid alterations relative to the amino acid sequence selected from the group consisting of SEQ ID NOs: 87, 97, 104, 110, 117, 122, 126, 133, 139, 144, 148, 154, 158, 162, and 166.

58. The anti-hPD1 antibody of item 57, wherein the amino acid sequence comprised by the VH comprises no more than two amino acid alterations relative to the amino acid sequence selected from the group consisting of SEQ ID NOs: 87, 97, 104, 110, 117, 122, 126, 133, 139, 144, 148, 154, 158, 162, and 166.

59. The anti-hPD1 antibody of item 58, wherein the amino acid sequence comprised by the VH comprises no more than one amino acid alteration relative to the amino acid sequence selected from the group consisting of SEQ ID NOs: 87, 97, 104, 110, 117, 122, 126, 133, 139, 144, 148, 154, 158, 162, and 166.

60. The anti-hPD1 antibody of any one of items 55 to 59, wherein the amino acid alteration(s) is (are) (a) substitution(s), and the substitution(s) is (are) (a) partner-directing alteration(s).

61. The anti-hPD1 antibody of item 59, wherein the amino acid sequence comprised by the VH is selected from the group consisting of SEQ ID NOs: 87, 97, 104, 110, 117, 122, 126, 133, 139, 144, 148, 154, 158, 162, and 166.

62. The anti-hPD1 antibody of any one of items 55 to 61, further comprising a VL, which comprises a VL CDR1, a VL CDR2, and a VL CDR3 comprising, respectively, the amino acid sequences of SEQ ID NOs:176, 177, and 179.

63. The anti-hPD1 antibody of item 62, wherein the VL CDR1, VL CDR2, and VL CDR3 comprise, respectively, the amino acid sequences of SEQ ID NOs: 93, 94, and 95, SEQ ID NOs: 102, 94, and 95, SEQ ID NOs: 93, 108, and 95, SEQ ID NOs: 115, 94, and 95, SEQ ID NOs: 120, 94, and 95, SEQ ID NOs: 102, 108, and 95, SEQ ID NOs: 130, 108, and 131, SEQ ID NOs: 137, 94, and 131, SEQ ID NOs: 142, 94, and 131, or SEQ ID NOs: 130, 94, and 131.

64. The anti-hPD1 antibody of any one of items 55 to 61, comprising a VL comprising an amino acid sequence which comprises no more than four amino acid alterations relative to an amino acid sequence selected from the group consisting of SEQ ID NOs: 92, 101, 107, 114, 119, 124, 129, 136, 141, 146, 152, 156, 160, 164, 168, 182, and 183.

65. The anti-hPD1 antibody of item 64, wherein the amino acid sequence comprised by the VL comprises no more than three amino acid alterations relative to the amino acid sequence selected from the group consisting of SEQ ID NOs: 92, 101, 107, 114, 119, 124, 129, 136, 141, 146, 152, 156, 160, 164, 168, 182, and 183.

66. The anti-hPD1 antibody of item 65, wherein the amino acid sequence comprised by the VL comprises no more than two amino acid alterations relative to the amino acid sequence selected from the group consisting of SEQ ID NOs: 92, 101, 107, 114, 119, 124, 129, 136, 141, 146, 152, 156, 160, 164, 168, 182, and 183.

67. The anti-hPD1 antibody of item 66, wherein the amino acid sequence comprised by the VL comprises no more than one amino acid alteration relative to the amino acid sequence selected from the group consisting of SEQ ID NOs: 92, 101, 107, 114, 119, 124, 129, 136, 141, 146, 152, 156, 160, 164, 168, 182, and 183.

68. The anti-hPD1 antibody of any one of items 64 to 67, wherein the amino acid alteration(s) relative to SEQ ID NOs: 92, 101, 107, 114, 119, 124, 129, 136, 141, 146, 152, 156, 160, 164, 168, 182, or 183 is (are) (a) substitution(s), and the substitution(s) is (are) (a) partner-directing alteration(s).

69. The anti-hPD1 antibody of item 67, wherein the amino acid sequence comprised by the VL is selected from the group consisting of SEQ ID NOs: 92, 101, 107, 114, 119, 124, 129, 136, 141, 146, 152, 156, 160, 164, 168, 182, and 183.

70. The anti-hPD1 antibody of any one of items 64 to 69, wherein the VL comprises a VL CDR1, a VL CDR2, and a VL CDR3 comprising, respectively, the amino acid sequences SEQ ID NOs: 93, 94, and 95, SEQ ID NOs: 102, 94, and 95, SEQ ID NOs: 93, 108, and 95, SEQ ID NOs: 115, 94, and 95, SEQ ID NOs: 120, 94, and 95, SEQ ID NOs: 102, 108, and 95, SEQ ID NOs: 130, 108, and 131, SEQ ID NOs: 137, 94, and 131, SEQ ID NOs: 142, 94, and 131, or SEQ ID NOs: 130, 94, and 131.

71. An anti-hPD1 antibody comprising a VL,
wherein the VL comprises an amino acid sequence which comprises no more than four amino acid alterations relative to an amino acid sequence selected from the group consisting of SEQ ID NOs: 92, 101, 107, 114, 119, 124, 129, 136, 141, 146, 152, 156, 160, 164, and 168, and
wherein the anti-hPD1 antibody inhibits the interaction of hPD1 with hPDL1.

72. The anti-hPD1 antibody of item 71 comprising a VL CDR1, a VL CDR2, and a VL CDR3 comprising, respectively, the amino acid sequences of SEQ ID NOs: 93, 94, and 95, SEQ ID NOs: 102, 94, and 95, SEQ ID NOs: 93, 108, and 95, SEQ ID NOs: 115, 94, and 95, SEQ ID NOs: 120, 94, and 95, SEQ ID NOs: 102, 108, and 95, SEQ ID NOs: 130, 108, and 131, SEQ ID NOs: 137, 94, and 131, SEQ ID NOs: 142, 94, and 131, or SEQ ID NOs: 130, 94, and 131.

73. The anti-PD1 antibody of item 71 or 72, wherein the amino acid sequence comprised by the VL comprises no more than three amino acid alterations relative to the amino acid sequence selected from the group consisting of SEQ ID NOs: 92, 101, 107, 114, 119, 124, 129, 136, 141, 146, 152, 156, 160, 164, and 168.

74. The anti-PD1 antibody of item 73, wherein the amino acid sequence comprised by the VL comprises no more than two amino acid alterations relative to the amino acid sequence selected from the group consisting of SEQ ID NOs: 92, 101, 107, 114, 119, 124, 129, 136, 141, 146, 152, 156, 160, 164, and 168.

75. The anti-PD1 antibody of item 74, wherein the amino acid sequence comprised by the VL comprises no more than one amino acid alteration relative to the amino acid sequence selected from the group consisting of SEQ ID NOs: 92, 101, 107, 114, 119, 124, 129, 136, 141, 146, 152, 156, 160, 164, and 168.

76. The anti-PD1 antibody of any one of items 71 to 75, wherein the amino acid alteration(s) is (are) (a) substitution(s), and the substitution(s) is (are) (a) partner-directing alteration(s).

77. The anti-PD1 antibody of item 75, wherein the amino acid sequence comprised by the VL is selected from the group consisting of SEQ ID NOs: 92, 101, 107, 114, 119, 124, 129, 136, 141, 146, 152, 156, 160, 164, and 168.

78. The anti-hPD1 antibody of any one of items 71 to 77, further comprising a VH, which comprises a VH CDR1, a VH CDR2, and a VH CDR3 comprising, respectively, the amino acid sequences of SEQ ID NOs: 170, 172, and 174.

79. The anti-hPD1 antibody of item 78, wherein the VH CDR1, VH CDR2, and VH CDR3 comprise, respectively, the amino acid sequences of SEQ ID NOs: 88, 89, and 90, SEQ ID NOs: 98, 89 and 99, SEQ ID NOs: 105, 89, and 90, SEQ ID NOs: 105, 111, and 112, SEQ ID NOs: 105, 111, and 90, SEQ ID NOs: 88, 89, and 112, SEQ ID NOs: 88, 89, and 127, SEQ ID NOs: 88, 89, and 134, SEQ ID NOs: 98, 89, and 90, SEQ ID NOs: 98, 111, and 112, SEQ ID NOs: 149, 150, and 112, SEQ ID NOs: 105, 111, and 90, SEQ ID NOs: 149, 89, and 127, SEQ ID NOs: 88, 89, and 112, or SEQ ID NOs: 105, 89, and 127.

80. The anti-hPD1 antibody of any one of items 71 to 77, further comprising a VH comprising an amino acid sequence which comprises no more than four amino acid alterations relative to an amino acid sequence selected from the group consisting of: SEQ ID NOs: 87, 97, 104, 110, 117, 122, 126, 133, 139, 144, 148, 154, 158, 162, 166, 180, and 181.

81. The anti-hPD1 antibody of item 80, wherein the amino acid sequence comprised by the VH comprises no more than three amino acid alterations relative to the amino acid sequence selected from the group consisting of: SEQ ID NOs: 87, 97, 104, 110, 117, 122, 126, 133, 139, 144, 148, 154, 158, 162, 166, 180, and 181.

82. The anti-hPD1 antibody of item 81, wherein the amino acid sequence comprised by the VH comprises no more than two amino acid alterations relative to the amino acid sequence selected from the group consisting of: SEQ ID NOs: 87, 97, 104, 110, 117, 122, 126, 133, 139, 144, 148, 154, 158, 162, 166, 180, and 181.

83. The anti-hPD1 antibody of item 82, wherein the amino acid sequence comprised by the VH comprises no more than one amino acid alteration relative to the amino acid sequence selected from the group consisting of: SEQ ID NOs: 87, 97, 104, 110, 117, 122, 126, 133, 139, 144, 148, 154, 158, 162, 166, 180, and 181.

84. The anti-hPD1 antibody of any one of items 80 to 83, wherein the amino acid alteration(s) is (are) (a) substitution(s), and the substitution(s) is (are) (a) partner-directing alteration(s).

85. The anti-hPD1 antibody of item 83, wherein the amino acid sequence comprised by the VH is selected from the group consisting of: SEQ ID NOs: 87, 97, 104, 110, 117, 122, 126, 133, 139, 144, 148, 154, 158, 162, 166, 180, and 181.

86. The anti-PD1 antibody of any one of items 80 to 85, wherein the VH comprises a VH CDR1, a VH CDR2, and a VH CDR3 comprising, respectively, the amino acid sequences of SEQ ID NOs: 88, 89, and 90, SEQ ID NOs: 98, 89 and 99, SEQ ID NOs: 105, 89, and 90, SEQ ID NOs: 105, 111, and 112, SEQ ID NOs: 105, 111, and 90, SEQ ID NOs: 88, 89, and 112, SEQ ID NOs: 88, 89, and 127, SEQ ID NOs: 88, 89, and 134, SEQ ID NOs: 98, 89, and 90, SEQ ID NOs: 98, 111, and 112, SEQ ID NOs: 149, 150, and 112, SEQ ID NOs: 105, 111, and 90, SEQ ID NOs: 149, 89, and 127, SEQ ID NOs: 88, 89, and 112, or SEQ ID NOs: 105, 89, and 127.

87. An anti-hPD1 antibody comprising a VH CDR1, VH CDR2, VH CDR3, VL CDR1, VL CDR2, and VL CDR3, which comprise, respectively, the following amino acid sequences:
 (a) SEQ ID NOs: 88, 89, 90, 93, 94, and 95;
 (b) SEQ ID NOs: 98, 89, 99, 102, 94, and 95;
 (c) SEQ ID NOs: 105, 89, 90, 93, 108, and 95;
 (d) SEQ ID NOs: 105, 111, 112, 115, 94, and 95;
 (e) SEQ ID NOs: 105, 111, 90, 120, 94, and 95;
 (f) SEQ ID NOs: 88, 89, 112, 102, 108, and 95;
 (g) SEQ ID NOs: 88, 89, 127, 130, 108, and 131;
 (h) SEQ ID NOs: 88, 89, 134, 137, 94, and 131;
 (i) SEQ ID NOs: 98, 89, 90, 142, 94, and 131;
 (j) SEQ ID NOs: 98, 111, 112, 130, 94, and 131;
 (k) SEQ ID NOs: 149, 150, 112, 130, 94, and 131;
 (l) SEQ ID NOs: 105, 111, 90, 142, 94, and 131;
 (m) SEQ ID NOs: 149, 89, 127, 115, 94, and 95;
 (n) SEQ ID NOs: 88, 89, 112, 93, 94, and 95; or
 (o) SEQ ID NOs: 105, 89, 127, 102, 108, and 95,
wherein the anti-hPD1 antibody inhibits the interaction of hPD1 with hPDL1.

88. The anti-hPD1 antibody of item 87, wherein the VH and the VL of the anti-hPD1 antibody each comprise an amino acid sequence, which, together, comprise two sequences, wherein one of the two sequences comprises not more than four amino acid alterations relative to one sequence in a pair of sequences and the other of the two sequences comprises not more than four amino acid alterations relative to the other sequence in the pair of sequences, and wherein the pair of sequences is selected from the group consisting of: SEQ ID NOs: 87 (VH) and 92 (VL); SEQ ID NOs: 97 (VH) and 101 (VL); SEQ ID NOs: 104 (VH) and 107 (VL); SEQ ID NOs: 110 (VH) and 114 (VL); SEQ ID NOs: 117 (VH) and 119 (VL); SEQ ID NOs: 122 (VH) and 124 (VL); SEQ ID NOs; 126 (VH) and 129 (VL); SEQ ID NOs: 133 (VH) and 136 (VL); SEQ ID NOs: 139 (VH) and 141 (VL); SEQ ID NOs: 144 (VH) and 146 (VL); SEQ ID NOs: 148 (VH) and 152 (VL); SEQ ID NOs: 154 (VH) and 156 (VL); SEQ ID NOs: 158 (VH) and 160 (VL); SEQ ID NOs: 162 (VH) and 164 (VL); and SEQ ID NOs: 166 (VH) and 168 (VL).

89. The anti-hPD1 antibody of item 88, wherein one of the two sequences comprises not more than three amino acid alterations relative to one sequence in the pair of sequences and the other of the two sequences comprises not more than three amino acid alterations relative to the other sequence in the pair of sequences.

90. The anti-hPD1 antibody of item 89, wherein one of the two sequences comprises not more than two amino acid alterations relative to one sequence in the pair of sequences and the other of the two sequences comprises not more than two amino acid alterations relative to the other sequence in the pair of sequences.

91. The anti-hPD1 antibody of item 90, wherein one of the two sequences comprises not more than one amino acid alteration relative to one sequence in the pair of sequences and the other of the two sequences comprises not more than one amino acid alteration relative to the other sequence in the pair of sequences.

92. The anti-hPD1 antibody of any one of items 88 to 91, wherein the alteration(s) is (are) (a) substitution(s), and the substitution(s) is (are) (a) partner-directing alteration(s).

93. The anti-hPD1 antibody of item 91, wherein one of the two sequences comprises one sequence in the pair of sequences and the other of the two sequences comprises the other sequence in the pair of sequences.

94. The anti-hPD1 antibody of any one of items 55 to 93, which is a human, humanized, or primate IgG antibody.

95. The anti-hPD1 antibody of item 94, which is (1) an IgG4 antibody or (2) an IgG1 antibody comprising the alteration K409R. 96. The anti-hPD1 antibody of item 94, which is an IgG1 antibody.

97. The anti-hPD1 antibody of any one of items 94 to 96, wherein the heavy chain (HC) or the light chain (LC) contains a first partner-directing alteration at one or more positions selected from the group consisting of positions 44, 105, 147, 168 and 181 in the HC and positions 43, 100, 131, 174, and 178 in the LC, wherein the partner-directing alteration is a substitution where a charged amino acid replaces another amino acid, wherein the substituted, charged amino acid of the partner-directing alteration forms part of a charge pair of contacting amino acids within the antibody, and wherein the contacting amino acids of the charge pair are selected from the group consisting of:

(a) 44R/K (HC) and 100D/E (LC) or 44D/E (HC) and 100R/K (LC);

(b) 105R/K (HC) and 43D/E (LC) or 105D/E (HC) and 43R/K (LC);

(c) 147R/K (HC) and 131D/E (LC) or 147D/E (HC) and 131R/K (LC);

(d) 168R/K (HC) and 174D/E (LC) or 168D/E (HC) and 174R/K (LC); and (e) 181R/K (HC) and 178D/E (LC) or 181D/E (HC) and 178R/K (LC).

98. The anti-hPD1 antibody of item 97, further comprising a second partner-directing alteration, wherein the second partner-directing alteration is a substitution of a charged amino acid for another amino acid, and wherein the substituted, charged amino acids of the first and second partner-directing alterations form the charge pair of contacting amino acids.

99. The anti-hPD1 antibody of item 97 or 98, wherein the anti-hPD1 antibody is an IgG1 antibody, wherein the HC or LC of the anti-hPD1 antibody contains a third partner-directing alteration at an amino acid in the HC or the LC, wherein the third partner-directing alteration is a cysteine substitution, and wherein the substituted cysteine of the third partner-directing alteration contacts a cysteine (1) in the HC if the third partner-directing alteration is in the LC or (2) in the LC if the third partner-directing alteration is in the HC, thereby forming a contacting pair of cysteines.

100. The anti-hPD1 antibody of item 99, wherein the contacting pair of cysteines is at positions selected from the group consisting of:

(a) position 126 of the HC and position 121 or 124 in the LC;

(b) position 128 in the HC and position 118 in the LC;

(c) position 133 in the HC and position 117 or 209 in the LC;

(d) position 134 or 141 in the HC and position 116 in the LC;

(e) position 168 in the HC and position 174 in the LC;

(f) position 170 in the HC and position 162 or 176 in the LC;

(g) position 173 in the HC and position 160 in the LC; and (h) position 183 in the HC and position 176 in the LC.

101. The anti-hPD1 antibody of item 100, wherein the contacting pair of cysteines is at a pair of positions selected from the group consisting of:

(a) position 126 of the HC and position 124 in the LC;

(b) position 128 of the HC and position 118 in the LC;

(c) position 133 of the HC and position 117 or 209 in the LC;

(d) position 134 of the HC and position 116 in the LC;

(e) position 168 of the HC and position 174 in the LC;

(f) position 170 of the HC and position 162 or 176 in the LC; and (g) position 173 in the HC and position 160 in the LC.

102. The anti-hPD1 antibody of any one of items 99 to 101, wherein if the third partner-directing alteration is in the HC, then the LC comprises a fourth partner-directing alteration which is a cysteine substitution at an amino acid contacting the amino acid of the third partner-directing alteration, or if the third partner-directing alteration is in the LC, then the HC comprises a fourth partner-directing alteration, which is a cysteine substitution at an amino acid contacting the amino acid of the third partner-directing alteration.

103. The anti-hPD1 of item 97 or 98, wherein the anti-hPD1 antibody is an IgG4 antibody, wherein the HC or LC of the anti-hPD1 antibody contains a third partner-directing alteration at an amino acid in the HC or LC, wherein the third partner-directing alteration is a cysteine substitution, and wherein the substituted cysteine of the third partner-directing alteration contacts a cysteine (1) in the HC if the third partner-directing alteration is in the LC or (2) in the LC if the second partner-directing alteration is in the HC, thereby forming a contacting pair of cysteines.

104. The anti-hPD1 antibody of item 103, wherein the contacting pair of cysteines is at positions within the HC and LC selected from the group consisting of:
    (a) position 126 in the HC and position 121 or 124 in the LC;
    (b) position 127 in the HC and position 121 in the LC;
    (c) position 128 in the HC and position 118 in the LC;
    (d) position 141 in the HC and position 116 in the LC;
    (e) position 168 in the HC and position 174 in the LC; and
    (f) position 170 or 173 in the HC and position 162 in the LC.

105. The anti-hPD1 antibody of item 103 or 104, wherein
    if the third partner-directing alteration is in the HC, then the LC comprises a fourth partner-directing alteration, which is a cysteine substitution at an amino acid contacting the amino acid of the third partner-directing alteration, or
    if the third partner-directing alteration is in the LC, then the HC comprises a fourth partner-directing alteration, which is a cysteine substitution at an amino acid contacting the amino acid of the third partner-directing alteration.

106. The anti-hPD1 antibody of any one of items 55 to 105, which comprises the alterations D399K/R and K/R409E/D.

107. An anti-hPD1 antibody, which comprises the amino acid sequences of SEQ ID NOs: 185 and 187.

108. A mixture of antibodies comprising the anti-hCTLA4 antibody of any one of items 1 to 54 and the anti-hPD1 antibody of any one of items 55 to 107, 109. The mixture of antibodies of item 108, comprising the anti-hCTLA4 antibody of item 8 and the anti-hPD1 antibody of item 61.

110. The mixture of antibodies of item 108 or 109, wherein the mixture is produced in a single host cell line.

111. The mixture of antibodies of item 110, which comprises not more than three major species of antibodies.

112. The mixture of antibodies of item 111, which comprises not more than two major species of antibodies.

113. One or more polynucleotide(s), which encode(s) the anti-hCTLA4 antibody of any one of items 1 to 54, the anti-hPD1 antibody of any one of items 55 to 107, or the mixture of antibodies of any one of items 108 to 112.

114. The polynucleotide(s) of item 113, which encode(s) the mixture of antibodies of any one of items 108 to 112.

115. One or more vector(s), which comprise(s) the polynucleotide(s) of item 113 or 114.

116. The vector(s) of item 115, which is (are) (a) viral vector(s).

117. The vector(s) of item 116, which is (are) (an) oncolytic viral vector(s),

118. The vector(s) of item 116 or 117, which is (are) (a) retroviral, adenoviral, adeno-associated viral (AAV), vaccinia viral, modified vaccinia viral Ankara (MVA), herpes viral, lentiviral, measles viral, coxsackie viral, Newcastle Disease viral, reoviral, or poxviral vector(s).

119. A pharmaceutical composition comprising the anti-hCTLA4 antibody of any one of items 1 to 54, the anti-hPD1 antibody of any one of items 55 to 107, the mixture of antibodies of any one of items 108 to 112, the polynucleotide(s) of item 113 or 114, or the vector(s) of any one of items 115 to 118.

120. A host cell, into which the polynucleotide(s) of item 113 or 114 or the vector(s) of item 115 or 116 has (have) been introduced.

121. The host cell of item 120, which is a mammalian cell.

122. The host cell of item 121, which is a CHO cell or a mouse myeloma cell.

123. A method for making an antibody or a mixture of antibodies comprising culturing the host cell of any one of items 120 to 122 and recovering the antibody or mixture of antibodies from the culture medium or the cell mass.

124. A method for treating a patient having a solid tumor or a hematological malignancy comprising administering to the patient the anti-hCTLA4 antibody of any one of items 1 to 54, the anti-hPD1 antibody of any one of items 55 to 107, the mixture of any one of items 108 to 112, the polynucleotide(s) of item 113 or 114, the vector(s) of any one of item 115 to 118, or the pharmaceutical composition of item 119.

125. The method of item 124, comprising administering the anti-hCTLA4 antibody, the anti-hPD1 antibody, or the mixture of antibodies.

126. The method of item 124 or 125, wherein the patient has melanoma, non-small cell lung cancer, small cell lung cancer, gastric cancer, bladder cancer, clear cell renal carcinoma, Hodgkin's lymphoma, or head and neck squamous cell cancer.

127. The method of any one of items 124 to 126, further comprising administering an additional therapy before, after, and/or concurrently with the anti-hCTLA4 antibody, the anti-hPD1 antibody, or the mixture of antibodies, the polynucleotide(s), the vector(s), or the pharmaceutical composition, wherein the additional therapy is selected from the group consisting of immunomodulatory molecules, radiation, a chemotherapeutic agent, a targeted biologic, a targeted inhibitor, and/or an oncolytic virus.

128. The method of item 127, wherein the additional therapy is radiation or a chemotherapeutic agent.

129. The method of item 127, wherein the additional therapy is a targeted biologic, a targeted inhibitor, and/or a immunomodulatory molecule selected from the group consisting of: an antagonist of PDL1, TIGIT, CCR4, CCR8, CSFR1a, B7H3, B7H4, CD96, or CD73; an agonist of GITR, 41BB, OX40, or CD40; an oncolytic virus such as talimogene laherparepvec (IMLYGIC™); a bispecific T cell engager (BiTE) such as blinatumomab; an indoleamine 2, 3 dioxygenase (IDO) inhibitor; an anti-angiogenic agent such as bevacizumab; an antibody-drug conjugate; and a tyrosine kinase inhibitor.

130. A method for inducing or enhancing an immune response in a patient comprising administering to the patient the anti-hCTLA4 antibody of any one of item 1 to 54, the anti-hPD1 antibody of any one of items 55 to 107, the mixture of any one of items 108 to 112, the polynucleotide(s) of item 113 or 114, the vector(s) of any one of items 115 to 118, or the pharmaceutical composition of item 119.

131. The method of item 130, comprising administering the mixture of antibodies, one or more vector(s) encoding the mixture of antibodies, or a pharmaceutical composition comprising the mixture of antibodies or the vector(s) encoding the mixture of antibodies.

132. The method of item 130 or 131, wherein the patient has melanoma, non-small cell lung cancer, small cell lung cancer, gastric cancer, bladder cancer, clear cell renal carcinoma, Hodgkin's lymphoma, or head and neck squamous cell cancer.

133. The method of any one of items 130 to 132, further comprising administering an additional therapy before, after, and/or concurrently with the anti-hCTLA4 antibody, the anti-hPD1 antibody, the mixture of antibodies, the polynucleotide(s), or the vector(s), wherein the additional therapy is selected from the group consisting of immunomodulatory molecules, radiation, a chemotherapeutic agent, a targeted biologic, a targeted inhibitor, and/or an oncolytic virus.

134. The method of item 133, wherein the additional therapy is radiation or a chemotherapeutic agent.

135. The method of item 133, wherein the additional therapy is a targeted biologic, a targeted inhibitor, and/or an immunomodulatory molecule selected from the group consisting of: an antagonist of PDL1, TIGIT, CCR4, CCR8, CSFR1a, B7H3, B7H4, CD96, or CD73; an agonist of GITR, 41BB, OX40, or CD40; an oncolytic virus such as talimogene laherparepvec (IMLYGIC™); a bispecific T cell engager (BiTE) such as blinatumomab; an indoleamine 2, 3 dioxygenase (IDO) inhibitor; an anti-angiogenic agent such as bevacizumab; an antibody-drug conjugate; and a tyrosine kinase inhibitor.

136. A method for treating a patient having an infection comprising administering to the patient the anti-hCTLA4 antibody of any one of items 1 to 54, the anti-hPD1 antibody of any one of items 55 to 107, the mixture of any one of items 108 to 112, the polynucleotide(s) of item 113 or 114, the vector(s) of any one of items 115 to 118, or the pharmaceutical composition of item 119.

137. An anti-human CTLA4 (hCTLA4) antibody comprising a heavy chain variable domain (VH) comprising a VH complementarity determining region 1 (CDR1), a VH complementarity determining region 2 (CDR2), and a VH complementarity determining region 3 (CDR3) comprising, respectively, the amino acid sequences of SEQ ID NOs: 3, 4, and 5, SEQ ID NOs: 3, 13 and 5, SEQ ID NOs: 3, 20, and 21, SEQ ID NOs: 3, 24, and 25, SEQ ID NOs: 3, 31, and 5, SEQ ID NOs: 3, 37, and 5, SEQ ID NOs: 3, 43, and 5, SEQ ID NOs: 3, 46, and 47, SEQ ID NOs: 3, 59, and 5, SEQ ID NOs: 3, 65, and 21, or SEQ ID NOs: 3, 70, and 21.

138. The anti-hCTLA4 antibody of item 137, wherein the VH comprises the amino acid sequence of SEQ ID NO:82.

139. The anti-hCTLA4 antibody of item 138, wherein the VH comprises the amino acid sequence of SEQ ID NO:83.

140. The anti-hCTLA4 antibody of item 139, wherein the VH comprises an amino acid sequence selected from the group consisting of SEQ ID NOs: 2, 12, 19, 23, 30, 36, 42, 45, 52, 58, 64, and 69.

141. An anti-hCTLA4 antibody comprising a light chain variable domain (VL) comprising a VL CDR1, a VL CDR2, and a VL CDR3 comprising, respectively, the amino acid sequences of SEQ ID NOs: 8, 9, and 10, SEQ ID NOs: 16, 9 and 17, SEQ ID NOs: 28, 9, and 17, SEQ ID NOs: 34, 9, and 17, SEQ ID NOs: 40, 9, and 10, SEQ ID NOs: 50, 9, and 17, SEQ ID NOs: 55, 9, and 56, SEQ ID NOs: 40, 9, and 62, SEQ ID NOs: 16, 9, and 62, or SEQ ID NOs: 73, 9, and 62.

142. The anti-hCTLA4 antibody of item 141, wherein the VL comprises the amino acid sequence of SEQ ID NO:84.

143. The anti-hCTLA4 antibody of item 142, wherein the VL comprises the amino acid sequence of SEQ ID NO:85.

144. The anti-hCTLA4 antibody of item 143, wherein the VL comprises an amino acid sequence selected from the group consisting of SEQ ID NOs: 7, 15, 27, 33, 39, 49, 54, 61, 67, and 72.

145. The anti-hCTLA4 antibody of any one of items 137 to 140, further comprising a VL comprising a VL CDR1, a VL CDR2, and a VL CDR3 comprising, respectively, the amino acid sequences of SEQ ID NOs: 8, 9, and 10, SEQ ID NOs: 16, 9 and 17, SEQ ID NOs: 28, 9, and 17, SEQ ID NOs: 34, 9, and 17, SEQ ID NOs: 40, 9, and 10, SEQ ID NOs: 50, 9, and 17, SEQ ID NOs: 55, 9, and 56, SEQ ID NOs: 40, 9, and 62, SEQ ID NOs: 16, 9, and 62, or SEQ ID NOs: 73, 9, and 62.

146. The anti-hCTLA4 antibody of item 145, comprising a VH CDR1, VH CDR2, VH CDR3, VL CDR1, VL CDR2, and VL CDR3, which comprise, respectively, the following amino acid sequences:
(a) SEQ ID NOs: 3, 4, 5, 8, 9, and 10;
(b) SEQ ID NOs: 3, 13, 5, 16, 9, and 17;
(c) SEQ ID NOs: 3, 20, 21, 16, 9, and 17;
(d) SEQ ID NOs: 3, 24, 25, 28, 9, and 17;
(e) SEQ ID NOs: 3, 31, 5, 34, 9, and 17;
(f) SEQ ID NOs: 3, 37, 5, 40, 9, and 10;
(g) SEQ ID NOs: 3, 43, 5, 28, 9, and 17;
(h) SEQ ID NOs: 3, 46, 47, 50, 9, and 17;
(i) SEQ ID NOs: 3, 31, 5, 55, 9, and 56;
(j) SEQ ID NOs: 3, 59, 5, 40, 9, and 62;
(k) SEQ ID NOs: 3, 65, 21, 16, 9, and 62; or
(l) SEQ ID NOs: 3, 70, 21, 73, 9, and 62.

147. The anti-hCTLA4 antibody of item 145, wherein the VL comprises the amino acid sequence of SEQ ID NO:84 and the VH comprises the amino acid sequence of SEQ ID NO:82.

148. The anti-hCTLA4 antibody of item 147, wherein the VL comprises the amino acid sequence of SEQ ID NO:85 and the VH comprises the amino acid sequence of SEQ ID NO:83.

149. The anti-hCTLA4 antibody of item 148, wherein the VL comprises an amino acid sequence selected from the group consisting of SEQ ID NOs: 7, 15, 27, 33, 39, 49, 54, 61, 67, and 72.

150. The anti-hCTLA4 antibody of item 149, wherein the VH and VL comprise, respectively, amino acid sequences selected from the group consisting of: SEQ ID NOs: 2 and 7; SEQ ID NOs: 12 and 15; SEQ ID NOs: 19 and 15; SEQ ID NOs: 23 and 27; SEQ ID NOs: 30 and 33; SEQ ID NOs: 36 and 39; SEQ ID NOs: 42 and 27; SEQ ID NOs: 45 and 49; SEQ ID NOs: 52 and 54; SEQ ID NOs: 58 and 61; SEQ ID NOs: 64 and 67; and SEQ ID NOs: 69 and 72.

151. The anti-hCTLA4 antibody of any one of items 137 to 150, which is a human, humanized or primate IgG antibody. 152. The anti-hCTLA4 antibody of item 151, which is an IgG4 antibody or an IgG1 antibody comprising the alteration K409R.

153. The anti-hCTLA4 antibody of item 151, which is an IgG1 antibody.

154. The anti-hCTLA4 antibody of any one of items 151 to 153,
wherein the heavy chain (HC) and/or the light chain (LC) contain at least one partner-directing alteration at one or more sites selected from the group consisting of positions 44, 105, 147, 168 and 181 in the HC and positions 43, 100, 131, 174, and 178 in the LC,
wherein the partner-directing alteration is a substitution where a charged amino acid replaces another amino acid,
wherein the substituted, charged amino acid of the partner-directing alteration forms part of a charge pair of contacting amino acids within the antibody, and
wherein the contacting pair of amino acids that form the charge pair are selected from the group consisting of:
(a) 44R/K (HC) and 100D/E (LC) or 44D/E (HC) and 100R/K (LC);
(b) 105R/K (HC) and 43D/E (LC) or 105D/E (HC) and 43R/K (LC);
(c) 147R/K (HC) and 131D/E (LC) or 147D/E (HC) and 131R/K (LC);

(d) 168R/K (HC) and 174D/E (LC) or 168D/E (HC) and 174R/K (LC); and (e) 181R/K (HC) and 178D/E (LC) or 181D/E (HC) and 178R/K (LC).

155. The anti-hCTLA4 antibody of item 151, 152, or 154, wherein the anti-hCTLA4 antibody is an IgG1 antibody, wherein the HC or LC of the anti-hCTLA4 antibody contains a second partner-directing alteration at an amino acid in the HC or the LC, wherein the second partner-directing alteration is a substitution where a cysteine replaces another amino acid, and wherein the substituted cysteine of the second partner-directing alteration contacts a cysteine (1) in the HC if the second partner-directing alteration is in the LC or (2) in the LC if the second partner-directing alteration is in the HC.

156. The anti-hCTLA4 antibody of item 155, wherein the contacting pairs of cysteines are at pairs of positions within the HC and LC selected from the group consisting of:

(a) the amino acids at position 126 of the HC and position 121 in the LC;

(b) the amino acids at position 170 in the HC and position 162 in the LC;

(c) the amino acids at position 170 in the HC and position 176 in the LC;

(d) the amino acids at position 173 in the HC and position 160 in the LC; and (e) the amino acids at position 183 in the HC and position 176 in the LC.

157. The anti-hCTLA4 antibody of item 155 or 156, wherein if the second partner-directing alteration is in the HC, then the LC comprises a third partner-directing alteration which is a cysteine substitution at an amino acid contacting the amino acid of the second partner-directing alteration, or if the second partner-directing alteration is in the LC, then the HC comprises a third partner-directing alteration, which is a cysteine substitution at an amino acid contacting the amino acid of the second partner-directing alteration.

158. The anti-hCTLA4 antibody of any one of items 151, 152, and 154, wherein the anti-hCTLA4 antibody is an IgG4 antibody, wherein the HC or LC of the anti-hCTLA4 antibody contains a second partner-directing alteration at an amino acid in the HC or LC, wherein the second partner-directing alteration is a substitution where a cysteine replaces another amino acid, and wherein the substituted cysteine of the second partner-directing alteration contacts a cysteine (1) in the HC if the second partner-directing alteration is in the LC or (2) in the LC if the second partner-directing alteration is in the HC.

159. The anti-hCTLA4 antibody of item 158, wherein the contacting pairs of cysteines are at pairs of positions within the HC and LC selected from the group consisting of:

(a) the amino acids at position 170 in the HC and position 162 in the LC;

(b) the amino acids at position 173 in the HC and position 162 in the LC; and (c) the amino acids at position 183 in the HC and position 176 in the LC.

160. The anti-hCTLA4 antibody of item 159, wherein if the second partner-directing alteration is in the HC, then the LC comprises a third partner-directing alteration, which is a cysteine substitution at an amino acid contacting the amino acid of the second partner-directing alteration, or if the second partner-directing alteration is in the LC, then the HC comprises a third partner-directing alteration, which is a cysteine substitution at an amino acid contacting the amino acid of the second partner-directing alteration.

161. The anti-hCTLA4 antibody of any one of items 151 to 160, which comprises the alterations D399K/R and K409D/E.

162. The anti-hCTLA4 antibody of any one of items 151 to 161, wherein the Fc portion of the antibody comprises one or more alterations that increase clearance of the antibody the in vivo.

163. The anti-hCTLA4 antibody of item 162, wherein the Fc portion of the antibody comprises at least one of the following alterations: M252A, M252L, M252S, M252R, R255K or H435R.

164. An anti-hPD1 antibody comprising a VH comprising a VH CDR1, a VH CDR2, and a VH CDR3 comprising, respectively, the amino acid sequences of SEQ ID NOs: 88, 89, and 90, SEQ ID NOs: 98, 89 and 99, SEQ ID NOs: 105, 89, and 90, SEQ ID NOs: 105, 111, and 112, SEQ ID NOs: 105, 111, and 90, SEQ ID NOs: 88, 89, and 112, SEQ ID NOs: 88, 89, and 127, SEQ ID NOs: 88, 89, and 134, SEQ ID NOs: 98, 89, and 90, SEQ ID NOs: 98, 111, and 112, SEQ ID NOs: 149, 150, and 112, SEQ ID NOs; 105, 111, and 90, SEQ ID NOs: 149, 89, and 127, or SEQ ID NOs: 105, 89, and 127.

165. The anti-hPD1 antibody of item 164, wherein the VH comprises the amino acid sequence of SEQ ID NO:180.

166. The anti-hPD1 antibody of item 165, wherein the VH comprises the amino acid sequence of SEQ ID NO:181.

167. The anti-hPD1 antibody of item 166, wherein the VH comprises an amino acid sequence selected from the group consisting of SEQ ID NOs: 87, 97, 104, 110, 117, 122, 126, 133, 139, 144, 148, 154, 158, 162, and 166.

168. An anti-hPD1 antibody comprising a VL comprising a VL CDR1, a VL CDR2, and a VL CDR3 comprising, respectively, the amino acid sequences of SEQ ID NOs: 93, 94, and 95, SEQ ID NOs: 102, 94, and 95, SEQ ID NOs: 93, 108, and 95, SEQ ID NOs: 115, 94, and 95, SEQ ID NOs: 120, 94, and 95, SEQ ID NOs: 102, 108, and 95, SEQ ID NOs: 130, 108, and 131, SEQ ID NOs: 137, 94, and 131, SEQ ID NOs: 142, 94, and 131, or SEQ ID NOs: 130, 94, and 131.

169. The anti-hPD1 antibody of item 168, wherein the VL comprises the amino acid sequence of SEQ ID NO:182.

170. The anti-hPD1 antibody of item 169, wherein the VL comprises the amino acid sequence of SEQ ID NO:183.

171. The anti-hPD1 antibody of item 170, wherein the VL comprises an amino acid sequence selected from the group consisting of SEQ ID NOs: 92, 101, 107, 114, 119, 124, 129, 136, 141, 146, 152, 156, 160, 164, and 168.

172. The anti-hPD1 antibody of any one of items 164 to 167, further comprising a VL comprising a VL CDR1, a VL CDR2, and a VL CDR3 comprising, respectively, the amino acid sequences of SEQ ID NOs: 93, 94, and 95, SEQ ID NOs: 102, 94, and 95, SEQ ID NOs: 93, 108, and 95, SEQ ID NOs: 115, 94, and 95, SEQ ID NOs: 120, 94, and 95, SEQ ID NOs: 102, 108, and 95, SEQ ID NOs: 130, 108, and 131, SEQ ID NOs: 137, 94, and 131, SEQ ID NOs: 142, 94, and 131, or SEQ ID NOs; 130, 94, and 131.

173. The anti-hPD1 antibody of item 172, comprising a VH CDR1, VH CDR2, VH CDR3, VL CDR1, VL CDR2, and VL CDR3, which comprise, respectively, the following amino acid sequences:

(a) SEQ ID NOs: 88, 89, 90, 93, 94, and 95;

(b) SEQ ID NOs: 98, 89, 99, 102, 94, and 95;

(c) SEQ ID NOs: 105, 89, 90, 93, 108, and 95;

(d) SEQ ID NOs: 105, 111, 112, 115, 94, and 95;

(e) SEQ ID NOs: 105, 111, 90, 120, 94, and 95;

(f) SEQ ID NOs: 88, 89, 112, 102, 108, and 95;
(g) SEQ ID NOs: 88, 89, 127, 130, 108, and 131;
(h) SEQ ID NOs: 88, 89, 134, 137, 94, and 131;
(i) SEQ ID NOs: 98, 89, 90, 142, 94, and 131;
(j) SEQ ID NOs: 98, 111, 112, 130, 94, and 131;
(k) SEQ ID NOs: 149, 150, 112, 130, 94, and 131;
(l) SEQ ID NOs: 105, 111, 90, 142, 94, and 131;
(m) SEQ ID NOs: 149, 89, 127, 115, 94, and 95;
(n) SEQ ID NOs: 88, 89, 112, 93, 94, and 95; or
(o) SEQ ID NOs: 105, 89, 127, 102, 108, and 95.

174. The anti-hPD1 antibody of item 172 or 173, wherein the VL comprises the amino acid sequence of SEQ ID NO:182.

175. The anti-hPD1 antibody of item 174, wherein the VL comprises the amino acid sequence of SEQ ID NO:183.

176. The anti-hPD1 antibody of item 175, wherein the VL comprises an amino acid sequence selected from the group consisting of SEQ ID NOs: 92, 101, 107, 114, 119, 124, 129, 136, 141, 146, 152, 156, 160, 164, and 168.

177. The anti-hPD1 antibody of item 174, wherein the VH and VL comprise, respectively, amino acid sequences selected from the group consisting of: SEQ ID NOs: 87 and 92; SEQ ID NOs: 97 and 101; SEQ ID NOs: 104 and 107; SEQ ID NOs: 110 and 114; SEQ ID NOs: 117 and 119; SEQ ID NOs: 122 and 124; SEQ ID NOs: 126 and 129; SEQ ID NOs: 133 and 136; SEQ ID NOs: 139 and 141; SEQ ID NOs: 144 and 146; SEQ ID NOs: 148 and 152; SEQ ID NOs: 154 and 156; SEQ ID NOs: 158 and 160; SEQ ID NOs: 162 and 164; and SEQ ID NOs: 166 and 168.

178. The anti-hPD1 antibody of any one of items 164 to 177, which is a human, humanized, or primate IgG antibody.

179. The anti-hPD1 antibody of item 178, which is an IgG4 antibody or an IgG1 antibody comprising the alteration K409R.

180. The anti-hPD1 antibody of item 178, which is an IgG1 antibody.

181. The anti-hPD1 antibody of any one of items 178 to 180,
wherein the HC and/or LC contain at least one partner-directing alteration at one or more sites selected from the group consisting of positions 44, 105, 147, 168 and 181 in the HC and positions 43, 100, 131, 174, and 178 in the LC,
wherein the partner-directing alteration is a substitution where a charged amino acid replaces another amino acid,
wherein the substituted, charged amino acid of the partner-directing alteration forms part of a charge pair within the antibody, and
wherein the contacting pair of amino acids that form the charge pair are selected from the group consisting of:
(a) 44R/K (HC) and 100D/E (LC) or 44D/E (HC) and 100R/K (LC);
(b) 105R/K (HC) and 43D/E (LC) or 105D/E (HC) and 43R/K (LC);
(c) 147R/K (HC) and 131D/E (LC) or 147D/E (HC) and 131R/K (LC);
(d) 168R/K (HC) and 174D/E (LC) or 168D/E (HC) and 174R/K (LC); and
(e) 181R/K (HC) and 178D/E (LC) or 181D/E (HC) and 178R/K (LC).

182. The anti-hPD1 antibody of item 178, 179, or 181,
wherein the anti-hPD1 antibody is an IgG1 antibody,
wherein the HC or LC of the anti-hCTLA4 antibody contains a second partner-directing alteration at an amino acid in the HC or the LC,
wherein the second partner-directing alteration is a substitution where a cysteine replaces another amino acid, and
wherein the substituted cysteine of the second partner-directing alteration contacts a cysteine (1) in the HC if the second partner-directing alteration is in an LC or (2) in the LC if the second partner-directing alteration is in an HC.

183. The anti-hPD1 antibody of item 182, wherein the contacting pairs of cysteines are at pairs of positions within the HC and LC selected from the group consisting of:
(a) the amino acids at position 126 of the HC and position 121 in the LC;
(b) the amino acids at position 170 in the HC and position 162 in the LC;
(c) the amino acids at position 170 in the HC and position 176 in the LC;
(d) the amino acids at position 173 in the HC and position 160 in the LC; and
(e) the amino acids at position 183 in the HC and position 176 in the LC, 184. The anti-hPD1 antibody of claim 182 or 183, wherein
if the second partner-directing alteration is in the HC, then the LC comprises a third partner-directing alteration, which is a cysteine substitution at an amino acid contacting the amino acid of the second partner-directing alteration, or
if the second partner-directing alteration is in the LC, then the HC comprises a third partner-directing alteration, which is a cysteine substitution at an amino acid contacting the amino acid of the second partner-directing alteration.

185. The anti-hPD1 antibody of any one of items 178, 179, and 181,
wherein the anti-hPD1 antibody is an IgG4 antibody,
wherein the HC or LC of the anti-hPD1 antibody contains a second partner-directing alteration at an amino acid in the HC or LC,
wherein the second partner-directing alteration is a substitution where a cysteine replaces another amino acid,
wherein the substituted cysteine of the second partner-directing alteration contacts a cysteine (1) in the HC if the second partner-directing alteration is in the LC or (2) in the LC if the second partner-directing alteration is in the HC.

186. The anti-hPD1 antibody of item 185, wherein the contacting pairs of cysteines are at pairs of positions within the HC and LC selected from the group consisting of:
(a) the amino acids at position 170 in the HC and position 162 in the LC;
(b) the amino acids at position 173 in the HC and position 162 in the LC; and
(c) the amino acids at position 183 in the HC and position 176 in the LC.

187. The anti-hPD1 antibody of item 186, wherein
if the second partner-directing alteration is in the HC, then the LC comprises a third partner-directing alteration, which is a cysteine substitution at an amino acid contacting the amino acid of the second partner-directing alteration, or
if the second partner-directing alteration is in the LC, then the HC comprises a third partner-directing alteration, which is a cysteine substitution at an amino acid contacting the amino acid of the second partner-directing alteration.

188. The anti-hPD1 antibody of any one of items 178 to 187, which comprises the alterations D399K/R and K409D/E.

189. A mixture of antibodies comprising the anti-hCTLA4 antibody of any one of items 137 to 163 and the anti-hPD1 antibody of any one of items 164 to 188.

190. The mixture of antibodies of item 189, comprising the anti-hCTLA4 antibody of item 151 and the anti-hPD1 antibody of item 178.

191. The mixture of antibodies of items 190, wherein the Fc portion of the anti-hCTLA4 antibody comprises one or more alterations that increase clearance of the anti-hCTLA4 antibody in vivo.

192. The mixture of antibodies of item 191, wherein the Fc portion of the anti-hCTLA4 antibody comprises at least one of the following alterations: M252A, M252L, M252S, M252R, R255K or H435R.

193. The mixture of antibodies of any one of items 189 to 192, wherein the mixture is produced in a single host cell line.

194. The mixture of antibodies of item 193, which comprises not more than three major species of antibodies.

195. The mixture of antibodies of any one of items 190 to 194,
wherein the HC and/or the LC of either one of or both the anti-hCTLA4 antibody and the anti-hPD1 antibody contain(s) at least one partner-directing alteration at one or more sites selected from the group consisting of positions 44, 105, 147, 168 and 181 in the HCs and positions 43, 100, 131, 174, and 178 in the LCs,
wherein the partner-directing alteration is a substitution where a charged amino acid replaces any other amino acid,
wherein the substituted, charged amino acid of the partner-directing alteration forms part of a charge pair of amino acids within either or both cognate HC/LC pairs, and
wherein the contacting pair of amino acids that form the charge pair are selected from the group consisting of:
(a) 44R/K (HC) and 100D/E (LC) or 44D/E (HC) and 100R/K (LC);
(b) 105R/K (HC) and 43D/E (LC) or 105D/E (HC) and 43R/K (LC);
(c) 147R/K (HC) and 131D/E (LC) or 147D/E (HC) and 131R/K (LC);
(d) 168R/K (HC) and 174D/E (LC) or 168D/E (HC) and 174R/K (LC); and
(e) 181R/K (HC) and 178D/E (LC) or 181D/E (HC) and 178R/K (LC).

196. The mixture of antibodies of any one of items 190 to 195,
wherein the heavy and/or light chains of either one or both of the anti-hCTLA4 antibody and the anti-hPD1 antibody contain(s) a second partner-directing alteration in an HC or LC,
wherein the antibody in which the second partner-directing alteration occurs is an IgG1 antibody,
wherein the second partner-directing alteration is a substitution where a cysteine replaces another amino acid, and
wherein the substituted cysteine of the second partner-directing alteration contacts a cysteine (1) in the cognate HC if the second partner-directing alteration is in the LC of one or both antibodies or (2) in the cognate LC if the second partner-directing alteration is in the HC of one or both antibodies.

197. The mixture of antibodies of item 196, wherein the contacting pairs of cysteines are at pairs of positions within the cognate HC/LC pair(s) of either or both antibodies selected from the group consisting of:
(a) the amino acids at position 126 of the HC and position 121 in the LC;
(b) the amino acids at position 170 in the HC and position 162 in the LC;
(c) the amino acids at position 170 in the HC and position 176 in the LC;
(d) the amino acids at position 173 in the HC and position 160 in the LC; and
(e) the amino acids at position 183 in the HC and position 176 in the LC.

198. The mixture of antibodies of item 196 or 197, wherein
if the second partner-directing alteration is in the HC(s) of one or both antibodies, then the cognate LC(s) comprise(s) a third partner-directing alteration, which is a cysteine substitution at an amino acid contacting the amino acid of the second partner-directing alteration, or
if the second partner-directing alteration is in the LC(s) of one or both antibodies, then the cognate HC(s) comprise(s) a third partner-directing alteration, which is a cysteine substitution at an amino acid contacting the amino acid of the second partner-directing alteration.

199. The mixture of antibodies of any one of items 190 to 195,
wherein the heavy and/or light chains of the anti-hCTLA4 antibody and/or the anti-hPD1 antibody contain(s) a fourth partner-directing alteration in an HC or LC,
wherein the antibody or antibodies in which the fourth partner-directing alteration occurs is an IgG4 antibody,
wherein the fourth partner-directing alteration is a substitution where a cysteine replaces another amino acid, and
wherein the substituted cysteine of the fourth partner-directing alteration contacts a cysteine (1) in the cognate HC if the fourth partner-directing alteration is in the LC of one or both antibodies or (2) in the cognate LC if the fourth partner-directing alteration is in the HC of one or both antibodies.

200. The mixture of antibodies of item 199, wherein the contacting pairs of cysteines are at pairs of positions within a cognate HC/LC pair selected from the group consisting of:
(a) the amino acids at position 170 in the HC and position 162 in the LC;
(b) the amino acids at position 173 in the HC and position 162 in the LC; and
(c) the amino acids at position 183 in the HC and position 176 in the LC.

201. The mixture of antibodies of item 200, wherein
if the fourth partner-directing alteration is in the HC(s) of one or both antibodies, then the cognate LC(s) comprise(s) a fifth partner-directing alteration, which is a cysteine substitution at an amino acid contacting the amino acid of the fourth partner-directing alteration, or
if the fourth partner-directing alteration is in the LC(s) of one or both antibodies, then the cognate HC(s) comprise(s) a fifth partner-directing alteration, which is a cysteine substitution at an amino acid contacting the amino acid of the fourth partner-directing alteration.

202. The mixture of antibodies of any one of items 189 to 201, wherein the mixture comprises not more than two major species of antibodies.

203. The mixture of antibodies of item 202, wherein (1) the anti-hPD1 antibody is an IgG4 antibody or an IgG1 antibody comprising the alteration K409R and (2) the anti-hCTLA4 antibody is an IgG1 antibody comprising the alterations D399K/R and K409D/E.

204. One or more polynucleotide(s), which encode the anti-hCTLA4 antibody of any one of items 137 to 163, the anti-hPD1 antibody of any one of items 164 to 188, or mixture of antibodies of any one of items 189 to 203.

205. The polynucleotide(s) of item 204, which encode(s) the mixture of antibodies of any one of items 189 to 203.

206. One or more vector(s), which comprise(s) the polynucleotide(s) of item 204 or 205.

207. The vector(s) of item 206, which is (are) (a) viral vector(s).

208. The vector(s) of item 207, which is (are) (an) oncolytic viral vector(s).

209. The vector(s) of item 207 or 208, which is (are) (a) retroviral, adenoviral, adeno-associated viral (AAV), vaccinia viral, modified vaccinia viral Ankara (MVA), herpes viral, lentiviral, measles viral, coxsackie viral, Newcastle Disease viral, reoviral, or poxviral vector(s).

210. A pharmaceutical composition comprising the anti-hCTLA4 antibody of any one of items 137 to 163, the anti-hPD1 antibody of any one of items 164 to 188, the mixture of antibodies of any one of items 189 to 203, the polynucleotide(s) of item 204 or 205, or the vector(s) of any one of items 206 to 209.

211. A host cell, into which the polynucleotide(s) of item 204 or 205 or the vector(s) of items 206 or 207 has (have) been introduced.

212. The host cell of item 211, which is a mammalian cell.

213. The host cell of item 212, which is a CHO cell or a mouse myeloma cell.

214. A method for making an antibody or a mixture of antibodies comprising culturing the host cell of any one of items 211 to 213 and recovering the antibody or mixture of antibodies from the culture medium or the cell mass.

215. A method for treating a patient having a solid tumor or a hematological malignancy comprising administering the anti-hCTLA4 antibody of any one of items 137 to 163, the anti-hPD1 antibody of any one of items 164 to 188, the mixture of any one of items 189 to 203, the polynucleotide(s) of item 204 or 205, the vector(s) of any one of items 206 to 209, or the pharmaceutical composition of item 210.

216. The method of item 215, comprising administering the anti-hCTLA4 antibody of item 146, the anti-hPD1 antibody of item 173, or the mixture of antibodies of item 189.

217. The method of item 215 or 216, wherein the patient has melanoma, non-small cell lung cancer, small cell lung cancer, gastric cancer, bladder cancer, clear cell renal carcinoma, Hodgkin's lymphoma, or head and neck squamous cell cancer.

218. The method of any one of items 216 to 217, further comprising administering an additional therapy before, after, and/or concurrently with the anti-hCTLA4 antibody, the anti-hPD1 antibody, the mixture of antibodies, the polynucleotide(s), the vector(s), or the pharmaceutical composition, wherein the additional therapy is selected from the group consisting of immunomodulatory molecules, radiation, a chemotherapeutic agent, a targeted biologic, a targeted inhibitor, and/or an oncolytic virus.

219. The method of item 218, wherein the additional therapy is radiation or a chemotherapeutic agent.

220. The method of item 218, wherein the additional therapy is an antagonist of PDL1, TIGIT, CCR4, CCR8, CSFR1a, B7H3, B7H4, CD96, or CD73, an agonist of GITR, 41BB, OX40, or CD40, an oncolytic virus such as talimogene laherparepvec (IMLYGIC™), a bispecific T cell engager (BiTE) such as blinatumomab, an indoleamine 2, 3 dioxygenase (IDO) inhibitor, an anti-angiogenic agent such as bevacizumab, an antibody-drug conjugate, or a tyrosine kinase inhibitor.

221. A method for inducing or enhancing an immune response in a patient comprising administering to the patient the anti-hCTLA4 antibody of any one of items 137 to 163, the anti-hPD1 antibody of any one of items 164 to 188, the mixture of any one of items 189 to 203, the polynucleotide(s) of item 204 or 205, the vector(s) of any one of items 206 to 209, or the pharmaceutical composition of item 210.

222. The method of item 221, comprising administering the mixture of antibodies of any one of items 189 to 203 or a vector comprising the polynucleotide(s) of item 206.

223. The method of item 221 or 222, wherein the patient has melanoma, non-small cell lung cancer, small cell lung cancer, gastric cancer, bladder cancer, clear cell renal carcinoma, Hodgkin's lymphoma, or head and neck squamous cell cancer.

224. The method of any one of items 221 to 223, further comprising administering an additional therapy before, after, and/or concurrently with the antibody, the mixture of antibodies, the polynucleotide(s), the vector(s), or the pharmaceutical composition, wherein the additional therapy is selected from the group consisting of immunomodulatory molecules, radiation, a chemotherapeutic agent, a targeted biologic, a targeted inhibitor, and/or an oncolytic virus 225. The method of item 224, wherein the additional therapy is radiation or a chemotherapeutic agent.

226. The method of item 224, wherein the additional therapy is an antagonist of PDL1, TIGIT, CCR4, CCR8, CSFR1a, B7H3, B7H4, CD96, or CD73, an agonist of GITR, 41BB, OX40, or CD40, an oncolytic virus such as talimogene laherparepvec (IMLYGIC™), a bispecific T cell engager (BiTE) such as blinatumomab, an indoleamine 2, 3 dioxygenase (IDO) inhibitor, an anti-angiogenic agent such as bevacizumab, an antibody-drug conjugate, or a tyrosine kinase inhibitor.

227. A method for treating a patient having an infection comprising administering to the patient the anti-hCTLA4 antibody of any one of items 137 to 163, the anti-hPD1 antibody of any one of items 164 to 188, or the mixture of any one of items 189 to 203.

228. The method of item 227, comprising administering the anti-hCTLA4 antibody of item 146, the anti-hPD1 antibody of item 173, or the mixture of item 193.

BRIEF DESCRIPTION OF THE FIGURES

FIG. 1: Amino acid sequences of anti-hCTLA4 antibody VH CDRs. Amino acids are identified with their one letter designation. The leftmost column states the name of each antibody as referred to herein. The CDRs for the VH of each antibody are shown in the same row to the right of the name, as indicated. Amino acids that vary from the amino acid at the same site in the CDRs of antibody 1E1 are shown in boldface italic type. Under the CDRs for the twelve antibodies is a consensus sequence for each CDR in plain boldface type. At sites in the consensus sequence that can vary, alternate amino acids that can occur at the site are shown below, with the most common amino acid (or one of two equally common amino acids that are more common than all others) shown in the full sequence of the CDR above the alternate amino acids.

FIG. 2: Amino acid sequences of anti-hCTLA4 antibody VL CDRs. The antibody names, CDR sequences, varying amino acids, and consensus CDR sequences are indicated as in FIG. 1.

FIG. 3: Amino acid sequences of anti-hCTLA4 VHs. The name of each antibody is indicated to the left of each row of sequence. The mature amino acid sequences of the VHs of twelve CTLA4 antibodies are shown. CDRs are underlined. The numbering according to Kabat et al., SEQUENCES OF PROTEINS OF IMMUNOLOGICAL INTEREST, FIFTH EDITION, U.S. Department of Health and Human Services, Public Health Service, National Institutes of Health, NIH Publication No. 91-3242, 1991, is shown above the sequence at 20 amino acid intervals. This numbering does not in all cases correspond to the actual number of amino acids because inserted amino acids (indicated by a #), which do not count in this numbering system, occur at a number of sites throughout the sequence. Amino acids that vary among the twelve sequences are shown in boldface type. An illustration of this numbering system, as applied to human VHs, is shown in Table 5 of International Application No. PCT/US2017/030676, which is incorporated herein by reference, and in Table 2 below.

FIG. 4: Amino acid sequences of anti-hCTLA4 VLs. CDRs and varying amino acids are indicated as in FIG. 3 using the numbering system of Kabat et al, supra. An illustration of this numbering system, as applied to VLs, is shown in Table 9 of International Application No. PCT/US2017/030676, which is incorporated herein by reference, and in Table 6 below. There are no inserted amino acids in these sequences.

FIG. 5: Amino acid sequences of anti-hPD1 antibody VH CDRs. Antibody names, CDR sequences, varying amino acids, and consensus sequences are indicated as in FIG. 1.

FIG. 6: Amino acid sequences of anti-hPD1 antibody VL CDRs. Antibody names, CDR sequences, varying amino acids, and consensus sequences are indicated as in FIG. 1.

FIG. 7: Amino acid sequences of anti-hPD1 VHs. The name of each antibody (which is a number) is indicated to the left of each row of sequence. All other indications are as described for FIG. 3.

FIG. 8: Amino acid sequences of anti-hPD1 VLs. All indications are as described for FIG. 7.

FIG. 18: Mass spectrometry of antibodies. Procedures are described in Example 11. The x axes show the deconvoluted mass, and the y axes show counts, which are reflective of the quantity of protein of a given mass. Panels A and B show data from a mixture of altered anti-PD1 #1 and altered anti-CTLA4 10D4 antibodies prepared in a single host cell line as described in Example 11.

FIG. 19: Mass spectrometry of antibodies. Procedures are described in Example 11. The x axes show the deconvoluted mass, and the y axes show counts, which are reflective of the quantity of protein of a given mass. Panels A and B show data from a mixture of altered anti-PD1 #1 and altered anti-CTLA4 11F4 antibodies prepared in a single host cell line as described in Example 11.

REFERENCE TO SEQUENCE LISTING

Figure 9:
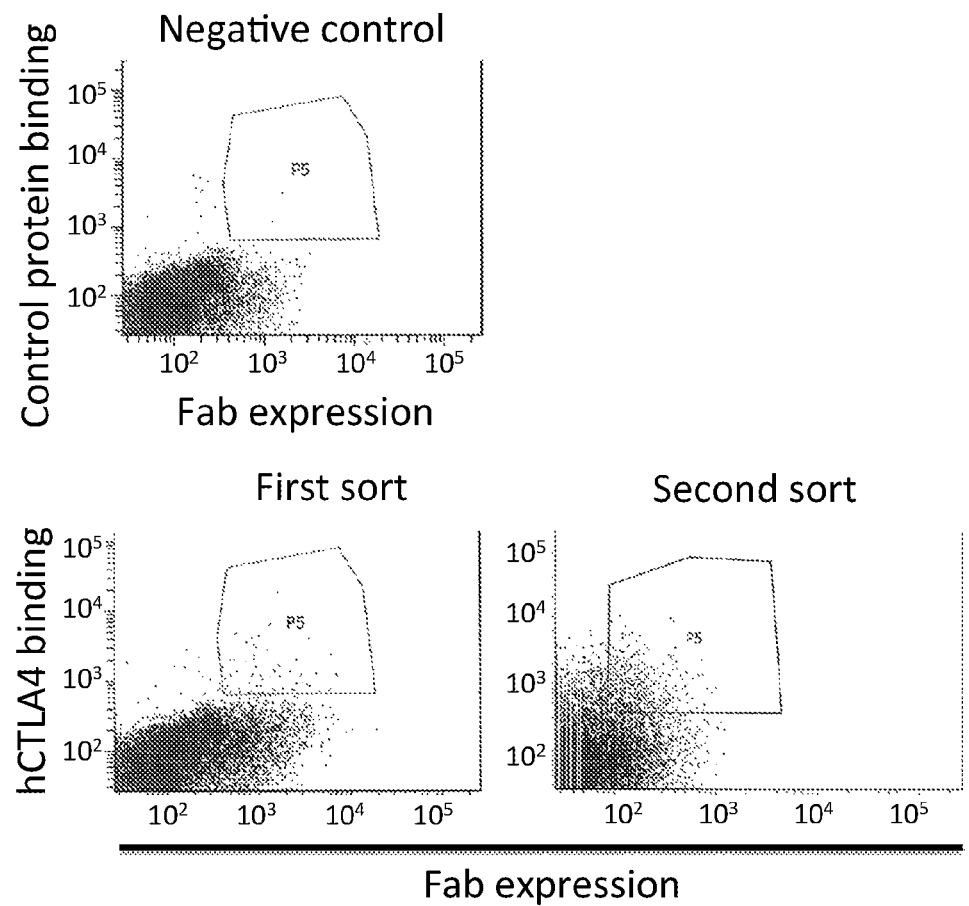
FIG. 9: Cell sorting to select anti-hCTLA4 Fab fragments. Procedures are described in detail in Example 1. The x axes indicate levels of expression of the displayed Fab fragments on the yeast cells as detected with a labeled antibody specific to the HA tag between the CH1 domain (CH1) of the displayed Fab fragments and a cell wall protein, agglutinin. The y axes indicate the amount of binding of a labeled negative control protein (a labeled PD1-Fc fusion protein) to the cells in the upper graph or amount of binding of a labeled hCTLA4:Fc fusion protein to the cells in the lower two graphs. The polygon labeled "PS" indicates the sorting window. The lower two panels show data from the first (at left) and second (at right) sorts in the selection procedure.

This application includes a sequence listing submitted electronically in a file entitled SB002WO_ST25.txt created Sep. 20, 2017 and having a size of 185 kilobytes (KB), which is incorporated herein by reference.

DETAILED DESCRIPTION

Described herein are antibodies that bind to human CTLA4 (hCTLA4), antibodies that bind to human PD1 (hPD1), mixtures of these antibodies, polynucleotides encoding these antibodies and mixtures, host cells containing such polynucleotides, and methods of treatment with these antibodies, mixtures, and polynucleotides. Further described herein are methods of making mixtures of these anti-hCTLA4 antibodies and anti-hPD1 antibodies utilizing a single host cell line for producing the mixture. The anti-hCTLA4 antibodies described herein can bind to both human and cynomolgus monkey CTLA4, can inhibit binding of the hCTLA4 ligands hB7-1 and/or hB7-2 to hCTLA4, and can enhance secretion of one or more cytokines, e.g., IL-2, by T cells. The anti-hPD1 antibodies described herein can inhibit binding of hPDL1 and/or hPDL2 to hPD1, can bind to both human and cynomolgus monkey PD1, and can enhance the proliferation and cytokine secretion of T cells in a primary response to an alloantigen and/or in a recall response to cytomegalovirus (CMV). A mixture of anti-hCTLA4 and anti-hPD1 antibodies can exhibit greater effects on T cell activation than either antibody alone.

Definitions

An "agonist," as meant herein, is a molecule that mimics or enhances the activity of a particular biologically active molecule. For example, a protein expressed on a cell surface might mediate known downstream effects due to its interaction with a cytokine that binds to it. An agonist of the protein could elicit similar, or even greater, downstream effects when it interacts with the protein, although it may or may not block or inhibit the binding of the cytokine to the protein.

An "alteration," as meant herein is a change in an amino acid sequence. Alterations can be insertions, deletions, or substitutions. An "alteration" is the insertion, deletion, or substitution of a single amino acid. If, for example, a deletion removes three amino acids from an amino acid sequence, then three alterations (in this case, deletions) have occurred. Alterations that are substitutions can be referred to by stating the amino acid present in the original sequence followed by the position of the amino acid in the original sequence followed by the amino acid replacing the original amino acid. For example, G133M means that the glycine at position 133 in the original sequence is replaced by a methionine. Further, 133M means that the amino acid at position 133 is methionine, but does not specify the identity of the original amino acid, which could be any amino acid including methionine. Finally, G133 means that glycine is the amino acid at position 133 in the original sequence.

An "alteration that disfavors heterodimers," as meant herein, is a substitution, insertion, or deletion of a single amino acid within a third heavy chain constant domain (CH3) amino acid sequence, optionally a human or primate CH3 amino acid sequence, where the substitution, insertion, or deletion disfavors the formation of heterodimers in the context of a mixture of antibodies. An antibody can comprise more than one alteration that disfavors heterodimers, and multiple alterations that disfavor heterodimers can occur at multiple sites in one or more antibodies in a mixture of antibodies. In some cases an alteration that disfavors heterodimers may have little or no effect alone but can inhibit heterodimer formation when one or more other alteration that disfavors heterodimer formation is present in the same antibody or in a different antibody in a mixture of antibodies. Included among the alterations can be the substitution of a charged residue for the residue present in the wild type sequence, which may or may not be charged. Alternatively, a substitution can create a steric clash that interferes with proper heavy chain/heavy chain (HC/HC) pairing such as a "protuberance" abutting against another "protuberance" or a "hole" abutting against another "hole," Protuberances or knobs and holes are described in U.S. Pat. No. 8,679,785, col. 12, line 12 to col. 13, line 2, which is incorporated herein by reference.

Whether one or more alteration(s) has (have) an effect on HC/HC heterodimer formation can be determined by introducing into host cells DNAs encoding two different Fc fragments that, when dimerized, form dimers of distinguishable sizes. For example, one could be a full-length IgG HC, which includes an Fc fragment, and the other could be a fragment including only the Fc fragment. Amounts of homo- and hetero-dimers produced could be determined by the sizes of these proteins as detected by Western blotting. Such amounts could be compared in samples coming from cells where the Fc regions do or do not contain alterations.

Alterations that disfavor heterodimers occur at "domain interface residues." Domain interface residues are discussed in U.S. Pat. No. 8,592,562 in Table 1 and accompanying text, which are incorporated herein by reference. Such domain interface residues are said to be "contacting" residues or are said to "contact" each other if they are predicted to be physically close, i.e., at most 12 angstroms (Å) between the alpha carbons (Cα, i.e., the carbon between the amino and the carboxyl moiety of the amino acid) of the two amino acids or at most 5.5 Å between a side chain heavy atom (any atom other than hydrogen) of one amino acid and any heavy atom of the other amino acid according to known structure models. Such structures are available online, for example, through the Protein Data Bank (available at http.www.rcsb.org/pdb/home/home.do) or through the INTERNATIONAL IMMUNOGENETICS INFORMATION SYSTEM® (IMGT; available at http://www.imgt.org). In Table 1 below, examples of contacting residues at the CH3/CH3 interface in a human IgG antibody are listed.

TABLE 1

Contacting residues at a human IgG CH3/CH3 interface

| Contacting residue in first CH3* | Residues in second CH3* having a heavy atom within 4.5 angstroms of a side chain heavy atom of the contacting amino acid in first CH3 |
|---|---|
| Q347 | K360 |
| Y349 | S354, D356, E357, K360 |
| T350 | S354, R355 |
| L351 | L351, P352, P353, S354, T366 |
| S354 | Y349, T350, L351 |
| R355 | T350 |
| D356 | Y349, K439 |
| E357 | Y349, K370 |
| K360 | Q347, Y349 |
| S364 | L368, K370 |
| T366 | L351, Y407 |
| L368 | S364, K409 |
| K370 | E357, S364 |
| N390 | S400 |
| K392 | L398, D399, S400, F405 |
| T394 | T394, V397, F405, Y407 |
| P395 | V397 |
| V397 | T393, T394, P395 |
| D399 | K392, K409 |
| S400 | N390, K392 |
| F405 | K392, T394, K409 |
| Y407 | T366, T394, Y407, S408, K409 |
| K409 | L368, D399, F405, Y407 |
| K439 | D356 |

*Numbering is according to Edelman et al. (1969), Proc. Natl. Acad. Sci. USA 63: 78-85, which is incorporated herein in its entirety Examples of alterations that disfavor heterodimers include, e.g., K/R409D plus D399K/R in a primate IgG HC in the context of a mixture of antibodies that includes another IgG antibody comprising 409R.

An "antagonist," as meant herein, is an agent that blocks or inhibits the activity of a particular biologically active molecule. For example, a particular protein may activate a biological pathway with known downstream effects when it interacts with its binding partner. An antagonist or inhibitor of that protein could lessen or eliminate those downstream effects, optionally by blocking or inhibiting interaction with the binding protein.

An "antibody," as meant herein, is a protein that contains at least one VH or VL. An antibody often contains both a VH and a VL. VHs and VLs are described in full detail in, e.g., Kabat et al., SEQUENCES OF PROTEINS OF IMMUNOLOGICAL INTEREST, FIFTH EDITION, U.S. Department of Health and Human Services, Public Health Service, National Institutes of Health, NIH Publication No. 91-3242, 1991, pp. xvi-xix and pp. 103-533, which are incorporated by reference herein. "Antibody" includes molecules having different formats such as single chain Fv antibodies (scFv, which contain a VH and a VL joined by a linker), Fab, F(ab')₂, Fab', scFv:Fc antibodies (as described in Carayannopoulos and Capra, Ch. 9 in FUNDAMENTAL IMMUNOLOGY, 3.sup.rd ed., Paul, ed., Raven Press, New York, 1993, pp. 284-286, which is incorporated herein by reference), and IgG antibodies as defined below, among many other possible formats.

An "antibody-drug conjugate," as meant herein, is an antibody as defined above conjugated to a drug or a toxin via a chemical linker. The linker is labile under certain conditions and can function to release the drug or toxin from the antibody in an intracellular environment. The drug or toxin can be cytotoxic and can be one of a large variety of cytotoxins including, e.g., maytansinoids, dolastatins, auristatin drug analogues, cryptophycin, duocarmycin derivatives such as CC-1065 analogs and duocarmycin, enediyne antibiotics including esperamicin and calicheamicin, and pyrolobenodiazepine. Antibody-drug conjugates are used as cancer therapeutics. Examples of such therapeutics include brentuximab vedotin (Adcetris®; Seattle Genetics/Millennium Pharmaceuticals) and ado-trastuzumab emtansine (Kadcyla®; Genentech/Roche).

A "charged" amino acid, as meant herein, is an acidic or basic amino acid that can have a charge at near-physiologic pH. These include the acidic amino acids glutamic acid (E) and aspartic acid (D), which are negatively charged at physiologic pH, and the basic amino acids arginine (R) and lysine (K), which are positively charged at physiologic pH. The weakly basic amino acid histidine, which can be partially charged at near-physiologic pH, is not within the definition of "charged" amino acid herein. To avoid confusion, a positive charge is considered to be "opposite" to a negative charge, as meant herein. Thus, for example, amino acid residues E and R are opposite in charge.

A "charge pair," as meant herein, is a pair of oppositely charged "contacting" amino acids, one on each of two different polypeptide chains. Thus, a charge pair is a pair of oppositely charged, contacting (as defined herein) amino acids on different polypeptide chains of a multimeric protein.

"Clearance" of an antibody in vivo refers to elimination of the antibody, which can be detected as elimination or a lessening in amount of the antibody in the bloodstream or in other tissues of a mammal. Generally, to determine a rate of clearance, the antibody will be administered to the mammal, and subsequently blood or tissue of the mammal will be periodically sampled and quantitatively tested for the presence of the antibody. From such tests, an in vivo half-life ($T_{1/2}$) and/or an Area Under the Curve (AUC) value can be derived. A decrease in $T_{1/2}$ or AUC indicates an increase in clearance, as meant herein. An exemplary method for determining whether clearance of an altered human IgG antibody in a mouse has increased or decreased relative to the unaltered antibody includes the following steps. The unaltered and altered antibodies can each be injected subcutaneously, e.g., under the skin over the shoulders, into separate mice. Whole blood samples of about 0.1 mL can be collected at each time point by retro-orbital sinus puncture. The blood can be clotted and processed to obtain serum. Serum samples can be assayed for the presence of human antibody using an antibody specific for a human Fc, for example a commercially-sold immunoassay system such as one of those available from Gyros U.S., Inc., Warren, N.J., USA. Blood samples can be collected, for example, at 0, 0.5, 2, 8, 24, 72, 120, 168, 240, 312, 384, and 480 hours after injection. Pharmacokinetic parameters can be estimated from serum concentrations using, for example, Phoenix® 6.3 software (Pharsight, Sunnyvale, Calif., USA).

A "chemotherapeutic agent" targets dividing cells and interferes with processes that are tied to cell division, for example, DNA replication, RNA synthesis, protein synthesis, the assembly, disassembly, or function of the mitotic spindle, and/or the synthesis or stability of molecules that play a role in these processes, such as nucleotides or amino acids. Thus, a chemotherapeutic agent can kill both cancer cells and other dividing cells. Chemotherapeutic agents are well-known in the art. They include, for example, the following agents: alkylating agents (e.g., busulfan, temozolomide, cyclophosphamide, lomustine (CCNU), streptozotocin, methyllomustine, cis-diamminedi-chloroplatinum, thiotepa, and aziridinylbenzo-quinone); inorganic ions (e.g., cisplatin and carboplatin); nitrogen mustards (e.g., melphalan hydrochloride, chlorambucil, ifosfamide, and mechlorethamine HCl); nitrosoureas (e.g., carmustine (BCNU)); anti-neoplastic antibiotics (e.g., adriamycin (doxorubicin), daunomycin, mithramycin, daunorubicin, idarubicin, mitomycin C, and bleomycin); plant derivatives (e.g., vincristine, vindesine, vinblastine, vinorelbine, paclitaxel, docetaxel, VP-16, and VM-26); antimetabolites (e.g., methotrexate with or without leucovorin, 5-fluorouracil with or without leucovorin, 5-fluorodeoxyuridine, 6-mercaptopurine, 6-thioguanine, gemcitabine, cytarabine, 5-azacytidine, hydroxyurea, deoxycoformycin, and fludarabine); podophyllotoxins (e.g., etoposide, irinotecan, and topotecan); as well as actinomycin D, dacarbazine (DTIC), mAMSA, procarbazine, hexamethylmelamine, pentamethylmelamine, L-asparaginase, and mitoxantrone. See, e.g., Cancer: Principles and Practice of Oncology, 4.sup.th Edition, DeVita et al., eds., J.B. Lippincott Co., Philadelphia, Pa. (1993), the relevant portions of which are incorporated herein by reference.

Other chemotherapeutic agents include those that act by the same general mechanism as those listed above. For example, agents that act by alkylating DNA, as do, for example, alkylating agents and nitrogen mustards, are considered chemotherapeutic agents. Agents that interfere with nucleotide synthesis, like, for example, methotrexate, cytarabine, 6-mercaptopurine, 5-fluorouracil, and gemcitabine, are considered to be chemotherapeutic agents. Mitotic spindle poisons are considered chemotherapeutic agents, as are, for example, paclitaxel and vinblastine. Topoisomerase inhibitors (e.g., podophyllotoxins), which interfere with DNA replication, are considered to be chemotherapeutic agents. Antibiotics that interfere with DNA synthesis by various mechanisms, examples of which are doxorubicin, bleomycin, and mitomycin, are considered to be chemotherapeutic agents. Agents that carbamoylate amino acids (e.g., lomustine, carmustine) or deplete asparagine pools (e.g., asparaginase) are also considered chemotherapeutic agents. Merck Manual of Diagnosis and Therapy, 17.sup.th Edition, Section 11, Hematology and Oncology, 144. Principles of Cancer Therapy, Table 144-2 (1999). Specifically included among chemotherapeutic agents are those that directly affect the same cellular processes that are affected by the chemotherapeutic agents listed above.

A "cognate" HC in the context of a mixture of antibodies, as meant herein, is the HC that a particular LC is known to pair with to form a binding site for a particular antigen. For example, if a known full-length IgG Antibody X binds to Antigen X, the Antibody X HC is the cognate HC of the Antibody X LC, and vice versa. Further, if the mixture also comprises an Antibody Y that binds to Antigen Y, the antibody Y HC is "non-cognate" with respect to the Antibody X LC and vice versa, and the Antibody Y LC is "non-cognate" with respect to the Antibody X HC and vice versa.

A "complementarity determining region" (CDR) is a hypervariable region within a VH or VL. Each VH and VL contains three CDRs called CDR1, CDR2, and CDR3. The CDRs form loops on the surface of the antibody and are primarily responsible for determining the binding specificity of an antibody. The CDRs are interspersed between four more conserved framework regions (called FR1, FR2, FR3, and FR4) as follows: FR1-CDR1-FR2-CDR2-FR3-CDR3-FR4. Positions of CDRs are indicated in, for example, FIGS. 3 and 7 (for a VH) and FIGS. 4 and 8 (for a VL). Kabat et al. position the VH CDRs as follows: CDR1 is at positions 31-35 (with possible insertions numbered 35A and 35B); CDR2 is at positions 50-65 (with possible insertions numbered 52A-52C); and CDR3 is at positions 95-102 (with possible insertions numbered 100A-100K). Kabat et al., supra, at xvii. Kabat et al. position the VL CDRs as follows: CDR1 is at positions 24-34 (with possible insertions numbered 27A-27F); CDR2 is at positions 50-56; and CDR3 is at positions 89-97 (with possible insertions numbered 95A-95F). Kabat et al., supra, at xvii, which is incorporated herein by reference.

A treatment or drug is considered to be administered "concurrently" with another treatment or drug if the two treatments/drugs are administered within the same small time frame, for example on the same day, or within the same more extended time frame. Such a more extended time frame can include a situation where, for example, one treatment/drug is administered once per week and the other is administered every 4 days. Although the two treatments/drugs may never or rarely be administered on the same day, the two treatments/drugs are administered on an ongoing basis during a common period of weeks, months, or longer. Similarly, if one drug is administered once per year and the other is administered weekly, they are considered to be administered "concurrently" if the drug administered weekly is administered during the year before and/or after the administration of the drug that is administered once per year. Hence, as meant herein, "concurrent" administration of the two treatments/drugs includes ongoing treatment with two different treatments/drugs that goes on in a common time period.

A "conservative" amino acid substitution, as meant herein, is the substitution of an amino acid with a different amino acid having similar properties, such as similar polarity, hydrophobicity, or volume. Conservative substitutions include replacement of an amino acid with another amino acid within the same group, where the groups of amino acids include the following: (1) hydrophobic amino acids, which include alanine, leucine, isoleucine, valine, proline, phenylalanine, tryptophan, and methionine; (2) uncharged polar amino acids, which include glycine, serine, threonine, cysteine, tyrosine, asparagine, and glutamine; (3) basic amino acids, which include arginine, lysine, and histidine; and (4) acidic amino acids, which include aspartic acid and glutamic acid. Conservative substitutions also include the substitution of (1) A with V, L, or I, (2) R with K, Q, or N, (3) N with Q, H, K, R, (4) D with E, (5) C with S or A, (6) Q with N, (7) E with D, (8), G with P or A, (9) H with N, Q, K, or R, (10) I with L, V, M, A, or F, (11) L with I, V, M, A, or F, (12) K with R, Q, or N, (13) M with L, F, or I, (14) F with L, V, I, A, or Y, (15) P with A, (16) S with T, A, or G, (17) T with S, (18) W with Y or F, (19) Y with W, F, T, or S, and (20) V with I, M, L, F, or A.

A "cysteine substitution," as meant herein, is an amino acid substitution where a cysteine replaces another amino acid.

Two or more antibodies are "different," as meant herein, if the amino acid sequences of all the polypeptide chains included in the antibody are not "the same," as meant herein.

A "heavy chain (HC)," as meant herein, comprises at least a VH, CH1, hinge, CH2, and CH3. An HC including all of these domains could also be referred to as a "full-length HC" or an "IgG HC." Some isotypes such as IgA or IgM can contain additional sequences, such as the IgM CH4 domain. The numbering system of Kabat et al., supra, is used for the VH (see FIGS. 3 and 7), and the EU system (Edelman et al. (1969), Proc. Natl. Acad. Sci, USA 63: 78-85, which is incorporated herein in its entirety) is used for the CH1, hinge, CH2, and CH3. The use of these well-known numbering systems can lead to a difference between an actual amino acid position in a sequence disclosed herein and a number assigned to that position using the Kabat or Edelman numbering system. However, one of skill in the art can assign a Kabat or Edelman number to any particular position in a disclosed antibody sequence with reference to tables disclosed herein below showing how Kabat or Edelman numbers can be assigned with reference to the conserved features of antibody sequences, which can be located in disclosed sequences. Tables 2-5 below illustrate this numbering on generalized HC sequences.

TABLE 2

Consensus sequence of human VHs

| 1 | 2 | 3 | 4 | 5 | 6 | 7 | 8 | 9 | 10 | 11 | 12 | 13 | 14 | 15 |
|---|---|---|---|---|---|---|---|---|----|----|----|----|----|----|
|   |   |   | L |   |   |   | G |   |    |    |    |    | P  |    |
| 16 | 17 | 18 | 19 | 20 | 21 | 22 | 23 | 24 | 25 | 26 | 27 | 28 | 29 | 30 |
|    | S  | V  |    | L  | S  | C  |    |    |    | G  |    |    |    |    |
|    | T  | L  |    | V  | T  |    |    |    |    |    |    |    |    |    |
| 31 | 32 | 33 | 34 | 35 | 35A | 35B | 36 | 37 | 38 | 39 | 40 | 41 | 42 | 43 |
|    |    |    |    |    |     |     | W  |    | R  | Q  |    |    | G  | K  |
|    |    |    |    |    |     |     |    |    |    |    |    |    |    | Q  |
| *44* | 45 | 46 | 47 | 48 | 49 | *50* | *51* | *52* | *52A* | *52B* | *52C* | 53 | 54 | 55 |
| G  | L  |    | W  |    |    |      |      |      |       |       |       |    |    |    |
| 56 | 57 | 58 | 59 | *60* | *61* | *62* | *63* | *64* | *65* | 66 | 67 | 68 | 69 | 70 |
|    |    |    |    |      |      |      |      |      |      | R  |    |    |    |    |
| 71 | 72 | 73 | 74 | 75 | 76 | 77 | 78 | 79 | 80 | 81 | 82 | 82A | 82B | 82C |
|    |    |    | S  |    |    |    |    |    | L  |    |    |     |     |     |
| 83 | 84 | 85 | 86 | 87 | 88 | 89 | 90 | 91 | 92 | 93 | 94 | *95* | *96* | *97* |
|    |    |    | D  |    |    |    | Y  |    | C  |    |    |      |      |      |
| *98* | *99* | *100* | *100A* | *100B* | *100C* | *100D* | *100E* | *100F* | *100G* | *100H* | *100I* | *100J* | | |
| *100K* | 101 | 102 | 103 | 104 | *105* | 106 | 107 | 108 | 109 | 110 | 111 | 112 | 113 | |
|        |     |     | W   |     | Q     | G   |     |     | V   |     | V   | S   |     | |

(SEQ ID NO: 196)

TABLE 2: This table shows conserved amino acids based on the human VH amino acid sequences (I-III) in Kabat et al. (supra). Numbering is according to Kabat et al., supra.
Site numbers within the CDRs are written in *bold italics*.
Position numbers with letters after them, e.g., 100A, with the exception of 82A-82C, may or may not be filled by an amino acid due to the varying lengths of CDRs. Positions 82A-82C, which are in a framework region, are always filled by an amino acid in a human VH, as meant herein.
A single boldface amino acid at a particular position indicates an "invariant" amino acid in all three classes of human VHs as described by Kabat et al. (supra).
At sites of interest where the amino acid at a given position is most commonly one amino acid or either of two amino acids, those amino acids are indicated in plain text.
Site numbers in <u>underlined boldface</u> indicate positions that are described as being altered herein or in the Examples of PCT/US2017/030676.
Positions where no amino acid is designated did not meet the criteria stated above.

Amino acid sequences are "different," as meant herein, if they have one or more amino acid substitution, deletion, or insertion relative to each other, with the caveat that such "different" amino acid sequences are not considered different if the differences are due solely to post-translational modifications, that is, if the amino sequences could be encoded by the same DNA sequence.

An "Fc fragment," "Fc region," or "Fc portion," as meant herein, consists essentially of a hinge domain (hinge), a second heavy chain constant domain (CH2), and a CH3 from an HC, although it may further comprise regions downstream from the CH3 in some isotypes such as IgA or IgM.

Table 2 shows that there are numerous conserved amino acids having conserved spacing that would allow alignment of any VH sequence with the conserved amino acids spaced as shown above by eye. Alternatively, a novel sequence could be aligned with a known VH sequence using alignment software, for example, alignment software available on the International ImMunoGeneTics (IMGT) Information System® (for example, IMGT/DomainGapAlign, which is available at http/www.imgt.org or CLUSTAL Omega (Sievers et al., (2011), Molecular Systems Biology 7(1): 539).

Table 3 below shows a consensus amino acid sequence of CH1s.

TABLE 3

CH1 consensus

| 118 | 119 | 120 | 121 | 122 | 123 | 124 | 125 | 126 | 127 | 128 | 129 | 130 | 131 | 132 |
|---|---|---|---|---|---|---|---|---|---|---|---|---|---|---|
|  |  |  |  |  | P |  |  |  | P |  |  |  | L |  |
| 133 R/K | 134 | 134 | 136 | 137 | 138 | 139 | 140 | 141 | 142 | 143 | 144 | 145 | 146 | 147 |
|  |  |  |  |  |  |  |  |  |  |  |  | C | L |  | K |
| 148 | 149 | 150 | 151 | 152 | 153 | 154 | 155 | 156 | 157 | 158 | 159 | 160 | 161 | 162 |
|  |  |  | P |  |  |  |  |  | W |  |  |  |  |  |
| 163 | 164 | 165 | 166 | 167 | 168 | 169 | 170 | 171 | 172 | 173 | 174 | 175 | 176 | 177 |
|  |  |  |  |  | H |  | F |  |  | V |  |  | A |  |
| 178 | 179 | 180 | 181 | 182 | 183 | 184 | 185 | 186 | 187 | 188 | 189 | 190 | 191 | 192 |
|  |  |  | T |  | S | S |  |  |  |  |  |  |  |  |
| 193 | 194 | 195 | 196 | 197 | 198 | 199 | 200 | 201 | 202 | 203 | 204 | 205 | 206 | 207 |
|  |  |  |  |  |  |  | C |  |  |  |  |  |  |  |

TABLE 3-continued

CH1 consensus

| 208 | 209 | 210 | 211 | 212 | 213 | 214 | 215 |
|---|---|---|---|---|---|---|---|

(SEQ ID NO: 197)

TABLE 3: The numbering is according to Edelman et al. (supra).
The single amino acids shown in boldface below the numbers are "invariant" residues according to Kabat et al. (supra) from alignments of CH1s from a variety of species.
Sites selected for alteration described herein or in PCT/US2017/030676 (131, 133, 147, 168, 170, 173, 176, 181, and 183) are shown in <u>underlined boldface</u>. At these sites, the most common one or two amino acids in the 63 primate CH1 sequences reported in Kabat et al. (supra) are shown in plain text.
Positions where no amino acid is designated were not "invariant" and were not selected for alteration.

Table 4 below shows an alignment human CH1s of the IgG1, IgG2, IgG3 and IgG4 isotypes. This alignment highlights the very strong conservation of sequence among these closely-related CH1s.

TABLE 4

Alignment of human IgG1, IgG2, IgG3, and IgG4 CH1s

```
         118 120       130       140       150       160       170    177
          *   *         *         *         *         *         *      *
IgG1 ASTKGPSVFPLAPSSKSTSGGTAALGCLVKDYFPEPVTVSWNSGALTSVHTFPAVLQSS

IgG2 ASTKGPSVFPLAPCSRSTSESTAALGCLVKDYFPEPVTVSWNSGALTSVHTFPAVLQSS

IgG3 ASTKGPSVFPLAPCSRSTSESTAALGCLVKDYFPEPVTVSWNSGALTSVHTFPAVLQSS

IgG4 ASTKGPSVFPLAPCSRSTSESTAALGCLVKDYFPEPVTVSWNSGALTSVHTFPAVLQSS 178 180       190       200       210  215
          *   *         *         *         *    *
IgG1 GLYSLSSVVTVPSSSLGTQTYICNVNHKPSNTKVDKKV (SEQ ID NO: 198)

IgG2 GLYSLSSVVTVPSSNFGTQTYTCNVDHKPSNTKVDKTV (SEQ ID NO: 199)

IgG3 GLYSLSSVVTVPSSSLGTQTYTCNVNHKPSNTKVDKRV (SEQ ID NO: 200)

IgG4 GLYSLSSVVTVPSSSLGTKTYTCNVDHKPSNTKVDKRV (SEQ ID NO: 201)
```

The amino acid sequences of representative CH1s of human IgG1, IgG2, IgG3 and IgG4 antibodies were obtained from IMGT web page, accession numbers J00228, J00230, X03604, and K01316, respectively, and aligned with CLUSTALW software.
Residues are numbered according to the EU system of Edelman et al., supra. "Invariant" residues according to Kabat et al., supra are shown in boldface.
These residues are highly conserved, but not completely invariant.
Residues that are underlined and in boldface italics are sites at which substitutions have been made and tested as reported in the Examples below or in PCT/US2017/030676.

Table 5 below shows an alignment of human IgG Fc regions of the four human IgG subclasses, IgG1, IgG2, IgG3, and IgG4. This alignment shows the differences between these subclasses, as well as the high sequence conservation.

TABLE 5

Amino acid sequences of human IgG Fc regions

```
IgG1 ----------------------------------------

IgG2 ----------------------------------------

IgG3 ELKTPLGDTTHTCPRCPEPKSCDTPPPCPRCPEPKSCDTPPPCPRCP

IgG4 ----------------------------------------

216       226       236       246       256       266
          *         *         *         *         *         *
IgG1 EPKSCDKTHTCPPCPAPELLGGPSVFLFPPKPKDTLMISRTPEVTCVVVDVSHEDPEVKF

IgG2 ERKCCVE---CPPCPAPPVA-GPSVFLFPPKPKDTLMISRTPEVTCVVVDVSHEDPEVQF

IgG3 EPKSCDTPPPCPRCPAPELLGGPSVFLFPPKPKDTLMISRTPEVTCVVVDVSHEDPEVQF

IgG4 ESKYG---PPCPSCPAPEFLGGPSVFLFPPKPKDTLMISRTPEVTCVVVDVSQEDPEVQF
```

TABLE 5-continued

Amino acid sequences of human IgG Fc regions

```
        276        286        296        306        316        326
         *          *          *          *          *          *
IgG1 NWYVDGVEVHNAKTKPREEQYNSTYRVVSVLTVLHQDWLNGKEYKCKVSNKALPAPIEKT

IgG2 NWYVDGMEVHNAKTKPREEQFNSTFRVVSVLTVVHQDWLNGKEYKCKVSNKGLPAPIEKT

IgG3 KWYVDGVEVHNAKTKPREEQYNSTFRVVSVLTVLHQDWLNGKEYKCKVSNKALPAPIEKT

IgG4 NWYVDGVEVHNAKTKPREEQFNSTYRVVSVLTVLHQDWLNGKEYKCKVSNKGLPSSIEKT 336        346        356        366        376        386
         *          *          *          *          *          *
IgG1 ISKAKGQPREPQVYTLPPSREEMTKNQVSLTCLVKGFYPSDIAVEWESNGQPENNYKTTP

IgG2 ISKTKGQPREPQVYTLPPSREEMTKNQVSLTCLVKGFYPSDIAVEWESNGQPENNYKTTP

IgG3 ISKTKGQPREPQVYTLPPSREEMTKNQVSLTCLVKGFYPSDIAVEWESSGQPENNYNTTP

IgG4 ISKAKGQPREPQVYTLPPSQEEMTKNQVSLTCLVKGFYPSDIAVEWESNGQPENNYKTTP 396        406        416        426        436        446
         *          *          *          *          *          *
IgG1 PVLDSDGSFFLYSKLTVDKSRWQQGNVFSCSVMHEALHNHYTQKSLSLSPGK (SEQ ID NO: 202)

IgG2 PMLDSDGSFFLYSKLTVDKSRWQQGNVFSCSVMHEALHNHYTQKSLSLSPGK (SEQ ID NO: 203)

IgG3 PMLDSDGSFFLYSKLTVDKSRWQQGNIFSCSVMHEALHNRFTQKSLSLSPGK (SEQ ID NO: 204)

IgG4 PVLDSDGSFFLYSRLTVDKSRWQEGNVFSCSVMHEALHNHYTQKSLSLSLGK (SEQ ID NO: 205)
```

A "human," nucleotide or amino acid sequence, protein, or antibody is one that occurs naturally in a human or one that is identical to such a sequence or protein except for a small number of alterations as explained below. Many human nucleotide and amino acid sequences are reported in, e.g., Kabat et al., supra, which illustrates the use of the word "human" in the art. A "human" amino acid sequence or antibody, as meant herein, can contain one or more insertions, deletions, or substitutions relative to a naturally-occurring sequence, with the proviso that a "human" amino acid sequence does not contain more than 10 insertions, deletions, and/or substitutions of a single amino acid per every 100 amino acids. Similarly, a human nucleotide sequence does not contain more than 30 insertions, deletions, and/or substitutions of a single nucleotide per every 300 nucleotides. In the particular case of a VH or VL sequence, the CDRs are expected to be extremely variable, and, for the purpose of determining whether a particular VH or VL amino acid sequence (or the nucleotide sequence encoding it) is a "human" sequence, the CDRs (or the nucleotides encoding them) are not considered part of the sequence.

A "humanized" antibody, as meant herein, is an antibody where the antibody is of non-human origin but has been engineered to be human as much as possible, thereby hopefully reducing immunogenicity in humans while retaining antibody stability and binding properties. Generally, this means that most or all of the constant domains and the framework regions of the variable domains are human, or nearly human sequences, while the CDRs originate from a different organism. However, merely grafting CDRs from, e.g., a mouse antibody, into a human framework may not produce an antibody with the desired properties, and further modification may be required. In recent years, a variety of approaches to streamline and improve the results of humanization have been developed. See, e.g., Choi et al. (2015), mAbs 7(6): 1045-1057 and references cited therein.

An "IgG antibody," as meant herein, comprises (1) two HCs, each comprising a VH, a CH1, a hinge domain, a CH2, and a CH3 and (2) two light chains (LCs), each comprising a VL and a LC constant domain (CL). The heavy chains of an IgG antibody are of an IgG isotype, for example, IgG1, IgG2, IgG3, or IgG4. These domains are described in, e.g., Kabat et al., supra, pp. xv-xix and 647-699, which pages are incorporated herein by reference. The numbering system of Kabat et al., supra, is used for VHs and VLs (see FIGS. 3, 4, 7, and 8), and the EU system (Edelman et al. (1969), Proc. Natl. Acad. Sci. USA 63: 78-85, which is incorporated herein in its entirety) is used for CLs, CH1s, hinges, CH2s, and CH3s.

An "immunomodulatory molecule," as meant herein, is a molecule that interacts with a component, for example a protein, that can mediate the activity of the immune system, thereby regulating the activity of the immune system. The activity of the immune system can be assessed in a mixed lymphocyte reaction (MLR) assay as described in Example 8 below, and an immunomodulatory molecule can either increase or decrease the activity of the immune system. As an example, the anti-hPD1 antibodies described herein are immunomodulatory molecules by this definition.

"Inhibition" of the interaction between hCTLA4 and human CD80 (hCD80, also known as human B-lymphocyte activation antigen B7-1 (hB7-1)) and/or human CD86 (hCD86, also known as human B-lymphocyte activation antigen B7-2 (hB7-2)) by an antibody, as meant herein, can be measured using the CTLA4 luciferase reporter assay employing Raji cells that express B7-1 and B7-2 as described in Example 4. An antibody that "inhibits" the interaction of hCTLA4 with hB7-1/hB7-2 if it has an $IC_{50}$ in this assay that is no more than 20, 15, 10, or 5 times as high as that of anti-CTLA4 antibody 7A4.

Similarly, "inhibition" of the interaction between hPD1 and hPDL1 by an anti-hPD1 antibody can be measured by the PD1 dual reporter assay using CHO-K1 cells and Jurkat T cells described in Example 7. An antibody that "inhibits"

the interaction between hPD1 and hPDL1 if it has an IC$_{50}$ in this assay that is no more than 20, 15, 10, or 5 times as high as that of anti-hPD1 antibody #9.

An "inhibitor," as meant herein, is similar to an "antagonist" as defined above, except that it refers to a small molecule (as opposed to a protein or polynucleotide), whereas an antagonist is a more general term referring to any kind of molecule. For example, "tyrosine kinase inhibitor" refers to a small molecule that antagonizes a tyrosine kinase. To avoid any confusion, this association of the term "inhibitor" with small molecules does not extend to the verb "inhibit" or the noun "inhibition." For example, a large molecule, such as an antibody, can inhibit the interaction of, e.g., PD1 and PDL1 Further, "inhibition" of an interaction need not be mediated by a small molecule to be "inhibition," as meant herein.

A "light chain (LC)," as meant herein, comprises a VL and a CL, which can be a kappa (CLκ) or lambda (CLλ) domain. These domains, including exemplary amino acid sequences thereof, are described in, e.g., Kabat et al., supra, pages xiii-lix, 103-309, and 647-660, which are incorporated herein by reference. The numbering system used herein for the VL is that described in Kabat et al., supra, and the EU numbering system used for the CL is that described in Edelman et al., supra. Tables 6 and 7 below illustrate the application of these systems to a variety of light chain sequences. One of skill in the art can use such information to assign Kabat or Edelman numbers to particular positions in the sequences disclosed herein.

TABLE 6

Consensus sequence of human VLs

| 1 | 2 | 3 | 4 | 5 | 6 | 7 | 8 | 9 | 10 | 11 | 12 | 13 | | | 14 | | 15 | |
|---|---|---|---|---|---|---|---|---|----|----|----|----|----|----|----|----|----|----|
| 16 | 17 | 18 | 19 | 20 | 21 | 22 | 23 | *24* | *25* | *26* | *27* | *27A* | *27B* | *27C* | *27D* | *27E* | *27F* | |
| G | | | | | | | C | | | | | | | | | | | |
| *28* | *29* | *30* | *31* | *32* | *33* | *34* | 35 | 36 | 37 | 38 | 39 | 40 | 41 | 42 | <u>43</u> | 44 | | |
| | | | | | | | W | | | | | | | | A | P | | |
| | | | | | | | | | | | | | | | S | | | |
| | | | | | | | | | | | | | | | P | | | |
| 45 | 46 | 47 | 48 | 49 | *50* | *51* | *52* | *53* | *54* | *55* | *56* | 57 | 58 | 59 | 60 | | | |
| | | | | | | | | | | | | | I/V | P | | | | |
| 61 | 62 | 63 | 64 | 65 | 66 | 67 | 68 | 69 | 70 | 71 | 72 | 73 | 74 | 75 | | | | |
| R | F | S | G | S | | | | | | | | L | | | | | | |
| 76 | 77 | 78 | 79 | 80 | 81 | 82 | 83 | 84 | 85 | 86 | 87 | 88 | *89* | *90* | | | | |
| | | | | | | | | A/G | | Y | Y/F | | | | | | | |
| *91* | *92* | *93* | *94* | *95* | *95A* | *96* | *97* | 98 | 99 | <u>100</u> | 101 | 102 | 103 | 104 | | | | |
| | | | | | | | | F | G | Q/G | G | T | | | | | | |
| 105 | 106 | 106A | 107 | 108 | 109 | | | | | | | | | | | | | |

(SEQ ID NO: 206)

TABLE 6: The numbering is according to Kabat et al. (supra).

Numbers in *bold italics* indicate the positions of the CDRs. Position numbers with letters after them, e.g., 27A, may or may not be filled by an amino acid, due to the varying lengths of CDRs.
Invariant residues for all human light chains in Kabat et al. (supra) are shown as bold letters indicating the amino acid found at that position.
At selected sites, the one to three most common amino acids found at that site are indicated in plain text.
In addition, many other amino acids are invariant or highly conserved within some subgroups of kappa or lambda VLs, which can aid in categorizing a particular amino acid sequence as a VL. Sites selected for alteration herein, as reported in the Examples below or in PCT/US2017/030676, are indicated by <u>boldface underlined</u> type.
Positions where no amino acid is designated and/or the number is not shown in <u>boldface underlined</u> type do not meet the criteria stated above.

TABLE 7

Consensus sequence and numbering for CLs

| | 108 | 109 | 110 | 111 | 112 | 113 | 114 | 115 | 116 | <u>117</u> | 118 | 119 | 120 | 121 | 122 | 123 |
|---|---|---|---|---|---|---|---|---|---|---|---|---|---|---|---|---|
| κ | | | | | | P | | | | I | | | P | P | | |
| λ | | | | | | P | | | | L | | | P | P | | |
| | 124 | 125 | 126 | 127 | 128 | 129 | 130 | <u>131</u> | 132 | 133 | 134 | 135 | 136 | 137 | 138 | 139 |
| κ | | | | | | | | S | | | V | C | | | | |
| λ | | | | | | | | A | | | V | C | | | | |
| | 140 | 141 | 142 | 143 | 144 | 145 | 146 | 147 | 148 | 149 | 150 | 151 | 152 | 153 | 154 | 155 |
| κ | | P | | | | | V | | W | | | | | | | |
| λ | | P | | | | | V | | W | | | | | | | |
| | 156 | 157 | 158 | 159 | <u>160</u> | 161 | <u>162</u> | 163 | 164 | 165 | 166 | 167 | 168 | 169 | 170 | 171 |
| κ | | | | | Q | | S | | T | | | | | | | |
| λ | | | | | E | | T | | P | | | | | | | |
| | 172 | 173 | <u>174</u> | 175 | <u>176</u> | 177 | 178 | 179 | 180 | 181 | 182 | 183 | 184 | 185 | 186 | 187 |
| κ | | | S | | S | S | T | L | T | L | | | | | | |
| λ | | | A/M | | S | S | Y | L | S | L | | | | | | |
| | 188 | 189 | 190 | 191 | 192 | 193 | 194 | 195 | 196 | 197 | 198 | 199 | 200 | 201 | 202 | 203 |
| κ | | | | | | | C | | | | H | | | | | |
| λ | | | | | | | C | | | | H | | | | | |

TABLE 7-continued

Consensus sequence and numbering for CLs

| | 204 | 205 | 206 | 207 | 208 | 209 | 210 | 211 | 212 | 213 | 214 |
|---|---|---|---|---|---|---|---|---|---|---|---|
| κ | | | | | | F | | | | | C |
| λ | | | | | | V | | | | | C |

(SEQ ID NO: 207)
(SEQ ID NO: 208)

TABLE 7: The numbering is according to Edelman et al. (supra), which is the same as the numbering of Kabat et al. (supra) for CLs.
The amino acids shown in bold below the numbers are "invariant" residues according to Kabat et al. (supra) from alignments of both kappa and lambda CLs from a variety of species.
As indicated at selected sites (131, 160, 162, 174, 176, and 178), amino acids conserved in the ten human kappa chains (top) and 28 human lambda chains (below) reported in Kabat et al. (supra) are shown in plain text. In cases where either of two different amino acids are found at one of these sites, the more common amino acid is shown prior to the less common, e.g., A/M.
Bold underlined numbers indicate sites that were altered as reported in the Examples below or in PCT/US2017/030676. In addition, many other amino acids are invariant or highly conserved within some subgroups of CLκ or CLλ domains, which can aid in categorizing a particular amino acid sequence as a CL. Positions where no amino acid is designated and/or the number is not shown in boldface underlined type do not meet the criteria stated above.

A "partner-directing alteration," as meant herein, is a substitution, insertion, or deletion of a single amino acid at the HC/LC interface within a VH, CH1, VL, or CL amino acid sequence, optionally a substitution of a charged amino acid or a cysteine for the naturally occurring amino acid, which causes an HC and LC, optionally a human and/or primate HC and LC, to associate more strongly. More specifically, an "HC partner-directing alteration" is an alteration in a VL or CL that can, sometimes only in the presence of an "LC partner-directing alteration" at a "contacting" residue in a VH or CH1, cause an HC and LC to associate more strongly. Similarly, an "LC partner-directing alteration" is an alteration in a VH or CH1 that can, sometimes only in the presence of an "HC partner-directing alteration" at a "contacting" residue in a VL or CL, cause an HC and LC to associate more strongly. In some embodiments, a contacting pair of HC and LC partner-directing alterations can be substitutions of charged amino acids having opposite charges. In other embodiments, a charged amino acid already exists at one of the contacting sites of the HC or LC so that alteration of only one chain is required to create a pair of oppositely charged residues at contacting sites in a cognate HC/LC pair, i.e., a charge pair. In other embodiments, cysteine residues can be introduced at contacting sites so that disulfide bridges in a cognate HC/LC pair can form. In further embodiments, HC- and LC-partner-directing alterations can be substitutions or pre-existing amino acids that create a knob and a hole (or a protuberance and a cavity) at contacting residues as described in U.S. Pat. No. 8,679,785, the relevant portions of which are incorporated herein by reference. The HC can be of the IgG, IgA, IgD, IgM, or IgE isotype, optionally IgG1, IgG2, IgG3, or IgG4. HC- and LC-partner-directing alterations occur at contacting amino acid positions that form part of the HC/LC interface. Interface residues in the CLs and CH1s include those within 4.5 Å, as explained in U.S. Pat. No. 8,592,562, Tables 4 and 5 and accompanying text in columns 10 and 11, all of which is incorporated herein by reference. These positions in human CH1s and CLs are catalogued in Table 8 below.

TABLE 8

Contacting residues between CH1 and CL

| CH1 residue | $CL_\kappa$ residue | CLλ residue |
|---|---|---|
| 125 | 123 | 119 |
| 126 | 121, 123, 124 | 117, 119, 120 |
| 127 | 121 | 117, 119 |
| 128 | 118, 133 | 114, 129 |
| 129 | 118 | 114 |
| 130 | 118 | |
| 139 | 116 | |
| 140 | 116 | |
| 141 | 116, 118, 135 | 112, 114 |
| 142 | 118 | 114 |
| 143 | | 114 |
| 145 | 124, 131 | 127, 129, 173 |
| 147 | 124, 131 | 125, 127 |
| 148 | | 125 |
| 168 | 137, 138, 174 | 133, 163, 169 |
| 169 | 164 | |
| 170 | 135, 162, 164, 174, 176 | 131, 133, 169, 171 |
| 171 | 162, 164 | 158, 161, 171 |
| 172 | | 158 |
| 173 | 160, 162 | 156, 158, 173 |
| 174 | 160 | 156 |
| 175 | 160 | 156 |
| 176 | | 156 |
| 181 | | 173 |
| 182 | | 173 |
| 183 | 176 | 129, 131, 173 |
| 185 | 135 | 114, 131 |
| 187 | 137 | |
| 213 | 123 | 119 |
| 218 | 122 | |

In the particular case of contacting residues on the interface between a VH and a VL, pairs of residues, one in the VH and one in the VL, suitable for alteration can be selected using the following criteria: (1) the residues are buried or partially buried, i.e., inaccessible in the tertiary structure of a full-length antibody, (2) the residues are spatially close, that is, where the Cα of the two amino acids are within about 12 Å, or where there is at most 5.5 Å between a side chain heavy atom (any atom other than hydrogen) of one amino acid and any heavy atom of the other amino acid according to known structure models, (3) the residues are highly conserved, although they need not be totally invariant, and (4) the residues are not within or interacting with the CDRs. Examples of such contacting residues include, without limitation, the following: position 44 (VH) and position 100 (VL); position 39 (VH) and position 38 (VL); and position 105 (VH) and position 43 (VL).

To a first approximation, a change in the strength of HC/LC association due to HC- and/or LC-partner-directing alterations can be measured by "chain drop out" experiments as described in Example 11.

To confirm or, in some cases, clarify results from chain drop out experiments, the sizes Fab fragments arising in transfectants containing DNAs encoding the HC and LC of a first antibody (Mab1) and the HC and LC of a second antibiody (Mab2) can be determined by mass spectrometry as described in Example 11 herein, in Thompson et al. (2014), mAbs 6:1, 197-203 (which is incorporated herein in its entirety), and in FIG. 15 and in Example 5 of U.S. Provisional Application 62/342,167 (which are incorporated herein by reference). In most cases, cognate and non-cognate pairs can be distinguished by mass using such techniques. If non-cognate pairs are major species in cells transfected with DNAs encoding an unaltered Mab1 HC and LC and an unaltered Mab2 HC and LC and are not major species in cells transfected with DNAs encoding Mab1 HC and LC and Mab2 HC and LC, wherein at least one of these antibodies comprises a partner-directing alteration, then it is considered herein that at least one of the alterations is a favorable partner-directing alteration.

Examples of partner-directing alterations include alterations that create, partially or wholly, any of the following charge pairs: 44D/E (VH) and 100R/K (VL); 44R/K (VH) and 100D/E (VL); 105R/K (VH) and 43D/E (VL); 105D/E (VH) and 43R/K (VL); 147D/E (CH1) and 131R/K (CL); 147R/K (CH1) and 131D/E (CL); 168D/E (CH1) and 174R/K (CL); 168R/K (CH1) and 174D/E (CL); 181R/K (CH1) and 178E/D (CL); and 181E/D (CH1) and 178R/K (CL). In addition, partner-directing alterations include substitutions where cysteine is substituted for another amino acid such that contacting pairs of cysteines exist in the HC and LC of the antibody, for example any of the following pairs: 126C (CH1) and 121C (CL); 126C (CH1) and 124C (CL); 127C (CH1) and 121C (CL); 128C (CH1) and 118C (CL); 133C (CH1) and 117C (CL); 133C (CH1) and 209C (CL); 123C (CH1) and 116C (CL); 141C (CH1) and 116C (CL); 168C (CH1) and 174C (CL); 170C (CH1) and 162C (CL); 183C (CH1) and 176C (CL); 173C (CH1) and 160C (CL); 170C (CH1) and 176C (CL); and 173C (CH1) and 162C (CL).

A "major species" of antibody in the context of a mixture of antibodies, as meant herein, is a particular antibody that makes up at least 10% of the total amount of antibodies within the mixture. To determine how many major species are in a mixture of antibodies, low pH CEX chromatography as described in Example 5 and shown in FIG. 14 of U.S. Provisional Application 62/342,167 (which portions of U.S. Provisional Application 62/342,167 are incorporated herein by reference) can be performed. This method is described by Chen et al. (2010), Protein Science, 19:1191-1204, which is incorporated herein in its entirety. Briefly, it employs a Thermo PROPAC™ WCX-10 weak CEX column, 4×250 mm, preceded by a 50 mm guard column (PROPAC™ WCX-10G) using a Waters Alliance 2695 high performance liquid chromatography (HPLC) system. Chromatography can be run with a linear gradient from 100% Buffer A (20 mM sodium acetate pH 5.2) to 100% Buffer B (20 mM sodium acetate with 250 mM sodium chloride pH 5.2) over 30 minutes. The column can be washed with high salt (1M sodium chloride) and re-equilibrated to starting condition of Buffer A. Antibodies can be detected in the column outflow by absorbance at 214 nm. Relative amounts of the detected peaks can be determined using EMPOWER™ software (Waters Corp., Milford, Mass., USA). Low pH CEX can distinguish between different full-length antibody species and can be used to quantitate relative amounts of specific antibody species in a mixture.

A "minor species" of antibody within a mixture of antibodies, as meant herein, comprises less than 10% of the total amount of antibodies in the mixture. This can be determined by low pH CEX chromatography as described in the definition of "major species."

The terms "nucleic acid" and "polynucleotide" are used interchangeably herein.

A "primate," nucleotide or amino acid sequence or a protein is one which occurs naturally in nucleic acids or proteins found in a primate or one that is identical to such a sequence or protein except for a small number of alterations as explained below. Primates include animals from a number of families including, without limitation, prosimians (including lemurs), new world monkeys, chimpanzees, humans, gorillas, orangutans, gibbons, and old world monkeys. Specific primate species include, without limitation, *Homo sapiens, Macaca mulata* (rhesus macaque), *Macaca fascicularis* (cynomolgus monkey), and *Pan troglodytes* (chimpanzee), among many others. Many primate nucleotide and amino acid sequences are known in the art, e.g., those reported in, e.g., Kabat et al., supra. Generally, a "primate" amino acid sequence, as meant herein, can contain one or more insertions, deletions, or substitutions relative to a naturally-occurring primate sequence, with the proviso that a "primate" amino acid sequence does not contain more than 10 insertions, deletions, and/or substitutions of a single amino acid per every 100 amino acids. Similarly, a primate nucleotide sequence does not contain more than 30 insertions, deletions, and/or substitutions of a single nucleotide relative to a naturally-occurring primate sequence per every 300 nucleotides. In the particular case of a VH or VL sequence, the CDRs are expected to be extremely variable, and, for the purpose of determining whether a particular VH or VL amino acid sequence (or the nucleotide sequence encoding it) is a "primate" sequence, the CDRs (or the nucleotides encoding them) are not considered part of the sequence.

Two amino acid sequences are "the same," as meant herein, if the two sequences could be encoded by the same DNA sequence. That is, amino acid sequences that differ only as a result of post-translational modifications, e.g., elimination of a carboxyl-terminal lysine or cyclization of N-terminal glutamate or glutamine residues, are "the same" as meant herein.

A "targeted biologic," as meant herein, is a protein that can influence an aspect of a cell's biological status via its interaction with another specific molecule (which can be a protein). For example, a "targeted biologic" may influence a cell's ability to live, to proliferate, to produce specific cytokines or proteins, etc. As an example, the anti-hPD1 antibodies described herein are "targeted biologics" since they interact with PD1, which causes a number of biological effects in T cells including an increase in proliferation and an increase in IFNγ production.

Similarly, a "targeted inhibitor," as meant herein, is small molecule that can influence an aspect of a cell's biological status via its interaction with a specific cellular molecule (which can be a protein). For example, a "tyrosine kinase inhibitor" is a small molecule that affects the activity of tyrosine kinase (which affects a variety of cell functions) via its interaction with tyrosine kinase.

As meant herein, a "treatment" for a particular disease or condition refers to a course of action, which can comprise administration of one or more antibodies or polynucleotides encoding one or more antibodies, that results in a lessening of one or more symptoms or a decrease or interruption in an expected progression of the disease or condition in a human patient, an animal model system considered to be reflective of the disease or condition, or an in vitro cell-based assay considered to be reflective of the disease or condition. This can be ascertained by an objective measurement of symptoms in humans or animals or by measurement of various parameters in cell-based assays, for example, production of one or more cytokines, e.g., IFNγ, cell proliferation, cell death, etc. For example, for a cancer "treatment," the treatment can result in a decrease in tumor volume, an absence of expected tumor metastasis in a human or in an animal model system, an increase in survival time, or an increase in progression-free or disease-free survival time in a human or animal suffering from cancer. A cancer treatment may also result in an increase in indices indicating activation of the immune system in a cell-based assay, for example, proliferation of T cells and/or increased production of cytokines, e.g., IFNγ and/or IL-2, by T cells.

Variable Domains of Anti-hCTLA4 Antibodies

In one aspect variable domains of anti-hCTLA4 antibodies are provided herein that have unique, but closely related, amino acid sequences. These antibodies can bind to both human and cynomolgus monkey CTLA4 and can inhibit the interaction of hCTLA4 with hB7-1 and/or hB7-2. In one aspect these, antibodies can be human, humanized, or primate IgG antibodies, which can be IgG1, IgG2, IgG3, or IgG4 antibodies. In some embodiments they can comprise alterations that increase in vivo clearance of an antibody. Such alterations include, for example, M252A, M252L, M252S, M252R, R255K or H435R.

FIGS. 1 and 2 show alignments of the CDRs of the VH and VLs of the anti-hCTLA4 antibodies whose selection is described in Example 1. FIGS. 3 and 4 show alignments of the VHs and VLs of the selected anti-hCTLA4 antibodies. Only eight sites vary over the entire length of the VHs, and only five sites vary over the entire length of the VLs. Thus, the sequences these selected antibodies are closely related. Consensus sequences for these anti-hCTLA4 VHs and VLs are provided in SEQ ID NOs: 82 and 83 (VH) and SEQ ID NOs: 84 and 85 (VL).

In one aspect, a VH of an anti-hCTLA4 antibody contains a VH CDR1, a VH CDR2, and a VH CDR3 which comprise the amino acid sequences SEQ ID NO:3 (CDR1), SEQ ID NO: 74 or 75 (CDR2), and SEQ ID NO: 76 or 77 (CDR3). SEQ ID NOs: 74, 75, 76 and 77 are consensus sequences (see FIG. 1) where several amino acids can vary within a limited range of amino acids. Further, the VH CDR1, VH CDR2, and VH CDR3 can comprise, respectively, the amino acid sequences of SEQ ID NOs: 3, 4, and 5, SEQ ID NOs: 3, 13 and 5, SEQ ID NOs: 3, 20, and 21, SEQ ID NOs: 3, 24, and 25, SEQ ID NOs: 3, 31, and 5, SEQ ID NOs: 3, 37, and 5, SEQ ID NOs: 3, 43, and 5, SEQ ID NOs: 3, 46, and 47, SEQ ID NOs: 3, 59, and 5, SEQ ID NOs: 3, 65, and 21, or SEQ ID NOs: 3, 70, and 21. Antibodies comprising a VH which comprises any one of these sets of CDR sequences can inhibit the interaction of hCTLA4 with hB7-1/hB7-2.

Further, a VH can comprise the amino acid sequence of any one of SEQ ID NOs: 2, 12, 19, 23, 30, 36, 42, 45, 52, 58, 64, 69, 82, or 83 or can comprise slightly altered versions of these sequences. For example, a VH can comprise one or more partner-directing alteration(s), which can be (an) amino acid substitution(s) relative to any one of SEQ ID NOs: 2, 12, 19, 23, 30, 36, 42, 45, 52, 58, 64, 69, 82, and 83. In some embodiments, a VH can comprise no more than 6, 5, 4, 3, 2, or 1 amino acid alterations relative to any one of any one of SEQ ID NOs: 2, 12, 19, 23, 30, 36, 42, 45, 52, 58, 64, 69, 82, and 83. These amino acid alterations can be substitutions and/or can be partner-directing alterations. VHs comprising such altered sequences can be part of antibodies that can inhibit the interaction of hCTLA4 with hB7-1 and/or hB7-2.

Similarly, a VL of an anti-hCTLA4 antibody can comprise a VL CDR1, VL CDR2 and VL CDR3, which comprise the amino acid sequences of SEQ ID NO: 78 or 79 (CDR1), SEQ ID NO:9 (CDR2), and SEQ ID NO: 80 or 81 (CDR3). SEQ ID NO: 78, 79, 80 and 81 (see FIG. 2) are consensus sequences that each vary at two amino acid positions within a limited range of amino acids. Further, a VL CDR1, VL CDR2, and VL CDR3 can comprise, respectively, the amino acid sequences of SEQ ID NOs: 8, 9, and 10, SEQ ID NOs: 16, 9 and 17, SEQ ID NOs: 28, 9, and 17, SEQ ID NOs: 34, 9, and 17, SEQ ID NOs: 40, 9, and 10, SEQ ID NOs: 50, 9, and 17, SEQ ID NOs: 55, 9, and 56, SEQ ID NOs: 40, 9, and 62, SEQ ID NOs: 16, 9, and 62, or SEQ ID NOs: 73, 9, and 62. Antibodies comprising a VL which comprises any one of these sets of CDR sequences can inhibit the interaction of hCTLA4 with hB7-1/hB7-2.

Further, a VL of an anti-hCTLA4 antibody can comprise the amino acid sequence of any one of SEQ ID NOs: 7, 15, 27, 33, 39, 49, 54, 61, 67, 72, 84, and 85 or can comprise slightly altered versions of these sequences. For example, a VL can comprise one or more partner-directing alteration(s), which can be (an) amino acid substitution(s) relative to any one of SEQ ID NOs: 7, 15, 27, 33, 39, 49, 54, 61, 67, 72, 84, and 85. In some embodiments, a VL can comprise no more than 6, 5, 4, 3, 2, or 1 amino acid alterations relative to any one of any one of SEQ ID NOs: 7, 15, 27, 33, 39, 49, 54, 61, 67, 72, 84, and 85. These amino acid alterations can be substitutions and/or can be partner-directing alterations. VLs comprising such altered sequences can be part of antibodies that can inhibit the interaction of hCTLA4 with hB7-1 and/or hB7-2.

In another aspect, an anti-hCTLA4 antibody can comprise a VH CDR1, VH CDR2, VH CDR3, VL CDR1, VL CDR2, and VL CDR3, which have the amino acid sequences of SEQ ID NOs: 3, 4, 5, 8, 9, and 10, SEQ ID NOs: 3, 13, 5, 16, 9, and 17, SEQ ID NOs: 3, 20, 21, 16, 9, and 17, SEQ ID NOs: 3, 24, 25, 28, 9, and 17, SEQ ID NOs: 3, 31, 5, 34, 9, and 17, SEQ ID NOs: 3, 37, 5, 40, 9, and 10, SEQ ID NOs: 3, 43, 5, 28, 9, and 17, SEQ ID NOs: 3, 46, 47, 50, 9, and 17, SEQ ID NOs: 3, 31, 5, 55, 9, and 56, SEQ ID NOs: 3, 59, 5, 40, 9, and 62, SEQ ID NOs: 3, 65, 21, 16, 9, and 62, or SEQ ID NOs: 3, 70, 21, 73, 9, and 62. Antibodies comprising such sets of CDR sequences can inhibit the interaction of hCTLA4 with hB7-1/hB7-2.

In a further aspect, the VH and VL can comprise, respectively, the amino acid sequences of any one of the following groups of two amino acid sequences: SEQ ID NOs: 2 (VH) and 7 (VL); SEQ ID NOs: 12 (VH) and 15 (VL); SEQ ID NOs: 19 (VH) and 15 (VL); SEQ ID NOs: 23 (VH) and 27 (VL); SEQ ID NOs: 30 (VH) and 33 (VL); SEQ ID NOs: 36 (VH) and 39 (VL); SEQ ID NOs: 42 (VH) and 27 (VL); SEQ ID NOs: 45 (VH) and 49 (VL); SEQ ID NOs: 52 (VH) and 54 (VL); SEQ ID NOs: 58 (VH) and 61 (VL); SEQ ID NOs: 64 (VH) and 67 (VL); SEQ ID NOs: 69 (VH) and 72 (VL); and SEQ ID NOs: 83 (VH) and 85 (VL). In some embodiments, the VH and VL can comprise slightly altered versions of one of these groups of two sequences. For example, a VH and can comprise one or more partner-directing alteration(s), which can be (an) amino acid substitution(s), relative to one sequence in one of the groups of two sequences, and the VL can comprise one or more partner-directing alteration(s), which can be (an) amino acid substitution(s), relative to the other sequence in the same group of two sequences. A VH and VL that form an antibody or a portion thereof can each comprise an amino acid sequence which comprises no more than 6, 5, 4, 3, 2, or 1 amino acid alterations, optionally substitutions, relative to the first (VH) and the second (VL) amino acid sequence in a group of two sequences. These alterations can be partner-directing alterations. VHs and VLs comprising such altered sequences can be part of antibodies that can inhibit the interaction of hCTLA4 with hB7-1 and/or hB7-2.

Variable Domains of Anti-hPD1 Antibodies

In one aspect, provided herein are variable domains of anti-hPD1 antibodies that have unique, but closely related, amino acid sequences. These antibodies can bind to both human and cynomolgus monkey PD1 and can inhibit the interaction of hPD1 with hPDL1. In one aspect these, antibodies can be human, humanized, or primate IgG antibodies, which can be IgG1, IgG2, IgG3, or IgG4 antibodies.

FIGS. 5 and 6 show alignments of the CDRs of the VHs and VLs of the anti-hPD1 antibodies, the selection of which is described in Example 2. FIGS. 7 and 8 show alignments of the amino acid sequences of VHs and VLs, respectively, of the selected anti-hPD1 antibodies. VHs and VLs both vary at ten sites. Thus, the sequences these selected antibodies are closely related. Consensus sequences of these VHs and VLs are provided in SEQ ID NOs: 180 and 181 (VH) and SEQ ID NOs: 182 and 183 (VL).

In one aspect, a VH of an anti-hPD1 antibody contains a VH CDR1, a VH CDR2, and a VH CDR3 which comprise the amino acid sequences SEQ ID NOs: 169 or 170 (CDR1), 171 or 172 (CDR2), and 173 or 174 (CDR3). These are consensus sequences (FIG. 5) where at least one amino acid in each CDR can vary within a limited range of amino acids. Further, the VH CDR1, VH CDR2, and VH CDR3 can comprise, respectively, the amino acid sequences of SEQ ID NOs: 88, 89, and 90, SEQ ID NOs: 98, 89 and 99, SEQ ID NOs: 105, 89, and 90, SEQ ID NOs: 105, 111, and 112, SEQ ID NOs: 105, 111, and 90, SEQ ID NOs: 88, 89, and 112, SEQ ID NOs: 88, 89, and 127, SEQ ID NOs: 88, 89, and 134, SEQ ID NOs: 98, 89, and 90, SEQ ID NOs: 98, 111, and 112, SEQ ID NOs: 149, 150, and 112, SEQ ID NOs: 105, 111, and 90, SEQ ID NOs: 149, 89, and 127, SEQ ID NOs: 88, 89, and 112, or SEQ ID NOs: 105, 89, and 127. Antibodies comprising a VH which comprises any one of these sets of CDR sequences can inhibit the interaction of hPD1 with hPDL1.

Further, the VH can comprise the amino acid sequence of any one of SEQ ID NOs: 87, 97, 104, 110, 117, 122, 126, 133, 139, 144, 148, 154, 158, 162, 166, 180, and 181 or can comprise slightly altered versions of these sequences. For example, a VH can comprise one or more partner-directing alteration(s), which can be (an) amino acid substitution(s) relative to any one of SEQ ID NOs: 87, 97, 104, 110, 117, 122, 126, 133, 139, 144, 148, 154, 158, 162, 166, 180, and 181. In some embodiments, a VH can comprise no more than 6, 5, 4, 3, 2, or 1 amino acid alterations, which can be substitutions, relative to any one of any one of SEQ ID NOs: 87, 97, 104, 110, 117, 122, 126, 133, 139, 144, 148, 154, 158, 162, 166, 180, and 181. These alterations can be partner-directing alterations. VHs comprising such altered sequences can be part of antibodies that can inhibit the interaction of hPD1 with hPDL1.

Similarly, a VL of an anti-hPD1 antibody can have a VL comprising a VL CDR1, VL CDR2 and VL CDR3, which comprise the amino acid sequences of SEQ ID NOs: 175 or 176 (CDR1), 177 (CDR2), and 178 or 179 (CDR3). These are consensus sequences (see FIG. 6) where at least one amino acid in each CDR can vary within a limited range of amino acids. Further, the VL CDR1, VL CDR2, and VL CDR3 can comprise, respectively, the amino acid sequences of SEQ ID NOs: 93, 94, and 95, SEQ ID NOs: 102, 94, and 95, SEQ ID NOs: 93, 108, and 95, SEQ ID NOs: 115, 94, and 95, SEQ ID NOs: 120, 94, and 95, SEQ ID NOs: 102, 108, and 95, SEQ ID NOs: 130, 108, and 131, SEQ ID NOs: 137, 94, and 131, SEQ ID NOs: 142, 94, and 131, SEQ ID NOs: 130, 94, and 131, SEQ ID NOs: 142, 94, and 131, SEQ ID NOs: 115, 94, and 95, or SEQ ID NOs: 102, 108, and 95. Antibodies comprising a VL which comprises any one of these sets of CDR sequences can inhibit the interaction of hPD1 with hPDL1.

The VL can comprise the amino acid sequence of any one of SEQ ID NOs: 92, 101, 107, 114, 119, 124, 129, 136, 141, 146, 152, 156, 160, 164, 168, 182, and 183 or can comprise slightly altered versions of these sequences. For example, a VL can comprise one or more partner-directing alteration(s), which can be (an) amino acid substitution(s) relative to any one of SEQ ID NOs: 92, 101, 107, 114, 119, 124, 129, 136, 141, 146, 152, 156, 160, 164, 168, 182, and 183. In some embodiments, a VL can comprise no more than 6, 5, 4, 3, 2, or 1 amino acid alterations, which can be substitutions, relative to any one of any one of SEQ ID NOs: 92, 101, 107, 114, 119, 124, 129, 136, 141, 146, 152, 156, 160, 164, 168, 182, and 183. These alterations can be partner-directing alterations. VLs comprising such altered sequences can be part of antibodies that can inhibit the interaction of hCTLA4 with hB7-1 and/or hB7-2.

In another aspect, an anti-hPD1 antibody can comprise a VH CDR1, VH CDR2, VH CDR3, VL CDR1, VL CDR2, and VL CDR3, which have the amino acid sequences of SEQ ID NOs: 88, 89, 90, 93, 94, and 95, SEQ ID NOs: 98, 89, 99, 102, 94, and 95, SEQ ID NOs: 105, 89, 90, 93, 108, and 95, SEQ ID NOs: 105, 111, 112, 115, 94, and 95, SEQ ID NOs: 105, 111, 90, 120, 94, and 95, SEQ ID NOs: 88, 89, 112, 102, 108, and 95, SEQ ID NOs: 88, 89, 127, 130, 108, and 131, SEQ ID NOs: 88, 89, 134, 137, 94, and 131, SEQ ID NOs: 98, 89, 90, 142, 94, and 131, SEQ ID NOs: 98, 111, 112, 130, 94, and 131, SEQ ID NOs: 149, 150, 112, 130, 94, and 131, SEQ ID NOs: 105, 111, 90, 142, 94, and 131, SEQ ID NOs: 149, 89, 127, 115, 94, and 95, SEQ ID NOs: 88, 89, 112, 93, 94, and 95, or SEQ ID NOs: 105, 89, 127, 102, 108, and 95. Antibodies comprising such sets of CDR sequences can inhibit the interaction of hPD1 with hPDL1.

In a further aspect, the VH and VLs of an anti-hPD1 antibody can comprise, respectively, the amino acid sequences of any one of the following groups of two amino acid sequences: SEQ ID NOs: 87 (VH) and 92 (VL); SEQ ID NOs: 97 (VH) and 101 (VL); SEQ ID NOs: 104 (VH) and 107 (VL); SEQ ID NOs: 110 (VH) and 114 (VL); SEQ ID NOs: 117 (VH) and 119 (VL); SEQ ID NOs: 122 (VH) and 124 (VL); SEQ ID NOs: 126 (VH) and 129 (VL); SEQ ID NOs: 133 (VH) and 136 (VL); SEQ ID NOs: 139 (VH) and 141 (VL); SEQ ID NOs: 144 (VH) and 146 (VL); SEQ ID NOs: 148 (VH) and 152 (VL); SEQ ID NOs: 154 (VH) and 156 (VL); SEQ ID NOs: 158 (VH) and 160 (VL); SEQ ID NOs: 162 (VH) and 164 (VL); SEQ ID NOs: 166 (VH) and 168 (VL); SEQ ID NOs: 180 (VH) and 182 (VL); and SEQ ID NOs: 181 (VH) and 183 (VL). In some embodiments, a VH and VL can comprise slightly altered versions of one of these groups of two sequences. For example, a VH and can comprise one or more partner-directing alteration(s), which can be (an) amino acid substitution(s), relative to one sequence in one of the groups of two sequences, and the VL can comprise one or more partner-directing alteration(s), which can be (an) amino acid substitution(s), relative to the other sequence in the same group of two sequences. A VH and VL that form an antibody or a portion thereof can each comprise an amino acid sequence which comprises no more than 6, 5, 4, 3, 2, or 1 amino acid alterations, which can be substitutions, relative to the first (VH) and second (VL) amino acid sequence in a group of two sequences. These alterations can be partner-directing alterations. VHs and VLs comprising such altered sequences can be part of antibodies that can inhibit the interaction of hPD1 with hPDL1.

Additional Aspects of Anti-hPD1 and/or Anti-hCTLA4 Antibodies

The anti-hCTLA4 and anti-hPD1 antibodies described herein can be human, humanized, or primate antibodies and/or IgG antibodies, for example IgG1, IgG2, IgG3, or IgG4 antibodies. Such IgG antibodies can comprise partner-directing alterations, such as HC and/or LC partner-directing alterations. Further, such IgG antibodies can comprise one or more alteration(s) that disfavor(s) heterodimers. Such alterations can improve the chances that a single host cell line into which DNAs encoding at least two different IgG antibodies have been introduced will produce no more than two or three different major species of antibodies.

The partner-directing alteration(s) can form part of charge pairs or pairs of contacting cysteines within an IgG anti-hCTLA4 and/or anti-hPD1 antibody as described herein, optionally a human or primate IgG antibody. For example, partner-directing alterations include alterations (including amino acid substitutions) that create, partially or wholly, any one of following charge pairs: 44D/E (VH) and 100R/K (VL); 44R/K (VH) and 100D/E (VL); 105R/K (VH) and 43D/E (VL); 105D/E (VH) and 43R/K (VL); 147D/E (CH1) and 131R/K (CL); 147R/K (CH1) and 131D/E (CL); 168D/E (CH1) and 174R/K (CL); 168R/K (CH1) and 174D/E (CL); 181R/K (CH1) and 178E/D (CL); and 181E/D (CH1) and 178R/K (CL). If a charged amino acid already exists at one of these sites, only one partner-directing alteration will be necessary to create the charge pair. In other situations, two partner-directing alterations, one in the HC and one in the LC, will be needed to create the charge pair. In addition, partner-directing alterations include substitutions where cysteine is substituted for another amino acid such that contacting pairs of cysteines are created, which can form disulfide bridges. In a human IgG1 antibody, these can include the following pairs: 126 (CH1) and 121 (CL), 170C (CH1) and 162C (CL), 170 (CH1) and 176 (CL), 173 (CH1) and 160 (CL), and 183 (CH1) and 176 (CL). In a human IgG4 antibody, these can include the following pairs: 170C (CH1) and 162C (CL), 173C (CH1) and 162C (CL), and 183 (CH1) and 176 (CL). The contacting cysteine pair in a cognate CH1/CL pair in one antibody in mixture of antibodies can be located at a different position than that of the another antibody in the mixture, which can increase the selectivity in formation of cognate HC/LC pairs. Those portions of U.S. Provisional Application 62/342,267 that describe partner-directing alterations, i.e., pages 33-36 and Examples 1-3 and 5, including figures referred to therein, are incorporated herein by reference.

Well known methods can be used to create DNAs encoding HCs and/or LCs containing partner-directing alterations. Such methods are described in Examples 1 and 2 below and include methods such as artificial synthesis of DNA sequences (for example by commercial vendors such as, e.g., Integrated DNA Technologies, Coralville, Iowa USA or Genewiz, South Plainfield, N.J., USA, among many others) and joining of DNA segments by Gibson reaction (i.e., overlap PCR) as described in, e.g., Gibson Assembly® Master Mix Instruction Manual, New England Biolabs Inc. (NEB), Version 3.3, NEB catalog no. #E2611S/L, NEB Inc., Ipswich, Mass., USA. The designing, making, and testing of partner-directing alterations is described in detail in U.S. Provisional Application 62/342,267. Examples 1-3 and 5 and FIGS. 4-7 and 12-15 of U.S. Provisional Application 62/342,267 are incorporated herein by reference. Once DNAs encoding the antibodies are made, the antibodies can be made in transfected host cells as described in, e.g., Example 1 below.

In further embodiments, an anti-hCTLA4 and/or anti-hPD1 antibody as described herein can comprise one or more alteration(s) that disfavor(s) HC/HC heterodimer formation. In U.S. Provisional Application 62/342,267, it is shown that heterodimers were not readily detectable in cells transfected with two different IgG antibodies where one of the antibodies is either an IgG4 antibody or an IgG1 antibody comprising the substitution K409R in its HC and the other antibody is an IgG1 antibody comprising the substitutions D399K/R and K409D/E. Example 4 and FIGS. 8-11 of U.S. Provisional Application 62/342,267 are incorporated herein by reference.

Mixtures of Anti-hCTLA4 and Anti-hPD1 Antibodies

In another aspect, mixtures of anti-hCTLA4 and anti-hPD1 antibodies are described herein. In the treatment of some conditions, blocking or inhibiting both CTLA4 and PD1 can be beneficial. See, e.g., Larkin et al. (2015), New Engl. J. Med. 373(1): 23-34. The antibody mixture can comprise the particular anti-hPD1 and anti-hCTLA4 antibodies described herein.

In some embodiments, a mixture of an anti-hPD1 and an anti-hCTLA4 antibody can be made in a single host cell line into which DNA encoding both of the antibodies has been introduced. Such methods have been described in detail in U.S. Provisional Application 62/342,167 and in International Application PCT/US2017/030676, and the portions of U.S. Provisional Application 62/342,167 and PCT/US2017/030676 that describe such methods are incorporated herein by reference. Production of an antibody mixture in a single host cell line, as compared to production in two separate cell lines, is much more efficient and cost-effective since it requires developing and running only one commercial process rather than two. The antibodies in mixtures produced in a single host cell line can comprise one or more HC and/or LC partner-directing alteration(s) and/or one or more alteration(s) that disfavor(s) heterodimers. Such alterations can limit the number of antibody species formed in the host cell line due to promiscuous pairing of the two different HCs and LCs and/or HC/HC heterodimer formation. See, e.g. FIG. 3 of U.S. Provisional Application 62/342,167, which is incorporated herein by reference. This can reduce the number of purification steps required to produce a mixture comprising at most three or at most two different antibodies from a single host cell line containing DNA encoding two different HCs and two different LCs.

Exemplary HC and LC partner-directing alterations, one or more of which can be included in the anti-hCTLA4 and/or anti-hPD1 antibodies in an antibody mixture, are listed in Table 9 below.

TABLE 9

Exemplary partner-directing alterations

| | Antibody 1* | | | | Antibody 2* | | | |
|---|---|---|---|---|---|---|---|---|
| | HC1 | | LC1 | | HC2 | | LC2 | |
| | VH | CH1@ | VL | CL | VH | CH1@ | VL | CL |
| 1# | 44E/D | | 100 R/K | | 44R/K | | 100 E/D | |
| 2 | 105 R/K | | 43E/D | | 105 E/D | | 43R/K | |
| 3 | | 147 R/K | 131 E/D | | | 147 E/D | 131 R/K | |
| 4 | | 168 E/D | 174 R/K | | | 168 R/K | 174 E/D | |
| 5 | | 181 R/K | 178 E/D | | | 181 E/D | 178 R/K | |
| 6 | | 126C | 121C | | | 133C | | 209C |
| 7 | | 168C | 174C | | | 133C | | 117C |
| 8 | | 170C | 162C | | | 183C | | 176C |
| 9 | | 173C | 160C | | | 170C | | 162C |
| 10 | | 173C | 160C | | | 183C | | 176C |
| 11 | | 170C | 176C | | | 173C | | 160C |
| 12 | | 170C | 176C | | | 183C | | 176C |
| 13 | | 170C | 162C | | | 170C | | 176C |
| 14 | | 173C | 162C | | | 170C | | 176C |
| 15 | | 173C | 162C | | | 173C | | 160C |
| 16 | | 173C | 162C | | | 170C | | 162C |

*Antibodies 1 and 2 are different antibodies. For the purposes of this table, they are interchangeable.
The alterations listed in a single row for heavy and light chains of a single first antibody (e.g., HC1 and LC1) can occur together as listed. However, the second antibody in the mixture may or may not contain the alterations listed in the same row for Antibody 2. In some embodiments, an antibody can comprise the alterations listed in two or more rows, e.g., 105R/K and 147R/K in a heavy chain and 43E/D and 131E/D in a light chain.
@Not all alterations are suitable for all IgG subtypes.

Alterations that disfavor heterodimers can also be included in the anti-hCTLA4 and/or the anti-hPD1 antibody when they are part of an antibody mixture, assuming that both antibodies are IgG antibodies. In one embodiment, one antibody can be an IgG4 antibody (which has a naturally occurring arginine at position 409) or an IgG1 antibody that has been altered so as to have an arginine at position 409, i.e., has the alteration K409R, and the other antibody has the alterations 399K/R and 409D/E.

In some embodiments, the anti-hCTLA4 antibody in an antibody mixture can comprise one or more alterations that increase the clearance of the antibody in vivo. Such alterations can include, for example, one or more of the following: M252A, M252L, M252S, M252R, R255K, and H435R. Other alterations having such effects can also be used. If a particular alteration within an IgG constant domain of an antibody has the effect of increasing in vivo clearance (as defined herein above) of, for example, a particular human, humanized, or primate IgG antibody, it is herein defined to be an alteration that increases in vivo clearance of any human, humanized, or primate IgG antibody comprising such an altered constant domain.

Methods of Making Antibodies and Mixtures of Antibodies

Generally, individual antibodies can be produced by introducing DNA encoding the antibody into a host cell, culturing the host cell under conditions suitable for production of the antibody by the cell, and recovering the antibody from the cell mass or the cell supernatant. The DNA can be introduced by transfection, transformation, electroporation, bombardment with microprojectiles, microinjection, lipofection, etc. Thereafter, the antibody can be purified to eliminate components other than the desired antibody, for example, host cell proteins, medium components, and/or undesired antibody species, for example, species of an IgG antibody that do not contain two heavy and two light chains. Such purification steps can include, for example, selective precipitation, column chromatography, dialysis, etc.

Antibodies produced individually by the methods described immediately above can be mixed to produce a mixture. Alternatively, mixtures of antibodies can be produced in a similar way except that DNA encoding both antibodies can be introduced into the host cell, either simultaneously or sequentially. A host cell containing DNAs encoding two different IgG antibodies, i.e., two different heavy and light chains, can potentially produce up to ten different IgG antibody species, due to promiscuous HC/HC and HC/LC pairing. To limit this number of species, the antibodies can comprise HC and LC partner-directing alterations and/or alterations that disfavor heterodimers. Such alterations can limit the number of major antibody species produced by the host cell. Such mixtures can be purified as described above.

One of skill in the art will appreciate that producing a mixture of antibodies in a single host cell line, rather than in two host cell lines, represents a significant increase in ease and efficiency of production relative to developing and running two commercial production processes. Development of a commercial production process for any one antibody requires optimization of a myriad of factors including, e.g., the expression system, the host cell line (if a cell line is used for expression), the cell culture process (including physical variables such as using stirred tank vs. perfusion vs. many other culture methods, as well as the medium and feeding strategy used to grow the host cell line), and antibody purification and formulation. Moreover, once a process is developed, it must be characterized and validated and transferred to a manufacturing facility for current good manufacturing practices (cGMP) production. See, e.g., Li et al. (2010), mAbs 2(5): 466-477. Thus, it is clear that production of an antibody mixture in a single process, versus production in two processes, represents a significant increase in ease and efficiency of production, not to mention a significant decrease in cost.

Polynucleotides and Vectors

Provided are polynucleotides, e.g., DNA or other nucleic acids, encoding the antibodies and mixtures of antibodies described herein. Using the guidance provided herein, one of skill in the art could combine known or novel nucleic acid sequences encoding antibodies and modify them by known methods to create polynucleotides encoding the antibodies and the mixtures of antibodies described herein, which comprise VH and VL amino acid sequences described herein. Such VH and VL sequences are disclosed, for example, in FIGS. 3, 4, 7, and 8 and throughout this Specification. In some embodiments, (a) polynucleotide(s) can encode an HC and/or LC comprising alterations with respect to the amino acid sequences disclosed in FIGS. 3, 4, 7, and 8, such as partner-directing alterations. Such alterations can be amino acid substitutions. In addition, such (a) polynucleotide(s) can encode an HC and/or an LC comprising one or more partner-directing alterations outside of the variable domains and/or one or more alterations that disfavor heterodimers. Exemplary nucleic acid sequences encoding VH or VLs described herein include SEQ ID NOs: 1, 6, 11, 14, 18, 22, 26, 29, 32, 35, 38, 41, 44, 48, 51, 53, 57, 60, 63, 66, 68, 71, 86, 91, 96, 100, 103, 106, 109, 113, 116, 118, 121, 123, 125, 128, 132, 135, 138, 140, 143, 145, 147, 151, 153, 155, 157, 159, 161, 163, 165, 167, 184, 186, 188, 190, 192, and 194. Numerous nucleic acid sequences encoding human, mammalian, and primate immunoglobulin constant domains, for example the CL, CH1, hinge, CH2, and CH3 are known in the art. See, e.g., Kabat et al., supra. Optionally, polynucleotide sequences encoding variable domains described herein can be combined with polynucleotide sequences encoding such constant domains to create antibodies in any of a variety of formats, e.g., IgG, IgM, IgD, IgE, IgA, bispecific formats, scFv, scFv-Fc, Fabs, BiTE (scFc-linker-scFv), Fab-scFv, IgG-scFv. In some embodiments, these antibodies can comprise partner-directing alterations and/or alterations that disfavor heterodimers. In some embodiments these antibodies can be mammalian antibodies, optionally human, humanized, or primate antibodies.

Methods of modifying polynucleotides are well-known in the art. Perhaps the most straightforward method for creating a modified polynucleotide is to synthesize a polynucleotide having the desired sequence. A number of companies, e.g., DNA 2.0 (Menlo Park, Calif., USA), BlueHeron (Bothell, Wash.), Genewiz (South Plainfield, N.J.), Gen9 (Cambridge, Mass.), and Integrated DNA Technologies (Coralville, Iowa), provide this service. Other known methods of introducing mutations, for example site-directed mutagenesis using polymerase chain reaction (PCR), can also be employed. See, e.g., Zoller (1991), Curr. Opin. Biotechnol. 2(4): 526-531; Reikofski and Tao (1992), Biotechnol. Adv. 10(4): 535-547.

Vector(s) that contain(s) polynucleotides, optionally DNA, encoding the antibodies and mixtures thereof described herein can be any vector(s) suitable for expression of the antibodies in a chosen host cell. The vector can include a selectable marker for selection of host cells containing the vector and/or for maintenance and/or amplification of the vector in the host cell. Such markers include, for example, (1) genes that confer resistance to antibiotics or other toxins, e.g., ampicillin, tetracycline, or kanamycin for prokaryotic host cells, (2) genes that complement auxotrophic deficiencies of the cell, or (3) genes whose operation supplies critical nutrients not available from complex or defined media. Specific selectable markers can be the kanamycin resistance gene, the ampicillin resistance gene, and the tetracycline resistance gene. A zeocin resistance or neomycin resistance gene may also be used for selection in both prokaryotic and eukaryotic host cells. A dihydrofolate reductase (DHFR) gene and/or a promoterless thymidine kinase gene can be used in mammalian cells, as is known in the art. See, e.g., Kingston et al. 2002, AMPLIFICATION USING CHO CELL EXPRESSION VECTORS, Current Protocols in Molecular Biology, Ch. 16, Unit 16.23, Wiley 2002.

In addition, a vector can contain one or more other sequence elements necessary for the maintenance of the vector and/or the expression of the inserted sequences encoding the antibodies or antibody mixtures described herein. Such elements include, for example, an origin of replication, a promoter, one or more enhancers, a transcriptional terminator, a ribosome binding site, a polyadenylation site, a polylinker insertion site for exogenous sequences (such as the DNA encoding an antibody or mixture of antibodies described herein), and an intervening sequence between two inserted sequences, e.g., DNAs encoding an HC and an LC. These sequence elements can be chosen to function in the desired host cells so as to promote replication and/or amplification of the vector and expression of the heterologous sequences inserted into the vector. Such sequence elements are well known in the art and available in a large array of commercially available vectors.

DNA encoding one or more antibodies can be introduced into a host cell using any appropriate method including, for example, transfection, transduction, lipofection, transformation, bombardment with microprojectiles, microinjection, or electroporation. In some embodiments, DNA encoding two full-length antibodies can be introduced into the host cells. Such methods are known in the art and described in, e.g., Kaestner et al. (2015), Bioorg. Med. Chem. Lett. 25: 1171-1176, which is incorporated herein by reference.

In some embodiments, the polynucleotides encoding the antibodies or the mixtures of antibodies can be carried on one or more viral vector(s), optionally oncolytic viral vector(s). Examples of such viral vectors include adenovirus, adeno-associated virus (AAV), retrovirus, vaccinia virus, modified vaccinia virus Ankara (MVA), herpes virus, lentivirus, Newcastle Disease virus, measles virus, coxsackievirus, reovirus, and poxvirus vectors. In such embodiments, these viral vectors containing polynucleotides encoding the antibody or mixture of antibodies described herein can be administered to patients to treat a disease. In a cancer patient, for example, such viral vectors containing polynucleotides encoding an antibody or mixture of antibodies can be administered directly to a tumor or a major site of cancer cells in the patient, for example by injection, inhalation (for a lung cancer), topical administration (for a skin cancer), and/or administration to a mucus membrane (through with the nucleic acids can be absorbed), among many possibilities. Alternatively, such viral vectors can be administered systemically, for example, orally, topically, via a mucus membrane, or by subcutaneous, intravenous, intraarterial, intramuscular, or peritoneal injection as described herein. Similarly, polynucleotides encoding a mixture of antibodies as described herein, which can be encased in liposomes, can be administered to a patient suffering from a disease.

Pharmaceutical Compositions and Methods of Administration

The antibodies, antibody mixtures, polynucleotides, and vectors described herein can be administered in a pharmaceutically acceptable formulation. Numerous pharmaceutical formulations are known in the art. Many such formulations are described in REMINGTON: THE SCIENCE AND PRACTICE OF PHARMACY, 21$^{st}$ ed., Lippincott Williams & Wilkins, Philadelphia, Pa., 2005, the relevant portions of which are incorporated herein by reference. Such a pharmaceutically acceptable formulation can be, for example, a liquid such as a solution or a suspension, a solid such as a pill, a capsule, a paste, or a gel. A liquid formulation can contain, for example, one or more of the following components: a buffer, an excipient, a salt, a sugar, a detergent, and a chelating agent. It can be designed to preserve the function of the antibody, antibody mixture, polynucleotide, or vector and to be well tolerated by the patient.

Polynucleotides and proteins such as antibodies are usually administered parenterally, as opposed to orally. Depending on the formulation, oral administration could subject the protein or polynucleotide to the acidic environment of the stomach, which could inactivate the protein or polynucleotide. In some embodiments, a specific formulation might allow oral administration of a specific protein or polynucleotide where the protein or polynucleotide is either insensitive to stomach acid or is adequately protected from the acidic environment, e.g., by a specific coating on a pill or capsule. The formulations could also be administered via a mucus membrane, including, for example, intranasal, vaginal, rectal, or oral administration, or administration as an inhalant. The formulations could also be administered topically in some embodiments. Commonly, antibodies and polynucleotides are administered by injection of a liquid formulation. Injection can be, for example, subcutaneous, intravenous, intraarterial, intralesional (e.g., intratumoral), intramuscular, or peritoneal.

Host Cells Containing Polynucleotides Encoding an Antibody or a Mixture of Antibodies A host cell containing one or more polynucleotide(s) encoding one or more antibodies can be any of a variety of cells suitable for the expression of a recombinant protein. These include, for example, gram negative or gram positive prokaryotes, for example, bacteria such as *Escherichia coli, Bacillus subtilis*, or *Salmonella typhimurium*. In other embodiments, the host cell can be a eukaryotic cell, including such species as *Saccharomyces cerevisiae, Schizosaccharomyces pombe*, or eukaryotes of the genus *Kluyveromyces, Candida,* Spodotera, or any cell capable of expressing heterologous polypeptides. In further embodiments, the host cell can be a mammalian cell. Many mammalian cell lines suitable for expression of heterologous polypeptides are known in the art and can be obtained from a variety of vendors including, e.g., American Type Culture Collection (ATCC). Suitable mammalian host cell lines include, for example, the COS-7 line (ATCC CRL 1651) (Gluzman et al., 1981, Cell 23:175), L cells, C127 cells, 3T3 cells (ATCC CCL 163), Chinese hamster ovary (CHO) cells, or their derivatives such as Veggie CHO and related cell lines, which grow in serum-free media (Rasmussen et al., 1998, Cytotechnology 28: 31), CHO-K1 and CHO pro-3 cell lines and their derivatives such as the DUKX-X11 and DG44 cell lines, which are deficient in dihydrofolate reductase (DHFR) activity, HeLa cells, baby hamster kidney (BHK) cells (e.g., ATCC CRL 10), the CVI/EBNA cell line derived from the African green monkey kidney cell line CVI (ATCC CCL 70) as described by McMahan et al., 1991, EMBO J. 10: 2821, human embryonic kidney (HEK) cells such as 293, 293 EBNA or MSR 293, human epidermal A431 cells, human CoIo205 cells, HL-60 cells, U937 cells, HaK cells, Jurkat cells, HepG2/3B cells, KB cells, NIH 3T3 cells, S49 cells, and mouse myeloma cells, including NS0 and Sp2/0 cells. Other prokaryotic, eukaryotic, or mammalian cell types that are capable of expression of a heterologous polypeptide could also be used.

Methods of Treatment

The anti-hCTLA4 antibodies, anti-hPD1 antibodies, mixtures thereof, and/or polynucleotides encoding such antibodies or mixtures described herein, optionally contained within one or more vectors, e.g., oncolytic viral vectors, can be used to enhance an immune response and/or to treat a variety of conditions including, for example, infections, immunodeficiency disorders, and various cancers such as melanoma, non-small cell lung cancer, head and neck squamous cell cancer, small cell lung cancer, gastric cancer, bladder cancer, clear cell renal sarcoma, and Hodgkin's lymphoma. Whether an immune response has been enhanced, as meant herein, can be assessed by a mixed lymphocyte reaction (MLR) assay as described below in Example 8.

The anti-hCTLA4 antibodies, anti-hPD1 antibodies, mixtures thereof, and/or polynucleotide(s) encoding such antibodies or mixtures can be administered with an additional therapy, which is administered before, after, and/or concurrently with the antibody, mixture of antibodies, or polynucleotide(s). The additional therapy can be selected from the group consisting of immunomodulatory molecules, radiation, a chemotherapeutic agent, a targeted biologic, a targeted inhibitor, and/or an oncolytic virus.

In some embodiments the additional therapy can be an antagonist of PDL1, TIGIT, CCR4, CCR8, CSFR1a, B7H3, B7H4, CD96, or CD73, an agonist of GITR, 41BB, OX40, or CD40, an oncolytic virus such as talimogene laherparepvec (IMLYGIC™), a bispecific T cell engager (BiTE) such as blinatumomab, an indoleamine 2, 3 dioxygenase (IDO) inhibitor, an anti-angiogenic agent such as bevacizumab, an antibody-drug conjugate, or a tyrosine kinase inhibitor.

If the additional therapy is a chemotherapeutic, it can, for example, be busulfan, temozolomide, cyclophosphamide, lomustine (CCNU), streptozotocin, methyllomustine, cis-diamminedi-chloroplatinum, thiotepa, aziridinylbenzo-quinone, cisplatin, carboplatin, melphalan hydrochloride, chlorambucil, ifosfamide, mechlorethamine HCl, carmustine (BCNU)), adriamycin (doxorubicin), daunomycin, mithramycin, daunorubicin, idarubicin, mitomycin C, bleomycin, vincristine, vindesine, vinblastine, vinorelbine, paclitaxel, docetaxel, VP-16, VM-26, methotrexate with or without leucovorin, 5-fluorouracil with or without leucovorin, 5-fluorodeoxyuridine, 5-fluorouracil, 6-mercaptopurine, 6-thioguanine, gemcitabine, cytarabine, 5-azacytidine, hydroxyurea, deoxycoformycin, fludarabine, etoposide, irinotecan, topotecan, actinomycin D, dacarbazine (DTIC), mAMSA, procarbazine, hexamethylmelamine, pentamethylmelamine, L-asparaginase, mitoxantrone. See, e.g., Cancer: Principles and Practice of Oncology, 4.sup.th Edition, DeVita et al., eds., J.B. Lippincott Co., Philadelphia, Pa. (1993), the relevant portions of which are incorporated herein by reference.

With regard to the antibodies or mixtures thereof, they can be administered to a patient in a therapeutically effective dose at appropriate intervals. For example, a single dose of a single antibody or antibody mixture can be from about 0.01 milligram per kilogram of body weight (mg/kg) to about 50 mg/kg, from about 0.05 mg/kg to about 10 mg/kg, from about 0.1 mg/kg to about 10 mg/kg, or from about 0.5 mg/kg to about 7 mg/kg. A single dose can be at a dose of about 0.05 mg/kg, 0.1 mg/kg, 0.5 mg/kg, 1 mg/kg, 2 mg/kg, 3 mg/kg, 4 mg/kg, 5, mg/kg, 6 mg/kg, 7 mg/kg, 8 mg/kg, 9 mg/kg, or 10 mg/kg. Similarly, a single dose of an antibody or antibody mixture can be from about 0.37 milligrams per square meter of skin surface area ($mg/m^2$) to about 1850 $mg/m^2$, from about 0.5 $mg/m^2$ to about 370 $mg/m^2$, from about 3.7 $mg/m^2$ to about 370 $mg/m^2$, or from about 18.5 $mg/m^2$ to about 259 $mg/m^2$. A single dose can be about 10 $mg/m^2$, 20 $mg/m^2$, 37 $mg/m^2$, 74 $mg/m^2$, 111 $mg/m^2$, 148 $mg/m^2$, 185 $mg/m^2$, 222 $mg/m^2$, 259 $mg/m^2$, 296 $mg/m^2$, 333, $mg/m^2$, or 370 $mg/m^2$. Similarly, a single dose of an antibody or antibody mixture can be administered at a dose from about 0.62 mg to about 3100 mg, from about 1 mg to about 620 mg, from about 6.2 mg to about 620 mg, or from about 10 mg to about 434 mg. A single dose can be about 0.5 1, 3, 6, 10, 15, 20, 25, 30, 35, 40, 45, 50, 60, 70, 80, 90, or 100 mg.

Doses of antibodies, mixtures of antibodies, or polynucleotides encoding them can be administered once or twice or at time intervals over a period of time. For example, doses can be administered every day, every other day, twice a week, once a week, once every ten days, once every two weeks, once every three weeks, once per month, or once every two, three, four, five, six, seven eight, nine, ten, eleven, or twelve months. Dosing can continue, for example, for about one to four weeks, for about one to six months, for about six months to a year, for about one to two years, or for up to five years. In some cases, dosing can be discontinued and restarted. In some embodiments, a mixture comprising an anti-hCTLA4 and an anti-hPD1 antibody can be administered so that both antibodies can be administered simultaneously. After one or more doses of the mixture, the anti-hPD1 antibody alone can be administered. In some embodiments, dosing with the anti-hPD1 antibody can continue for a period of time. In some embodiments, dosing with the antibody or mixture of antibodies can be discontinued and resumed one or more times.

In the case of one or more polynucleotide(s) encoding the antibody or mixtures of antibodies described herein, doses can, for example, be from about $5 \times 10^9$ copies the of the polynucleotide(s) per kilogram of body weight (copies/kg) to about $10^{15}$ copies/kg, from about $10^{10}$ copies/kg to about $10^{14}$ copies/kg, or from about $5 \times 10^{10}$ copies/kg to about $5 \times 10^{13}$ copies/kg. Alternatively, doses can be about $10^{10}$, $10^{11}$, $10^{12}$, $10^{13}$, $5 \times 10^{13}$, $10^{14}$, $2 \times 10^{14}$, $3 \times 10^{14}$, $4 \times 10^{14}$, $5 \times 10^{14}$, $6 \times 10^{14}$, $7 \times 10^{14}$, $8 \times 10^{14}$, $9 \times 10^{14}$, or $10^{15}$ copies of the polynucleotide(s). Frequency of dosing can be adjusted as needed and can be as described above or, for example, every day, every other day, twice a week, once a week, once every ten days, once every two weeks, once every three weeks, once per month, or once every two, three, four, five, six, seven eight, nine, ten, eleven, or twelve months.

Having described the invention in general terms above, the specific Examples below are offered to exemplify the invention, not limit its scope. It is understood that various changes and modifications may be made to the invention that are in keeping with the spirit of the invention described herein and would be apparent to one of skill in the art. Such changes and modifications are within the scope of the invention described herein, including in the appended claims.

EXAMPLES

Example 1: Making Anti-hCTLA4 Antibodies

A DNA library encoding a variety of anti-hCTLA4 Fab fragments, which were randomized at selected positions, was created as follows. The library was based on human germline VH (IGHV3-33*01-IGHJ4*01) and VL (IGKV3-20*01-IGKJ3*01) framework regions. Overlapping single-stranded oligonucleotides, 69 to 99 bases long, were used to assemble cDNAs encoding heavy and light chain variable regions. Using degenerate synthetic oligonucleotides, eight and five conservatively randomized codons were introduced into DNA encoding the VH and VLs, respectively. The conservatively randomized codons were randomized such that only conservative amino acid substitutions were expected to result from the randomization. For example, a G-G-C codon encoding glycine could be conservatively randomized using A/G-C/G-C to encode glycine, alanine, serine or threonine. The oligonucleotides were mixed and assembled into VH and VL libraries separately by polynucleotide chain reaction (PCR). DNA encoding a CL kappa (Ck) fragment followed by the self-cleaving 2A peptide (Pep2A; see, e.g., Kim et al. (2011), PLOS ONE, http://dx.doi.org/10.1371/journal.pone.0018556) and a signal peptide for the downstream VH was amplified using a gBlock® (Integrated DNA Technologies (IDT), Coralville, Iowa, USA) as template for PCR. All oligonucleotides were synthesized by IDT. All amplifications were carried out with the Pfu DNA polymerase.

To display the library of randomized Fab fragments in yeast, *Saccharomyces cerevisiae* cells were electroporated with a linearized vector having sequence encoding signal peptide SP1 on one end (which is preceded by a galactose-inducible promoter) and sequence encoding a CH1 on the other end (followed by be sequence encoding agglutinin) plus the three PCR fragments described above encoding (1) SP1-VL-Ck(part), (2) Ck-R6-Pep2A-SP2, and (3) SP2-VH-CH1(part), in which the VL and VH were conservatively randomized at selected sites. PCR fragment (1) overlaps the SP1 end of the vector and the Ck end of PCR fragment 2. The SP2 end of PCR fragment (2) overlaps PCR fragment 3 on its SP2 end, and the CH1 end of PCR fragment 3 overlaps the vector on its CH1 end. Since all of these overlaps are within the range of 30 to 60 base pairs, homologous recombination in yeast enables the fragments to assemble into a single vector containing an insert having the following order of sequence elements: SP1-VL-Ck-R6-Pep2A-SP2-VH-CH1-HA-agglutinin, where R6 encodes six consecutive arginine residues, and HA is an HA tag, i.e., a small peptide derived from human influenza hemagglutinin that has been extensively used as a protein tag. Expression of these sequences is driven by a galactose inducible promoter upstream from SP1. Transformants were grown on selective agar plates made with yeast medium containing dextrose and lacking uracil. The vector contains a gene that complements the inability of the host yeast strain to make uracil. The library sizes, i.e., the total number of transformants, were in the range of about $2 \times 10^8$ to $3 \times 10^8$ transformants. The estimated complexities of the libraries were less than about $10^7$, meaning that less than about $10^7$ different combinations of nucleotide sequences encoding Fab fragments existed within each library. These estimates were based on the number of possible combinations that could occur given the conservative randomization at the sites that were varied.

To assess the actual diversity and quality of the library, DNA segments encoding the Fab fragments from 50 randomly picked yeast clones were examined. The VH and VL DNA fragments of these clones were amplified by yeast colony PCR and sequenced by Genewiz Inc., Seattle, Wash. See, e.g. Dudaite et al. (2015), *Direct PCR from Yeast Cells*, Application Note, Thermo Scientific. DNA sequence analysis revealed that 70% of the sequences encoded in-frame VHs and CH1s and in-frame VLs and CLs, and the DNA encoding the VH and VLs contained the designed and expected variations at the targeted sites.

To screen the libraries, *S. cerevisiae* cells were grown in medium lacking uracil and containing dextrose, the cells were spun down and resuspended in medium lacking uracil and containing galactose to induce Fab expression. Yeast cells were labeled with an ALEXA FLUOR® 488-labeled antibody specific for the HA tag and a complex of streptavidin-allophycocyanin (streptavidin-APC) and biotinylated hCTLA4:Fc fusion protein, i.e., the extracellular region of hCTLA4 fused to the Fc region of IgG1, to simultaneously detect levels of Fab displayed by the cells and levels of hCTLA4 bound by the displayed Fab fragments. A negative control was labeled with the anti-HA tag antibody and a complex of streptavidin-APC and an irrelevant biotinylated protein (biotinylated PD1). Samples were sorted on a FACSARIA™ flow cytometer (BD Biosciences, San Jose, Calif.) with a sorting window as shown in FIG. 9 and collected at an event rate of 4,000 cells/sec. A total of 1×10⁸ cells were screened during the first round of fluorescence-activated cell sorting (FACS), and 0.5% of the population was collected. The collected cells were grown at 30° C. on agar plates made with yeast medium containing dextrose and lacking uracil. Yeast cells from these plates were scraped into liquid medium containing dextrose and lacking uracil, and cultured at 30° C. prior to induction in liquid medium containing galactose and lacking uracil for next round of sorting. Two rounds of sorting were performed. The first sort was done in enrichment mode, i.e., done using a fast sorting speed to enable the sorting of many cells, using 500 nM of the complex of streptavidin-APC and biotinylated hCTLA4:Fc for labeling, and the second sort was done in purification mode, i.e., done using a slow sorting speed, and used 0.6 nM of the complex of streptavidin-APC and biotinylated hCTLA4 for labeling. FIG. 9 shows the FACS analyses of a negative control and the first and second rounds of cell sorting. A polygon labeled "PS" in FIG. 9 indicates the gated sorting window.

To increase the chances of getting true positives, the collected cells were re-sorted for a third time and plated on agar plates made with medium containing dextrose but lacking uracil to obtain individual colonies. To confirm that the Fab fragments expressed on the yeast cells obtained from the third sort could bind to hCTLA4, 96 of these yeast colonies were randomly picked, induced, and subjected to FACS analysis using the complex of streptavidin-APC and biotinylated hCTLA4:Fc and the ALEXA FLUOR®-labeled antibody specific for the HA tag. Of these yeast clones, 95% bound both hCTLA4:Fc and the antibody specific for the HA tag. DNA sequencing revealed that 40% of these yeast clones expressed Fab fragments having unique sequences. To identify the strongest hCTLA4 binders, 32 yeast clones that showed strong binding to hCTLA4:Fc and also expressed Fab fragments having unique VH/VL sequences, were subjected to additional FACS analyses using varying concentrations of biotinylated hCTLA4:Fc to identify those that could bind hCTLA4:Fc at the lowest concentrations.

The Fab fragments from the twelve yeast clones that showed the strongest binding to hCTLA4:Fc were converted to human IgG1 format by inserting DNA encoding the VH from a single clone into a mammalian expression vector encoding the signal peptide VκlO2/O12 and the remainder of the human IgG1 HC, and inserting DNA encoding the VL from the same clone into another mammalian expression vector encoding the signal peptide VκlO2/O12 and a Ck domain. *Escherichia coli* cells were transformed with the ligated mixture, and bacterial clones containing the correct heavy and light chain sequences were identified by DNA sequencing. Mammalian expression constructs encoding correct heavy and light chain sequences were co-transfected into EXPI293™ cells (ThermoFisher Scientific, Waltham, Mass., USA), and the resulting transfectants were cultured under conditions conducive to expression. Antibodies in the resulting cell supernatants were purified using a Protein A column. Amino acid sequences of the VH and VLs of the twelve Fab fragments that were converted to IgG1 format are shown in FIGS. 3 and 4. As indicated in these figures, these antibodies are designated herein as the 1E1, 2F1, 3G1, 4H1, 5B2, 6E3, 7A4, 8B4, 9C4, 10D4, 11F4, and 12G4 antibodies. The amino acid sequences of the VH and VL CDRs are shown in FIGS. 1 and 2, respectively.

Example 2: Making Anti-hPD1 Antibodies

To select anti-hPD1 antibodies, libraries were constructed, sorted, and tested in essentially the same way as described above for the anti-hCTLA4 antibodies, except that nine and seven conservatively randomized codons were introduced into the DNA encoding the VH and VL, respectively.

Figure 10:
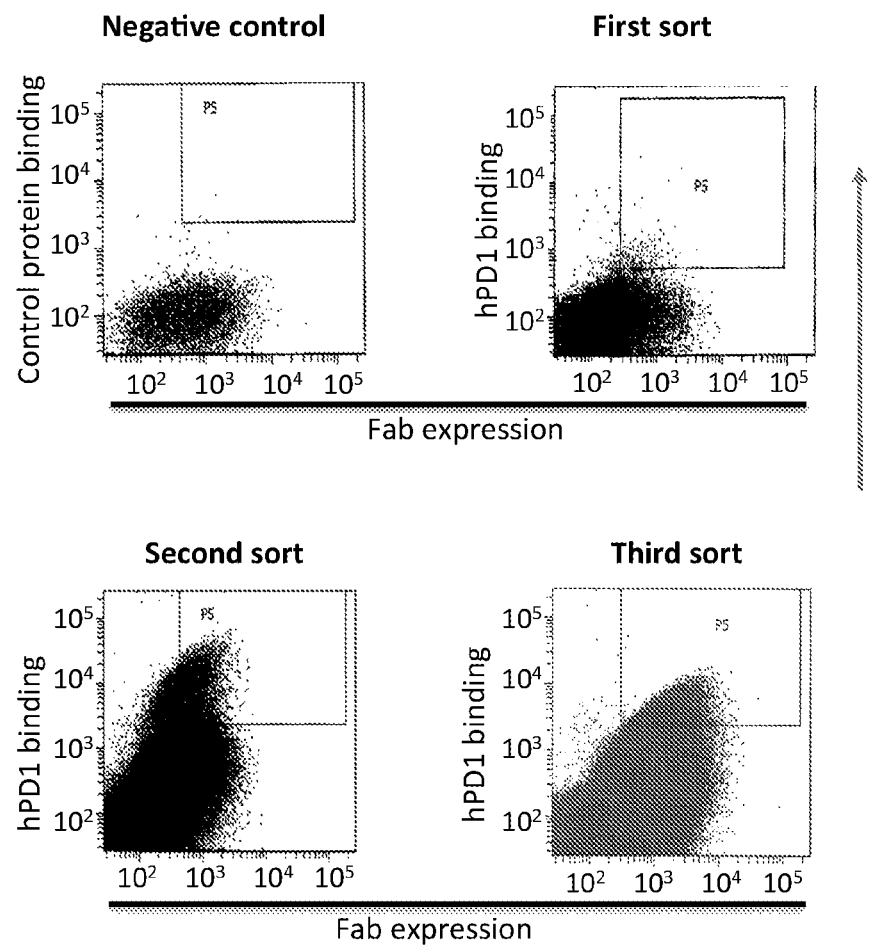
FIG. 10: Cell sorting to select anti-hPD1 Fab fragments. Procedures are described in detail in Example 2. Indications are as in FIG. 9. As indicated, the upper right, lower left, and lower right panels contain data from the first, second, and third rounds of sorting, respectively, in which anti-hPD1 antibody was detected with a labeled hPD1 protein. The upper left panel contains data from a sorting using a negative control protein (a biotinylated human PDL1 protein) for detection.

FACS was used to select yeast cells expressing Fab fragments binding to hPD1 as described above for the anti-hCTLA4 antibodies, with a few exceptions. A biotinylated monovalent hPD1 was made by fusing DNA encoding the extracellular region of hPD1 to a hexahistidine tag and an AVITAG™ (Avidity L.L.C., Colorado, USA). The hPD1-His6-AVITAG™ fusion protein was biotinylated in vivo by co-transfecting plasmid DNA encoding the BirA biotin-protein ligase and the hPD1-His6-AVITAG™ fusion protein and adding biotin in the growth medium. The biotinylated hPD1-His6-AVITAG™ fusion protein was purified through a nickel-nitrilotriacetic acid (Ni-NTA) agarose column. This biotinylated hPD1 protein was used instead of biotinylated hCTLA4:Fc. A total of 3 rounds of sorting were performed using 500 nM, 5 nM, and 0.05 nM biotinylated hPD1 consecutively for labeling in the first, second, and third rounds. As in the anti-hCTLA4 selection, a negative control was performed using an unrelated biotinylated protein. Results of these FACS analyses are shown in FIG. 10. The first two sorts were done in enrichment mode, that is, with a fast sorting speed, and the last sort was done in purification mode, that is, with a slow sorting speed.

Following the third sort, the collected cells were re-sorted and plated on agar plates made with yeast medium containing dextrose and lacking uracil. Three hundred colonies were randomly picked, cultured in medium containing dextrose and lacking uracil, induced in medium containing galactose and lacking uracil, and analyzed by FACS as described above. DNAs encoding the VL and VHs of each individual clone were amplified by PCR reactions and sequenced. Among the 300 colonies, 95% produced Fab fragments that bound hPD1 as determined by FACS, and 50% contained DNA encoding unique Fab fragments.

To further characterize the Fab fragments, yeast cells expressing unique anti-hPD1 Fab fragments were grown in medium containing galactose and lacking uracil. The cells were heated at 75° C. for 5 minutes and then stained with biotinylated hPD1 followed with streptavidin-APC. Thereafter, the cells were subjected to FACS analysis. The 100 yeast clones that produced Fab fragments having the strongest hPD1 binding were identified by titrating the amount of hPD1 added to the cells prior to FACS analysis. Those clones that produced a strong signal for hPD1 binding at low hPD1 concentrations were considered strong binders.

Fifteen Fab fragments that exhibited both good temperature stability and strong binding to hPD1 were selected for conversion to the human IgG4 format. The amino acid sequences of the VH and VLs of these Fab fragments are shown in FIGS. 7 and 8. As indicated in these figures, these antibodies are designated herein by numbers from 1 to 15. The amino acid sequences of the VH and VL CDRs are shown in FIGS. 5 and 6, respectively.

Anti-hPD1 antibodies were produced essentially as described above for the anti-hCTLA4 antibodies, except that the DNAs encoding the VHs were inserted into a vector encoding the CH1, hinge, CH2, and CH3 of a human IgG4 antibody, rather than a human IgG1 antibody.

Example 3: Binding of Anti-hCTLA4 Antibodies to Cell Surface-Expressed hCTLA4

The following experiment was done to determine whether the anti-hCTLA4 antibodies selected as described in Example 1 could bind to hCTLA4 when expressed on a cell surface. About $1\times10^5$ Jurkat T cells expressing hCTLA4 (Promega CS186907) were incubated in wells of a microtiter plate containing varying concentrations of the selected anti-hCTLA4 antibodies for 30 minutes at 4° C. in FACS buffer (0.1% $NaN_3$ and 2% BSA in phosphate buffered saline (PBS, which contains 137 mM NaCl, 2.7 mM KCl, 10 mM $Na_2HPO_4$, and 1.8 mM $K_2HPO_4$)). After washing, the surface-bound anti-hCTLA4 antibodies were detected with a polyclonal anti-hIgG (Fc-specific) antibody labeled with fluorescein isothiocyanate (FITC)(anti-hIgG-FITC). Binding of anti-hCTLA4 antibodies were detected by flow cytometric analysis. The results were reported a geometric mean fluorescence intensity (MFI) using FlowJo software (FLOWJO, L.L.C., Ashland, Oreg., USA). $EC_{50}$ values were computed from these data using GraphPad Prism software (GraphPad, Inc., La Jolla, Calif., USA) and are shown in Table 10 below.

TABLE 10

$EC_{50}$'s of anti-hCTLA4 antibodies for binding to cell surface-expressed hCTLA4

| Antibody | $EC_{50}$ (pM) |
|---|---|
| 1E1 | 696.8 |
| 2F1 | 276.3 |
| 3G1 | 3101.0 |
| 4H1 | 189.1 |
| 5B2 | 2927.0 |
| 6E3 | 437.0 |
| 7A4 | 217.2 |
| 8B4 | 384.0 |
| 9C4 | 472.7 |
| 10D4 | 85.0 |
| 11F4 | 157.9 |
| 12G4 | 150.2 |

These data indicate that all twelve antibodies were able to bind to cell surface-expressed CTLA4, although there was variation in the strength of their binding as measured in this assay.

Example 4: Anti-hCTLA4 Antibody Inhibition of hCTLA4 Binding to hB7-1/hB7-2

Blocking or inhibition of the interaction of hCTLA4 with its ligands hB7-1 and/or hB7-2 by the anti-hCTLA4 antibodies was assessed in two different assay systems.

In a first assay, inhibition of hCTLA4 binding to hB7-1 and hB7-2 expressed on the surface of Raji cells was assessed. Raji cells, which are human cells, express high levels of hB7-1 and hB7-2. A soluble version of hCTLA4 comprising the extracellular domain of hCTLA4 fused to an Fc fragment (CTLA4-ECD_Fc) was pre-incubated in a microtiter plate with varying concentrations of selected anti-hCTLA4 antibodies in FACS buffer at room temperature (RT). After 30 minutes, $1\times10^5$ Raji cells were added to each well and incubated for another 30 minutes. CTLA4-ECD_Fc bound to Raji cells was detected with a non-blocking, anti-CTLA4 antibody (anti-human CD152 (CTLA4) (clone 14D3) labeled with PerCP-eFluor® 710, Affymetrix eBioscience catalog number 46-1529). Levels of bound CTLA4-ECD_Fc were detected by flow cytometric analysis, and binding of CTLA4-ECD_Fc was reported as an MFI. $IC_{50}$'s were calculated using GraphPad Prism software (GraphPad, Inc., La Jolla, Calif., USA).

TABLE 11

$IC_{50}$'s for inhibiting hCTLA4 binding to hB7-1/hB7-2 on Raji cells

| Antibody | $IC_{50}$ (nM) |
|---|---|
| 1E1 | 6.3 |
| 2F1 | 9.1 |
| 3G1 | 3.5 |
| 4H1 | 8.2 |
| 5B2 | 11.5 |
| 6E3 | 14.1 |
| 7A4 | 19.8 |
| 8B4 | 3.8 |
| 9C4 | 15.7 |
| 10D4 | 3.3 |
| 11F4 | 7.5 |
| 12G4 | 3.5 |

Figure 11:
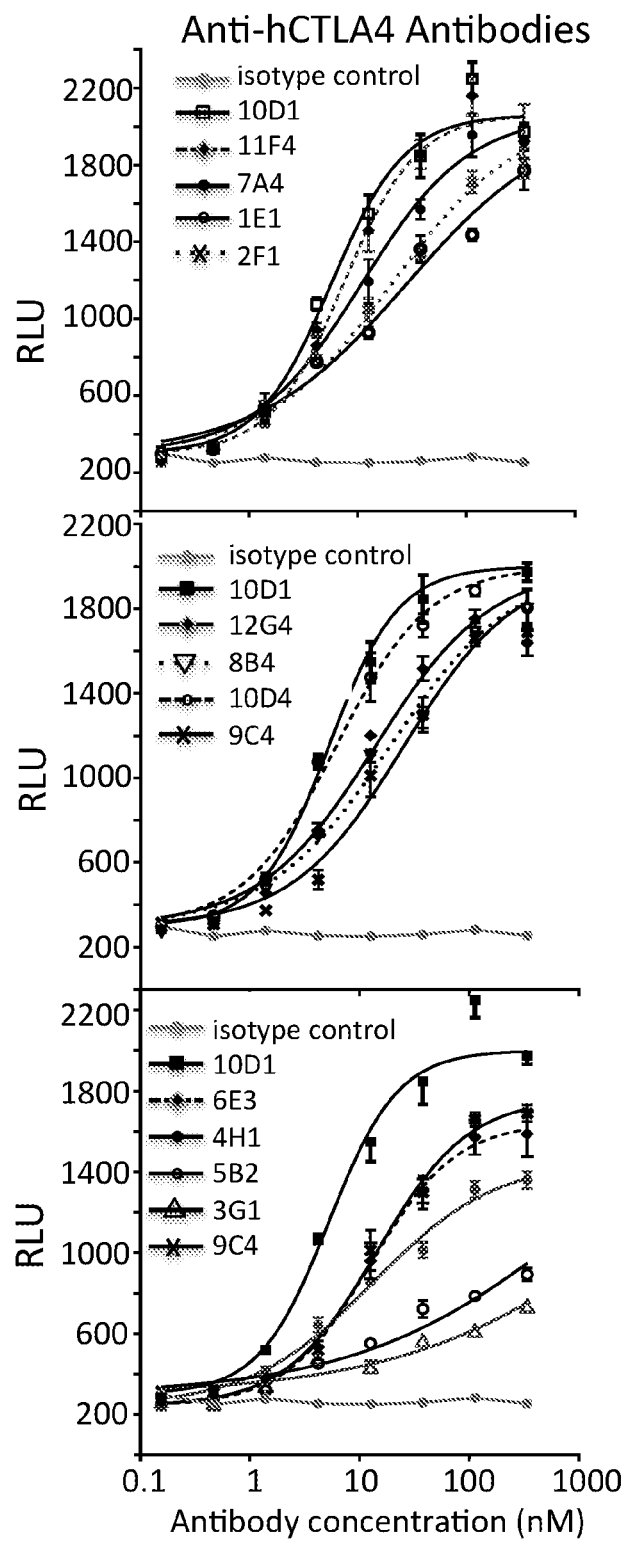
FIG. 11: Antibody inhibition of the interaction between hCTLA4 and hB7-1/hB7-2. Procedures for assaying inhibition of hCTLA4 and hB7-1/hB7-2 using engineered Jurkat T cells are described in Example 4, and numeric results from the assay are reported in Table 12. The meaning of symbols identifying samples is indicated in the legends in the upper left corner of each panel. The 10D1 antibody is a positive control anti-CTLA4 antibody. The x axes indicate the concentration of the indicated anti-hCTLA4 antibody used (nM), and the y axes indicate the relative luminescent units (RLU) as a mean plus or minus a standard error of the mean (±SEM).

In a second inhibition assay, the CTLA4 Dual-Cell Reporter Assay (Promega CS186907) was used to assess the functional effect of the anti CTLA4 antibodies on CTLA4 activity. In this assay, anti-CD3 activation of Jurkat cells, which are human cells expressing a luciferase reporter driven by an IL-2 promotor, induces luciferase production, which can be inhibited by hB7-1 or hB7-2 (from added Raji cells) engagement of hCTLA4 expressed on the same Jurkat cell. Anti-CTLA4 antibodies that bind hCTLA4 and inhibit or block hB7-1 or hB7-2 binding remove the inhibitory signal blocking the IL-2 pathway, thereby restoring the luciferase signal in the dual-cell reporter system The assay was performed essentially according to the manufacturer's instructions as described in brief below. The engineered Jurkat T cells expressing CTLA4 in assay medium (RPMI 1640 medium (see, e.g., ATCC® 30-2001™) containing 10% fetal bovine serum (FBS)) were distributed into a half area 96-well plate (Costar, catalog number 3688) using $5\times10^4$ cells in 15 μL per well. In a separate microtiter plate, serial dilutions of each of test antibody were made. Then each well containing the Jurkat T cells received two 15 μL additions, one containing a test antibody dilution and the other containing $5\times10^4$ Raji cells (which express hB7-1 and hB7-2) and anti-CD3 antibody. The microplate was incubated for 16 hours at 37° C. in 5% $CO_2$. After incubation, 40 μL of Bio-Glo™ reagent (Promega, catalog number G7941) was added to each well, following the manufacturer's instructions. Luciferase activity was detected using an EnVision 2103 Multilabel Reader (PerkinElmer). The data were plotted as Relative Luminescence Units (RLU) and analyzed using GraphPad Prism software to determine the $IC_{50}$ values. FIG. 11 and Table 12 below show that all 12 anti-hCTLA4 antibodies caused increased luciferase expression compared to a negative control antibody that did not bind to CTLA4 (an isotype-matched control). These data strongly suggest that the tested anti-hCTLA4 antibodies inhibited the hCTLA4 interaction with hB7-1 and/or hB7-2, thereby decreasing functional inhibition of the IL-2 pathway. The antibody 10D1 is an anti-hCTLA4 antibody (ipilimumab) used as a positive control.

TABLE 12

$IC_{50}$'s for inhibiting hCTLA4 interaction with hB7-1/B7-2

| Anti-hCTLA4 antibody | $IC_{50}$ (nM) |
|---|---|
| 1E1 | 28.19 |
| 2F1 | 20.53 |

TABLE 12-continued

IC$_{50}$'s for inhibiting hCTLA4 interaction with hB7-1/B7-2

| Anti-hCTLA4 antibody | IC$_{50}$ (nM) |
| --- | --- |
| 3G1 | >340 |
| 4H1 | 73.75 |
| 5B2 | >340 |
| 6E3 | 29.96 |
| 7A4 | 10.86 |
| 8B4 | 19.01 |
| 9C4 | 25.32 |
| 10D4 | 6.123 |
| 11F4 | 7.393 |
| 12G4 | 13.94 |
| 10D1 | 5.19 |

Example 5: Effects of Anti-hCTLA4 Antibodies on T Cell Activation

The ability of the selected anti-hCTLA4 antibodies to boost T cell activation was tested in an in vitro Staphylococcal Enterotoxin B (SEB) T cell activation assay. Human peripheral blood mononuclear cells (PBMCs) from three different donors were pre-activated with 0.5 µg/ml OKT3 (an anti-CD3 antibody that can activate T cells) for 3 days in complete RPMI-1640 medium (Invitrogen RPMI-1640 plus 5% FBS). PBMCs (mostly consisting of activated T cells at day 3) were harvested, washed three times with warm medium, and rested for 2 days. Then the rested, pre-activated PBMCs were distributed in the wells of a 96-well microtiter plate using $3 \times 10^4$ cells/well. Thereafter, the following additions were made to each well: SEB to a final concentration of 100 ng/ml, $1 \times 10^4$ PBMCs that had been previously depleted of autologous CDT$^+$ T cells, and varying concentrations of each antibody being tested. Culture supernatants were harvested two days later, and levels of IL-2 were determined by enzyme linked immunosorbent assay (ELISA).

Figure 12:
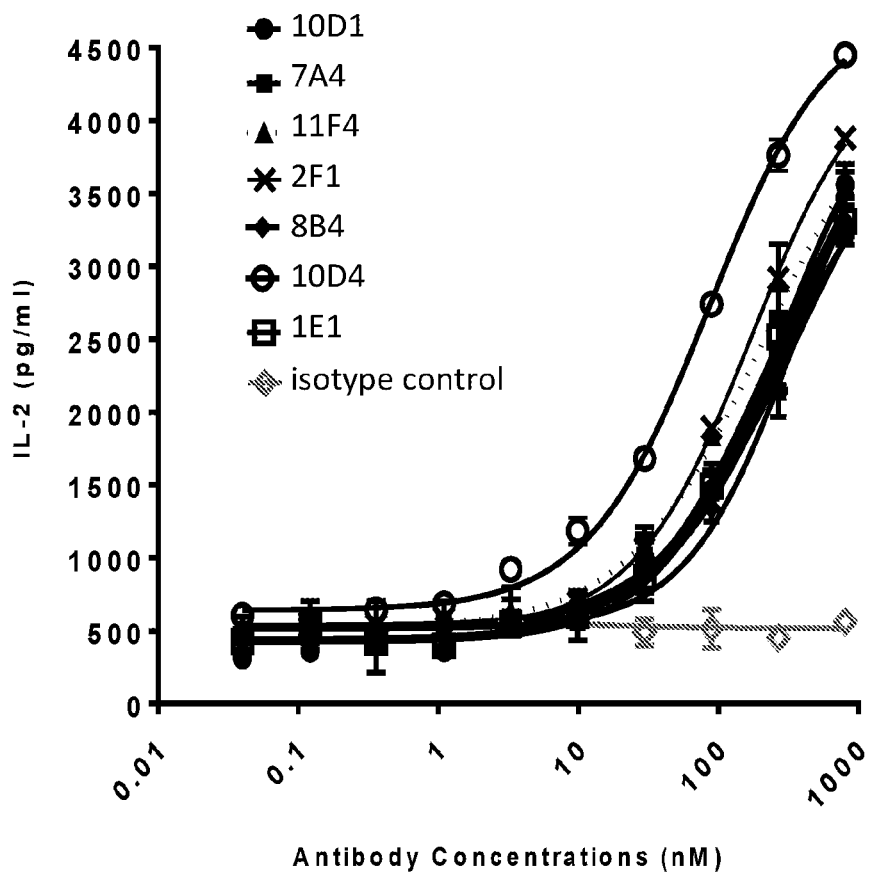
FIG. 12: Potency of anti-hCTLA4 antibodies in a Staphylococcal Enterotoxin B (SEB) T cell activation assay. Procedures are described in Example 5. Identity of the samples is stated in the legend in the upper left of the graph. The antibody 10D1 is a positive control anti-CTLA4 antibody. The x axis indicates the concentration (nM) of antibody used in the assays, and the y axis indicates the levels of interleukin-2 (IL-2) (pg/ml) detected in the samples.

FIG. 12 and Table 13 below show the results from duplicate samples from a single donor (which were representative of experiments performed with other donors). These results show that all the anti-hCTLA4 antibodies tested were able to increase production of IL-2. Among the antibodies tested, 10D4 was the most potent. The antibody designated 10D1 is an anti-hCTLA4 human IgG1 kappa antibody (ipilimumab) used as a positive control.

TABLE 13

EC$_{50}$'s for production of IL-2

| Antibody | EC$_{50}$ (nM) |
| --- | --- |
| 1E1 | 293 |
| 2F1 | 170 |
| 7A4 | 363 |
| 8B4 | 319 |
| 10D4 | 63 |
| 11F4 | 214 |
| 10D1 | 280 |

Example 6: Binding of Anti-hPD1 Antibodies to hPD1 Expressed on a Cell Surface The following experiment tested whether the selected anti-hPD1 antibodies can bind to native PD1 expressed on the surface of activated T cells. Human PBMCs were pre-activated with OKT3 (an anti-CD3 antibody) at a concentration of 1 µg/ml. After three days, the PBMCs, which were mostly activated T cells at this time, were distributed into a 96 well microtiter plate using $0.1 \times 10^6$ cells/well. Varying concentrations of the selected anti-hPD1 antibodies were added to the wells, and the plate was incubated at 4° C. for 30 minutes in FACS buffer (as described in Example 3). The antibody bound to CD4$^+$ T cells and CD4$^-$ T cells (which were predominately CD8$^+$ T cells) was detected using anti-hIgG-FITC and an anti-CD4 antibody labeled with allophycocyanin (anti-CD4-APC).

The samples were analyzed by flow cytometry (FACScalibur, BD), and binding was reported as an MFI. EC$_{50}$'s for binding were calculated using GraphPad Prism software. Data is reported in Table 14 below.

TABLE 14

EC50 values for binding of anti-hPD1 antibodies to hPD1 expressed on T cells

| | EC$_{50}$ (pM) | |
| --- | --- | --- |
| Antibody | CD4$^+$ cells | CD4$^-$ cells |
| Anti-hPD1 #1 | 918.0 | 1368.0 |
| Anti-hPD1 #2 | 398.0 | 416.0 |
| Anti-hPD1 #3 | 536.2 | 689.5 |
| Anti-hPD1 #4 | 672.1 | 884.9 |
| Anti-hPD1 #5 | 974.4 | 1123.0 |
| Anti-hPD1 #6 | 667.5 | 616.5 |
| Anti-hPD1 #7 | 439.1 | 569.2 |
| Anti-hPD1 #8 | 646.8 | 903.9 |
| Anti-hPD1 #9 | 1010.0 | 1484.0 |
| Anti-hPD1 #10 | 1067.0 | 1605.0 |
| Anti-hPD1 #11 | 33737.0 | 24657.0 |
| Anti-hPD1 #12 | 849.1 | 1158.0 |
| Anti-hPD1 #13 | 997.7 | 1463.0 |
| Anti-hPD1 #14 | 389.9 | 449.3 |
| Anti-hPD1 #15 | 720.1 | 627.5 |

These data show that all of the tested anti-hPD1 antibodies could bind to hPD1 expressed on T cells, although there was variation in the EC$_{50}$'s observed in this assay.

Example 7: Inhibition of the hPD1/hPDL1 Interaction by Anti-hPD1 Antibodies

Two different assays were used to assess the ability of the anti-hPD1 antibodies to inhibit the interaction of hPD1 and its ligand hPDL1. A dual cell reporter assay tested the ability of the selected anti-hPD1 antibodies to inhibit hPD1 function mediated by its interaction with hPDL1 (Promega catalog no. J1250, formerly catalog no. CS187106). The ability of the selected anti-hPD1 antibodies to inhibit hPDL1 binding to hPD1 was measured using an ALPHALISA® (PerkinElmer).

The PD1 dual reporter assay system relies on the fact that interaction of PDL1 with PD1 expressed on a T cell inhibits transcription from the promoter for the nuclear factor of activated T cells (NFAT) gene in a T cell induced by anti-CD3 antibody activation. The T cells used in the assay express hPD1 on their cell surface and contain a luciferase gene whose expression is driven by the NFAT promoter. If the hPD1 on the cell surface is engaged by hPDL1, luciferase production will be inhibited. This inhibition will be reversed when an anti-hPD1 antibody prevents binding of hPDL1 to hPD1.

The assay was performed as follows. CHO-K1 cells (see, e.g., ATCC® CCL-61™) expressing hPDL1 and an anti-CD3 ($4 \times 10^4$ cells per well in 50 µL of F-12 medium (see, e.g., ATCC® 30-2004™) with 10% FBS) were distributed into a half area 96-well plate (Costar, 3688) and incubated overnight. In a separate plate the next day, two-fold serial dilutions of each of test antibody were made in duplicate in assay medium (RPMI 1640 containing 2% FBS) starting at a concentration of 68 nM. Then the medium from each well containing CHO-K1 cells was removed and replaced with 20 µL from a well of the plate containing the diluted test antibodies and 20 µL of Jurkat T cells ($4 \times 10^4$) expressing hPD1 and containing the NFAT-luciferase reporter gene. The plate was incubated for 6 hours at 37° C. in 5% CO2. After incubation, 38 µL of Bio-Glo™ reagent (Promega catalog number G7941) was added to each well according to the manufacturer's instructions. Luciferase activity was read on an EnVision Multilabel Reader (PerkinElmer). The data were plotted as RLU and analyzed using GraphPad Prism software (GraphPad, Inc., La Jolla, Calif., USA) to determine $IC_{50}$ values.

Figure 13:
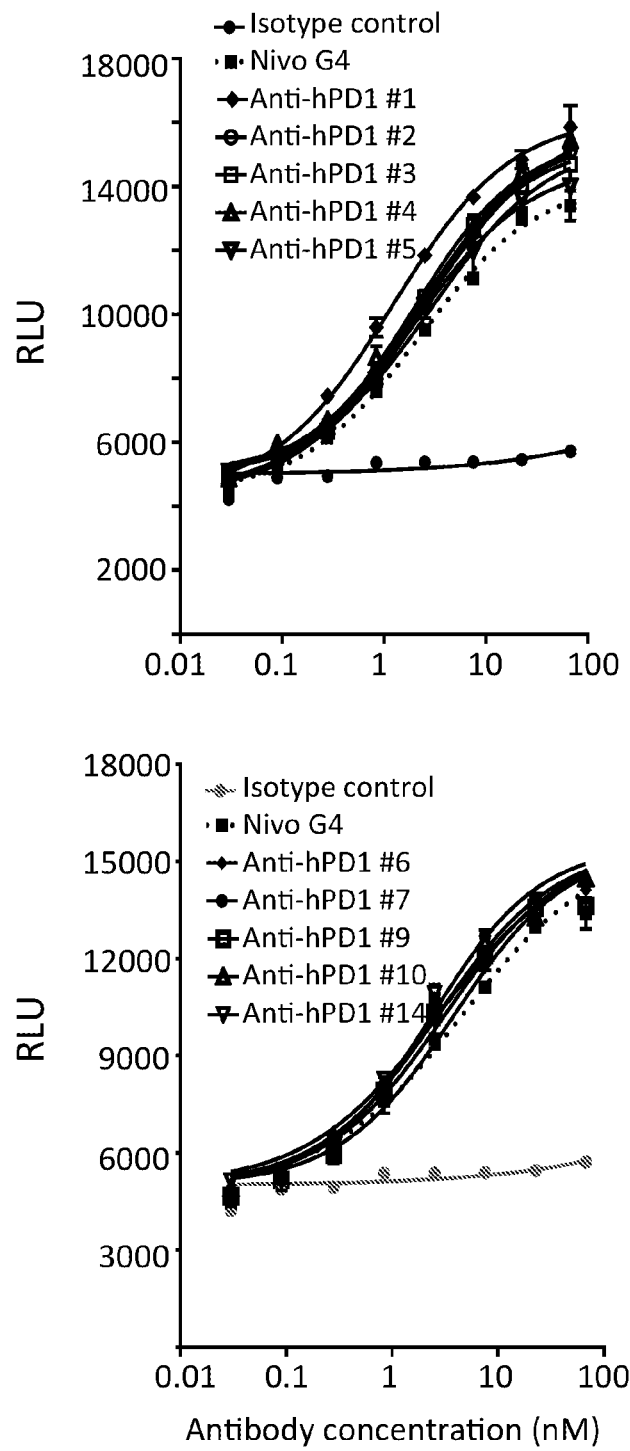
FIG. 13: Inhibition of the hPD1/hPDL1 interaction by anti-hPD1 antibodies. Procedures are described in Example 7. Identities of the antibody samples are indicated in the legends in the upper left corner of each panel. The x axes indicate the antibody concentration used in each sample (nM). The y axes indicate the mean RLU±SEM. Nivo G4 is a positive control anti-hPD1 antibody.

Data are shown in FIG. 13 and Table 15 below. All ten tested anti-hPD1 antibodies inhibited the PD1/PDL1 interaction compared to an isotype control 10D1 IgG4 (which is an anti-CTLA4 antibody). The tested antibodies were more potent than one positive control antibody having the variable domains of nivolumab, i.e., Nivo G4, an IgG4 anti-hPD1 antibody that inhibits the PD1/PDL1 interaction.

TABLE 15

$IC_{50}$'s for inhibiting PD1/PDL1 interaction

| Antibody | $IC_{50}$ (nM) |
| --- | --- |
| Anti-PD1 #1 | 1.181 |
| Anti-PD1 #2 | 2.453 |
| Anti-PD1 #3 | 2.37 |
| Anti-PD1 #4 | 2.032 |
| Anti-PD1 #5 | 3.004 |
| Anti-PD1 #6 | 3.848 |
| Anti-PD1 #7 | 2.392 |
| Anti-PD1 #9 | 3.135 |
| Anti-PD1 #10 | 2.691 |
| Anti-PD1 #14 | 2.694 |
| Nivo G4 | 4.587 |

Selected anti-hPD1 antibodies were also tested for inhibiting the interaction of hPD1 and its ligand hPDL1 using an ALPHALISA® assay (PerkinElmer, USA). Briefly, 10 µL containing a soluble, biotinylated version PD1 protein (which was biotinylated in vivo (see, e.g., Ashraf et al. (2004), Protein Expr, Purif. 33(2): 238-245) and contained only the extracellular region) and 10 µL containing an anti-hPD1 antibody at varying concentrations in ALPHALISA® immunoassay buffer (catalog number AL000, PerkinElmer) were mixed in wells of a 96-well half-area plate (PerkinElmer, USA) and incubated for one hour at RT. Then a soluble, glutathione S-transferase (GST)-tagged human PDL1 (containing only the extracellular domain; 10 µL at a concentration of 1 nM) was added, and the mixture was incubated for a further hour at RT, Next, 10 µL of GST acceptor beads (which can bind the GST-tagged PDL1) were added to a final concentration of 16 µg/mL, and the plates were shaken for an hour at RT. Finally, 10 µL of streptavidin donor beads (which can bind the biotinylated hPD1) were added to bring the final concentration of donor beads to 16 µg/mL, and the plates were incubated in the dark at RT for one hour. If hPD1 and hPDL1 bind or interact, the donor and acceptor beads will be brought close to each other, and a signal should therefore be detected. An antibody that inhibits this interaction or binding will decrease the signal, since the inhibiting antibody prevents physical proximity of the donor and acceptor beads.

Figure 14:
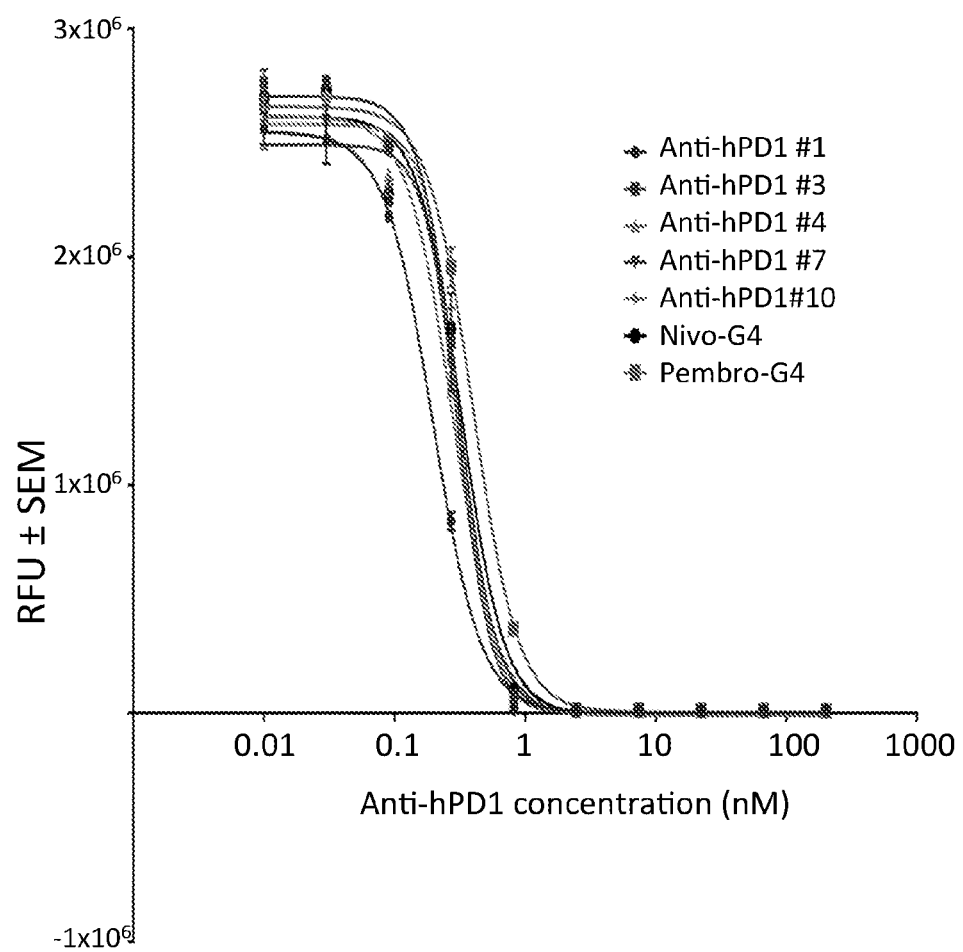
FIG. 14: Inhibition of the PD1/PDL1 interaction by anti-hPD1 antibodies. Procedures, i.e., the ALPHALISA® assay, are described in Example 7. Identities of the antibody samples are indicated in the legend in the upper right corner of the graph. The x axis indicates the concentrations of antibody (nM) used in the assays. They axis indicates the Relative Fluorescence Units (RFU)±SEM. Nivo-G4 and Pembro-G4 are positive control IgG4 anti-hPD1 antibodies.

Plates were read in an EnVision 2103 Multilabel Reader (PerkinElmer) using illumination at a wavelength of 680 nM and reading emission at a wavelength of about 615 mM. The results were plotted and $IC_{50}$ values were calculated using GraphPad Prism software. Results are shown in FIG. 14 and Table 16 below.

TABLE 16

$IC_{50}$'s for inhibiting PD1/PDL1 interaction

| Antibody | $IC_{50}$ (nM) |
| --- | --- |
| Anti-PD1 #1 | 0.1966 |
| Anti-PD1 #3 | 0.3055 |
| Anti-PD1 #4 | 0.3143 |
| Anti-PD1 #7 | 0.3070 |
| Anti-PD1 #10 | 0.2789 |
| Nivo-G4 | 0.3255 |
| Pembro-G4 | 0.3997 |

These data indicate that the tested antibodies were able to inhibit binding of hPDL1 to hPD1 more potently the two anti-hPD1 antibodies used as positive controls, Nivo-G4 and Pembro-G4.

Example 8: Testing Anti-hPD1 Antibodies in a Mixed Lymphocyte Reaction (MLR) Assay The potency of the selected anti-hPD1 antibodies in enhancing T cell activation was tested in an MLR assay. Briefly, monocyte-derived immature dendritic cells (iDCs) were used as stimulators. To prepare iDCs, monocytes were isolated from PBMCs using a Human Monocyte Isolation Kit (Miltenyi) and cultured for 6 days in complete RPMI medium containing 800 U/mL granulocyte-macrophage colony-stimulating factor (GM-CSF) and 500 U/mL interleukin-4 (IL-4). Thereafter, $2 \times 10^4$ cells from the cultured monocytes (now predominately iDCs) were cultured with $1 \times 10^5$ allogeneic CD3$^+$ T cells in the presence of selected anti-hPD1 antibodies at 37° C. in 96-well flat-bottom plates. It is expected that the iDCs will activate the T cells and that the activation will be greater if the negative PD1 pathway is not activated via a ligand-engaged hPD1 expressed on the surface of the T cells. Thus, if an anti-PD1 antibody can inhibit the interaction of hPD1 with its ligands, it is expected that the anti-hPD1 antibody could increase T cell activation.

Culture supernatants were collected after 5 days. IFNγ levels were measured using IFN-gamma DuoSet ELISA kit (R&D Systems). T cell proliferation was measured using CLICK-IT® Plus EdU Alexa Fluor® Flow Cytometry Assay Kit (Life Technologies, which is now part of ThermoFisher Scientific) following the manufacturer's instructions. Briefly, EdU at a final concentration of 15 µM was added on day five, 24 hours before harvest. Proliferation of T cell subsets is presented as percentage of EdU$^+$ cells among CD4$^+$ or CD4$^-$ (predominately CD8$^+$) T cell subsets. CD4$^+$ and CD4$^-$ cells were distinguished with a labeled anti-CD4 antibody.

Figure 15:
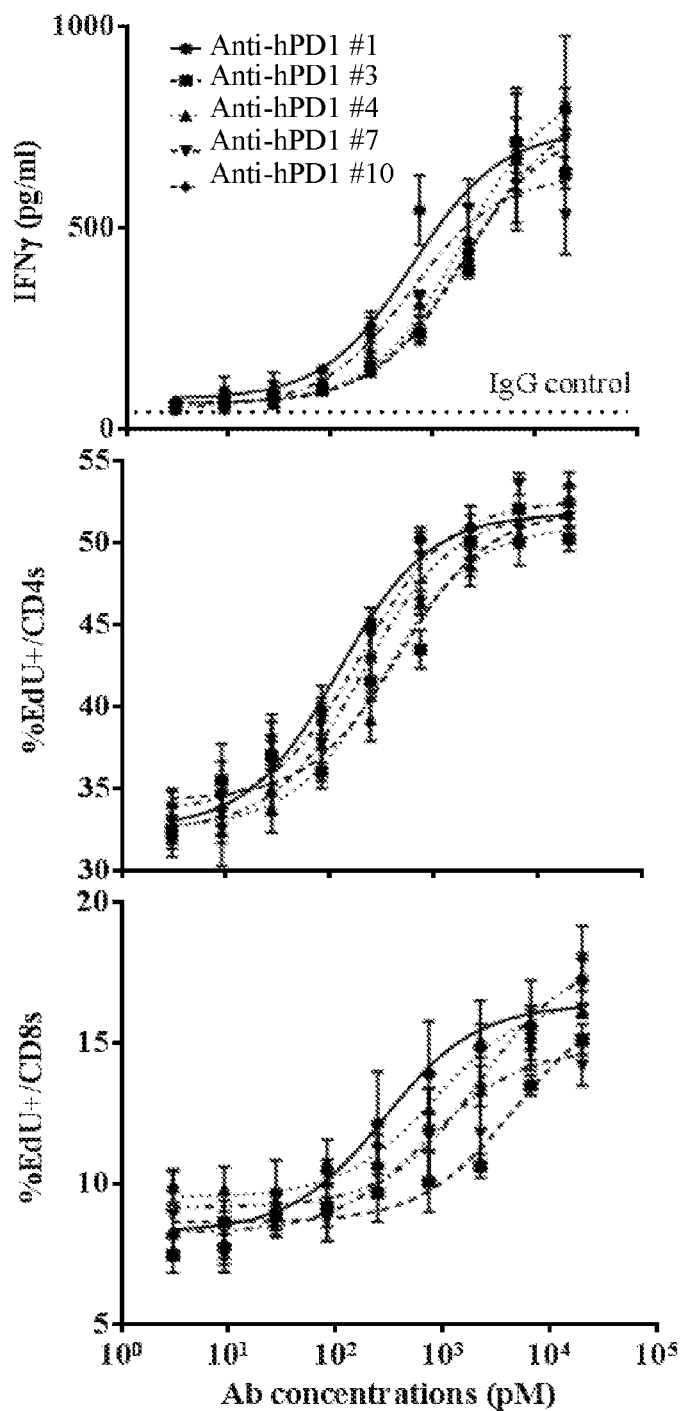
FIG. 15: Activity of anti-hPD1 antibodies in a mixed lymphocyte reaction (MLR) assay. Procedures are described in Example 8. Identities of the antibody samples in all panels are indicated in the legend the upper left corner of the top panel. In all panels, the x axis indicates the concentration of the tested antibody in each sample. In the top panel, they axis indicates the concentration of interferon gamma (IFNγ) detected in the samples. They axis in the middle and bottom panels indicates the percentage of $CD4^+$ (middle panel) or $CD8^+$ (bottom panel) T cells that stained with 5-ethynyl-2'-deoyuridine (EdU), which reflects the percentage of proliferating cells in the culture.

As shown in FIG. 15, the selected anti-hPD1 antibodies promoted IFNγ production and the proliferation of CD4$^+$ and CD8$^+$ T cells. $EC_{50}$ values for these antibodies were calculated using GraphPad Prism (GraphPad Software, Inc., La Jolla, Calif.) and are shown in Table 17 below. Results shown are representative of MLR assay results from 3

HLA-mismatched donor pairs. A control IgG did not increase IFNγ production over that of that observed with no addition (see FIG. 15).

TABLE 17

EC$_{50}$ values of selected anti-hPD1 antibodies in MLR assay

| Antibody | EC$_{50}$ for IFNγ production (pM) | EC$_{50}$ for CD4+ T cell proliferation (pM) | EC$_{50}$ for CD8+ T cell proliferation (pM) |
|---|---|---|---|
| Anti-PD1 #1 | 889.5 | 134.8 | 322.9 |
| Anti-PD1 #3 | 2218.0 | 365.3 | 3670.0 |
| Anti-PD1 #4 | 1542.0 | 391.2 | 534.3 |
| Anti-PD1 #7 | 1460.0 | 165.0 | 1518.0 |
| Anti-PD1 #10 | 2212.0 | 234.1 | 839.4 |

Example 9: Assay of Anti-hPD1 Antibodies for Cytomegalovirus (CMV) Recall Response To test the effects of selected anti-hPD1 antibodies on an antigen-specific T cell memory response, 1×10$^5$ PBMCs from CMV seropositive donors (Bentech, Seattle, Wash.) were stimulated with 1.5 µg/ml CMV lysate (Astarte Biologics) in the presence of varying antibody concentrations in 96-well round-bottom microtiter plates in complete RPMI-1640 media at 37° C. Culture supernatants were collected after 5 days to measure IFNγ levels. EC$_{50}$'s were calculated as described above.

Figure 16:
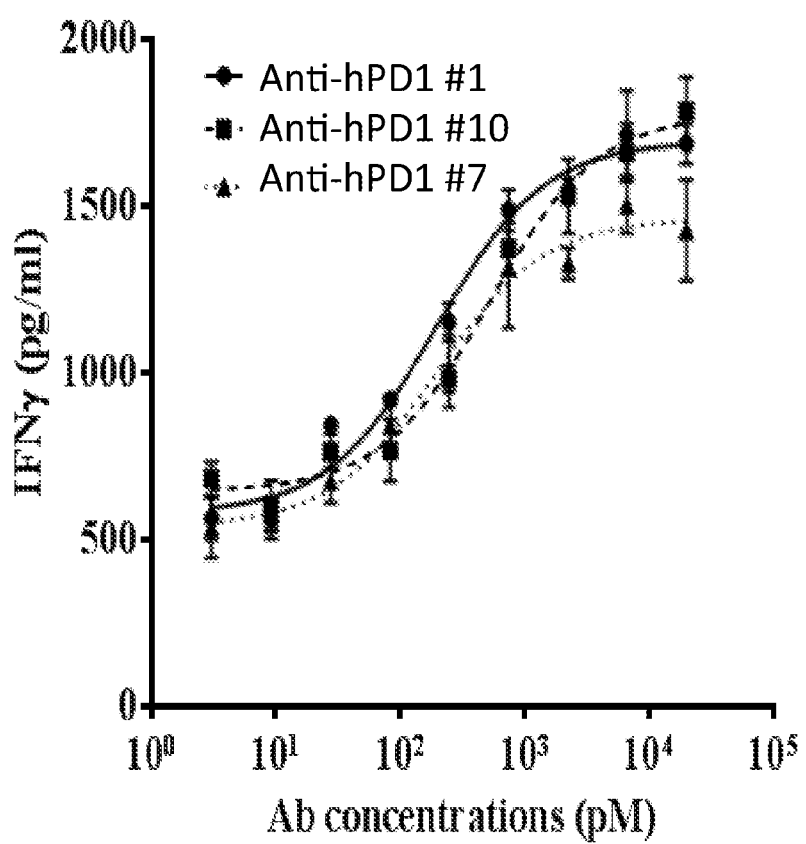
FIG. 16: Activity of anti-hPD1 antibodies in a cytomegalovirus (CMV) recall response assay. Procedures are described in Example 9. Identities of the antibody samples are indicated in the legend the upper left corner of the panel. The x axis indicates the concentration (pM) of the tested antibody in each sample. The y axis indicates the concentration of interferon gamma (IFNγ) detected in the samples.

Results are shown in FIG. 16 and Table 18 below. The anti-hPD1 antibodies boosted the antigen-specific IFNγ production by the PMBCs in response to the CMV lysate. Results are representative of two experiments using different CMV seropositive donors. A control IgG antibody did not increase IFNγ production in response to the CMV lysate at the same concentrations as did the anti-hPD1 antibodies, i.e., the EC$_{50}$ of the control IgG was greater than 10,000 pM. Data not shown.

TABLE 18

EC$_{50}$'s of anti-hPD1 antibodies for IFN γ production in CMV recall response assay

| Antibody | EC$_{50}$ (pM) |
|---|---|
| Anti-PD1 #1 | 209.0 |
| Anti-PD1 #10 | 376.1 |
| Anti-PD1 #7 | 516.1 |

Example 10: Binding Properties of Anti-hPD1 Antibodies

The association rate constant (k$_a$), dissociation rate constant (k$_d$), and equilibrium dissociation constant (K$_D$=k$_d$/k$_a$) for the binding of five different anti-hPD1 antibodies (#1, #3, #4, #7 and #10) to recombinant human (rhu) PD1 (extracellular domain only) was determined as described below. The same values were determined for the binding of two of these anti-hPD1 antibodies (#1 and #7) to the extracellular domain of a recombinant cynomolgus (rcyno) PD1.

Biosensor analysis was conducted at 25° C. in an HBS-EP buffer (10 mM HEPES, 150 mM NaCl, 3 mM EDTA, 0.005% polysorbate 20, 0.1% bovine serum albumin, pH 7.4) using a Biacore 3000 optical biosensor equipped with a CM5 sensor chip according to the manufacturer's general protocol. The auto sampler was maintained at ambient temperature. Goat anti-human IgG capture antibody (Jackson Laboratories; 109-005-098) was immobilized to flow cells 3 and 4 of the sensor chip using standard amine coupling chemistry. About 8000 resonance units (RU) of this antibody was immobilized on these chips. Flow cell 4 was used to analyze captured anti-hPD1 antibodies (about 100 to 200 RU were captured on flow cell 4), while flow cell 3 was used as the reference flow cell. Both analytes, recombinant human PD1 and recombinant cynomolgus PD1, were prepared in five concentrations for each antibody tested. The analyte concentrations tested ranged from 1.2 to 300 nM. All analyte dilutions were prepared in HPS-EP buffer. Each of the five analyte sample concentrations were run in duplicate and in a mixed order, as a means of assessing the reproducibility of binding and mitigating systematic bias to the order of injection. Multiple blank (running buffer) injections also were run and used to assess and subtract system artifacts. The association phase and dissociation phase for all analyte concentrations were monitored for 300 seconds and 1500 seconds, respectively, at a flow rate of 50 µL/min. Between antibody samples the surface of the flow cell was regenerated with 10 mM glycine, pH 1.5 for 30 seconds at a flow rate of 50 µL/min.

The data was aligned, double referenced, and fit using SCRUBBER 2™ software (BioLogic Software, Pty, Australia), which is a Surface Plasmon Resonance (SPR) data processing and non-linear least squares regression fitting program. A dissociation rate constant (k$_d$) was determined from the first 1500 seconds of the dissociation phase data. The dissociation rate constant was then applied as a fixed parameter in the global fit of the association phase data using a first order binding model to determine the association rate constant (k$_a$) and the analyte binding capacity of the surface (R$_{max}$).

Results are shown in Table 19 below. Among the antibodies tested, anti-hPD1 antibody #7 has the lowest K$_D$ for binding to both human and cynomolgus monkey PD1,

TABLE 19

Binding constants of anti-hPD1 antibodies

| Anti-hPD1 antibody | Analyte | R$_{max}$ (RU) | k$_a$ (1/Ms) | k$_d$ (1/s) | K$_D$ (nM) |
|---|---|---|---|---|---|
| #1 | rhu PD1 | 57.9 | 6.09E+04 | 1.33E−04 | 2.18 |
| #3 | rhu PD1 | 57.4 | 6.74E+04 | 3.48E−04 | 5.16 |
| #4 | rhu PD1 | 60 | 6.04E+04 | 2.79E−04 | 4.62 |
| #7 | rhu PD1 | 51.5 | 1.19E+05 | 3.54E−05 | 0.297 |
| #10 | rhu PD1 | 60.4 | 7.80E+04 | 7.15E−05 | 0.917 |
| #1 | rcyno PD1 | 32.3 | 1.18E+05 | 5.97E−04 | 5.06 |
| #7 | rcyno PD1 | 40.3 | 1.45E+05 | 5.79E−05 | 0.4 |

Example 11: Engineering Anti-hPD1 and Anti-hCTLA4 Antibodies for Production of a Pair of Antibodies in a Single Host Cell Line The goal of the following experiments was to obtain a host cell line that expressed only two major antibody species, an anti-hPD1 antibody and an anti-hCTLA4 antibody. Non-cognate HC/LC pairing and/or formation of HC/HC heterodimers could possibly lead to production of as many as ten different antibody species in a cell transfected with DNAs encoding two different HCs and two different LCs. We have observed that cells transfected with DNAs encoding an HC from an anti-hPD1 antibody and an LC from an anti-hCTLA4 antibody (or vice versa), i.e., a non-cognate HC/LC pair, can produce IgG antibody, indicating that promiscuous HC/LC occurs. Data not shown.

In the following experiment, the antibodies were altered so as to strengthen cognate HC/LC pairs, weaken non-cognate HC/LC pairs, and weaken HC/HC heterodimers. In Example 3 of U.S. Provisional Application 62/342,167 (which is incorporated herein by reference) altered versions of anti-hPD1 and anti-hCTLA4 antibodies are described. Variant pair 18C comprises an altered IgG4 anti-PD1 antibody (comprising HC1 and LC1) and an altered IgG1 anti-hCTLA4 antibody (comprising HC2 and LC2). These HCs and LCs contain the following alterations: HC1, G44D, Q105R, K147R, H168R, and V173C; LC1, V43D, G100R, S131D, S174D, and S162C; HC2, G44R, Q105D, V173C, K147D, H168D, D399R, and K409E; and LC2, A43R, P100D, Q160O, S131R, and S174R. U.S. Provisional Application 62/342,167, Table 18, which is incorporated herein by reference. These alterations create the following charge pairs in HC1/LC1: G44D/G100R, Q105R/V43D, K147R/S131D, and H168R/S174D. The following similar set of charge pairs is created in HC2/LC2: G44R/P100D, Q105D/A43R, K147D/S131R, and H168D/S174R. These alterations are also likely to weaken non-cognate HC/LC pairs since they create contacting residues with the same charge in non-cognate HC/LC pairs, e.g., G44D(HC1)/P100D(LC2). Contacting pairs of cysteine residues were also created in HC1/LC1 (V1730/51620) and HC2/LC2 (V1730/Q1600). Further, the alterations D399R and K409E in the anti-CTLA4 HC disfavor formation of HC/HC heterodimers, i.e., the HC of the anti-hPD1 antibody paired with the HC of the anti-hCTLA4 antibody, because it creates contacting residues with the same charge in heterodimers, e.g., D399R (HC2)/409R(HC1). The alterations in the 18C variant pair of antibodies were incorporated into HC and LC of anti-hPD1 antibody #1 (SEQ ID NOs: 185 and 187, respectively; referred to herein as altered anti-hPD1 antibody #1) and the HC and LC of two different anti-hCTLA4 antibodies, 10D4 (SEQ ID NOs: 189 and 191, respectively; referred to herein as altered anti-hCTLA4 10D4), and 11F4 (SEQ ID NOs: 193 and 195, respectively; referred to herein as altered anti-hCTLA4 11F4). In addition, the two altered anti-hCTLA4 antibodies include the additional alteration R255K in their HC, which increases in vivo clearance of the antibody.

To clarify any possible confusion about numbering of positions, applicants point out below the actual positions of selected alterations mentioned above in some sequences disclosed in the Sequence Listing appended hereto. For example, the alterations G44D, Q105R, K147R, H168R, and V173C are at positions 44, 111, 149, 170, and 175 respectively, in SEQ ID NO:185. Similarly, the alterations V43D, G100R, S131D, S162C, and S174D are at positions 49, 106, 137, 168, and 180 respectively, in SEQ ID NO:187.

DNAs encoding these altered antibodies were tested in "chain drop out" experiments, as explained in U.S. Provisional Application 62/342,167, Example 3, which is incorporated herein by reference. Briefly, five different combinations of DNAs were used in a set of five transfections done for each pair of altered anti-hPD1 and anti-hCTLA4 antibodies, i.e., (1) altered anti-hPD1 #1/altered anti-hCTLA4 10D4 and (2) altered anti-hPD1 #1/altered anti-hCTLA4 11F4. For each pair of antibodies, DNAs encoding the following HCs and LCs were transfected into EXPI293™ cells in five separate transfections: 1) HC1, LC1, HC2, and LC2; 2) HC1 and LC1; 3) HC1 and LC2; 4) HC2 and LC2; and 5) HC2 and LC1. The transfectants were cultured, and the culture supernatants were harvested and analyzed by SDS-PAGE and Western blotting. Antibodies were detected using an HRP-conjugated polyclonal goat-anti-human IgG (Fc-specific).

Figure 17:
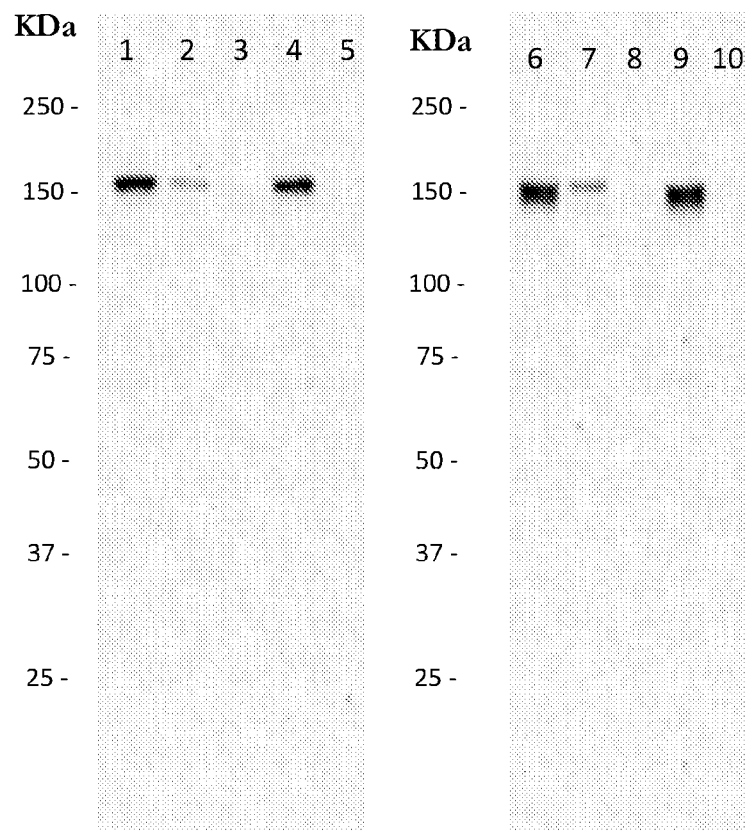
FIG. 17: Chain drop-out transient transfections to assess HC/LC pairing. Experiments are described in Example 11. Each set of five samples comes from transfections using various combinations of the DNAs encoding a first heavy chain (HC1) and a first light chain (LC1), which together encode a first antibody (anti-hPD1 #1), and a second heavy chain (HC2) and a second light chain (LC2), which together encode a second antibody (anti-hCTLA4 10D4 or 11F4). The combinations of DNAs used in the transfections encoded the following chains: lanes 1 and 6, HC1, LC1, HC2, and LC2; lanes 2 and 7, HC1 and LC1; lanes 3 and 8, HC1 and LC2; lanes 4 and 9, HC2 and LC2; and lanes 5 and 10, HC2 and LC1. The first and second of antibodies used were altered anti-hPD1 #1 and altered anti-hCTLA4 10D4 (left panel) or altered anti-hCTLA4 11F4 (right panel).

As can be seen in FIG. 17, when DNAs encoding HC1, LC1, HC2, and LC2 were co-transfected into EXPI293™ cells, IgG antibodies of around 150 kilodaltons (Kda) were detected in the supernatants (FIG. 17, lanes 1 and 6). When DNAs encoding HC1 and LC1 or HC2 and LC2 were co-transfected, full-length antibodies at around 150 Kda were also detected (FIG. 17, lanes 2, 4, 7, and 9), indicating that the cognate HC/LC pairs could form. However, when DNAs encoding non-cognate pairs HC1/LC2 and HC2/LC1 were co-transfected, no antibody was detected (FIG. 17, lanes 3, 5, 8, and 10), suggesting that the non-cognate HC/LC pairs do not form readily. Thus, these data suggest that the alterations in these antibodies reduced or eliminated non-cognate HC/LC pairing observed in the absence of the alterations.

To confirm these results, mass spectrometry was performed. To obtain enough material for analysis, DNAs encoding the HCs and LCs (HC1, LC1, HC2, and LC2) of each pair of altered antibodies, i.e., altered anti-hPD1 #1/altered anti-hCTLA4 10D4 and altered anti-hPD1 #1/altered anti-hCTLA4 11F4, were used to transfect cells on a larger scale. Antibodies in the culture supernatant were purified by Protein A affinity chromatography. These antibodies were subjected to mass spectrometry on Agilent 6224 accurate-mass time-of-flight (TOF) mass spectrometer equipped with an electrospray ionization (ESI) source.

Panels A and B of FIG. 18 show the results for the altered anti-hPD1 #1/altered anti-hCTLA4 10D4 pair. Panel A shows results over a broad range of sizes, and panel B zooms in on the size range of full length IgG antibodies, i.e., just under 150 Kda. Panel A shows two major peaks within the size range of full length IgG antibodies and a trace of a peak at about 75 Kda, possibly a half antibody containing an HC and an LC. Panel B shows a dominant peak at 145,473.16 daltons, which matches the predicted mass of full length altered anti-hCTLA4 10D4 (145477.80 daltons) with an error of 32 parts per million (ppm). A shorter peak at 147,065.89 daltons matches the predicted mass of altered anti-hPD1 #1 (147068.86 daltons) with an error of 20 ppm. By calculation of the area under the peaks, the altered anti-hCTLA4 10D4 and the altered anti-hPD1 #1 antibodies constituted, respectively, 72.8% and 27.2% of the mass of antibody in the mixture, as indicated in FIG. 18, panel B.

Panels A and B of FIG. 19 show the results for the altered anti-hPD1 #1/altered anti-hCTLA4 11F4 pair. Panel A shows results over a broad range of sizes, and panel B zooms in on the size range of full length IgG antibodies. Panel A shows two major peaks within the size range of full length IgG antibodies, and a trace of a peak at about 75 Kda. Panel B shows a dominant peak at 145,430.59 daltons, which matches the predicted mass of full length altered anti-hCTLA4 10D4 (145,427.68 daltons) with an error of 20 ppm. A shorter peak at 147,076.88 daltons matches to the predicted mass of altered anti-hPD1 #1 (147,068.86 daltons) with an error of 54.5 ppm. The altered anti-hCTLA4 11F4 and the altered anti-hPD1 #1 antibodies constituted, respectively, 70.9% and 29.1% of the mass of antibody in the mixture, as indicated in FIG. 19, panel B.

Tables 20 and 21 below show the predicted masses of all possible IgG species that could result from cognate or non-cognate HC/LC pairing and/or homo- or heterodimer formation of HCs. In Table 20 and 21, HC1 and LC1 are the HC and LC of altered anti-hPD1 #1. HC2 and LC2 are the HC and LC of altered anti-hCTLA4 10D4 (Table 20) and 11F4 (Table 21).

TABLE 20

Predicted masses of potential IgGs in cells transfected with DNAs encoding altered anti-hPD1 #1 and altered anti-hCTLA4 10D4

| Combination | Predicted mass (daltons) |
|---|---|
| HC1/LC1 + HC1/LC1 | 147068.86 |
| HC1/LC1 + HC1/LC2 | 146392.35 |
| HC1/LC1 + HC2/LC1 | 146949.84 |
| HC1/LC1 + HC2/LC2 | 146273.33 |
| HC1/LC2 + HC2/LC1 | 146273.33 |
| HC2/LC1 + HC2/LC1 | 146830.82 |
| HC1/LC2 + HC1/LC2 | 145715.84 |
| HC2/LC1 + HC2/LC2 | 146154.31 |
| HC1/LC2 + HC2/LC2 | 145596.82 |
| HC2/LC2 + HC2/LC2 | 145477.80 |

TABLE 21

Predicted masses of potential IgGs in cells transfected with DNAs encoding altered anti-hPD1 #1 and altered anti-hCTLA4 11F4

| Combination | Predicted mass (daltons) |
|---|---|
| HC1/LC1 + HC1/LC1 | 147068.86 |
| HC1/LC1 + HC1/LC2 | 146419.37 |
| HC1/LC1 + HC2/LC1 | 146897.76 |
| HC1/LC1 + HC2/LC2 | 146248.27 |
| HC1/LC2 + HC2/LC1 | 146248.27 |
| HC2/LC1 + HC2/LC1 | 146726.66 |
| HC1/LC2 + HC1/LC2 | 145769.88 |
| HC2/LC1 + HC2/LC2 | 146077.17 |
| HC1/LC2 + HC2/LC2 | 145598.78 |
| HC2/LC2 + HC2/LC2 | 145427.68 |

The mass spectrometry data, combined with the results from the chain drop out experiment described above, strongly suggest that a mixture containing only two major antibody species can be produced in a single host cell line.

Example 12: Luciferase Reporter Assays to Assess the Potency of the Altered Antibodies The following experiments tested the potency of altered (as described in Example 11) and unaltered versions of anti-hCTLA4 antibodies 10D4 or 11F4 and altered and unaltered versions of anti-hPD1 antibody #1, either alone or in mixtures containing altered anti-PD1 #1 and an altered CTLA4 antibody (either 10D4 or 11F4) produced by a single host cell line (as described in Example 11 above).

Figure 20:
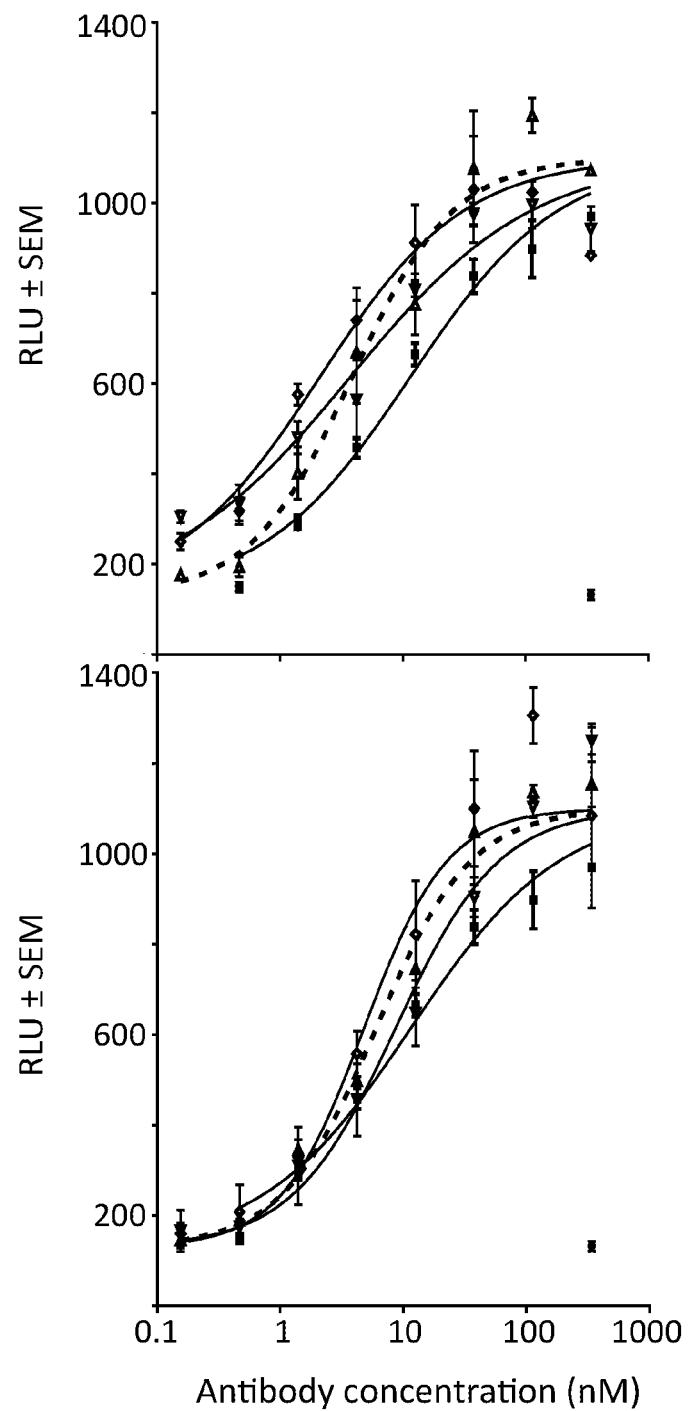
FIG. 20: Potency of altered and unaltered anti-hCTLA4 antibodies alone and in an antibody mixture. Procedures are described in Example 12. The x axes show the concentration of antibody used in each assay, and the y axes show RLU±SEM. The symbols and lines signify antibody samples as follows: filled squares joined by a solid line, anti-hCTLA4 antibody 10D1, a positive control, in both top and bottom panels; unfilled diamonds joined by a solid line, anti-hCTLA4 antibody 10D4 (top panel) or 11F4 (bottom panel); unfilled downward-pointing triangles joined by a solid line, anti-hCTLA4 antibody 10D4 (top panel) or 11F4 (bottom panel), both altered as described in Example 11; unfilled upward-pointing triangles joined by a dashed line, a mixture of altered anti-PD1 antibody #1 and altered anti-hCTLA4 antibody 10D4 (top panel) or altered anti-hCTLA4 antibody 11F4 (bottom panel), where the mixtures were made in a single cell line as described in Example 11; and the filled circle with error bars (which looks like a square) in the lower right corner of each panel, the value obtained for the negative control, which was an unrelated human IgG1 antibody.

This assay for anti-hCTLA4 potency is described in detail in Example 8 of U.S. Provisional Application 62/342,167, which is incorporated herein by reference. Briefly, Jurkat cells stably expressing CTLA4 and luciferase (from Promega Corporation, Madison, Wis., USA) were seeded into microtiter plates. Following one day of incubation, Raji cells expressing hCD80 (also called hB7-1) and hCD86 (also called hB7-2) were added to each well, along with an anti-hCTLA4 antibody (altered or unaltered 10D4 or 11F4 or the control antibody, 10D1) or one of the mixtures containing altered anti-hPD1 #1 and either altered anti-hCTLA4 10D4 or altered anti-hCTLA4 11F4. When a mixture of antibodies was used, the amount of anti-hCTLA4 antibody was determined based on the percentage of anti-hCTLA4 antibody in the mixture. See Example 11. The hCD80 and hCD86 expressed on the Raji cells can engage with the hCTLA4 on the Jurkat cells, activating an intracellular signaling pathway that inhibits expression of luciferase. If an anti-hCTLA4 antibody prevents hCTLA4 engagement with hCD80 and/or hCD86, luciferase expression will increase. A dilution series of the antibody or the mixtures was done so that different wells had different concentrations of the antibody or an antibody mixture. The plates were incubated at 37° C., and thereafter, BIO-GLO™ luciferase reagent (Promega, Cat no. G7941) was added. Plates were read in ENVISION® plate reader (PerkinElmer). The anti-hCTLA4 antibody 10D1, which has the same VH and VL as ipilimumab, was used as a positive control. An unrelated human IgG1 antibody (HuIgG1) was used as a negative control. Results are shown in FIG. 20 and Tables 22 and 23 below.

TABLE 22

Potency of anti-hCTLA4 antibody 10D4

| Antibody | $IC_{50}$ (nM) |
|---|---|
| Anti-CTLA4 10D1 (positive control) | 11.55 |
| Anti-CTLA4 10D4 | 2.12 |
| Altered anti-CTLA4 10D4 | 3.75 |
| Altered anti-CTLA4 10D4 and altered anti-PD1 #1 | 3.87 |

TABLE 23

Potency of anti-hCTLA4 antibody 11F4

| Antibody | $IC_{50}$ (nM) |
|---|---|
| Anti-CTLA4 10D1 (positive control) | 11.55 |
| Anti-CTLA4 11F4 | 4.80 |
| Altered anti-CTLA4 11F4 | 8.68 |
| Altered anti-CTLA4 11F4 and altered anti-PD1 #1 | 6.03 |

These results indicate that the $IC_{50}$'s of anti-hCTLA4 10D4, altered anti-hCTLA4 10D4, the mixture of altered anti-hCTLA4 10D4 with altered anti-hPD1 #1 were comparable, as were the $IC_{50}$'s of anti-hCTLA4 11F4, altered anti-hCTLA4 11F4, and the mixture of altered anti-hCTLA4 11F4 with altered anti-hPD1 #1. Thus, the alterations in the anti-CTLA4 antibodies 10D4 and 11F4 had little effect on their potency in this assay.

Figure 21:
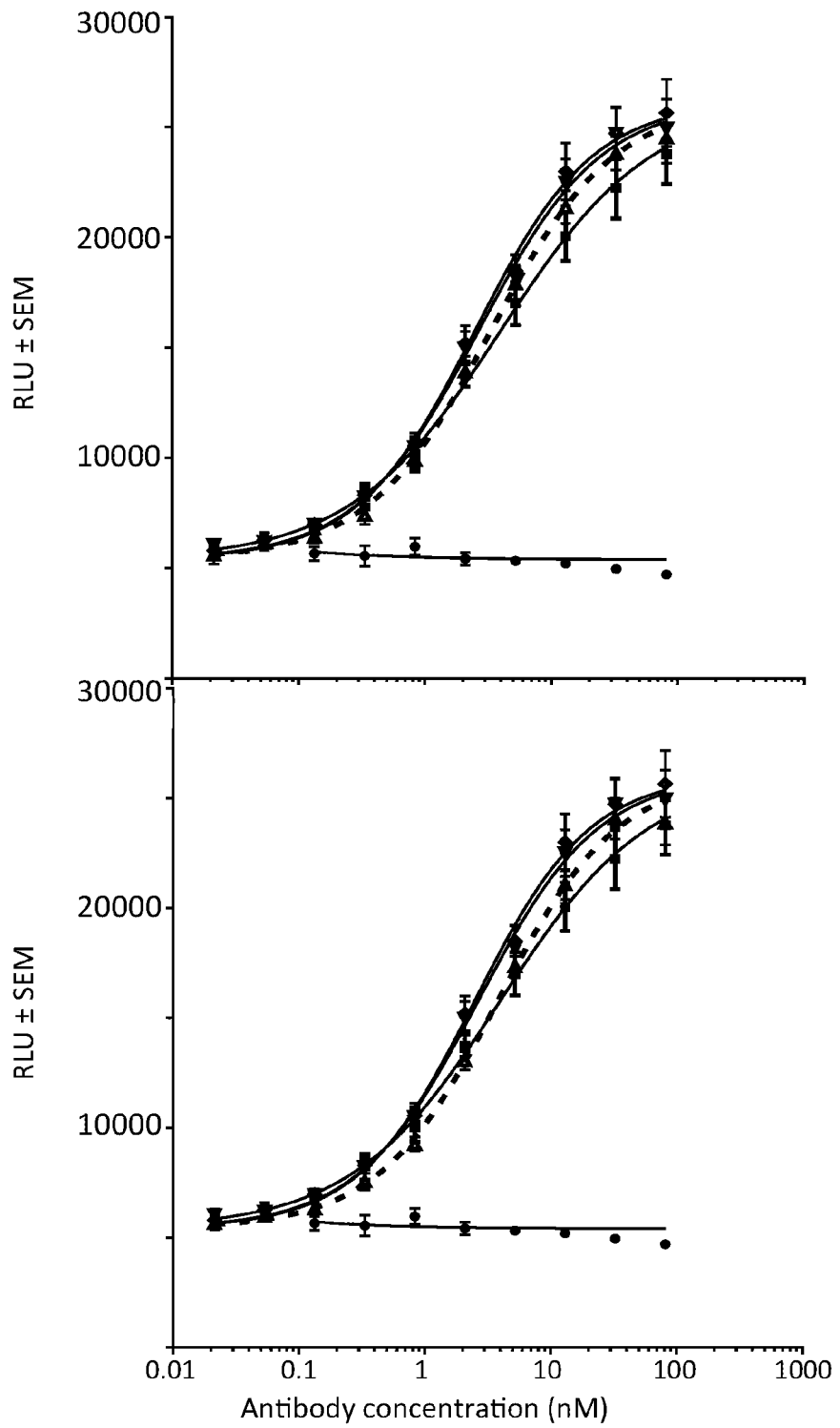
FIG. 21: Potency of altered and unaltered anti-hPD1 antibodies alone and in an antibody mixture. Procedures are described in Example 12. The x axes show the concentration of antibody used in each assay, and the y axes show RLU±SEM. The symbols and lines signify antibody samples as follows: filled squares joined by a solid line, anti-hPD1 antibody having the VH and VL of nivolumab, a positive control (both top and bottom panels); filled diamonds joined by a solid line, anti-hPD1 antibody #1 without alteration (both top and bottom panels); unfilled downward-pointing triangles joined by a solid line, anti-hPD1 antibody #1 altered as described in Example 11 (both top and bottom panels); unfilled upward-pointing triangles joined by a dashed line, a mixture of altered anti-hPD1 antibody #1 and altered anti-hCTLA4 antibody 10D4 (bottom panel) or altered anti-hCTLA4 antibody 11F4 (top panel), where the mixtures were made in a single cell line as described in Example 11; and filled circles joined by a solid line, an unrelated human IgG4 antibody, a negative control (both top and bottom panels).

The assay for anti-hPD1 potency is described in detail in Example 7 of U.S. Provisional Application 62/342,167, which is incorporated herein by reference. Briefly, Jurkat cells stably expressing hPD1 and luciferase (from Promega Corporation, Madison, Wis., USA) were seeded into 96-well plates ($4 \times 10^4$ cells/well in 20 µl). Following one day of incubation, CHO cells stably expressing hPDL1 ($5 \times 10^4$ cells/well in 20 µl) were added, along with a test antibody or antibody mixture (20 µl) at various dilutions. The hPDL1 expressed on the CHO cells can engage with the hPD1 on the Jurkat cells, activating an intracellular signaling pathway that inhibits expression of luciferase. If an antibody prevents hPD1/hPDL1 engagement, luciferase expression will increase. The plates were incubated at 37° C. in 5% $CO_2$ for 6 hours. BIO-GLO™ luciferase reagent (Promega, cat. no. G7941) was added (40 µl/well) to lyse the cells, and plates were read in ENVISION® plate reader (PerkinElmer). An IgG4 anti-hPD1 antibody comprising the same VH and VL as nivolumab (Nivo-G4) was used as a positive control, and an unrelated IgG4 antibody was used a negative control. The results are shown in FIG. 21 and Tables 24 and 25 below.

TABLE 24

Potency of anti-hPD1 antibody #1

| Antibody | IC$_{50}$ (nM) |
|---|---|
| Nivo-G4 | 3.95 |
| Anti-hPD1 #1 | 2.49 |
| Altered anti-hPD1 #1 | 2.65 |
| Altered anti-CTLA4 10D4 and altered anti-PD1 #1 | 3.80 |

TABLE 25

Potency of anti-hPD1 antibody #1

| Antibody | IC$_{50}$ (nM) |
|---|---|
| Nivo-G4 | 3.98 |
| Anti-hPD1 #1 | 2.50 |
| Altered anti-hPD1 #1 | 2.67 |
| Altered anti-CTLA4 11F4 and altered anti-PD1 #1 | 3.34 |

These data indicate that the alterations in altered anti-hPD1 antibody #1 had little effect on its potency. Further, the IC$_{50}$'s of the mixtures containing altered anti-hPD1 #1 and altered anti-hCTLA 10D4 or 11F4 produced in a single cell line as described in Example 11 were comparable to that of altered anti-PD1 #1 alone.

Example 13: Effects of Anti-hPD1 or Anti-hCTLA4 Antibodies or a Mixture Thereof on T Cell Activation The following experiment tests the effects on T cell activation of an IgG4 anti-hPD1 antibody, either of two IgG1 anti-hCTLA4 antibodies, or mixtures of the anti-hPD1 antibody with either of the anti-hCTLA4 antibodies.

Human PBMCs from a healthy donor were distributed in a 96-well U-bottom microtiter plate at 3×10$^5$ cells per well. Antibodies (or a control solution lacking antibodies) were added to each well. The following six different antibodies, combinations thereof, or a control solution lacking antibodies were used: 1) an IgG4 anti-hPD1 #1 antibody at 2.5 µg/ml; 2) an IgG1 anti-hCTLA4 #10D4 antibody at 10 µg/ml; 3) an IgG1 anti-hCTLA4 #11F4 antibody at 10 µg/ml; 4) a mixture of the anti-hPD1 #1 antibody at 2.5 µg/ml and the anti-hCTLA4 #10D4 antibody at 10 µg/ml; 5) a mixture of the anti-hPD1 #1 antibody at 2.5 µg/ml and the anti-hCTLA4 #11F4 antibody at 10 µg/ml; or 6) a control solution lacking antibodies. Staphylococcal Enterotoxin B (SEB) was added at varying concentrations (0, 0.6, 6, 60, or 600 ng/ml) to all wells. All conditions were tested in duplicate. Cells were incubated at 37° C. at 5% CO$_2$ for 4 days. On the fourth day, cell supernatants were collected and assayed to determine levels of IL-2 using ELISA. Absolute concentrations of IL-2 were determined by comparison to a standard curve generated using known quantities of IL-2.

Figure 22:
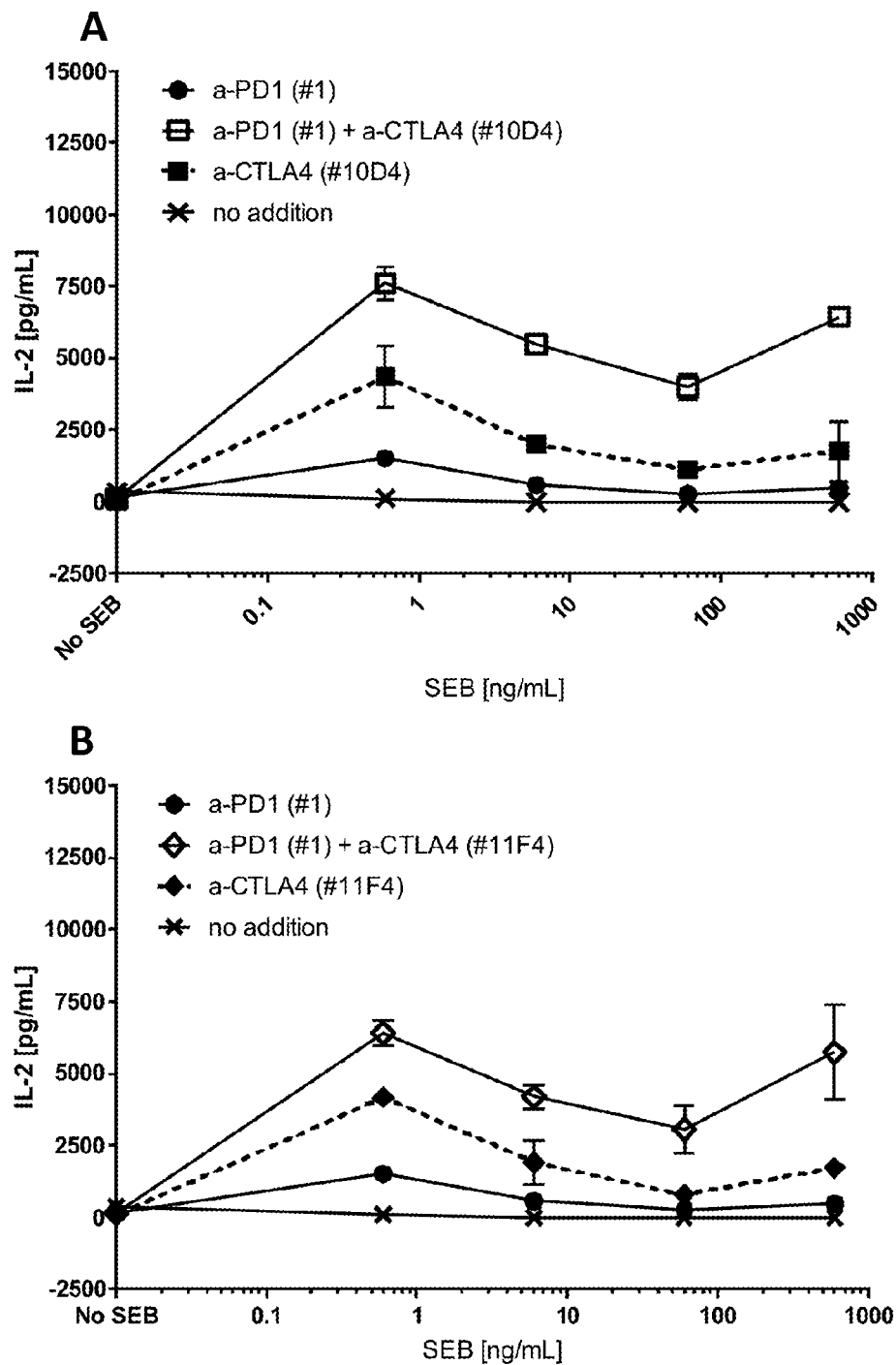
FIG. 22: Induction of IL-2 expression by anti-hPD1, anti-hCTLA4 antibodies, or combinations thereof. Procedures are described in Example 13. The antibodies added to the various samples are indicated in the legend in the upper left corner of each of panels A and B. The designation "a-PD1 (#1)" indicates the anti-hPD1 antibody 1, and the designations "a-CTLA4 (#10D4)" and "a-CTLA4 (#11F4)" indicate the anti-hCTLA4 antibodies 10D4 and 11F4, respectively. As indicated, the x axes show the concentrations of Staphylococal Enterotoxin B (SEB) in nanograms per milliliter (ng/mL) in the samples, and the y axes show the concentrations (picograms per milliliter (pg/mL)) of IL-2 detected in the cell supernatants of the samples.

Control samples to which no antibody was added showed no increase in IL-2 production. FIG. 22, panels A and B, solid lines with "X" symbol. Addition of the IgG4 anti-hPD1 #1 antibody slightly increased IL-2 production. FIG. 22, panels A and B, solid lines with filled circles. Addition of the IgG1 anti-hCTLA4 #10D4 or the IgG1 anti-hCTLA4 #11F4 antibody significantly increased IL-2 production. FIG. 22, panels A or B, dashed lines with filled squares or filled diamonds, respectively. Addition of a mixture of the anti-hPD1 antibody and the anti-hCTLA4 #10D4 or 11F4 antibody increased the IL-2 production more than the addition of any of these antibodies alone. FIG. 22, panels A and B, solid lines with open squares or open diamonds, respectively.

What is claimed is:

1. An anti-human cytotoxic T lymphocyte-associated 4 (anti-hCTLA4) antibody comprising a heavy chain variable domain (VH) and a light chain variable region (VL), each comprising a complementarity determining region 1 (CDR1), a CDR2, and a CDR3,
   wherein the anti-hCTLA4 antibody comprises a VH CDR1, VH CDR2, VH CDR3, VL CDR1, VL CDR 2, and VL CDR3 comprising, respectively, the following amino acid sequences: SEQ ID NOs: 3, 4, 5, 8, 9, and 10; SEQ ID NOs: 3, 13, 5, 16, 9, and 17; SEQ ID NOs: 3, 20, 21, 16, 9, and 17; SEQ ID NOs: 3, 24, 25, 28, 9, and 17; SEQ ID NOs: 3, 31, 5, 34, 9, and 17; SEQ ID NOs: 3, 37, 5, 40, 9, and 10; SEQ ID NOs: 3, 43, 5, 28, 9, and 17; SEQ ID NOs: 3, 46, 47, 50, 9, and 17; SEQ ID NOs: 3, 31, 5, 55, 9, and 56; SEQ ID NOs: 3, 59, 5, 40, 9, and 62; SEQ ID NOs: 3, 65, 21, 16, 9, and 62; or SEQ ID NOs: 3, 70, 21, 73, 9, and 62, and
   wherein the anti-hCTLA4 antibody inhibits interaction of hCTLA4 with human B-lymphocyte activation antigen B7-1 (hB7-1) and/or human B-lymphocyte activation antigen B7-2 (hB7-2).

2. The anti-hCTLA4 antibody of claim 1, wherein the VH comprises an amino acid sequence which comprises no more than four alterations relative to an amino acid sequence selected from the group consisting of SEQ ID NOs: 2, 12, 19, 23, 30, 36, 42, 45, 52, 58, 64, and 69, and/or the VL comprises an amino acid sequence which comprises no more than four amino acid alterations relative to an amino acid sequence selected from the group consisting of SEQ ID Nos: 7, 15, 27, 33, 39, 49, 54, 61, 67, and 72.

3. The anti-hCTLA4 antibody of claim 2,
   wherein the VH and the VL of the anti-hCTLA4 antibody each comprise an amino acid sequence, which, together, comprise two sequences,
   wherein one of the two sequences comprises not more than four amino acid alterations relative to one sequence in a VH/VL pair of sequences, and the other of the two sequences comprises not more than four amino acid alterations relative to the other sequence in the VH/VL pair of sequences, and
   wherein the VH/VL pair of sequences is selected from the group consisting of: SEQ ID NOs: 2 (VH) and 7 (VL); SEQ ID NOs: 12 (VH) and 15 (VL); SEQ ID NOs: 19 (VH) and 15 (VL); SEQ ID NOs: 23 (VH) and 27 (VL); SEQ ID NOs: 30 (VH) and 33 (VL); SEQ ID NOs: 36 (VH) and 39 (VL); SEQ ID NOs: 42 (VH) and 27 (VL); SEQ ID NOs: 45 (VH) and 49 (VL); SEQ ID NOs: 52 (VH) and 54 (VL); SEQ ID NOs: 58 (VH) and 61 (VL); SEQ ID NOs: 64 (VH) and 67 (VL); and SEQ ID NOs: 69 (VH) and 72 (VL).

4. The anti-CTLA4 antibody of claim 1, wherein
the VH CDR1, VH CDR2, VH CDR3, VL CDR1, VL CDR 2, and VL CDR3 comprise, respectively, the amino acid sequences of SEQ ID NOs: 3, 65, 21, 16, 9, and 62,
the VH comprises an amino acid sequence which comprises no more than four alterations relative to the amino acid sequence of SEQ ID NO: 64, and
the VL comprises an amino acid sequence which comprises no more than four alterations relative to the amino acid sequence of SEQ ID NO: 67.

5. One or more polynucleotide(s) encoding an anti-hCTLA4 antibody comprising a VH and a VL, each comprising a CDR1, a CDR2, and a CDR3,
wherein the anti-hCTLA4 antibody comprises a VH CDR1, VH CDR2, VH CDR3, VL CDR1, VL CDR 2, and VL CDR3 comprising, respectively, the following amino acid sequences: SEQ ID NOs: 3, 4, 5, 8, 9, and 10; SEQ ID NOs: 3, 13, 5, 16, 9, and 17; SEQ ID NOs: 3, 20, 21, 16, 9, and 17; SEQ ID NOs: 3, 24, 25, 28, 9, and 17; SEQ ID NOs: 3, 31, 5, 34, 9, and 17; SEQ ID NOs: 3, 37, 5, 40, 9, and 10; SEQ ID NOs: 3, 43, 5, 28, 9, and 17; SEQ ID NOs: 3, 46, 47, 50, 9, and 17; SEQ ID NOs: 3, 31, 5, 55, 9, and 56; SEQ ID NOs: 3, 59, 5, 40, 9, and 62; SEQ ID NOs: 3, 65, 21, 16, 9, and 62; or SEQ ID NOs: 3, 70, 21, 73, 9, and 62, and
wherein the anti-hCTLA4 antibody inhibits interaction of hCTLA4 with hB7-1 and/or hB7-2.

6. A host cell comprising one or more polynucleotide(s) encoding an anti-hCTLA4 antibody comprising a VH and a VL, each comprising a CDR1, a CDR2, and a CDR3,
wherein the anti-hCTLA4 antibody comprises a VH CDR1, VH CDR2, VH CDR3, VL CDR1, VL CDR 2, and VL CDR3 comprising, respectively, the following sequences: SEQ ID NOs: 3, 4, 5, 8, 9, and 10; SEQ ID NOs: 3, 13, 5, 16, 9, and 17; SEQ ID NOs: 3, 20, 21, 16, 9, and 17; SEQ ID NOs: 3, 24, 25, 28, 9, and 17; SEQ ID NOs: 3, 31, 5, 34, 9, and 17; SEQ ID NOs: 3, 37, 5, 40, 9, and 10; SEQ ID NOs: 3, 43, 5, 28, 9, and 17; SEQ ID NOs: 3, 46, 47, 50, 9, and 17; SEQ ID NOs: 3, 31, 5, 55, 9, and 56; SEQ ID NOs: 3, 59, 5, 40, 9, and 62; SEQ ID NOs: 3, 65, 21, 16, 9, and 62; or SEQ ID NOs: 3, 70, 21, 73, 9, and 62, and
wherein the anti-hCTLA4 antibody inhibits interaction of hCTLA4 with hB7-1 and/or hB7-2.

7. A method of treating a patient having a cancer or an infection comprising:
(a) administering to the patient an anti-hCTLA4 antibody comprising a VH and a VL, each comprising a CDR1, a CDR2, and a CDR3, wherein: (1) the anti-hCTLA4 antibody comprises a VH CDR1, VH CDR2, VH CDR3, VL CDR1, VL CDR 2, and VL CDR3 comprising, respectively, the following sequences: SEQ ID NOs: 3, 4, 5, 8, 9, and 10; SEQ ID NOs: 3, 13, 5, 16, 9, and 17; SEQ ID NOs: 3, 20, 21, 16, 9, and 17; SEQ ID NOs: 3, 24, 25, 28, 9, and 17; SEQ ID NOs: 3, 31, 5, 34, 9, and 17; SEQ ID NOs: 3, 37, 5, 40, 9, and 10; SEQ ID NOs: 3, 43, 5, 28, 9, and 17; SEQ ID NOs: 3, 46, 47, 50, 9, and 17; SEQ ID NOs: 3, 31, 5, 55, 9, and 56; SEQ ID NOs: 3, 59, 5, 40, 9, and 62; SEQ ID NOs: 3, 65, 21, 16, 9, and 62; or SEQ ID NOs: 3, 70, 21, 73, 9, and 62; and (2) the anti-hCTLA4 antibody inhibits interaction of hCTLA4 with hB7-1 and/or hB7-2; or
(b) administering to the patient one or more polynucleotide(s) encoding the anti-hCTLA4 antibody of (a).

8. A mixture comprising an anti-hCTLA4 antibody and an anti-hPD1 antibody, wherein:
(a) (1) the anti-hCTLA4 antibody comprises a VH and a VL, each comprising a CDR1, a CDR2, and a CDR3, (2) the anti-hCTLA4 antibody comprises a VH CDR1, VH CDR2, VH CDR3, VL CDR1, VL CDR 2, and VL CDR3 comprising, respectively, the following sequences: SEQ ID NOs: 3, 4, 5, 8, 9, and 10; SEQ ID NOs: 3, 13, 5, 16, 9, and 17; SEQ ID NOs: 3, 20, 21, 16, 9, and 17; SEQ ID NOs: 3, 24, 25, 28, 9, and 17; SEQ ID NOs: 3, 31, 5, 34, 9, and 17; SEQ ID NOs: 3, 37, 5, 40, 9, and 10; SEQ ID NOs: 3, 43, 5, 28, 9, and 17; SEQ ID NOs: 3, 46, 47, 50, 9, and 17; SEQ ID NOs: 3, 31, 5, 55, 9, and 56; SEQ ID NOs: 3, 59, 5, 40, 9, and 62; SEQ ID NOs: 3, 65, 21, 16, 9, and 62; or SEQ ID NOs: 3, 70, 21, 73, 9, and 62, and (3) the anti-hCTLA4 antibody inhibits interaction of hCTLA4 with hB7-1 and/or hB7-2, and
(b) (1) the anti-hPD1 antibody comprises a VH and a VL, each comprising a CDR1, a CDR2, and a CDR3, (2) the anti-hPD1 antibody comprises a VH CDR1, VH CDR2, VH CDR3, VL CDR1, VL CDR 2, and VL CDR3 comprising, respectively, the following sequences: SEQ ID NOs: 88, 89, 90, 93, 94, and 95; SEQ ID NOs: 98, 89, 99, 102, 94, and 95; SEQ ID NOs: 105, 89, 90, 93, 108, and 95; SEQ ID NOs: 105, 111, 112, 115, 94, and 95; SEQ ID NOs: 105, 111, 90, 120, 94, and 95; SEQ ID NOs: 88, 89, 112, 102, 108, and 95; SEQ ID NOs: 88, 89, 127, 130, 108, and 131; SEQ ID NOs: 88, 89, 134, 137, 94, and 131; SEQ ID NOs: 98, 89, 90, 142, 94, and 131; SEQ ID NOs: 98, 111, 112, 130, 94, and 131; SEQ ID NOs: 149, 150, 112, 130, 94, and 131; SEQ ID NOs: 105, 111, 90, 142, 94, and 131; SEQ ID NOs: 149, 89, 127, 115, 94, and 95; SEQ ID NOs: 88, 89, 112, 93, 94, and 95; or SEQ ID NOs: 105, 89, 127, 102, 108, and 95, and (3) the anti-hPD1 antibody inhibits the interaction of hPD1 with hPDL1.

9. The mixture of claim 8, wherein
(a) (1) the VH CDR1, VH CDR2, VH CDR3, VL CDR1, VL CDR 2, and VL CDR3 of the anti-hCTLA4 antibody comprise, respectively, the amino acid sequences of SEQ ID NOs: 3, 65, 21, 16, 9, and 62, (2) the VH of the anti-hCTLA4 antibody comprises an amino acid sequence which comprises no more than four alterations relative to the amino acid sequence of SEQ ID NO: 64, and (3) the VL of the anti-hCTLA4 antibody comprises an amino acid sequence which comprises no more than four alterations relative to the amino acid sequence of SEQ ID NO: 67, and
(b) (1) the VH CDR1, VH CDR2, VH CDR3, VL CDR1, VL CDR 2, and VL CDR3 of the anti-hPD1 antibody comprise, respectively, the amino acid sequences of SEQ ID NOs: 88, 89, 90, 93, 94, and 95, (2) the VH comprises an amino acid sequence which comprises no more than four alterations relative to the amino acid sequence of SEQ ID NO: 87, and (3) the VL comprises an amino acid sequence which comprises no more than four alterations relative to the amino acid sequence of SEQ ID NO: 92.

10. One or more polynucleotide(s) encoding a mixture comprising an anti-hCTLA4 antibody and an anti-hPD1 antibody, wherein
(a) (1) the anti-hCTLA4 antibody comprises a VH and a VL, each comprising a CDR1, a CDR2, and a CDR3, (2) the anti-hCTLA4 antibody comprises a VH CDR1, VH CDR2, VH CDR3, VL CDR1, VL CDR 2, and VL CDR3 comprising, respectively, the following amino acid sequences: SEQ ID NOs: 3, 4, 5, 8, 9, and 10; SEQ ID NOs: 3, 13, 5, 16, 9, and 17; SEQ ID NOs: 3, 20, 21, 16, 9, and 17; SEQ ID NOs: 3, 24, 25, 28, 9, and 17; SEQ ID NOs: 3, 31, 5, 34, 9, and 17; SEQ ID NOs: 3, 37, 5, 40, 9, and 10; SEQ ID NOs: 3, 43, 5, 28, 9, and 17; SEQ ID NOs: 3, 46, 47, 50, 9, and 17; SEQ ID NOs: 3, 31, 5, 55, 9, and 56; SEQ ID NOs: 3, 59, 5, 40, 9, and 62; SEQ ID NOs: 3, 65, 21, 16, 9, and 62; or SEQ ID NOs: 3, 70, 21, 73, 9, and 62, and (3) the anti-hCTLA4 antibody inhibits interaction of hCTLA4 with hB7-1 and/or hB7-2, and (b) (1) the anti-hPD1 antibody comprises a VH and a VL, each comprising a CDR1, a CDR2, and a CDR3, (2) the anti-hPD1 antibody comprises a VH CDR1, VH CDR2, VH CDR3, VL CDR1, VL CDR 2, and VL CDR3 comprising, respectively, the following amino acid sequences: SEQ ID NOs: 88, 89, 90, 93, 94, and 95; SEQ ID NOs: 98, 89, 99, 102, 94, and 95; SEQ ID NOs: 105, 89, 90, 93, 108, and 95; SEQ ID NOs: 105, 111, 112, 115, 94, and 95; SEQ ID NOs: 105, 111, 90, 120, 94, and 95; SEQ ID NOs: 88, 89, 112, 102, 108, and 95; SEQ ID NOs: 88, 89, 127, 130, 108, and 131; SEQ ID NOs: 88, 89, 134, 137, 94, and 131; SEQ ID NOs: 98, 89, 90, 142, 94, and 131; SEQ ID NOs: 98, 111, 112, 130, 94, and 131; SEQ ID NOs: 149, 150, 112, 130, 94, and 131; SEQ ID NOs: 105, 111, 90, 142, 94, and 131; SEQ ID NOs: 149, 89, 127, 115, 94, and 95; SEQ ID NOs: 88, 89, 112, 93, 94, and 95; or SEQ ID NOs: 105, 89, 127, 102, 108, and 95, and (3) the anti-hPD1 antibody inhibits the interaction of hPD1 with hPDL1.

11. A host cell comprising one or more polynucleotides encoding a mixture comprising an anti-hCTLA4 antibody and an anti-hPD1 antibody, wherein (a) (1) the anti-hCTLA4 antibody comprises a VH and a VL, each comprising a CDR1, a CDR2, and a CDR3, (2) the anti-hCTLA4 antibody comprises a VH CDR1, VH CDR2, VH CDR3, VL CDR1, VL CDR 2, and VL CDR3 comprising, respectively, the following amino acid sequences: SEQ ID NOs: 3, 4, 5, 8, 9, and 10; SEQ ID NOs: 3, 13, 5, 16, 9, and 17; SEQ ID NOs: 3, 20, 21, 16, 9, and 17; SEQ ID NOs: 3, 24, 25, 28, 9, and 17; SEQ ID NOs: 3, 31, 5, 34, 9, and 17; SEQ ID NOs: 3, 37, 5, 40, 9, and 10; SEQ ID NOs: 3, 43, 5, 28, 9, and 17; SEQ ID NOs: 3, 46, 47, 50, 9, and 17; SEQ ID NOs: 3, 31, 5, 55, 9, and 56; SEQ ID NOs: 3, 59, 5, 40, 9, and 62; SEQ ID NOs: 3, 65, 21, 16, 9, and 62; or SEQ ID NOs: 3, 70, 21, 73, 9, and 62, and (3) the anti-hCTLA4 antibody inhibits interaction of hCTLA4 with hB7-1 and/or hB7-2, and (b) (1) the anti-hPD1 antibody comprises a VH and a VL, each comprising a CDR1, a CDR2, and a CDR3, (2) the anti-hPD1 antibody comprises a VH CDR1, VH CDR2, VH CDR3, VL CDR1, VL CDR 2, and VL CDR3 comprising, respectively, the following amino acid sequences: SEQ ID NOs: 88, 89, 90, 93, 94, and 95; SEQ ID NOs: 98, 89, 99, 102, 94, and 95; SEQ ID NOs: 105, 89, 90, 93, 108, and 95; SEQ ID NOs: 105, 111, 112, 115, 94, and 95; SEQ ID NOs: 105, 111, 90, 120, 94, and 95; SEQ ID NOs: 88, 89, 112, 102, 108, and 95; SEQ ID NOs: 88, 89, 127, 130, 108, and 131; SEQ ID NOs: 88, 89, 134, 137, 94, and 131; SEQ ID NOs: 98, 89, 90, 142, 94, and 131; SEQ ID NOs: 98, 111, 112, 130, 94, and 131; SEQ ID NOs: 149, 150, 112, 130, 94, and 131; SEQ ID NOs: 105, 111, 90, 142, 94, and 131; SEQ ID NOs: 149, 89, 127, 115, 94, and 95; SEQ ID NOs: 88, 89, 112, 93, 94, and 95; or SEQ ID NOs: 105, 89, 127, 102, 108, and 95, and (3) the anti-hPD1 antibody inhibits the interaction of hPD1 with hPDL1.

12. A method of treating a patient having a cancer or an infection comprising:

(a) administering to the patient a mixture comprising an anti-hCTLA4 antibody and an anti-hPD1 antibody, wherein:

(1) (A) the anti-hCTLA4 antibody comprises a VH and a VL, each comprising a CDR1, a CDR2, and a CDR3, (B) the anti-hCTLA4 antibody comprises a VH CDR1, VH CDR2, VH CDR3, VL CDR1, VL CDR 2, and VL CDR3 comprising, respectively, the following amino acid sequences: SEQ ID NOs: 3, 4, 5, 8, 9, and 10; SEQ ID NOs: 3, 13, 5, 16, 9, and 17; SEQ ID NOs: 3, 20, 21, 16, 9, and 17; SEQ ID NOs: 3, 24, 25, 28, 9, and 17; SEQ ID NOs: 3, 31, 5, 34, 9, and 17; SEQ ID NOs: 3, 37, 5, 40, 9, and 10; SEQ ID NOs: 3, 43, 5, 28, 9, and 17; SEQ ID NOs: 3, 46, 47, 50, 9, and 17; SEQ ID NOs: 3, 31, 5, 55, 9, and 56; SEQ ID NOs: 3, 59, 5, 40, 9, and 62; SEQ ID NOs: 3, 65, 21, 16, 9, and 62; or SEQ ID NOs: 3, 70, 21, 73, 9, and 62, and (C) the anti-hCTLA4 antibody inhibits interaction of hCTLA4 with hB7-1 and/or hB7-2; and (2) (A) the anti-hPD1 antibody comprises a VH and a VL, each comprising a CDR1, a CDR2, and a CDR3, (B) the anti-hPD1 antibody comprises a VH CDR1, VH CDR2, VH CDR3, VL CDR1, VL CDR 2, and VL CDR3 comprising, respectively, the following amino acid sequences: SEQ ID NOs: 88, 89, 90, 93, 94, and 95; SEQ ID NOs: 98, 89, 99, 102, 94, and 95; SEQ ID NOs: 105, 89, 90, 93, 108, and 95; SEQ ID NOs: 105, 111, 112, 115, 94, and 95; SEQ ID NOs: 105, 111, 90, 120, 94, and 95; SEQ ID NOs: 88, 89, 112, 102, 108, and 95; SEQ ID NOs: 88, 89, 127, 130, 108, and 131; SEQ ID NOs: 88, 89, 134, 137, 94, and 131; SEQ ID NOs: 98, 89, 90, 142, 94, and 131; SEQ ID NOs: 98, 111, 112, 130, 94, and 131; SEQ ID NOs: 149, 150, 112, 130, 94, and 131; SEQ ID NOs: 105, 111, 90, 142, 94, and 131; SEQ ID NOs: 149, 89, 127, 115, 94, and 95; SEQ ID NOs: 88, 89, 112, 93, 94, and 95; or SEQ ID NOs: 105, 89, 127, 102, 108, and 95, and (C) the anti-hPD1 antibody inhibits the interaction of hPD1 with hPDL1; or (b) administering to the patient one or more polynucleotide(s) encoding the mixture of (a).

* * * * *